US012805188B2

(12) United States Patent
Ahn et al.

(10) Patent No.: US 12,805,188 B2
(45) Date of Patent: Nov. 17, 2026

(54) HETEROCYCLIC COMPOUND, LIGHT-EMITTING DEVICE INCLUDING THE HETEROCYCLIC COMPOUND, AND ELECTRONIC APPARATUS INCLUDING THE LIGHT-EMITTING DEVICE

(71) Applicant: Samsung Display Co., Ltd., Yongin-si (KR)

(72) Inventors: Heechoon Ahn, Yongin-si (KR); Hyeongmin Kim, Yongin-si (KR); Youngjin Park, Yongin-si (KR); Juhui Yun, Yongin-si (KR); Hyoyoung Lee, Yongin-si (KR); Yirang Im, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 983 days.

(21) Appl. No.: 17/895,499

(22) Filed: Aug. 25, 2022

(65) Prior Publication Data

US 2023/0172064 A1 Jun. 1, 2023

(30) Foreign Application Priority Data

Aug. 27, 2021 (KR) ........................ 10-2021-0114256

(51) Int. Cl.
*H10K 85/60* (2023.01)
*C07D 403/14* (2006.01)
(Continued)

(52) U.S. Cl.
CPC ....... *H10K 85/6572* (2023.02); *C07D 403/14* (2013.01); *C07D 405/14* (2013.01);
(Continued)

(58) Field of Classification Search
CPC ............. H10K 85/6572; H10K 85/342; H10K 85/654
See application file for complete search history.

(56) References Cited

U.S. PATENT DOCUMENTS 6,310,360 B1 10/2001 Forrest et al.
6,515,298 B2 2/2003 Forrest et al.
(Continued)

FOREIGN PATENT DOCUMENTS

CN 1402885 A 3/2003
CN 101253185 A 8/2008
(Continued)

OTHER PUBLICATIONS

Zhao et al., J. Org. Chem., 2017, 82, 1024-1033.*
(Continued)

*Primary Examiner* — Vu A Nguyen
(74) *Attorney, Agent, or Firm* — Womble Bond Dickinson (US) LLP

(57) ABSTRACT

A light-emitting device includes a first electrode, a second electrode facing the first electrode, an interlayer between the first electrode and the second electrode and including an emission layer, and at least one heterocyclic compound represented by Formula 1. An electronic apparatus including the light-emitting device is also provided:

[Formula 1]

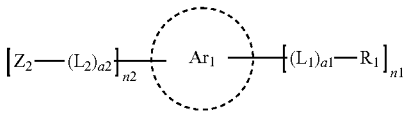

Formula 1 is the same as described herein.

19 Claims, 3 Drawing Sheets

10

(51) Int. Cl.

| | |
|---|---|
| ***C07D 405/14*** | (2006.01) |
| ***C07F 7/08*** | (2006.01) |
| ***C09K 11/06*** | (2006.01) |
| ***H10K 50/11*** | (2023.01) |
| ***H10K 59/12*** | (2023.01) |
| ***H10K 85/40*** | (2023.01) |

(52) U.S. Cl.

CPC ............ *C07F 7/0812* (2013.01); *C09K 11/06* (2013.01); *H10K 85/40* (2023.02); *H10K 85/654* (2023.02); *H10K 85/6574* (2023.02); *C09K 2211/1018* (2013.01); *H10K 50/11* (2023.02); *H10K 59/12* (2023.02)

(56) References Cited

U.S. PATENT DOCUMENTS 7,381,479 B2 6/2008 Lamansky et al.
7,393,599 B2 7/2008 Thompson et al.
7,585,573 B2 9/2009 Lee et al.
7,768,894 B2 8/2010 Kimmelmann et al.
7,776,458 B2 8/2010 Ragini et al.
7,990,046 B2 8/2011 Iwakuma et al.
8,106,199 B2 1/2012 JabbOur et al.
8,389,725 B2 3/2013 Li et al.
8,669,364 B2 3/2014 Li et al.
8,680,760 B2 3/2014 Cheng et al.
8,816,080 B2 8/2014 Li et al.
8,846,940 B2 9/2014 Li et al.
8,946,417 B2 2/2015 Jian et al.
9,051,344 B2 6/2015 Lin et al.
9,076,974 B2 7/2015 Li et al.
9,082,986 B2 7/2015 Kato et al.
9,203,039 B2 12/2015 Li et al.
9,221,857 B2 12/2015 Li et al.
9,224,963 B2 12/2015 Li et al.
9,238,668 B2 1/2016 Li et al.
9,312,502 B2 4/2016 Li et al.
9,324,957 B2 4/2016 Li et al.
9,379,361 B2 6/2016 Tsurutani et al.
9,382,273 B2 7/2016 Li et al.
9,425,415 B2 8/2016 Li et al.
9,458,182 B2 10/2016 Langer et al.
9,548,467 B2 1/2017 Archer
9,698,359 B2 7/2017 Li et al.
9,711,739 B2 7/2017 Li
9,786,858 B2 10/2017 Adamovich et al.
9,899,614 B2 2/2018 Li et al.
9,911,931 B2 3/2018 Szigethy et al.
9,972,793 B2 5/2018 Wu et al.
9,991,454 B2 6/2018 Kim et al.
10,177,329 B2 1/2019 Kim et al.
10,374,166 B2 8/2019 Hatakeyama et al.
10,381,580 B2 8/2019 Xia et al.
10,411,211 B2 9/2019 Tsukamoto et al.
10,483,328 B2 11/2019 Lee et al.
10,559,758 B2 2/2020 Park et al.
10,910,580 B2 2/2021 Choi et al.
11,393,988 B2 7/2022 Stoessel et al.
11,515,489 B2 11/2022 Wolohan et al.
11,758,804 B2 9/2023 Chen et al.
12,101,997 B2 9/2024 Hashimoto et al.
12,250,874 B2 3/2025 Ahn et al.
12,514,112 B2 12/2025 Um et al.
12,559,671 B2 2/2026 Shin et al.
12,598,909 B2 4/2026 Ahn et al.
2001/0008271 A1 7/2001 Ikeda et al.
2005/0287394 A1 12/2005 Yang et al.
2005/0287396 A1 12/2005 Nakamura et al.
2006/0103298 A1 5/2006 Lee
2008/0018221 A1 1/2008 Egen et al.
2008/0036373 A1 2/2008 Itoh et al.
2009/0295274 A1 12/2009 Hwang et al.
2010/0127616 A1 5/2010 Kai et al.
2010/0219397 A1 9/2010 Watanabe et al.
2010/0270916 A1 10/2010 Xia et al.
2011/0301351 A1 12/2011 Li et al.
2012/0121936 A1 5/2012 Baek et al.
2012/0215001 A1 8/2012 Li et al.
2012/0228583 A1 9/2012 Wu et al.
2012/0302753 A1 11/2012 Li et al.
2013/0105777 A1 5/2013 Adamovich et al.
2013/0200357 A1 8/2013 Ludemann et al.
2014/0077172 A1 3/2014 So et al.
2014/0309428 A1 10/2014 Egen et al.
2015/0041770 A1 2/2015 Lee
2015/0105556 A1 4/2015 Li et al.
2015/0126736 A1 5/2015 Cho et al.
2015/0137051 A1 5/2015 Jung et al.
2015/0137095 A1 5/2015 Xia et al.
2015/0318487 A1 11/2015 Ito et al.
2015/0349267 A1 12/2015 Vo et al.
2015/0380666 A1 12/2015 Szgethy et al.
2016/0028025 A1 1/2016 Ogiwara et al.
2016/0028027 A1 1/2016 Inoue et al.
2016/0028029 A1 1/2016 Li et al.
2016/0240799 A1 8/2016 Tsa et al.
2016/0336517 A1* 11/2016 Hirose ............... H10K 85/6572
2016/0372687 A1 12/2016 Murer et al.
2017/0018600 A1 1/2017 Ito et al.
2017/0062730 A1 3/2017 Ahn et al.
2017/0077420 A1 3/2017 Li et al.
2017/0098782 A1 4/2017 Choi et al.
2017/0117488 A1 4/2017 Ahn et al.
2017/0125699 A1 5/2017 Ahn et al.
2017/0149008 A9 5/2017 Forrest et al.
2017/0207398 A1 7/2017 Yang et al.
2017/0309841 A1 10/2017 Kim et al.
2018/0051003 A1 2/2018 Koo et al.
2018/0151816 A1 5/2018 Xia et al.
2018/0212165 A1 7/2018 Ji
2018/0261791 A1 9/2018 Yoo et al.
2018/0337349 A1 11/2018 Li et al.
2018/0337361 A1 11/2018 Lee et al.
2019/0058144 A1 2/2019 Lee et al.
2019/0109287 A1 4/2019 Wu et al.
2019/0119312 A1 4/2019 Chen et al.
2019/0225636 A1 7/2019 Bae et al.
2019/0280222 A1 9/2019 Kim et al.
2019/0296254 A1 9/2019 Ko et al.
2020/0002315 A1* 1/2020 Chung ................ C07D 519/00
2020/0028084 A1 1/2020 Song et al.
2020/0055886 A1 2/2020 Choi et al.
2020/0099001 A1 3/2020 Kim et al.
2020/0168819 A1 5/2020 Ahn et al.
2020/0190115 A1 6/2020 Hatakeyama et al.
2020/0199164 A1 6/2020 Kim et al.
2020/0258009 A1 8/2020 Colon
2020/0280003 A1 9/2020 Min et al.
2020/0295280 A1 9/2020 Jeon et al.
2020/0328359 A1 10/2020 Ko et al.
2020/0343455 A1 10/2020 Wei et al.
2021/0050530 A1 2/2021 Wu et al.
2021/0066617 A1 3/2021 Shin et al.
2021/0098714 A1 4/2021 Choi et al.
2021/0098716 A1 4/2021 Lee et al.
2021/0098721 A1 4/2021 Jung et al.
2021/0104682 A1 4/2021 Youngeun et al.
2021/0265575 A1 8/2021 Lee et al.
2021/0384450 A1 12/2021 Shin et al.
2021/0391546 A1 12/2021 Lee et al.
2022/0013737 A1 1/2022 Kang et al.
2022/0024958 A1 1/2022 Ko et al.
2022/0052276 A1 2/2022 Lee et al.
2022/0069235 A1 3/2022 Kim et al.
2022/0251121 A1 8/2022 Ahn et al.
2022/0407021 A1 12/2022 Shin et al.
2023/0172064 A1 6/2023 Ahn et al.
2023/0217807 A1 7/2023 Um et al.

(56) References Cited

U.S. PATENT DOCUMENTS

| | | | |
|---|---|---|---|
| 2023/0232714 | A1 | 7/2023 | Lee et al. |
| 2023/0279029 | A1 | 9/2023 | Fleetham et al. |

FOREIGN PATENT DOCUMENTS

| | | | | |
|---|---|---|---|---|
| CN | 103563118 | A | 2/2014 | |
| CN | 104370974 | A | 2/2015 | |
| CN | 104411702 | A | 3/2015 | |
| CN | 106232770 | A | 12/2016 | |
| CN | 106366069 | A * | 2/2017 | .......... C07D 413/04 |
| CN | 106795166 | A | 5/2017 | |
| CN | 107431084 | A | 12/2017 | |
| CN | 107501334 | A | 12/2017 | |
| CN | 111825660 | | 10/2020 | |
| CN | 112913040 | A | 6/2021 | |
| EP | 3750898 | A1 | 12/2020 | |
| EP | 3806175 | A1 | 4/2021 | |
| JP | 2004-234952 | A | 8/2004 | |
| JP | 2007-045742 | A | 2/2007 | |
| JP | 2010-215759 | A | 9/2010 | |
| JP | 2011-140475 | A | 7/2011 | |
| JP | 4729516 | B2 | 7/2011 | |
| JP | 2015-185728 | A | 10/2015 | |
| JP | 2017-120867 | A | 7/2017 | |
| JP | 6232052 | B2 | 11/2017 | |
| JP | 6550498 | B2 | 7/2019 | |
| JP | 2021-066689 | A | 4/2021 | |
| KR | 10-0730115 | B1 | 6/2007 | |
| KR | 10-2007-0106082 | A | 11/2007 | |
| KR | 10-2008-0014608 | A | 2/2008 | |
| KR | 10-2008-0037006 | A | 4/2008 | |
| KR | 10-2010-0118700 | A | 11/2010 | |
| KR | 10-2012-0021215 | A | 3/2012 | |
| KR | 10-2013-0048170 | A | 5/2013 | |
| KR | 10-2013-0115027 | A | 10/2013 | |
| KR | 10-2013-0118084 | A | 10/2013 | |
| KR | 10-2014-0041732 | A | 4/2014 | |
| KR | 10-2014-0096182 | A | 8/2014 | |
| KR | 10-2014-0134947 | A | 11/2014 | |
| KR | 10-2015-0020543 | | 2/2015 | |
| KR | 10-1502316 | B1 | 3/2015 | |
| KR | 10-1505152 | B1 | 3/2015 | |
| KR | 10-2015-0114791 | A | 10/2015 | |
| KR | 10-2016-0045604 | A | 4/2016 | |
| KR | 10-2016-0060569 | A | 5/2016 | |
| KR | 10-2016-0073482 | A | 6/2016 | |
| KR | 10-2016-0110764 | A | 9/2016 | |
| KR | 10-2016-0119155 | A | 10/2016 | |
| KR | 10-2017-0008358 | A | 1/2017 | |
| KR | 10-2017-0008673 | A | 1/2017 | |
| KR | 10-1693903 | B1 | 1/2017 | |
| KR | 10-2017-0040851 | A | 4/2017 | |
| KR | 10-2017-0103358 | A | 9/2017 | |
| KR | 10-2017-0122296 | A | 11/2017 | |
| KR | 10-2018-0027468 | A | 3/2018 | |
| KR | 10-2018-0104258 | A | 9/2018 | |
| KR | 10-2018-0115800 | A | 10/2018 | |
| KR | 10-2019-0000830 | A | 1/2019 | |
| KR | 10-2019-0013105 | A | 2/2019 | |
| KR | 10-2019-0089626 | A | 7/2019 | |
| KR | 10-2019-0107264 | A | 9/2019 | |
| KR | 10-2020-0001439 | A | 1/2020 | |
| KR | 10-2020-0021870 | A | 3/2020 | |
| KR | 10-2020-0034900 | A | 4/2020 | |
| KR | 10-2020-0062465 | | 6/2020 | |
| KR | 10-2020-0062465 | A | 6/2020 | |
| KR | 10-2020-0076583 | A | 6/2020 | |
| KR | 10-2020-0095395 | A | 8/2020 | |
| KR | 10-2020-0110577 | A | 9/2020 | |
| KR | 10-2214339 | B1 | 2/2021 | |
| KR | 10-2021-0028085 | A | 3/2021 | |
| KR | 10-2021-0041167 | A | 4/2021 | |
| KR | 10-2021-0059652 | A | 5/2021 | |
| KR | 10-2261645 | B1 | 6/2021 | |
| KR | 10-2021-0104219 | A | 8/2021 | |
| KR | 10-2021-0109549 | A | 9/2021 | |
| KR | 10-2021-0124922 | A | 10/2021 | |
| KR | 10-2021-0127076 | A | 10/2021 | |
| KR | 10-2021-0153188 | A | 12/2021 | |
| WO | WO 00/70655 | A2 | 11/2000 | |
| WO | WO 01/08230 | A1 | 2/2001 | |
| WO | WO 2008/096609 | A1 | 8/2008 | |
| WO | WO 2010/126234 | A1 | 4/2010 | |
| WO | WO 2012/121936 | A2 | 9/2012 | |
| WO | WO 2014/003440 | A1 | 1/2014 | |
| WO | WO 2015/000955 | A1 | 8/2015 | |
| WO | WO 2016/080749 | A1 | 5/2016 | |
| WO | WO 2017/082169 | A1 | 5/2017 | |
| WO | WO 2020/096167 | A1 | 5/2020 | |

OTHER PUBLICATIONS

Neugebauer Franz Alfred et al: "Aminyle, 6. tert.-Butyl-substituierte 9-Carbazolyl-Radikale, Carbazol- Radikalkationen und Carbazol-9-oxyl-Radikale", Chemische Berichte, vol. 105, No. 8, Aug. 1, 1972 (Aug. 1, 1972), pp. 2694-2713, XP093005844.

Hirohiko Fukagawa et al., "High-Efficiency Ultrapure Green Organic Light-Emitting Diodes", Materials Chemistry Frontiers, Jan. 29, 2018, 7 total pages.

Shi-Jian Su et al., "A host material with a small singlet-triplet exchange energy for phosphorescent organic light-emitting diodes: Guest, host, and exciplex emission", Organic Electronics, 2012, pp. 1937-1947.

H. Bock et al., ""d-Orbital Effects" in Silicon-Substituted π-Electron Systems. XI.' Syntheses and Properties of the someric Bis (trimethylsilyl)-1,3-butadienes", Journal of the American Chemical Society, Oct. 9, 1968, pp. 5694-5700.

"Analog Electronic Technology", with English Abstract, dated Jul. 31, 2010, pp. 157-159.

CAS reg No. 2422045-58-5, Jun. 10, 2020.

Esteruelas, Miguel A., et al., "Preparation of Phosphorescent Iridium(III) Complexes with a Dianionic C,C,C,C-Tetradentate Ligand," Inorg. Chem. (2018), 11 pages.

Holmes et al., "Blue organic electrophosphorescence using exothermic host-guest energy transfer", Applied Physics Letters, (2002) , vol. 82, pp. 2422-2424. (Year: 2002).

Huei-Ru Tsai et al. "Metal-Ligand Bonding Strength of Fluoro-Substituted Cyclometalated Iridium(III) Complexes from Raman and Infrared Spectra", J. Phys. Chem. 2011, vol. 115, p. 17163-17174 (Year: 2011).

Pang et al. "A Full-Color, Low-Power, Wearable Display for Mobile Applications," SPIE, Mar. 29, 2012, 5 pages.

Chinese Office Action dated Jan. 27, 2024, issued in Chinese Patent Application No. 201980068141.8.

Chinese Office Action for Chinese Patent Application No. 202010073332.8, mailed Mar. 18, 2024, 29 pages.

International Search Report issued in PCT/KR2019/009197 (English Version), mailed Oct. 21, 2019, 2 pages.

English Translation of International Preliminary Report issued in PCT/KR2019/009197, Search Authority search carried JUI on Feb. 22, 2021, 3 pages.

Extended European Search Report dated Jun. 11, 2021, issued in corresponding European Patent Application No. 21159426.2 (8 pages).

Extended European Search Report dated Jul. 21, 2021, issued in corresponding European Patent Application No. 21159425.4 (18 pages).

US Office Action dated Mar. 23, 2022, issued in U.S. Appl. No. 16/529,327.

US Office Action dated Jun. 6, 2022, issued in U.S. Appl. No. 16/666,327.

US Final Office Action dated Jul. 13, 2022, issued in U.S. Appl. No. 16/529,327.

US Notice of Allowance dated Sep. 21, 2022, issued in U.S. Appl. No. 16/529,327.

US Final Office Action dated Nov. 16, 2022, issued in U.S. Appl. No. 16/666,327.

(56) References Cited

OTHER PUBLICATIONS

US Notice of Allowance dated Feb. 2, 2023, issued in U.S. Appl. No. 16/529,327.
US Office Action dated Mar. 14, 2023, issued in U.S. Appl. No. 16/666,327.
US Final Office Action dated Sep. 13, 2023, issued in U.S. Appl. No. 16/666,327.
US Notice of Allowance dated Oct. 12, 2023, issued in U.S. Appl. No. 16/529,327.
US Office Action dated Apr. 18, 2024, issued in U.S. Appl. No. 16/666,327.
US Office Action dated May 16, 2024, issued in U.S. Appl. No. 16/529,327.
US Office Action dated May 20, 2024, issued in U.S. Appl. No. 17/447,249.
US Final Office Action dated Sep. 6, 2024, issued in U.S. Appl. No. 16/666,327.
US Final Office Action dated Sep. 26, 2024, issued in U.S. Appl. No. 16/529,327.
US Notice of Allowance dated Oct. 31, 2024, issued in U.S. Appl. No. 17/447,249.
US Office Action dated Feb. 13, 2025, issued in U.S. Appl. No. 16/666,327.
US Office Action dated Feb. 6, 2025, issued in U.S. Appl. No. 17/477,903.
US Office Action dated Mar. 24, 2025, issued in U.S. Appl. No. 16/529,327.
US Final Office Action dated May 16, 2025, issued in U.S. Appl. No. 17/477,903.
US Final Office Action dated Jul. 2, 2025, issued in U.S. Appl. No. 16/666,327.
US Final Office Action dated Jul. 16, 2025, issued in U.S. Appl. No. 16/529,327.
US Office Action dated Aug. 1, 2025, issued in U.S. Appl. No. 17/660,182.
US Notice of Allowance dated Aug. 5, 2025, issued in U.S. Appl. No. 17/477,903.
US Notice of Allowance dated Aug. 27, 2025, issued in U.S. Appl. No. 17/831,724.
US Notice of Allowance dated Sep. 23, 2025, issued in U.S. Appl. No. 16/666,327.
US Notice of Allowance dated Nov. 18, 2025, issued in U.S. Appl. No. 16/529,327.
US Final Office Action dated Dec. 9, 2025, issued in U.S. Appl. No. 17/660,182.
US Office Action dated Dec. 17, 2025, issued in U.S. Appl. No. 17/827,788.
US Office Action dated Apr. 1, 2026, issued in U.S. Appl. No. 17/976,568.
US Notice of Allowance dated Apr. 1, 2026, issued in U.S. Appl. No. 17/660,182.
US Office Action dated Apr. 1, 2026, issued in U.S. Appl. No. 18/108,516.
US Office Action dated Apr. 15, 2026, issued in U.S. Appl. No. 18/090,671.
US Office Action dated Jun. 3, 2026, issued in U.S. Appl. No. 17/827,788.

* cited by examiner

HETEROCYCLIC COMPOUND, LIGHT-EMITTING DEVICE INCLUDING THE HETEROCYCLIC COMPOUND, AND ELECTRONIC APPARATUS INCLUDING THE LIGHT-EMITTING DEVICE

CROSS-REFERENCE TO RELATED APPLICATION(S)

This application claims priority to and benefits of Korean Patent Application No. 10-2021-0114256 under 35 U.S.C. § 119, filed on Aug. 27, 2021 in the Korean Intellectual Property Office, the entire contents of which are incorporated herein by reference.

BACKGROUND

1. Technical Field

Embodiments relate to a heterocyclic compound, a light-emitting device including the heterocyclic compound, and an electronic apparatus including the light-emitting device.

2. Description of the Related Art

From among light-emitting devices, organic light-emitting devices are self-emissive devices that, as compared with devices of the related art, have wide viewing angles, high contrast ratios, short response times, and excellent characteristics in terms of luminance, driving voltage, and response speed, while producing full-color images.

In an example of organic light-emitting devices, a first electrode is located on a substrate, and a hole transport region, an emission layer, an electron transport region, and a second electrode are sequentially formed on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. These excitons transition from an excited state to a ground state, thereby generating light.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Embodiments include a heterocyclic compound, a light-emitting device including the heterocyclic compound, and an electronic apparatus including the light-emitting device.

Additional aspects will be set forth in part in the description, which follows and, in part, will be apparent from the description, or may be learned by practice of the embodiments of the disclosure.

According to embodiments, a heterocyclic compound may be represented by Formula 1.

[Formula 1]

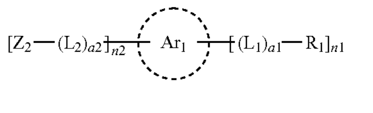

-continued

[Formula 2]

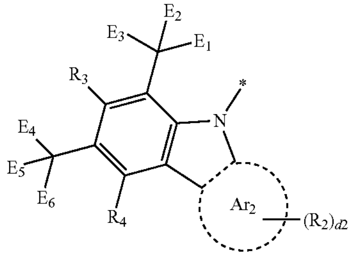

In Formula 1 and Formula 2, $Z_2$ may be a group represented by Formula 2, $Ar_1$ and $Ar_2$ may each independently be a $C_5$-$C_{60}$ carbocyclic group or a $C_1$-$C_{60}$ heterocyclic group, $L_1$ and $L_2$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, a1 and a2 may each independently be an integer from 1 to 3, $R_1$ to $R_4$ may each independently be:

Hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —B($Q_1$)($Q_2$), —C(═O)($Q_1$), —S(═O)$_2$($Q_1$), or —P(═O)($Q_1$)($Q_2$); or a group represented by Formula 2, $E_1$ to $E_6$ may each independently be a $C_1$-$C_{60}$ alkyl group unsubstituted or substituted with at least one $R_{10a}$, a $C_2$-$C_{60}$ alkenyl group unsubstituted or substituted with at least one $R_{10a}$, or a $C_2$-$C_{60}$ alkynyl group unsubstituted or substituted with at least one $R_{10a}$, d2 may be an integer from 0 to 10, n1 may be an integer from 1 to 10, n2 may be an integer from 1 to 5, indicates a binding site to a neighboring atom, $R_{10a}$ may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or $Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_6$ alkoxy group, a $C_3$-$C_{60}$ carbocyclic group, a $C_1$-$C_{60}$ heterocyclic group, or any combination thereof.

In an embodiment, the heterocyclic compound represented by Formula 1 may satisfy at least one of Conditions 1 and 2:

[Condition 1]

An is a π electron-deficient nitrogen-containing $C_1$-$C_{60}$ cyclic group,

[Condition 2]

at least one of $R_1$(s) in the number of n1 is —$Si(Q_1)(Q_2)(Q_3)$.

In an embodiment, n2 may be an integer from 1 to 3.

In an embodiment, the heterocyclic compound represented by Formula 1 may be represented by Formula 1-A:

[Formula 1-A]

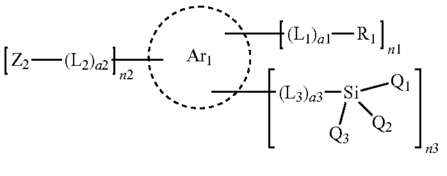

In Formula 1-A, $Z_2$, $Ar_1$, $L_1$, $L_2$, n1, n2, a1, a2, $R_1$, and $Q_1$ to $Q_3$ may each be the same as described in Formula 1, $L_3$ may be the same as described in connection with $L_1$ in Formula 1, a3 may be the same as described in connection with a1 in Formula 1, and n3 may be an integer from 0 to 10.

In an embodiment, An may be a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, an indenoanthracene group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group.

In an embodiment, $L_1$ and $L_2$ may each independently be:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-a fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ may be the same as described in Formula 1.

In an embodiment, $L_1$ and $L_2$ may each independently be:

a single bond; or a group represented by one of Formulae 3-1 to 3-40, which are explained below.

In an embodiment, the heterocyclic compound represented by Formula 1 is represented by one of Formulae 1-1 to 1-5:

1-1

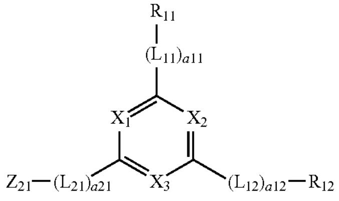

1-2

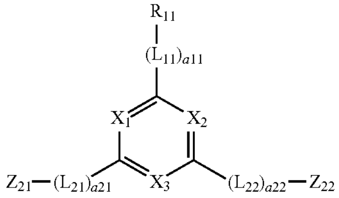

1-3

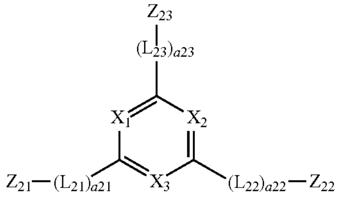

1-4

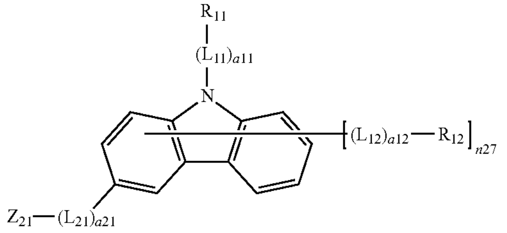

1-5

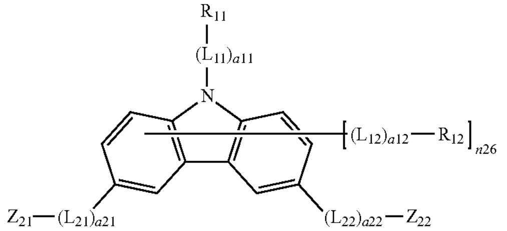

In Formulae 1-1 to 1-5, $X_1$ may be $C(R_{13})$ or N, $X_2$ may be $C(R_{14})$ or N, $X_3$ may be $C(R_{15})$ or N, $R_{11}$ to $R_{15}$ may each independently be the same as described in connection with $R_1$ in Formula 1, $L_{11}$ and $L_{12}$ may each independently be the same as described in connection with $L_1$ in Formula 1, a11 and a12 may each independently be the same as described in connection with a1 in Formula 1, n26 may be an integer from 1 to 6, n27 may be an integer from 1 to 7, $L_{21}$ to $L_{23}$ may each independently be the same as described in connection with $L_2$ in Formula 1, a21 to a23 may each independently be the same as described in connection with a2 in Formula 1, and $Z_{21}$ to $Z_{23}$ may each independently be the same as described in connection with $Z_2$ in Formula 1.

In an embodiment, at least one of $X_1$ to $X_3$ may be N.

In an embodiment, $R_{11}$ may be —$Si(Q_1)(Q_2)(Q_3)$, and $Q_1$ to $Q_3$ may each be the same as described in Formula 1.

In an embodiment, $E_1$ to $E_6$ may each independently be:

a $C_1$-$C_{20}$ alkyl group, a $C_2$-$C_{60}$ alkenyl group, or a $C_2$-$C_{60}$ alkynyl group; or a $C_1$-$C_{20}$ alkyl group, a $C_2$-$C_{60}$ alkenyl group, or a $C_2$-$C_{20}$ alkynyl group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof.

In an embodiment, the group represented by Formula 2 may be represented by Formula 2-1:

[Formula 2-1]

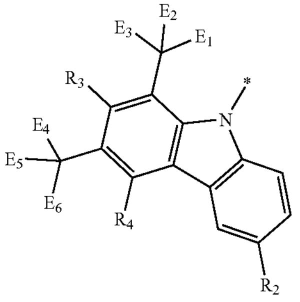

In Formula 2-1, $E_1$ to $E_6$ and $R_2$ to $R_4$ may each be the same as described in Formula 2, and * indicates a binding site to a neighboring atom.

In an embodiment, the heterocyclic compound may be one of Compounds 1 to 50, which are explained below.

According to embodiments, provided is a light-emitting device which may include a first electrode, a second electrode facing the first electrode, an interlayer between the first electrode and the second electrode and including an emission layer, and at least one heterocyclic compound represented by Formula 1.

In an embodiment, the first electrode may be an anode, the second electrode may be a cathode, and the interlayer may further include a hole transport region between the emission layer and the first electrode, and an electron transport region between the emission layer and the second electrode. The hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In an embodiment, the emission layer may include the at least one heterocyclic compound represented by Formula 1.

In an embodiment, the emission layer may further include an organometallic compound represented by Formula 401, which is explained below.

According to embodiments, provided is an electronic apparatus including the light-emitting device.

In an embodiment, the electronic apparatus may further include a thin-film transistor, wherein the thin-film transistor may include a source electrode and a drain electrode, and the first electrode of the light-emitting device may be electrically connected to the source electrode or the drain electrode.

In an embodiment, the electronic apparatus may further include a color filter, a color conversion layer, a touch screen layer, a polarizing layer, or any combination thereof.

BRIEF DESCRIPTION OF THE DRAWINGS

The above and other aspects, features, and advantages of embodiments of the disclosure will be more apparent from the following description taken in conjunction with the accompanying drawings, in which.

DETAILED DESCRIPTION OF THE EMBODIMENTS

Figure 1:
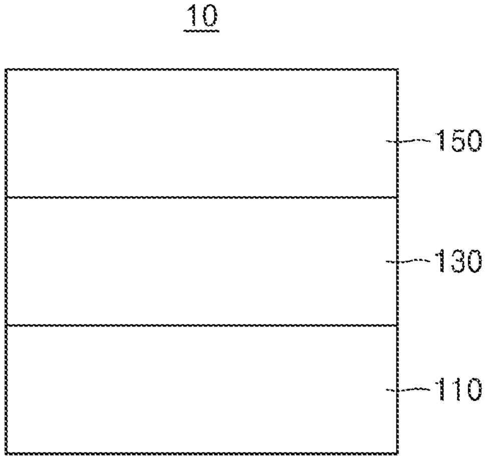
FIG. 1 is a schematic cross-sectional view of a light-emitting device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

In the specification and the claims, the term "at least one of" is intended to include the meaning of "at least one selected from the group of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

An aspect of the disclosure provides a heterocyclic compound which may be represented by Formula 1:

[Formula 1]

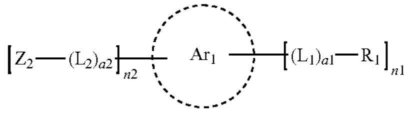

-continued

[Formula 2]

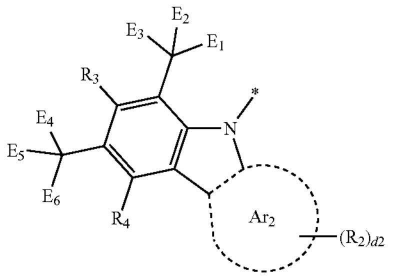

In Formula 1 and Formula 2, $Z_2$ may be a group represented by Formula 2, and $Ar_1$ and $Ar_2$ may each independently be a $C_5$-$C_{60}$ carbocyclic group or a $C_1$-$C_{60}$ heterocyclic group.

In an embodiment, An may be a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, an indenoanthracene group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group.

In an embodiment, $Ar_2$ may be a benzene group, a naphthalene group, an anthracene group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a pyridine group, a pyrimidine group, a pyrazine group, a pyridazine group, or a triazine group.

In Formula 1, $L_1$ and $L_2$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, $L_1$ and $L_2$ may each independently be:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-a fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ may be the same as described herein.

In embodiments, $L_1$ and $L_2$ may each independently be:

a single bond; or a group represented by one of Formulae 3-1 to 3-40:

3-1

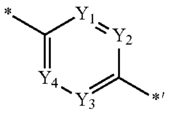

3-2

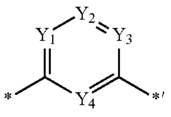

-continued
3-3
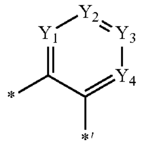
3-4
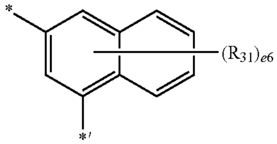
3-5
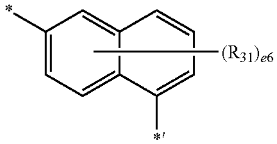
3-6
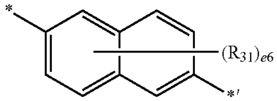
3-7
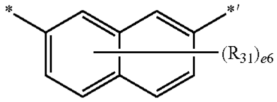
3-8
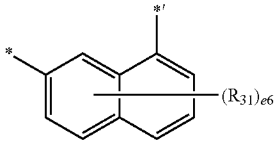
3-9
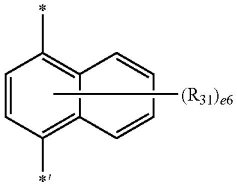
3-10
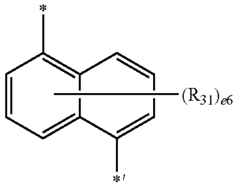
3-11
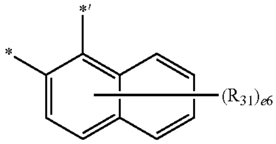
3-12
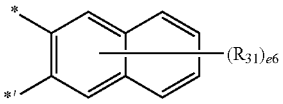
-continued
3-13
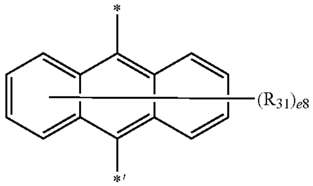
3-14
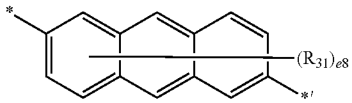
3-15
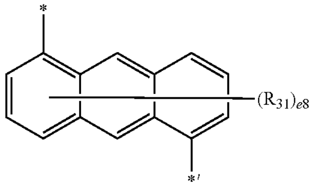
3-16
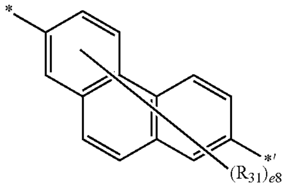
3-17
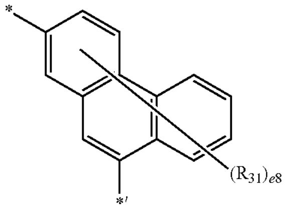
3-18
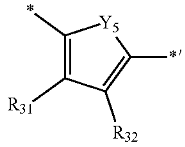
3-19
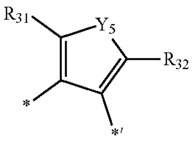
3-20
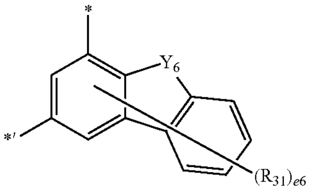
3-21
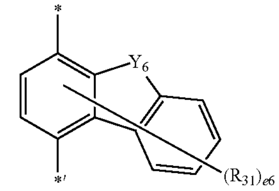

-continued
3-22
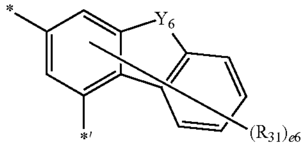
3-23
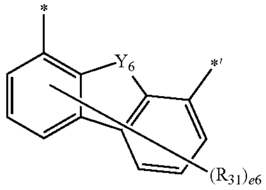
3-24
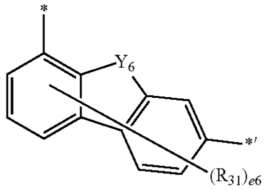
3-25
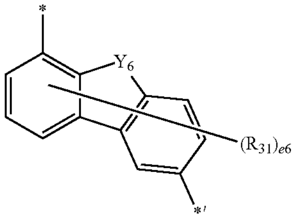
3-26
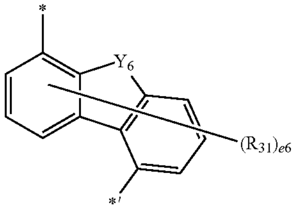
3-27
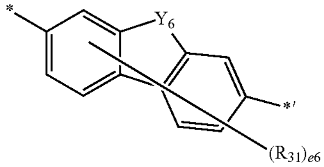
3-28
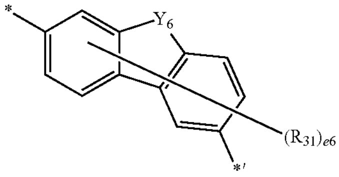
3-29
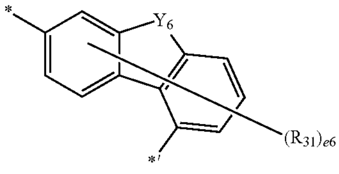
-continued
3-30
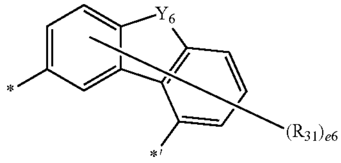
3-31
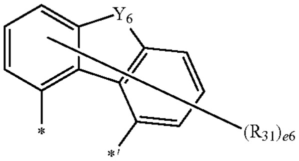
3-32
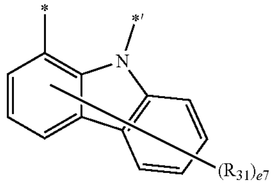
3-33
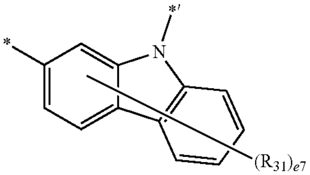
3-34
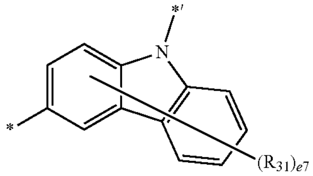
3-35
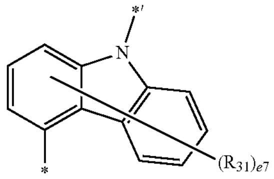
3-36
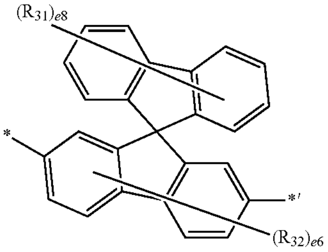

-continued 3-37

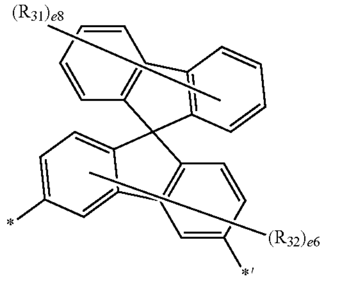

3-38

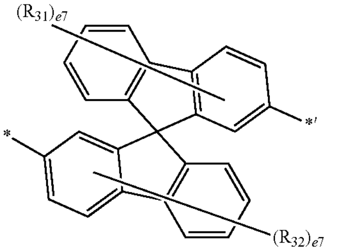

3-39

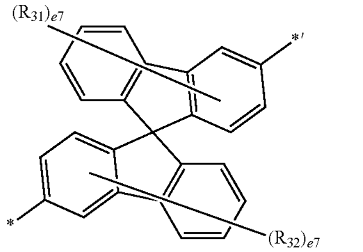

3-40

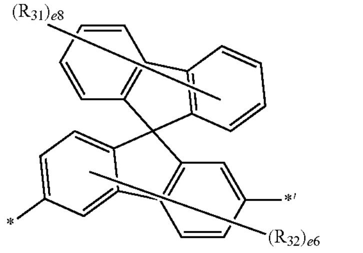

In Formulae 3-1 to 3-40, $Y_1$ may be N or $C(R_{33})$, $Y_2$ may be N or $C(R_{34})$, $Y_3$ may be N or $C(R_{35})$, $Y_4$ may be N or $C(R_{36})$, $Y_5$ may be 0, S, or Se, $Y_6$ may be O, S, Se, $N(R_{37})$, or $C(R_{37})(R_{38})$, $R_{31}$ to $R_{38}$ may each independently be:

hydrogen, deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $—Si(Q_{11})(Q_{12})(Q_{13})$, $—B(Q_{11})(Q_{12})$, $—C(=O)(Q_{11})$, $—S(=O)_2(Q_{11})$, $—P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group; or a $C_6$-$C_{60}$ arylthio group, each unsubstituted or substituted with deuterium, —F, —$C_1$, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $—Si(Q_{21})(Q_{22})(Q_{23})$, $—B(Q_{21})(Q_{22})$, $—C(=O)(Q_{21})$, $—S(=O)_2(Q_{21})$, $—P(=O)(Q_{21})(Q_{22})$, or any combination thereof; or $Si(Q_{31})(Q_{32})(Q_{33})$, $—B(Q_{31})(Q_{32})$, $—C(=O)(Q_{31})$, $—S(=O)_2(Q_{31})$, or $—P(=O)(Q_{31})(Q_{32})$, $Q_{11}$ to $Q_{13}$, $Q_{21}$ to $Q_{23}$, and $Q_{31}$ to $Q_{33}$ may each be the same as described herein, e6 may be an integer from 0 to 6, e7 may be an integer from 0 to 7, e8 may be an integer from 0 to 8, and

* and *' each indicate a binding site to a neighboring atom.

In Formula 1, a1 and a2 may each independently be an integer from 1 to 3.

In Formula 1 and Formula 2, $R_1$ to $R_4$ may each independently be:

hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $—Si(Q_1)(Q_2)(Q_3)$, $—B(Q_1)(Q_2)$, $—C(=O)(Q_1)$, $—S(=O)_2(Q_1)$, or $—P(=O)(Q_1)(Q_2)$; or a group represented by Formula 2.

In an embodiment, $R_3$ and $R_4$ may each independently be hydrogen or deuterium.

In Formula 2, $E_1$ to $E_6$ may each independently be a $C_1$-$C_{60}$ alkyl group unsubstituted or substituted with at least one $R_{10a}$, a $C_2$-$C_{60}$ alkenyl group unsubstituted or substituted with at least one $R_{10a}$, or a $C_2$-$C_{60}$ alkynyl group unsubstituted or substituted with at least one $R_{10a}$.

In embodiments, $E_1$ to $E_6$ may each independently be:

a $C_1$-$C_{20}$ alkyl group, a $C_2$-$C_{60}$ alkenyl group, or a $C_2$-$C_{60}$ alkynyl group; or a $C_1$-$C_{20}$ alkyl group, a $C_2$-$C_{60}$ alkenyl group, or a $C_2$-$C_{20}$ alkynyl group, each substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof.

In Formula 2, d2 may be an integer from 0 to 10.

In Formula 1, n1 may be an integer from 1 to 10.

In Formula 1, n2 may be an integer from 1 to 5.

In embodiments, n2 may be an integer from 1 to 3.

In Formula 2, * indicates a binding site to a neighboring atom.

In an embodiment, the heterocyclic compound represented by Formula 1 may satisfy at least one of Conditions 1 and 2:

[Condition 1]

An is a π electron-deficient nitrogen-containing $C_1$-$C_{60}$ cyclic group,

[Condition 2]

at least one of $R_1$(s) in the number of n1 is —Si($Q_1$)($Q_2$)($Q_3$).

In embodiments, the heterocyclic compound represented by Formula 1 may satisfy Condition 1 only, may satisfy Condition 2 only, or may satisfy both Conditions 1 and 2.

In an embodiment, the heterocyclic compound represented by Formula 1 may be represented by Formula 1-A:

[Formula 1-A]

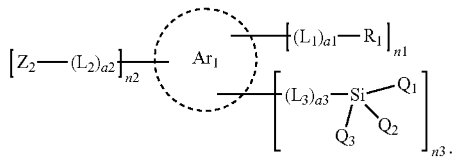

In Formula 1-A, $Z_2$, $Ar_1$, $L_1$, $L_2$, n1, n2, a1, a2, $R_1$, and $Q_1$ to $Q_3$ may each be the same as described herein, $L_3$ may be the same as described in connection with $L_1$, a3 may be the same as described in connection with a1, and n3 may be an integer from 0 to 10.

In an embodiment, n3 may be 0, 1, or 2.

In embodiments, the heterocyclic compound represented by Formula 1 may be represented by one of Formulae 1-1 to 1-5:

1-1

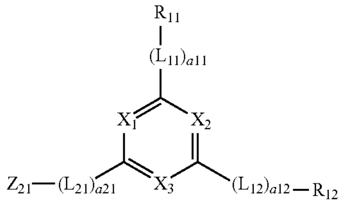

1-2

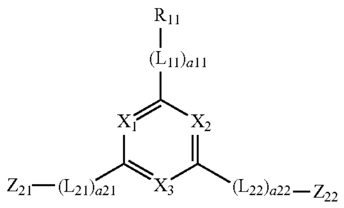

1-3

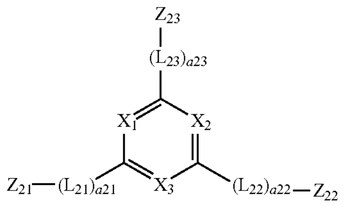

-continued 1-4

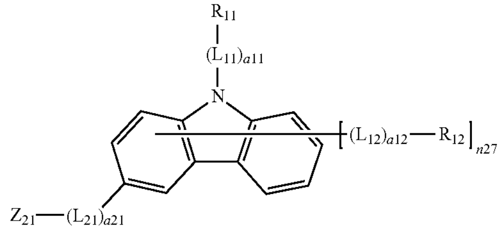

1-5

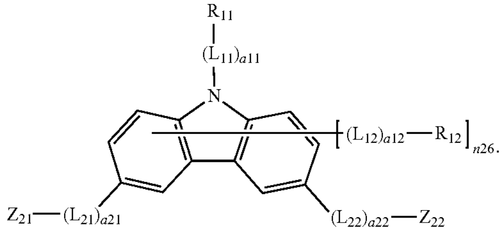

In Formulae 1-1 to 1-5, $X_1$ may be C($R_{13}$) or N, $X_2$ may be C($R_{14}$) or N, $X_3$ may be C($R_{15}$) or N, $R_{11}$ to $R_{15}$ may each independently be the same as described in connection with $R_1$, $L_{11}$ and $L_{12}$ may each independently be the same as described in connection with $L_1$, a11 and a12 may each independently be the same as described in connection with a1, n26 may be an integer from 1 to 6, n27 may be an integer from 1 to 7, $L_{21}$ to $L_{23}$ may each independently be the same as described in connection with $L_2$, a21 to a23 may each independently be the same as described in connection with a2, and $Z_{21}$ to $Z_{23}$ may each independently be the same as described in connection with $Z_2$.

In an embodiment, at least one of $X_1$ to $X_3$ may be N.

In an embodiment, $R_{11}$ may be —Si($Q_1$)($Q_2$)($Q_3$).

In an embodiment, in Formula 1-1, $R_{11}$ and $R_{12}$ may each independently be —Si($Q_1$)($Q_2$)($Q_3$).

In an embodiment, $Q_1$ to $Q_3$ may each be the same as described herein.

In an embodiment, the group represented by Formula 2 may be represented by Formula 2-1:

[Formula 2-1]

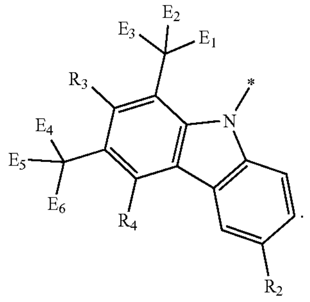

In Formula 2-1, $E_1$ to $E_6$ and $R_2$ to $R_4$ may each be the same as described herein, and indicates a binding site to a neighboring atom.

In an embodiment, $R_2$ may be:

hydrogen, deuterium, or a cyano group;

a group represented by Formula 2; or a group represented by one of Formulae 4-1 to 4-3:

4-1

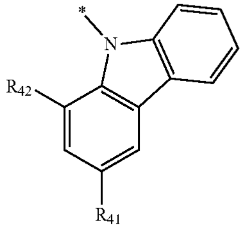

4-2

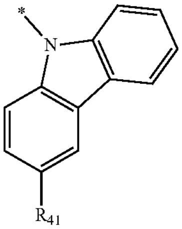

4-3

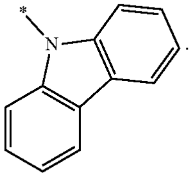

In Formulae 4-1 to 4-3, $R_{41}$ and $R_{42}$ may each independently be deuterium, —F, —Cl, —Br, —I, a hydroxyl group, a cyano group, a nitro group, an amidino group, a hydrazino group, a hydrazono group, $—CF_3$, $—CF_2H$, $—CFH_2$, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a phenanthridinyl group, an acridinyl group, a phenanthrolinyl group, a phenazinyl group, a carbazolyl group, a dibenzofuranyl group, a dibenzothiophenyl group, a dibenzosilolyl group, $—Si(Q_{31})(Q_{32})(Q_{33})$, $—N(Q_{31})(Q_{32})$, or $—B(Q_{31})(Q_{32})$, $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group, and indicates a binding site to a neighboring atom.

The group "$R_{10a}$" as used herein may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, $—Si(Q_{11})(Q_{12})(Q_{13})$, $—N(Q_{11})(Q_{12})$, $—B(Q_{11})(Q_{12})$, $—C(=O)(Q_{11})$, $—S(=O)_2(Q_{11})$, $—P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, $—Si(Q_{21})(Q_{22})(Q_{23})$, $—N(Q_{21})(Q_{22})$, $—B(Q_{21})(Q_{22})$, $—C(=O)(Q_{21})$, $—S(=O)_2(Q_{21})$, $—P(=O)(Q_{21})(Q_{22})$, or any combination thereof; or $Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, or $—P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a $C_3$-$C_{60}$ carbocyclic group, a $C_1$-$C_{60}$ heterocyclic group, or any combination thereof.

In embodiments, the heterocyclic compound represented by Formula 1 may be one of Compounds 1 to 50, but embodiments are not limited thereto:

1

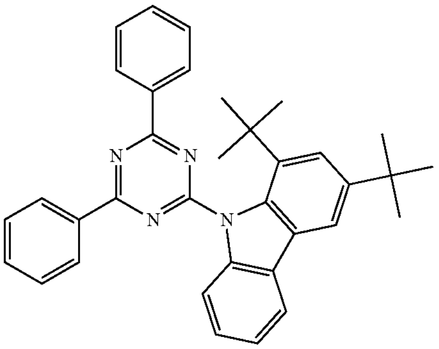

2

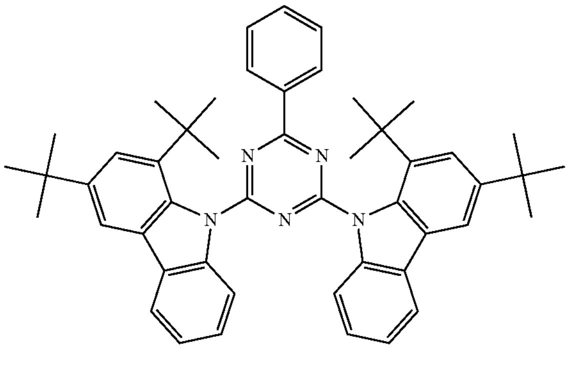

-continued
3
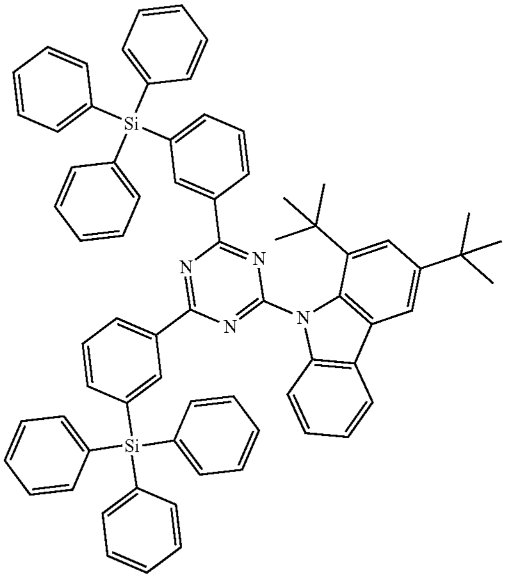
4
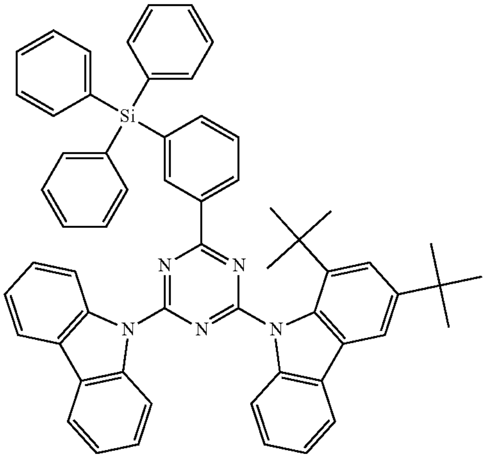
5
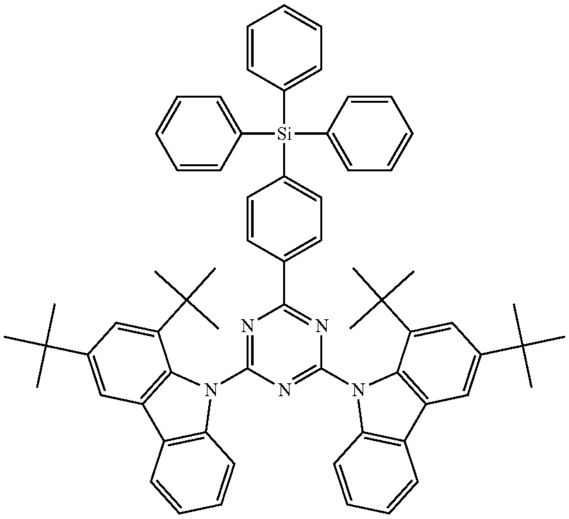
-continued
6
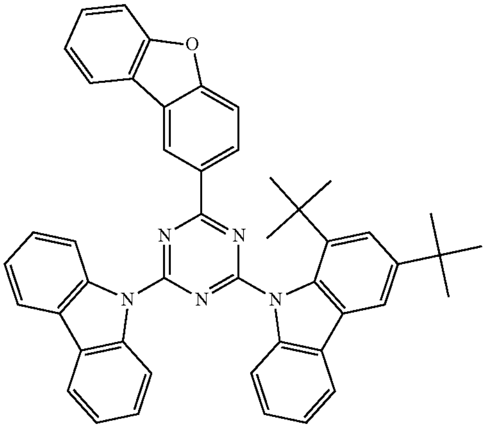
7
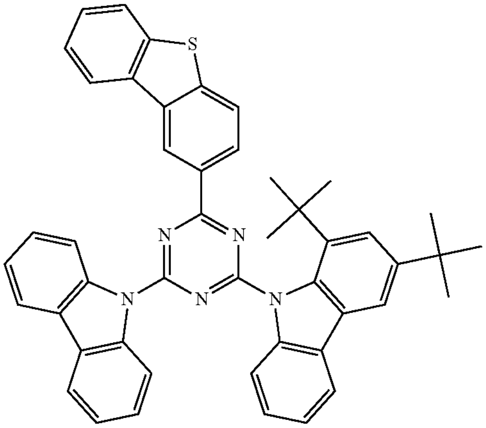
8
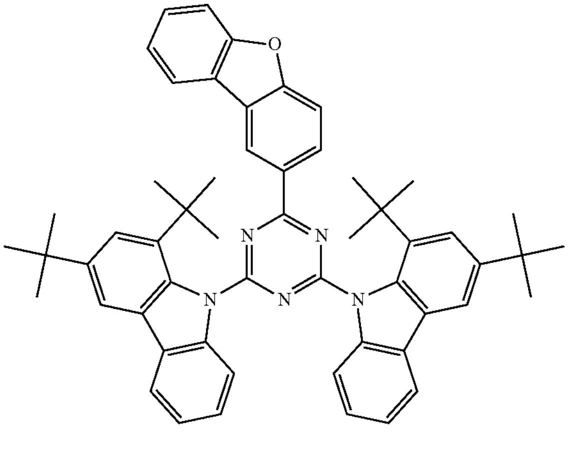

-continued
9
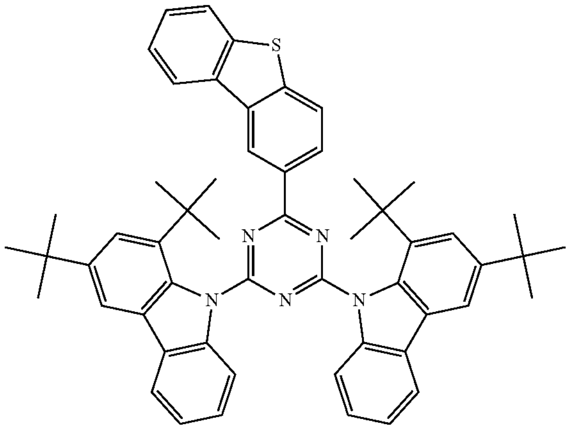
10
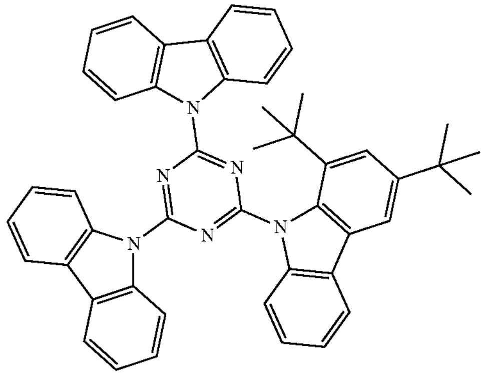
11
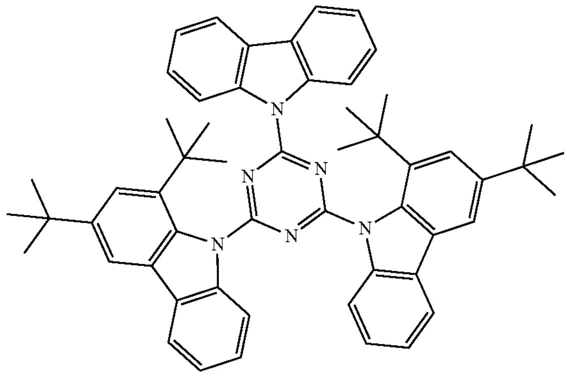
12
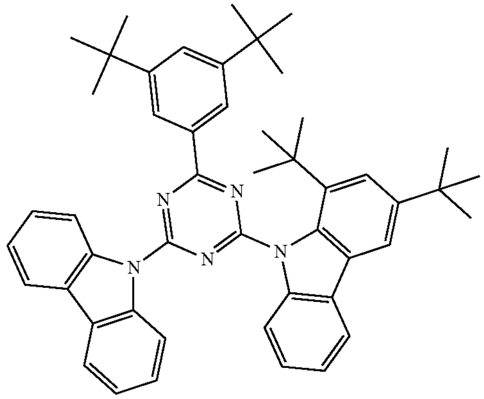
-continued
13
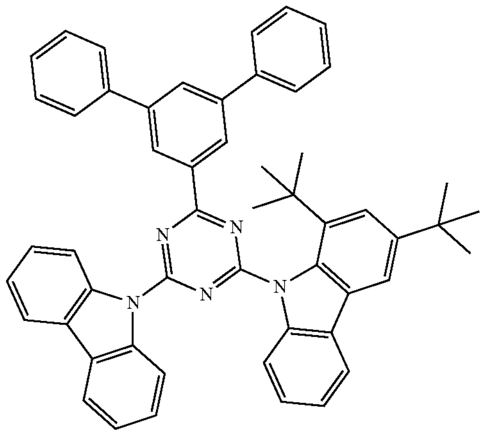
14
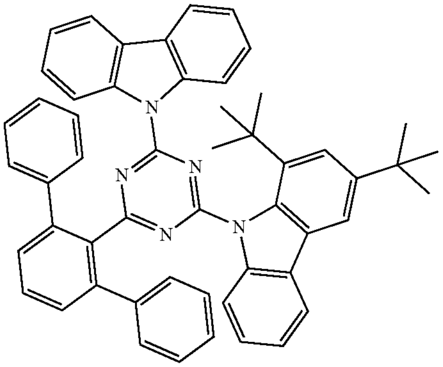
15
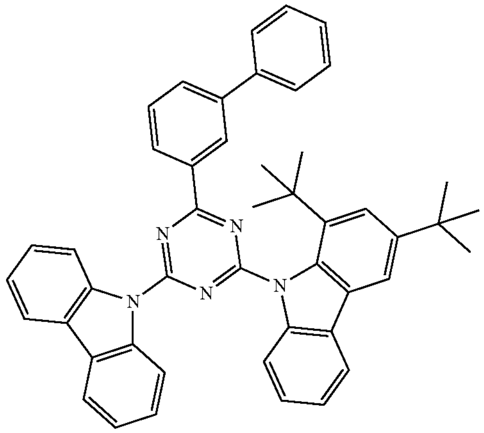

-continued
16
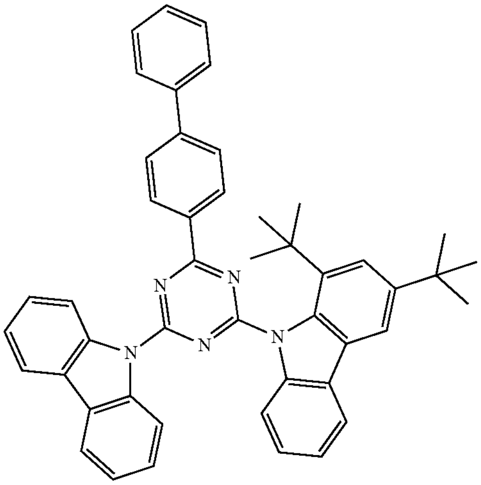
17
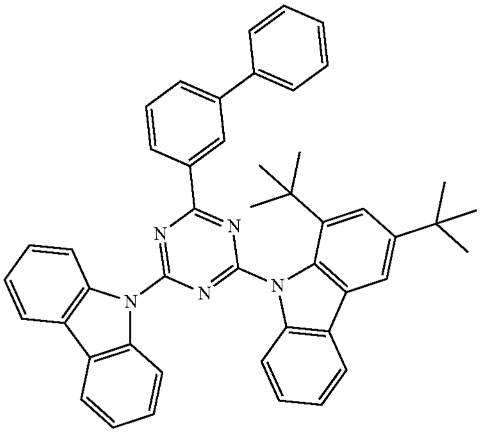
18
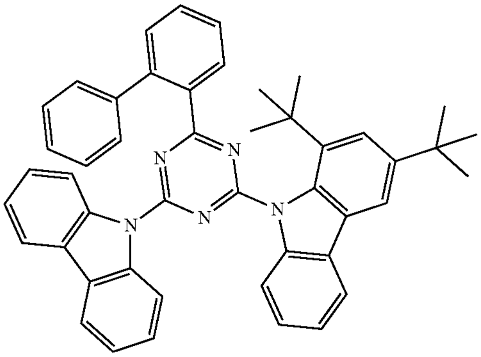
-continued
19
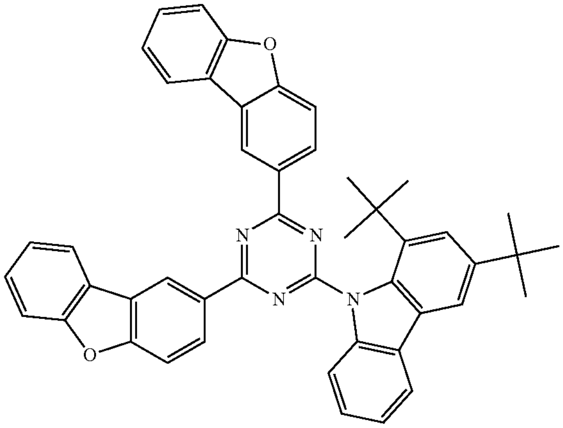
20
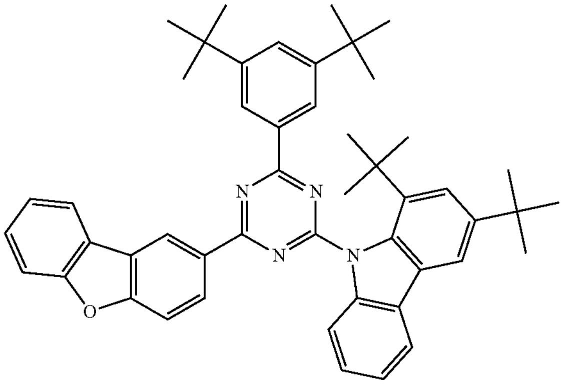
21
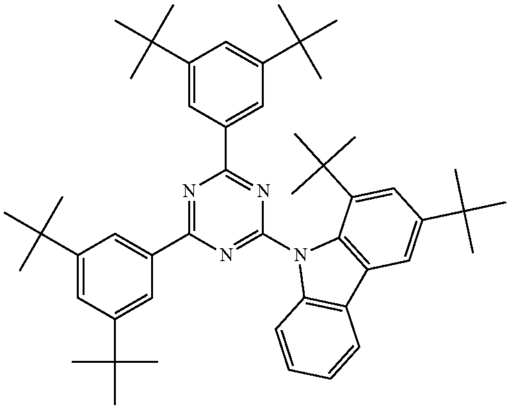

-continued
22
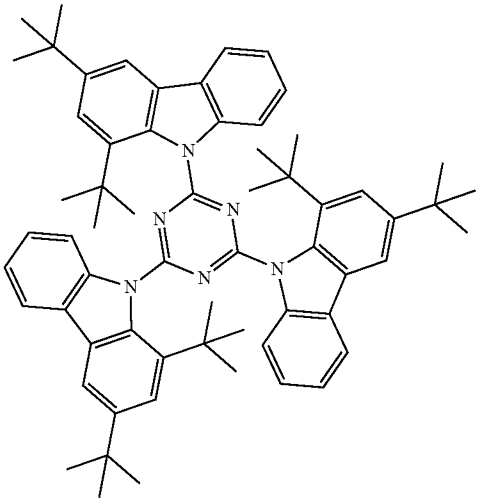
23
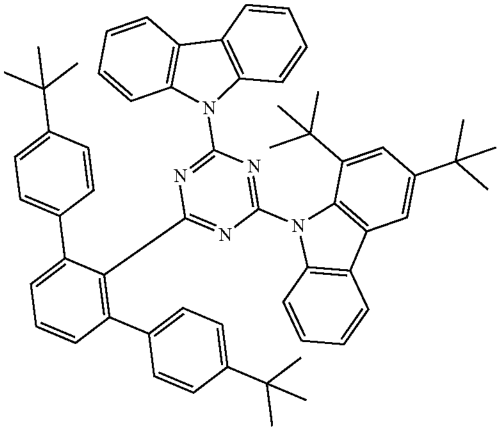
24
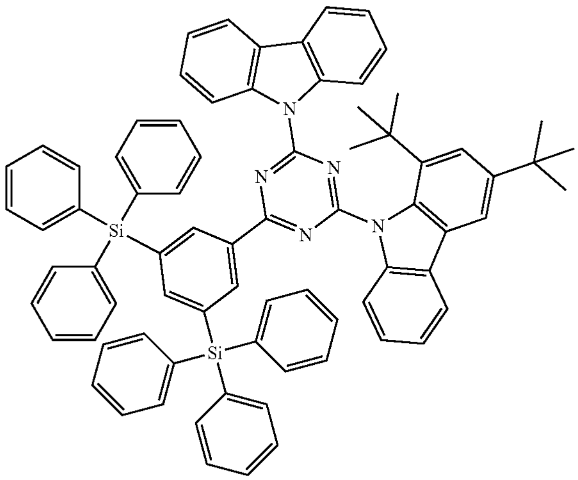
-continued
25
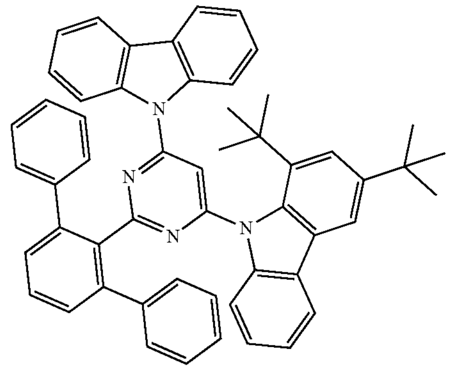
26
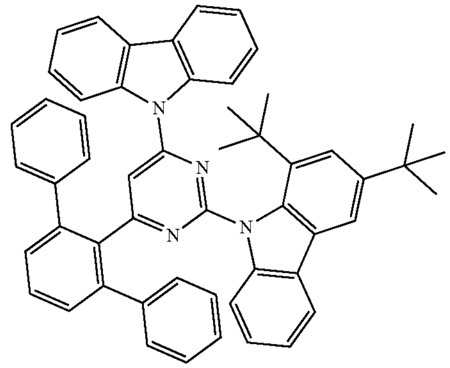
27
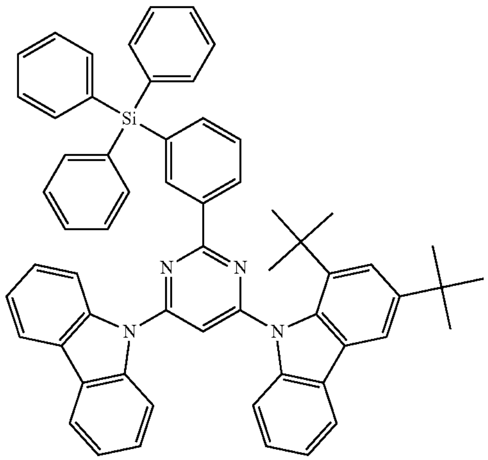

-continued
28
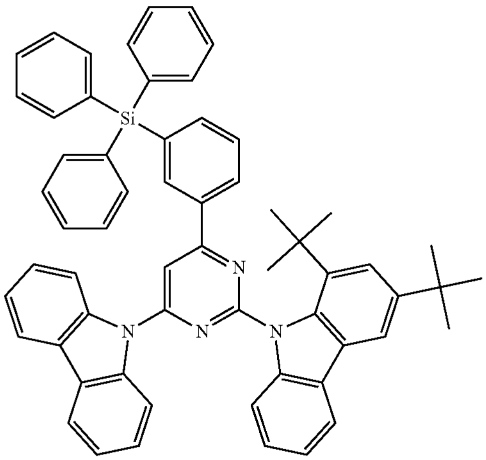
29
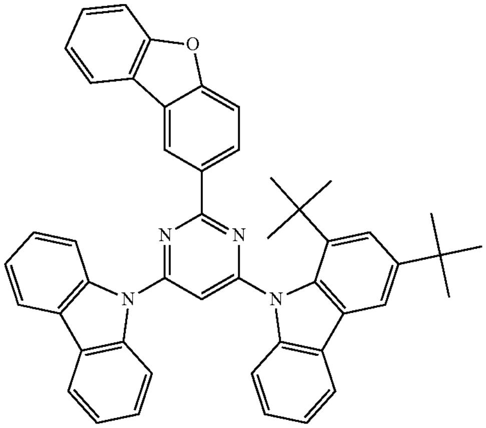
30
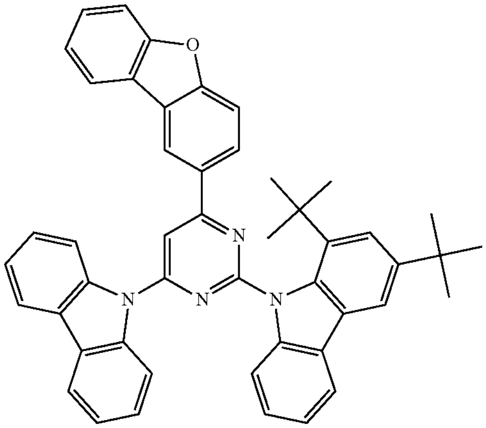
-continued
31
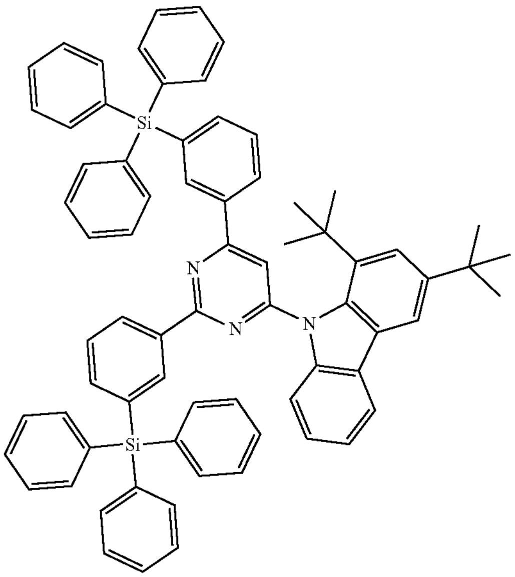
32
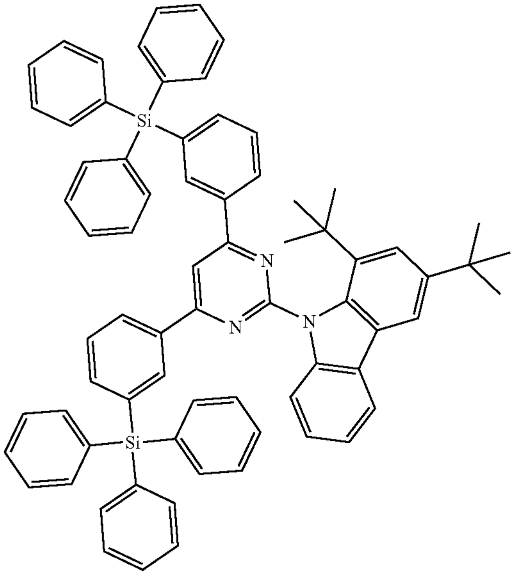

-continued
33
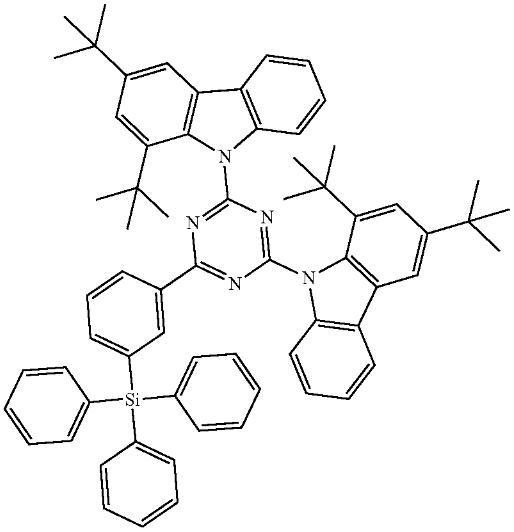
34
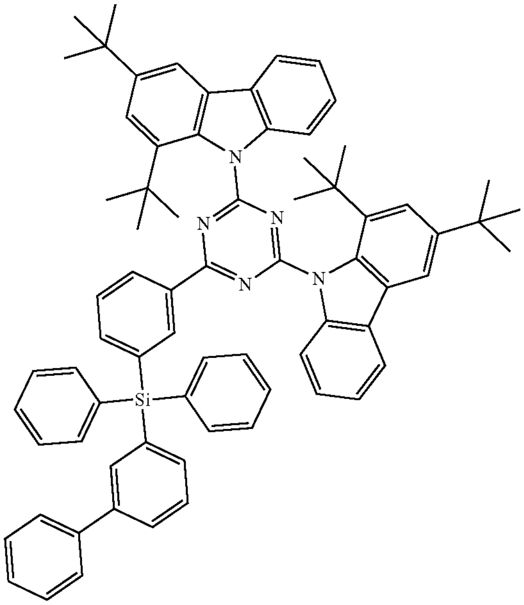
-continued
35
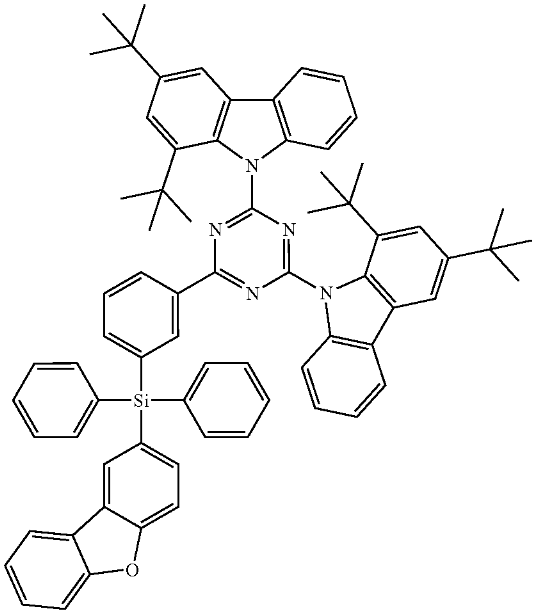
36
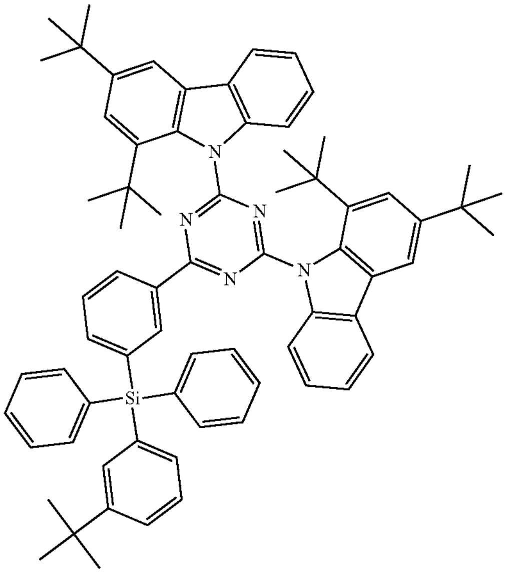

-continued
37
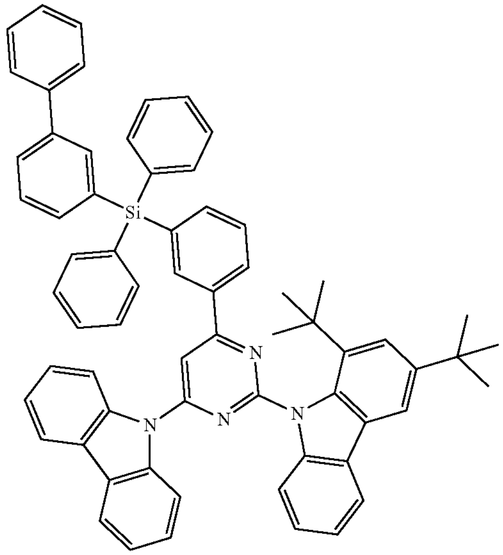
38
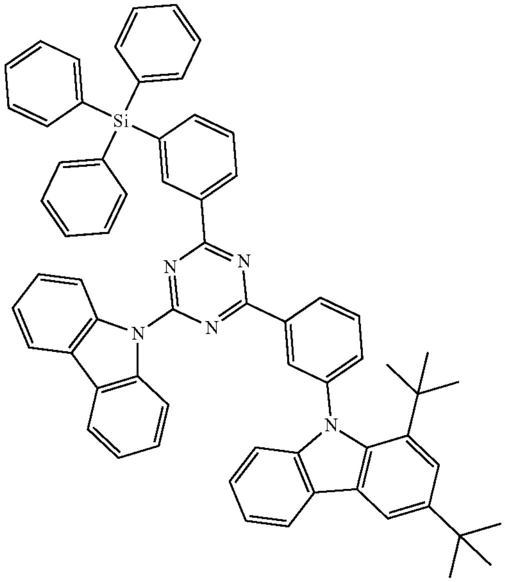
-continued
39
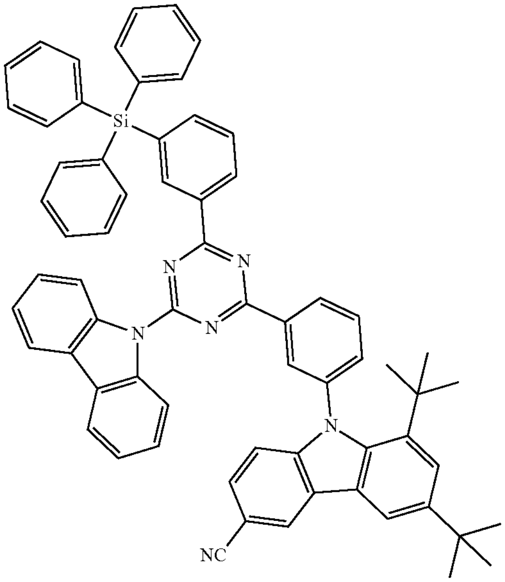
40
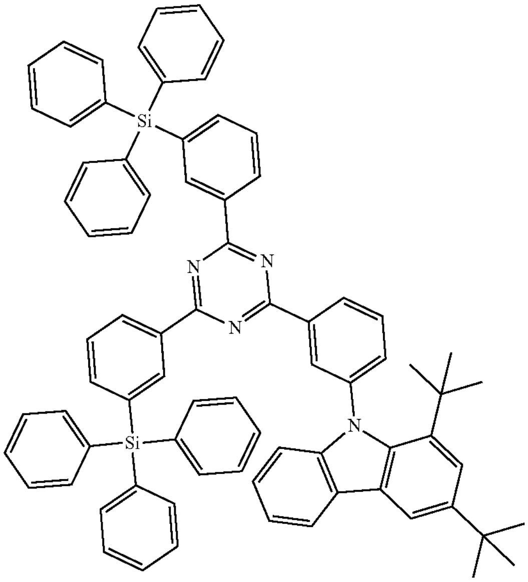

-continued
41
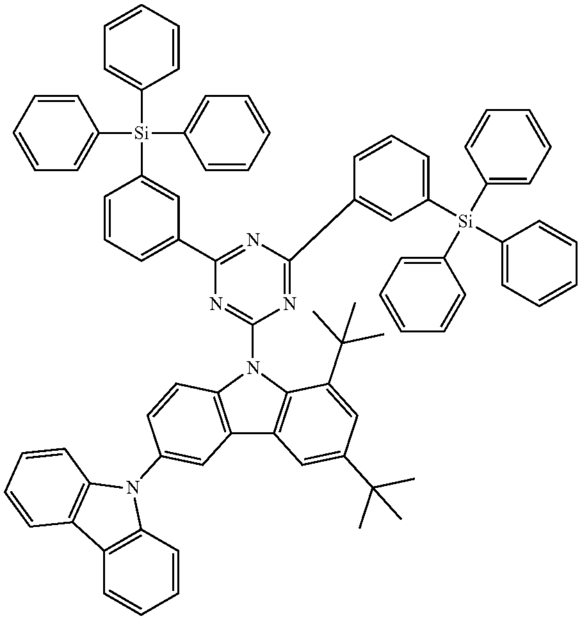
42
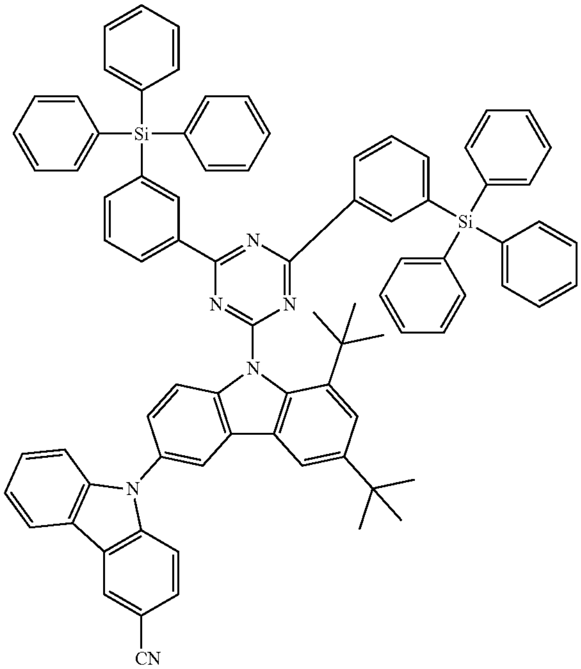
-continued
43
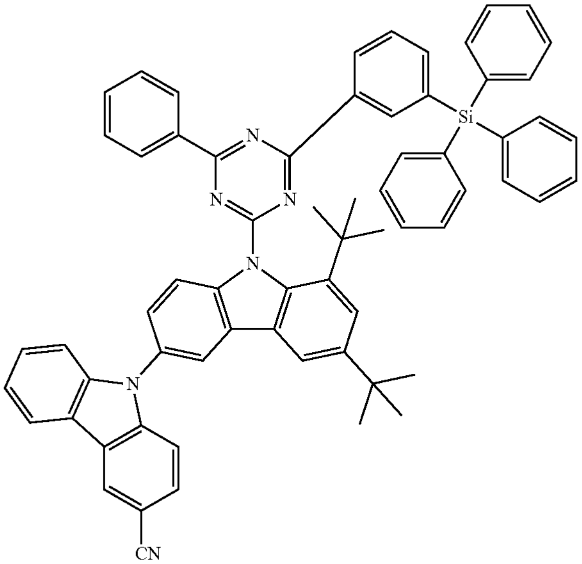
44
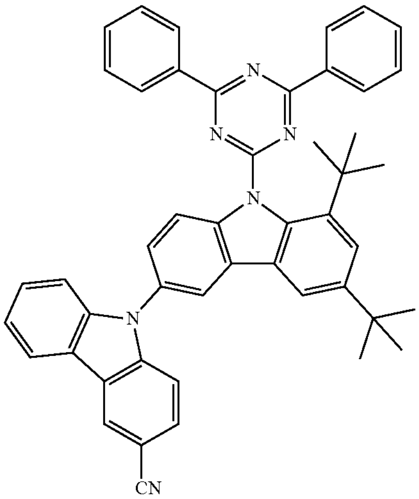
45
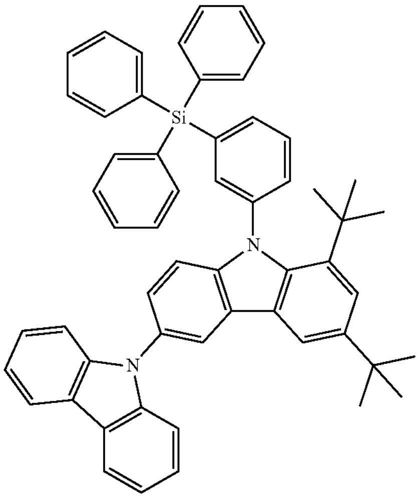

-continued
46
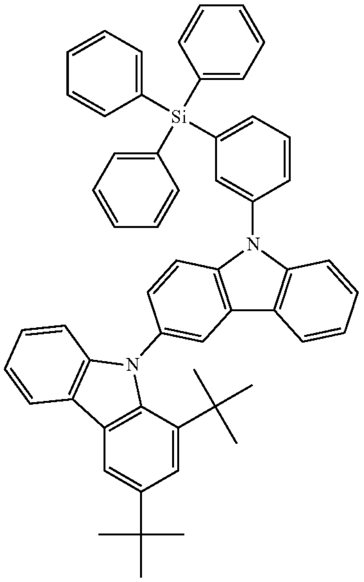
47
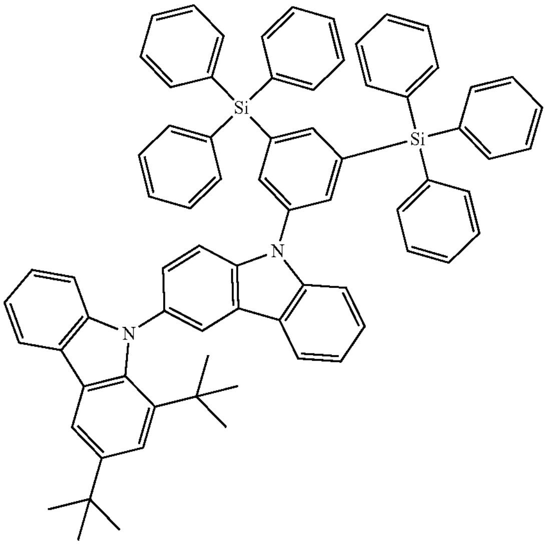
-continued
48
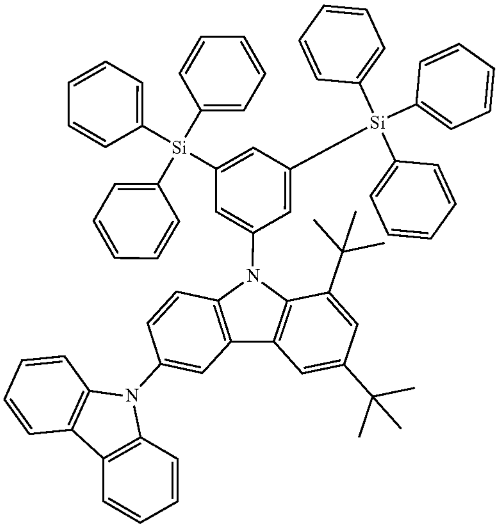
49
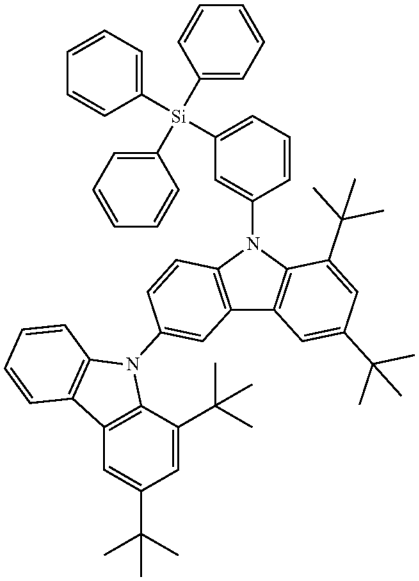

-continued

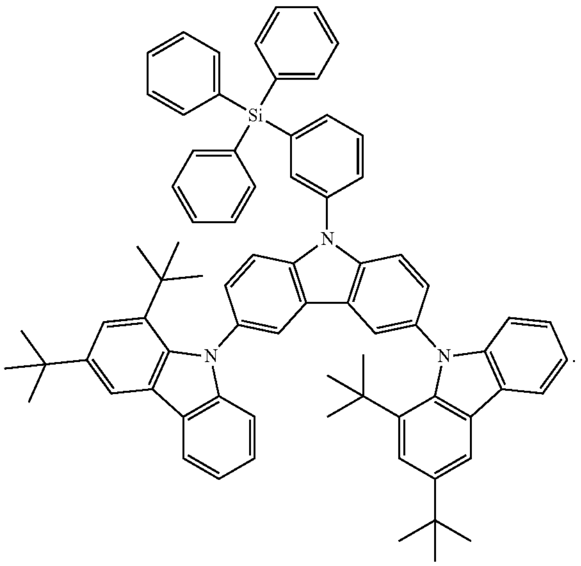

The heterocyclic compound represented by Formula 1 has a structure that includes a carbazole-based substituent in which a bulky substituent (for example, a t-butyl group) is located at the C1 and C3 positions.

As the heterocyclic compound represented by Formula 1 includes a carbazole-based substituent in which a bulky substituent is located at the C1 and C3 positions, degradation of color purity due to the formation of an exciplex between a host and a dopant may be suppressed, thereby having the advantage of improving the electrical stability of the molecule.

As the heterocyclic compound represented by Formula 1 includes at least one π electron-deficient nitrogen-containing $C_1$-$C_{60}$ cyclic group or at least one silyl group, the electron transport ability may be increased, and thus the heterocyclic compound may have advantageous characteristics in terms of luminescence efficiency and energy transfer.

Therefore, an electronic device, for example, an organic light-emitting device, employing the heterocyclic compound represented by Formula 1 may have low driving voltage, high EQE, high efficiency, and a long lifespan.

Methods of synthesizing the heterocyclic compound represented by Formula 1 should be readily apparent to those of ordinary skill in the art by referring to Examples described herein.

At least one heterocyclic compound represented by Formula 1 may be used in a light-emitting device (for example, an organic light-emitting device).

Another aspect of the disclosure provides a light-emitting device which may include a first electrode, a second electrode facing the first electrode, an interlayer between the first electrode and the second electrode and including an emission layer, and at least one heterocyclic compound represented by Formula 1, as described herein.

In an embodiment, the first electrode may be an anode, the second electrode may be a cathode, and the interlayer may further include a hole transport region between the emission layer and the first electrode and an electron transport region between the emission layer and the second electrode. The hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In an embodiment, the interlayer may include the at least one heterocyclic compound.

In an embodiment, the emission layer may include the at least one heterocyclic compound.

In an embodiment, the emission layer may include a host and a dopant, wherein an amount of the host may be greater than an amount of the dopant, and the host may include the at least one heterocyclic compound.

In an embodiment, the emission layer may further include a transition metal-containing compound.

In an embodiment, the emission layer may emit blue light or blue-green light.

In an embodiment, the emission layer may emit blue light or blue-green light, each having a maximum emission wavelength in a range of about 400 nm to about 500 nm.

As used herein, the expression the "(interlayer) includes at least one heterocyclic compound" may be construed as meaning the "(interlayer) may include one heterocyclic compound of Formula 1 or two different heterocyclic compounds of Formula 1".

In an embodiment, the interlayer may include only Compound 1 as the heterocyclic compound. In this regard, Compound 1 may be in the emission layer of the light-emitting device. In embodiments, the interlayer may include, as the heterocyclic compound, Compound 1 and Compound 2. In this regard, Compound 1 and Compound 2 may be in an identical layer (for example, Compound 1 and Compound 2 may all be in the emission layer), or may be in different layers (for example, Compound 1 may be in the emission layer and Compound 2 may be in the electron transport region).

The term "interlayer" as used herein refers to a single layer and/or all layers between the first electrode and the second electrode of the light-emitting device.

Another aspect of the disclosure provides an electronic apparatus including the light-emitting device. In an embodiment, the electronic apparatus may further include a thin-film transistor.

For example, the electronic apparatus may further include a thin-film transistor including a source electrode and a drain electrode, wherein the first electrode of the light-emitting device may be electrically connected to the source electrode or the drain electrode.

In an embodiment, the electronic apparatus may further include a color filter, a color conversion layer, a touch screen layer, a polarizing layer, or any combination thereof. For example, the electronic apparatus may be a flat panel display apparatus, but embodiments are not limited thereto.

More details for the electronic apparatus are the same as described herein.

[Description of FIG. 1]

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described with reference to FIG. 1.

[First Electrode 110]

In FIG. 1, a substrate may be further included under the first electrode 110 or on the second electrode 150. The substrate may be a glass substrate or a plastic substrate. In embodiments, the substrate may be a flexible substrate, and for example, may include plastics with excellent heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high-work function material that facilitates injection of holes.

The first electrode 110 may be a reflective electrode, a semi-transmissive electrode, or a transmissive electrode. In an embodiment, when the first electrode 110 is a transmissive electrode, a material for forming the first electrode 110 may include indium tin oxide (ITO), indium zinc oxide (IZO), tin oxide ($SnO_2$), zinc oxide (ZnO), or any combination thereof. In embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a structure consisting of a single layer or a structure including multiple layers. For example, the first electrode 110 may have a three-layered structure of ITO/Ag/ITO.

[Interlayer 130]

The interlayer 130 is located on the first electrode 110. The interlayer 130 may include an emission layer.

The interlayer 130 may further include a hole transport region between the first electrode 110 and the emission layer, and an electron transport region between the emission layer and the second electrode 150.

The interlayer 130 may further include, in addition to various organic materials, a metal-containing compound such as an organometallic compound, an inorganic material such as a quantum dot, and the like.

In an embodiment, the interlayer 130 may include two or more emitting units sequentially stacked between the first electrode 110 and the second electrode 150 and at least one charge generation layer between the two or more emitting units. When the interlayer 130 includes the two or more emitting units and the at least one charge generation layer as described above, the light-emitting device 10 may be a tandem light-emitting device.

[Hole Transport Region in Interlayer 130]

The hole transport region may have a structure consisting of a layer consisting of a single material, a structure consisting of a layer consisting of different materials, or a structure including multiple layers including different materials.

The hole transport region may include a hole injection layer, a hole transport layer, an emission auxiliary layer, an electron-blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron-blocking layer structure, wherein the layers of each structure may be stacked from the first electrode 110 in its respective stated order, but the structure of the hole transport region is not limited thereto.

The hole transport region may include a compound represented by Formula 201, a compound represented by Formula 202, or any combination thereof:

[Formula 201]

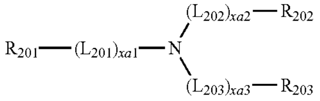

[Formula 202]

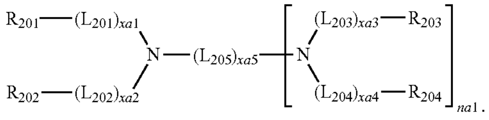

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of groups represented by Formulae CY201 to CY217:

CY201

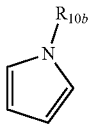

CY202

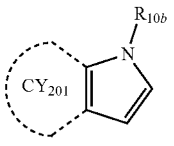

-continued

CY203

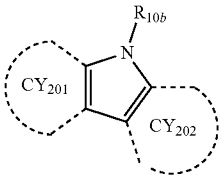

CY204

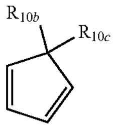

CY205

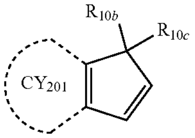

CY206

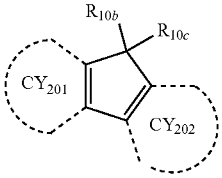

CY207

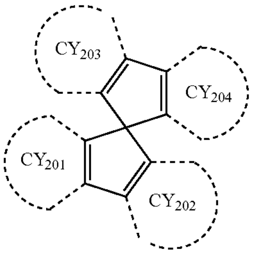

CY208

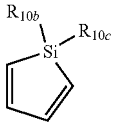

CY209

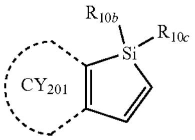

CY210

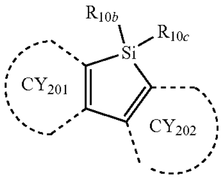

-continued

CY211

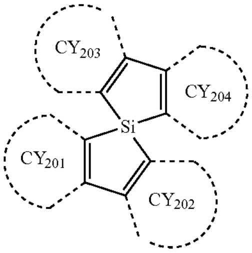

CY212

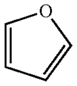

CY213

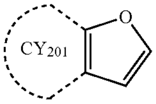

CY214

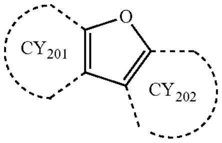

CY215

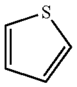

CY216

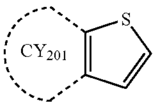

CY217

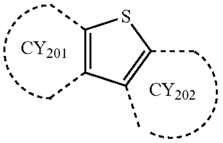

.

In Formulae CY201 to CY217, $R_{10b}$ and $R_{10c}$ may each independently be the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$ as described above.

In an embodiment, ring $CY_{201}$ to ring $CY_{204}$ in Formulae CY201 to CY217 may each independently be a benzene group, a naphthalene group, a phenanthrene group, or an anthracene group.

In embodiments, each of Formulae 201 and 202 may include at least one of groups represented by Formulae CY201 to CY203.

In embodiments, Formula 201 may include at least one of groups represented by Formulae CY201 to CY203 and at least one of groups represented by Formulae CY204 to CY217.

In embodiments, in Formula 201, xa1 may be 1, $R_{201}$ may be a group represented by one of Formulae CY201 to CY203, xa2 may be 0, and $R_{202}$ may be a group represented by one of Formulae CY204 to CY207.

In embodiments, each of Formulae 201 and 202 may not include a group represented by one of Formulae CY201 to CY203.

In embodiments, each of Formulae 201 and 202 may not include a group represented by one of Formulae CY201 to CY203, and may include at least one of groups represented by Formulae CY204 to CY217.

In embodiments, each of Formulae 201 and 202 may not include a group represented by one of Formulae CY201 to CY217.

For example, the hole transport region may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

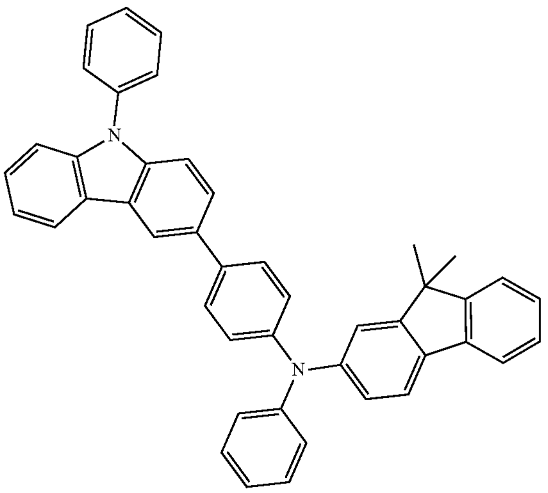

HT2

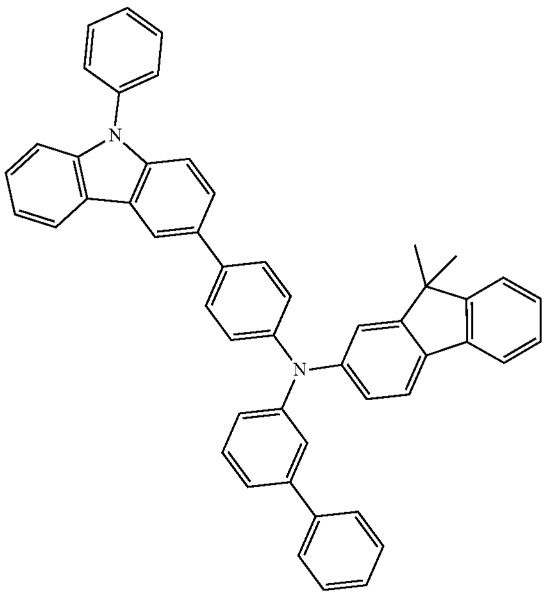

HT3

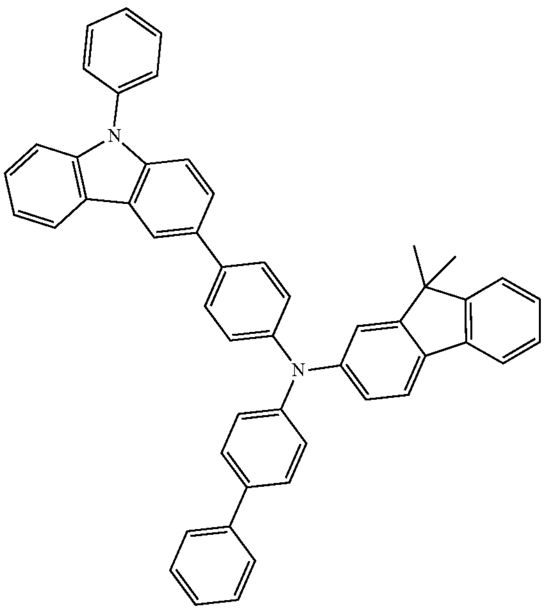

HT4

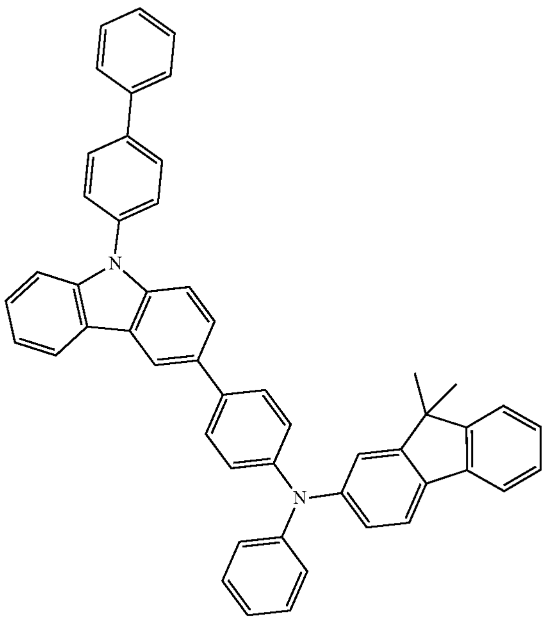

-continued
HT5
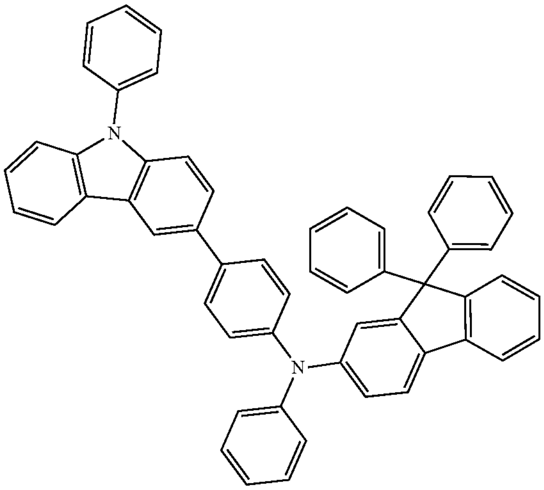
HT6
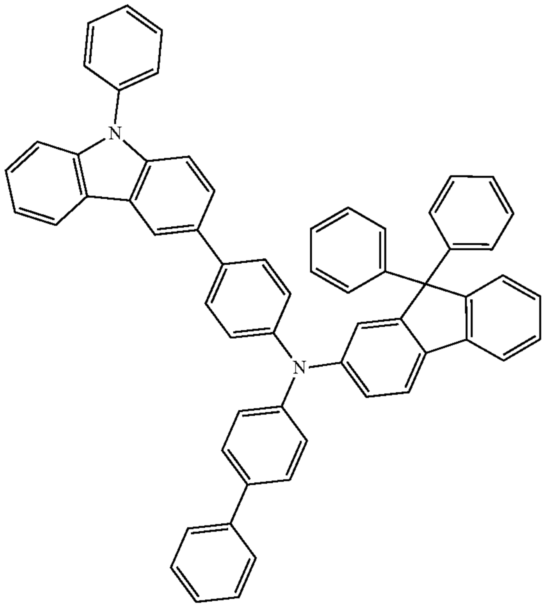
HT7
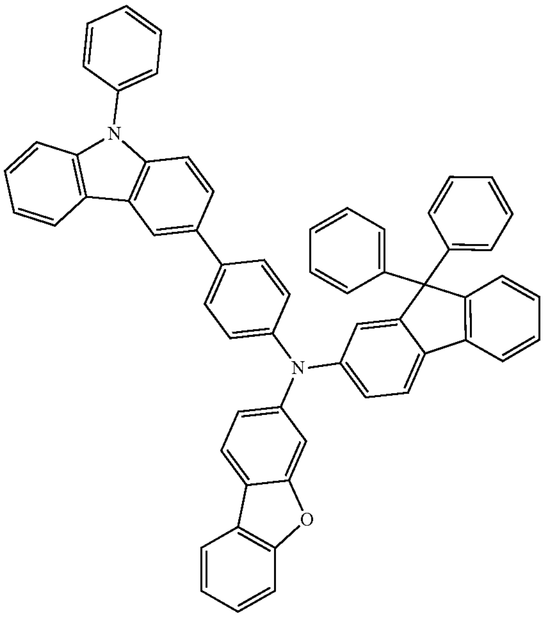
HT8
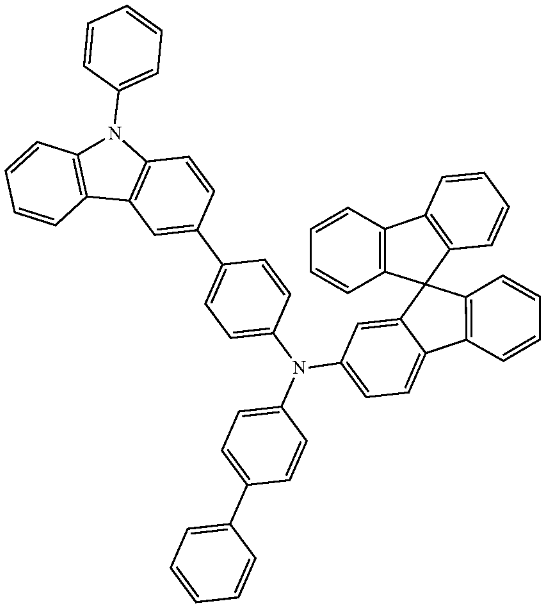

-continued
HT9
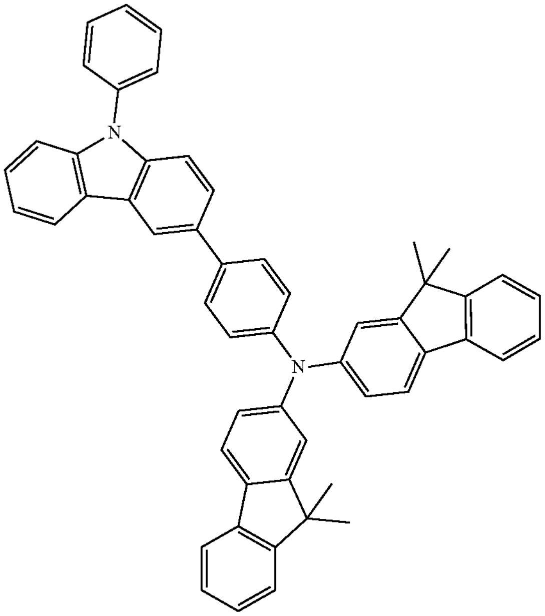
HT10
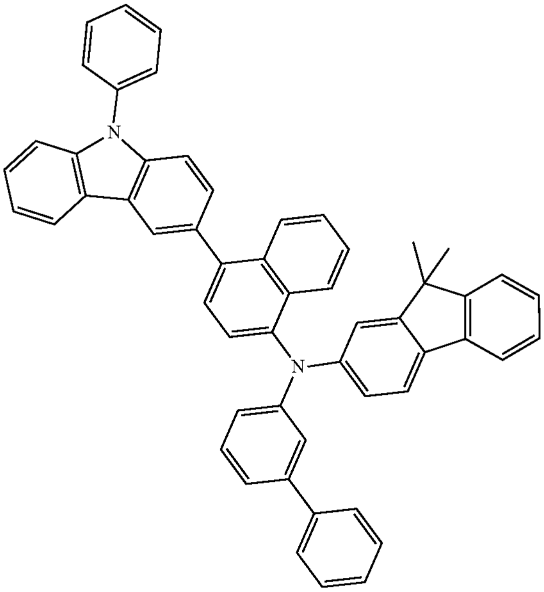
HT11
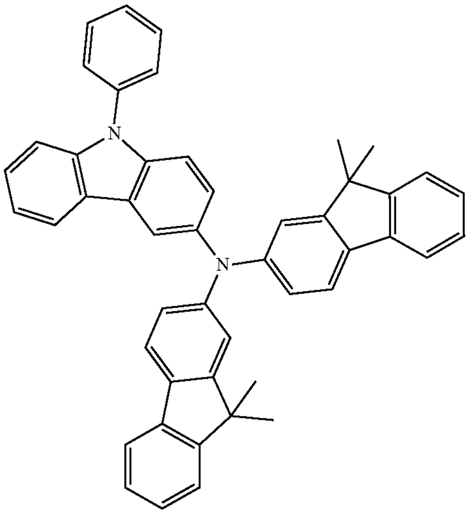
HT12
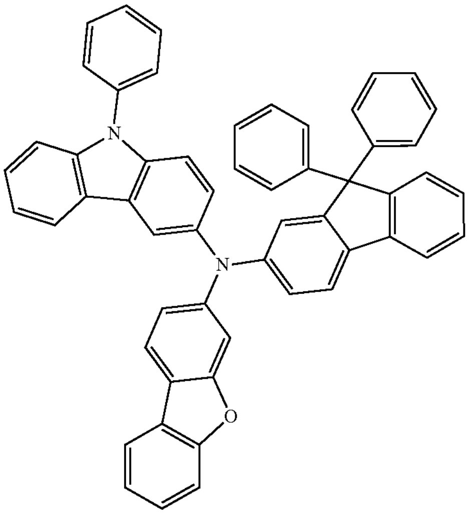

-continued
HT13
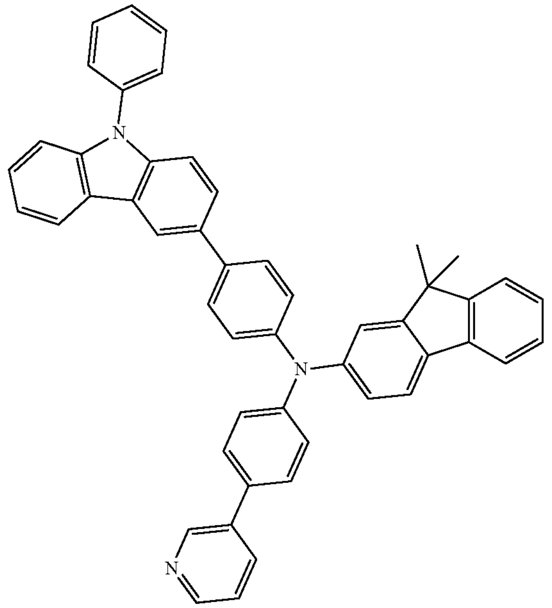
HT14
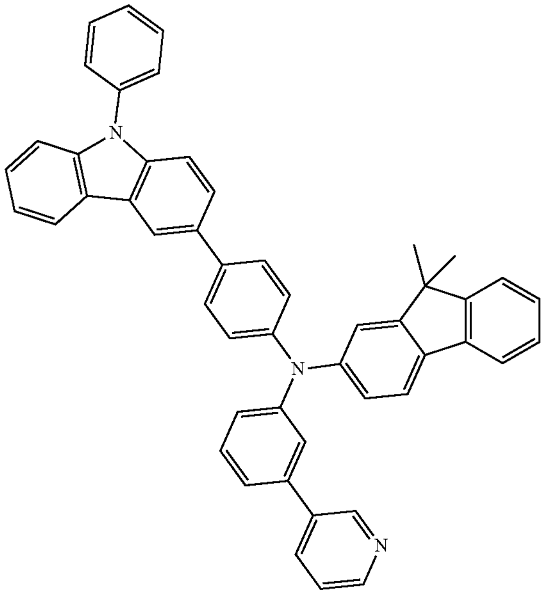
HT15
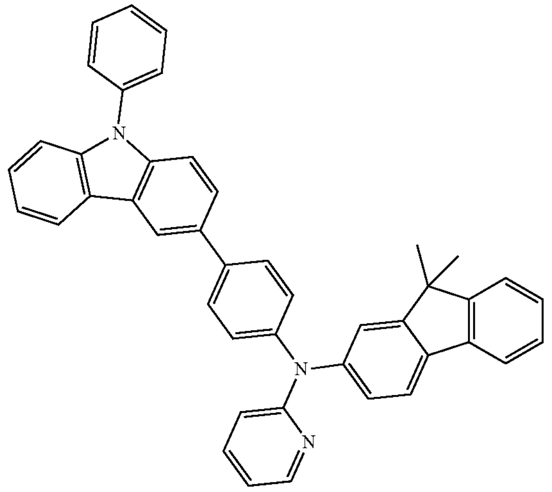
HT16
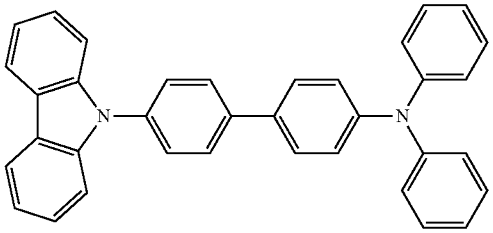
HT17
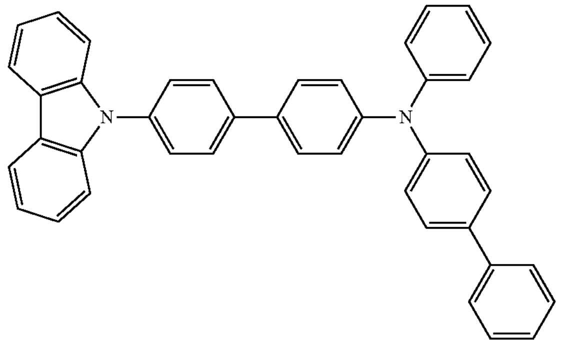
HT18
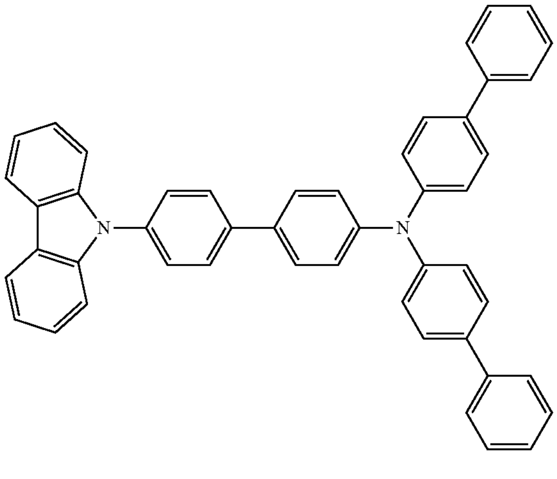

-continued
HT19
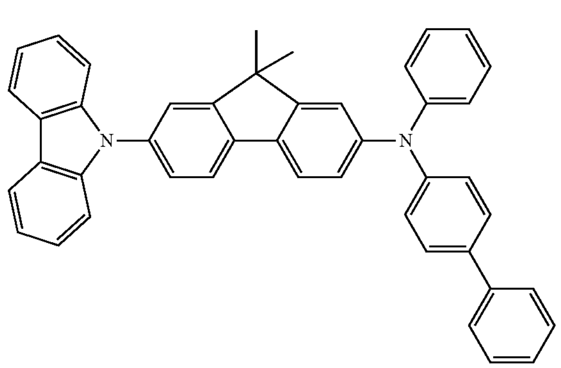
HT20
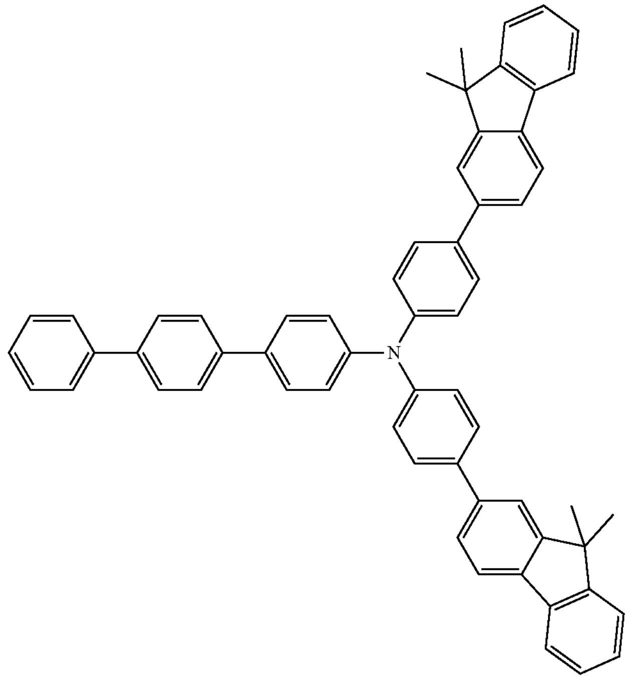
HT21
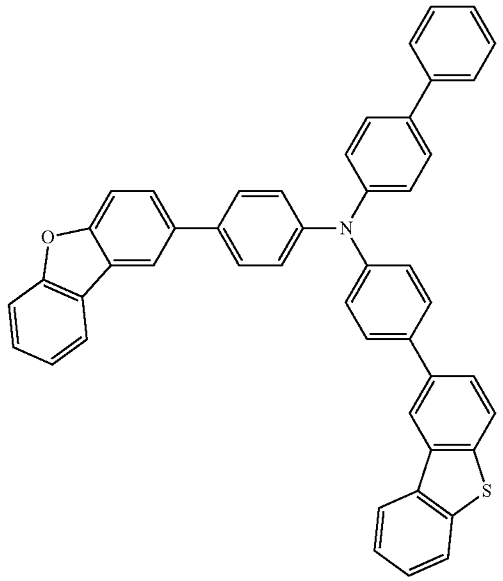
HT22
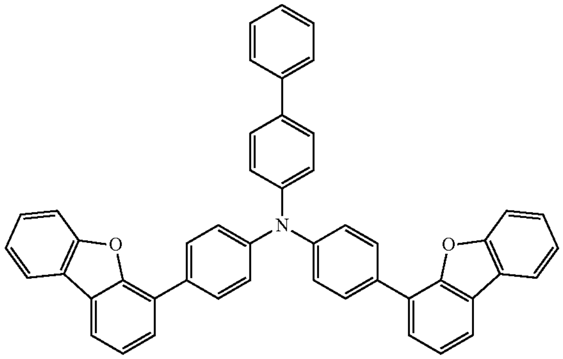

-continued
HT23
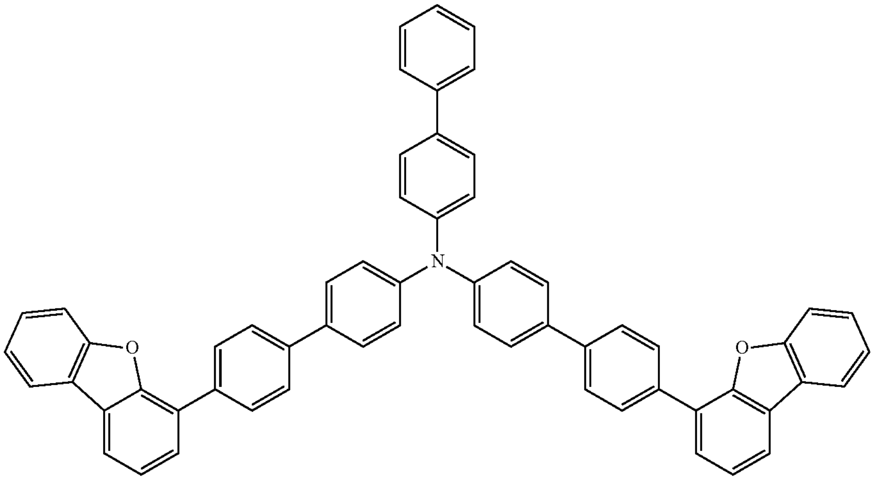
HT24
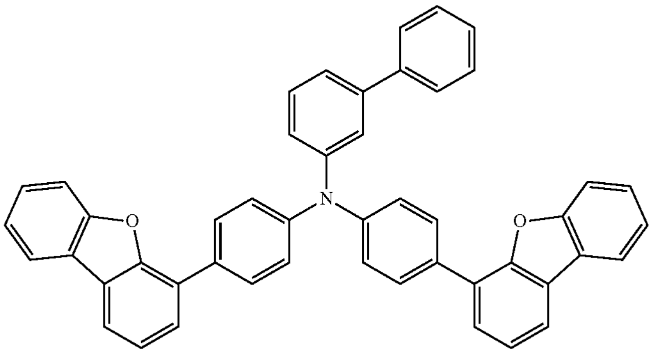
HT25
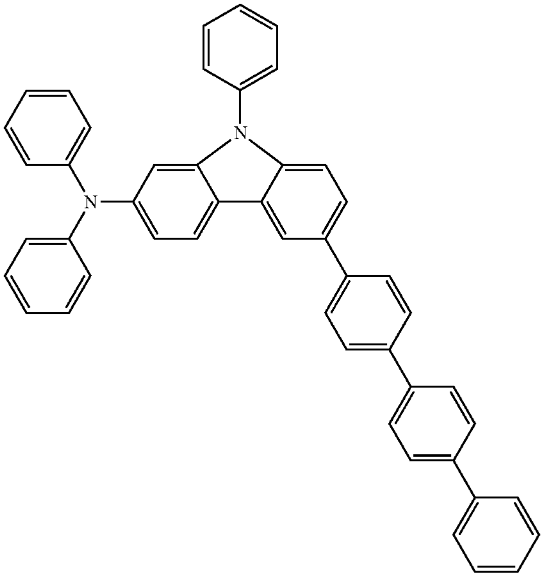
HT26
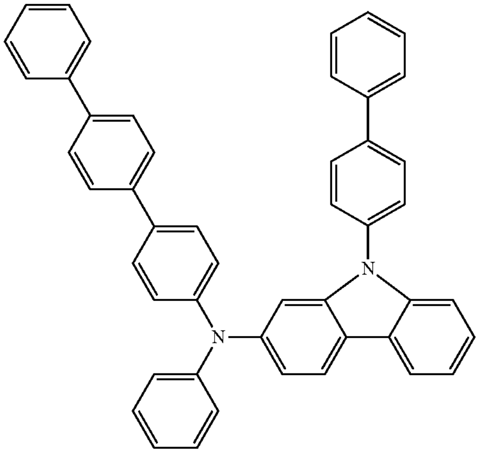

-continued
HT27
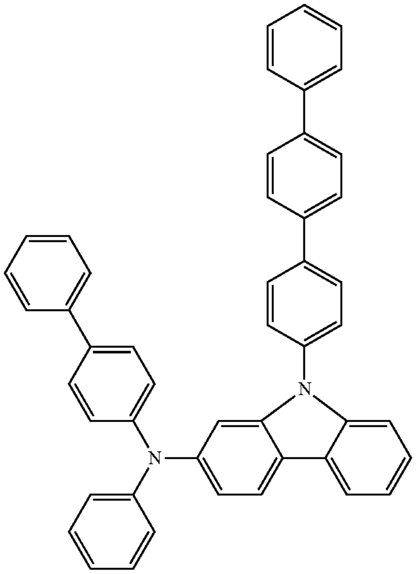
HT28
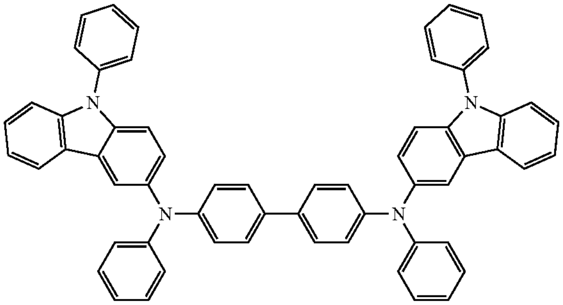
HT29
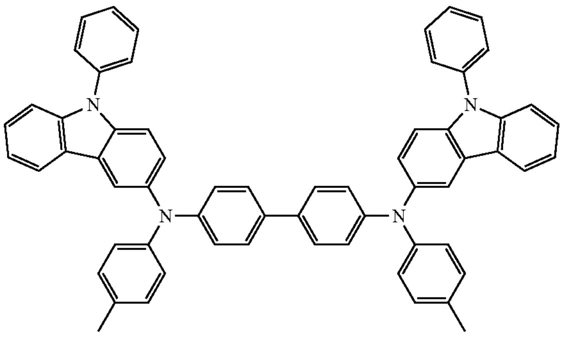
HT30
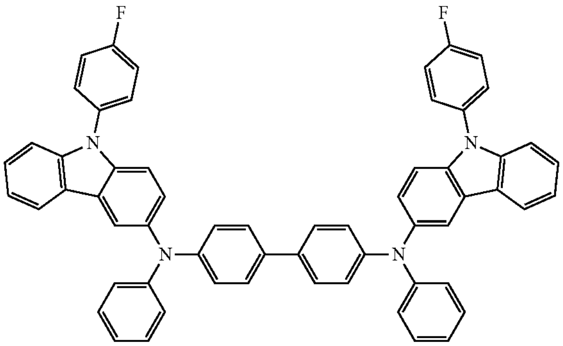
HT31
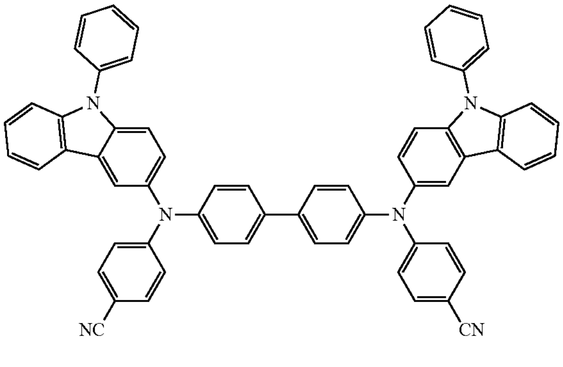
HT32
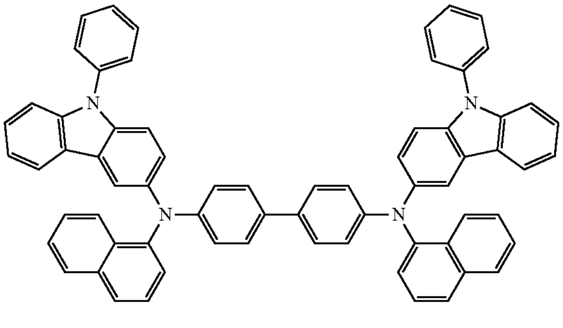

-continued
HT33
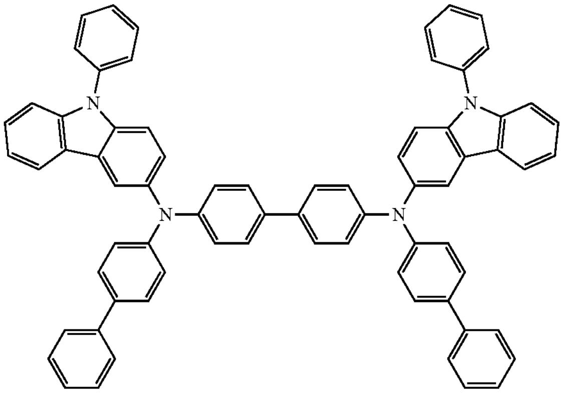
HT34
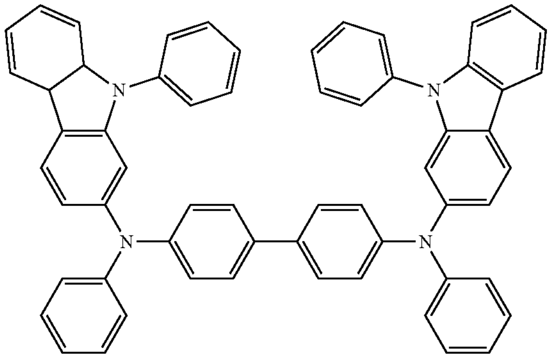
HT35
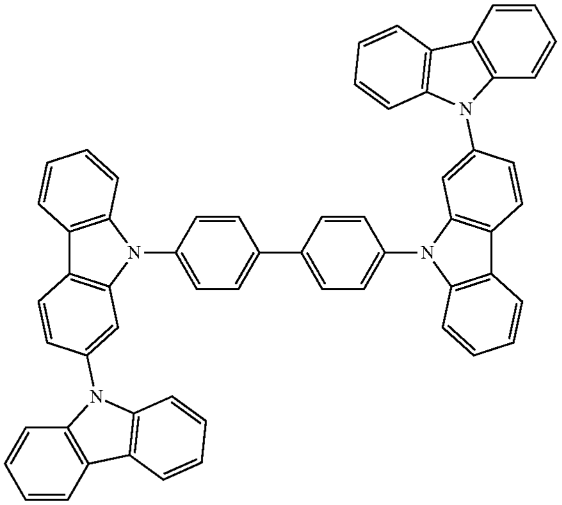
HT36
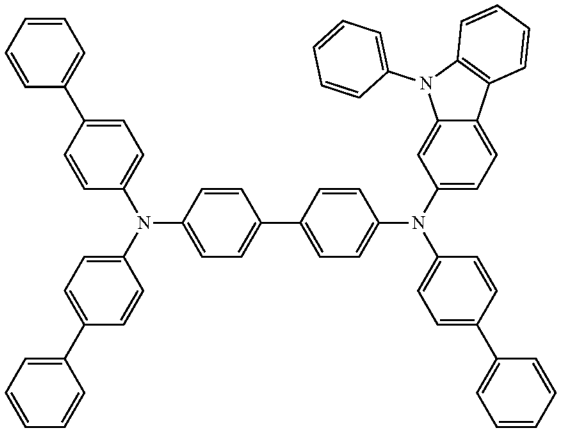
HT37
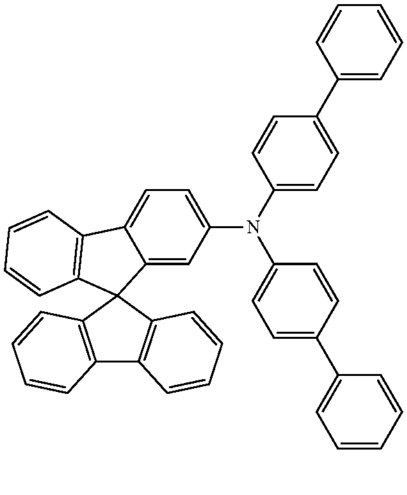
HT38
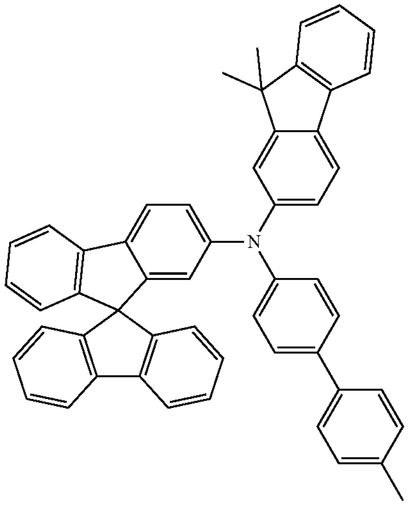

-continued
HT39
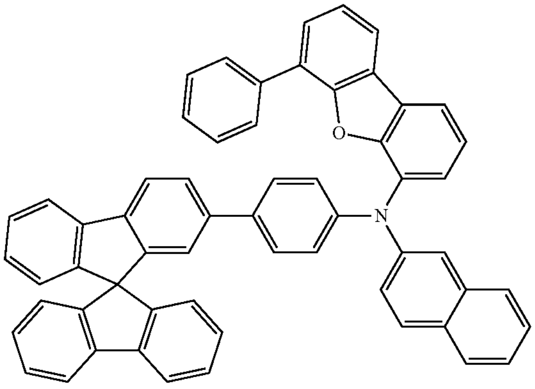
HT40
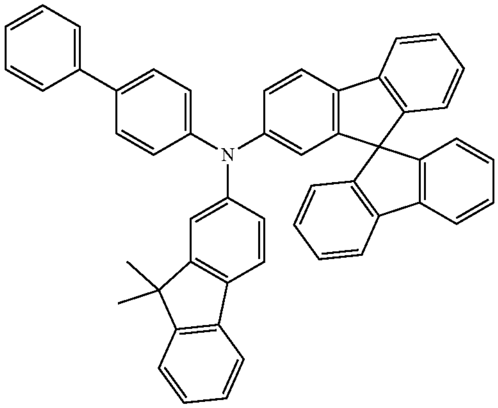
HT41
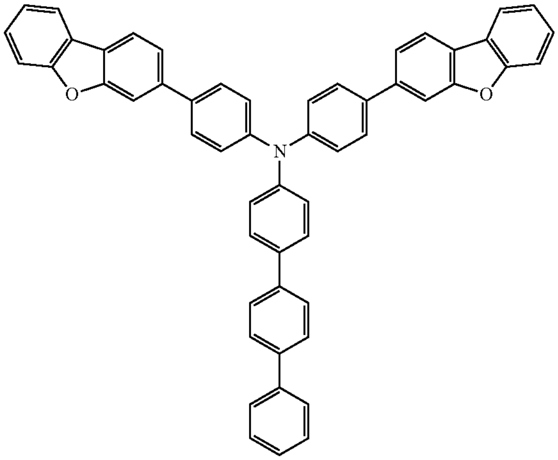
HT42
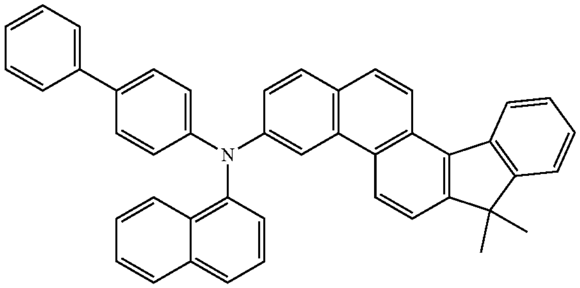
HT43
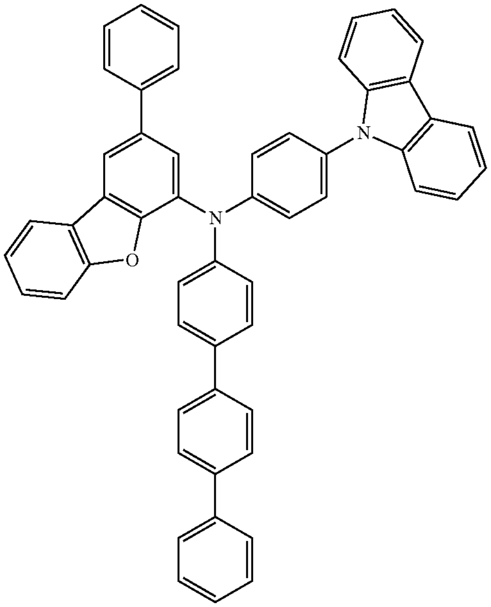
HT44
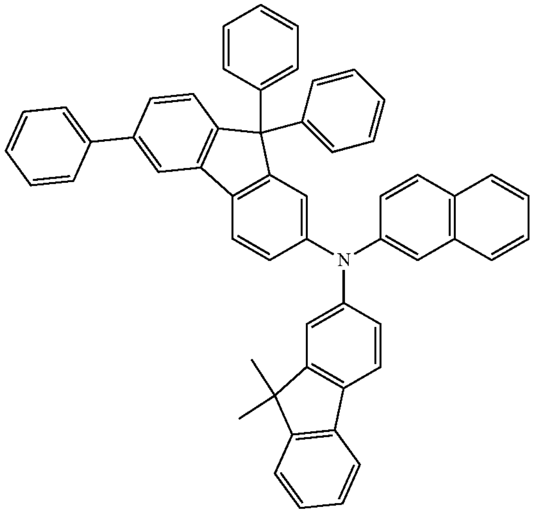

-continued
HT45
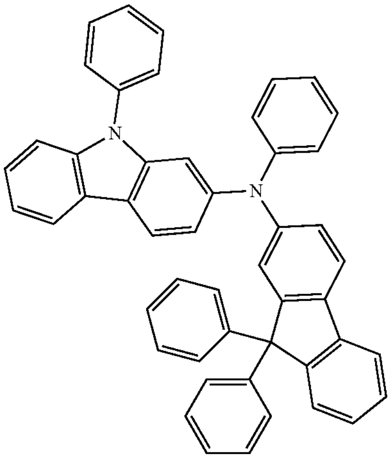
HT46
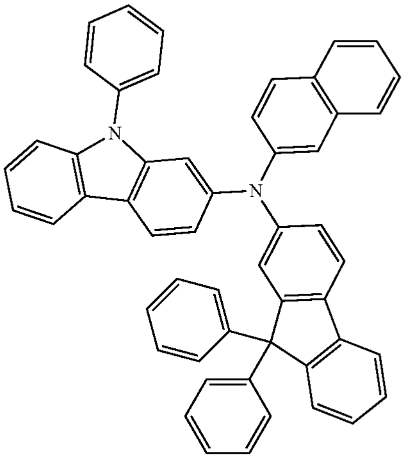
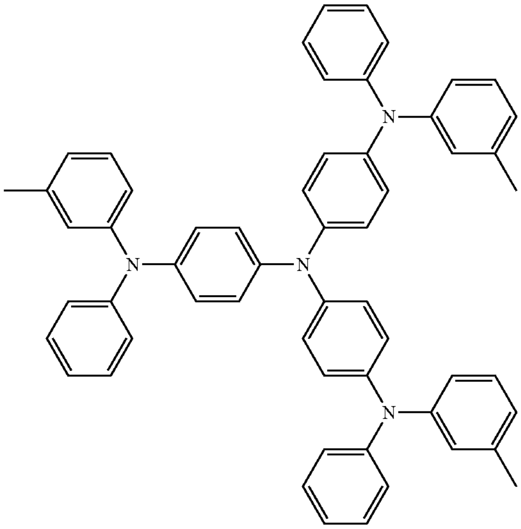
m-MTDATA
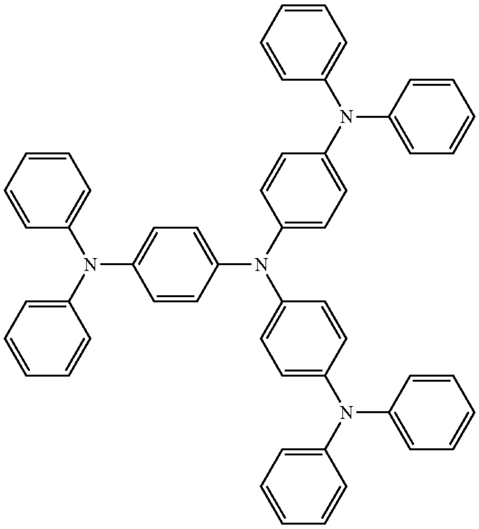
TDATA
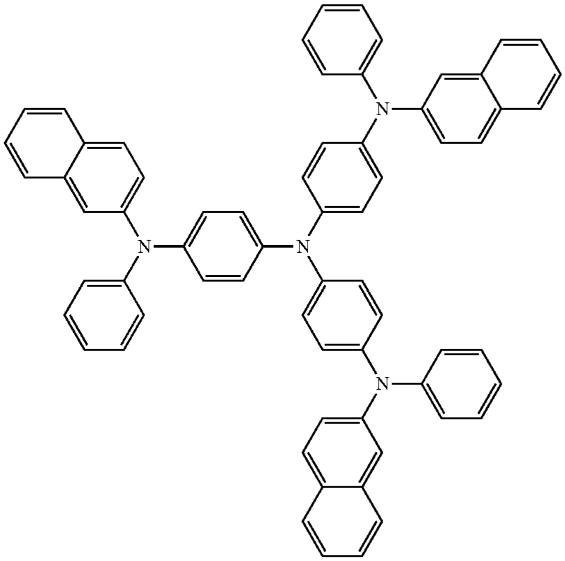
2-TNATA
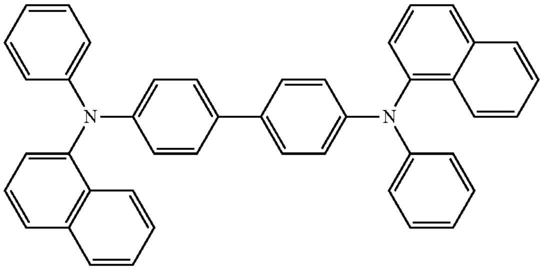
NPB -continued

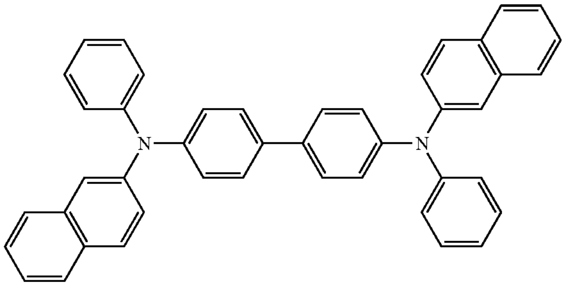

β-NPB

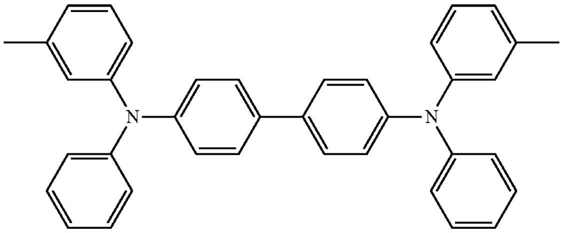

TPD

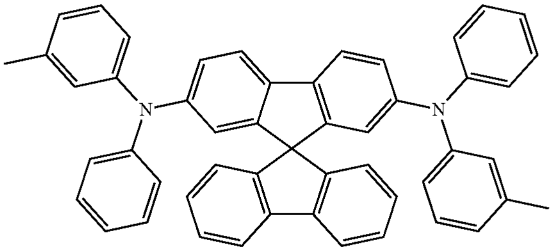

Spiro-TPD

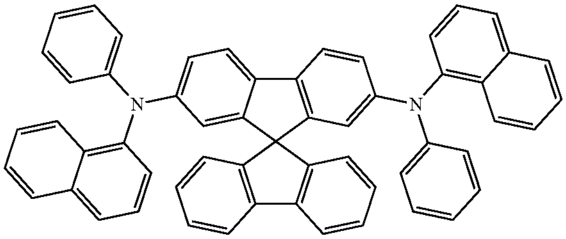

Spiro-NPB

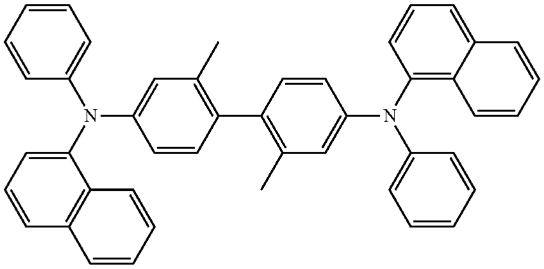

methylated-NPB

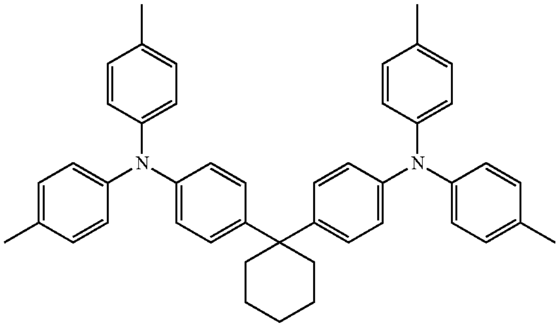

TAPC

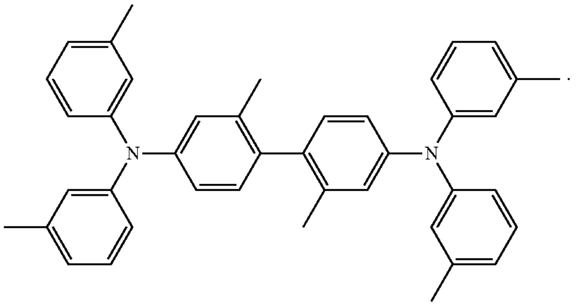

HMTPD

A thickness of the hole transport region may be in a range of about 50 Å to about 10,000 Å. For example, the thickness of the hole transport region may be in a range of about 100 Å to about 4,000 Å. When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of about 100 Å to about 1,000 Å. For example, the thickness of the hole transport layer may be in a range of about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to a wavelength of light emitted by the emission layer, and the electron blocking layer may block the leakage of electrons from the emission layer to the hole transport region. Materials that may be included in the hole transport region may be included in the emission auxiliary layer and the electron-blocking layer.

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

A lowest unoccupied molecular orbital (LUMO) energy level of the p-dopant may be about equal to or less than about −3.5 eV.

In an embodiment, the p-dopant may include a quinone derivative, a cyano group-containing compound, a compound including element EL1 and element EL2, or any combination thereof.

Examples of the quinone derivative may include TCNQ, F4-TCNQ, and the like.

Examples of the cyano group-containing compound may include HAT-CN, a compound represented by Formula 221, and the like:

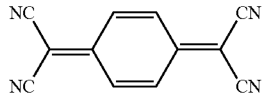

TCNQ

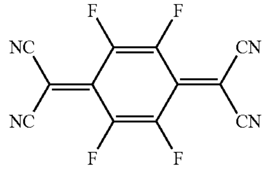

F4-TCNQ

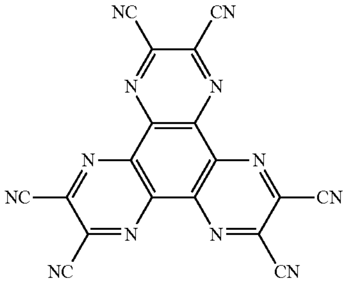

HAT-CN

[Formula 221]

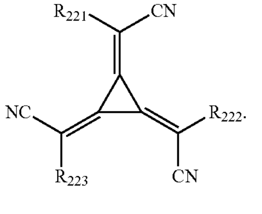

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; -A; a $C_1$-$C_{20}$ alkyl group substituted with a cyano group, —F, —Cl, —Br, —I, or any combination thereof; or any combination thereof.

In the compound including element EL1 and element EL2, element EL1 may be a metal, a metalloid, or any combination thereof, and element EL2 may be a non-metal, a metalloid, or any combination thereof.

Examples of the metal may include an alkali metal (for example, lithium (Li), sodium (Na), potassium (K), rubidium (Rb), cesium (Cs), and the like); an alkaline earth metal (for example, beryllium (Be), magnesium (Mg), calcium (Ca), strontium (Sr), barium (Ba), and the like); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), and the like); a post-transition metal (for example, zinc (Zn), indium (In), tin (Sn), and the like); a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), and the like); and the like.

Examples of the metalloid may include silicon (Si), antimony (Sb), tellurium (Te), and the like.

Examples of the non-metal may include oxygen (O), a halogen (for example, F, Cl, Br, I, and the like), and the like.

Examples of the compound including element EL1 and element EL2 may include a metal oxide, a metal halide (for example, a metal fluoride, a metal chloride, a metal bromide, a metal iodide, and the like), a metalloid halide (for example, a metalloid fluoride, a metalloid chloride, a metalloid bromide, a metalloid iodide, and the like), a metal telluride, or any combination thereof.

Examples of the metal oxide may include tungsten oxide (for example, WO, $W_2O_3$, $WO_2$, $WO_3$, $W_2O_5$, and the like), vanadium oxide (for example, VO, $V_2O_3$, $VO_2$, $V_2O_5$, and the like), molybdenum oxide (MoO, $Mo_2O_3$, $MoO_2$, $MoO_3$, $Mo_2O_5$, and the like), rhenium oxide (for example, $ReO_3$ and the like), and the like.

Examples of the metal halide may include an alkali metal halide, an alkaline earth metal halide, a transition metal halide, a post-transition metal halide, a lanthanide metal halide, and the like.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, $BaI_2$, and the like.

Examples of the transition metal halide may include a titanium halide (for example, $TiF_4$, $TiCl_4$, $TiBr_4$, $TiI_4$, and the like), a zirconium halide (for example, $ZrF_4$, $ZrCl_4$, $ZrBr_4$, $ZrI_4$, and the like), a hafnium halide (for example, $HfF_4$, $HfCl_4$, $HfBr_4$, $HfI_4$, and the like), a vanadium halide (for example, $VF_3$, $VCl_3$, $VBr_3$, $VI_3$, and the like), a niobium halide (for example, $NbF_3$, $NbCl_3$, $NbBr_3$, $NbI_3$, and the like), a tantalum halide (for example, $TaF_3$, $TaCl_3$, $TaBr_3$, $TaI_3$, and the like), a chromium halide (for example, $CrF_3$, $CrCl_3$, $CrBr_3$, $CrI_3$, and the like), a molybdenum halide (for example, $MoF_3$, $MoCl_3$, $MoBr_3$, MoI3, and the like), a tungsten halide (for example, $WF_3$, $WCl_3$, $WBr_3$, $WI_3$, and the like), a manganese halide (for example, $MnF_2$, $MnCl_2$, $MnBr_2$, $MnI_2$, and the like), a technetium halide (for example, $TcF_2$, $TcCl_2$, $TcBr_2$, $TcI_2$, and the like), a rhenium halide (for example, $ReF_2$, $ReCl_2$, $ReBr_2$, $ReI_2$, and the like), an iron halide (for example, $FeF_2$, $FeCl_2$, $FeBr_2$, $FeI_2$, and the like), a ruthenium halide (for example, $RuF_2$, $RuCl_2$, $RuBr_2$, $RuI_2$, and the like), an osmium halide (for example, $OsF_2$, $OsCl_2$, $OsBr_2$, $OsI_2$, and the like), a cobalt halide (for example, $CoF_2$, $CoCl_2$, $CoBr_2$, $C_{012}$, and the like), a rhodium halide (for example, $RhF_2$, $RhCl_2$, $RhBr_2$, $RhI_2$, and the like), an iridium halide (for example, $IrF_2$, $IrCl_2$, $IrBr_2$, $IrI_2$, and the like), a nickel halide (for example, $NiF_2$, $NiCl_2$, $NiBr_2$, $NiI_2$, and the like), a palladium halide (for example, $PdF_2$, $PdCl_2$, $PdBr_2$, $PdI_2$, and the like), a platinum halide (for example, $PtF_2$, $PtCl_2$, $PtBr_2$, $PtI_2$, and the like), a copper halide (for example, CuF, CuCl, CuBr, CuI, and the like), a silver halide (for example, AgF, AgCl, AgBr, AgI, and the like), a gold halide (for example, AuF, AuCl, AuBr, AuI, and the like), and the like Examples of the post-transition metal halide may include a zinc halide (for example, $ZnF_2$, $ZnCl_2$, $ZnBr_2$, $ZnI_2$, and the like), an indium halide (for example, $InI_3$ and the like), a tin halide (for example, $SnI_2$ and the like), and the like Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$ $SmBr_3$, YbI, $YbI_2$, $YbI_3$, $SmI_3$, and the like.

Examples of the metalloid halide may include an antimony halide (for example, $SbCl_5$ and the like) and the like.

Examples of the metal telluride may include an alkali metal telluride (for example, $Li_2Te$, $Na_2Te$, $K_2Te$, $Rb_2Te$, $Cs_2Te$, and the like), an alkaline earth metal telluride (for example, BeTe, MgTe, CaTe, SrTe, BaTe, and the like), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, and the like), a post-transition metal telluride (for example, ZnTe, and the like), a lanthanide metal telluride (for example, LaTe, CeTe, PrTe, NdTe, PmTe, EuTe, GdTe, TbTe, DyTe, HoTe, ErTe, TmTe, YbTe, LuTe, and the like), and the like.

[Emission Layer in Interlayer 130]

When the light-emitting device 10 is a full-color light-emitting device, the emission layer may be patterned into a red emission layer, a green emission layer, and/or a blue emission layer, according to a subpixel. In an embodiment, the emission layer may have a stacked structure of two or more layers of a red emission layer, a green emission layer, and a blue emission layer, wherein the two or more layers may contact each other or may be separated from each other to emit white light. In embodiments, the emission layer may include two or more materials of a red light-emitting material, a green light-emitting material, and a blue light-emitting material, wherein the two or more materials are mixed with each other in a single layer to emit white light.

In an embodiment, the emission layer may include a host and a dopant. The dopant may include a phosphorescent dopant, a fluorescent dopant, or any combination thereof.

In the emission layer, an amount of the dopant may be in a range of about 0.01 parts by weight to about 15 parts by weight, based on 100 parts by weight of the host.

In an embodiment, the emission layer may include a quantum dot.

In embodiments, the emission layer may include a delayed fluorescence material. The delayed fluorescence material may serve as a host or as a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within these ranges, excellent luminescence characteristics may be obtained without a substantial increase in driving voltage.

[Host]

In an embodiment, the host may include a compound represented by Formula 301:

[Formula 301]

$$[Ar_{301}]_{xb11}—[(L_{301})_{xb1}—R_{303}]_{xb21}$$

In Formula 301, $Ar_{301}$ and $L_{301}$ may each independently be a $C_3$-$C_{60}$ carbocyclic group unsubstituted or substituted with at least one $R_{10a}$ or a $C_1$-$C_6$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_6$ heterocyclic group unsubstituted or substituted with at least one $R_{10a}$, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, or —$P(=O)(Q_{301})(Q_{302})$, xb21 may be an integer from 1 to 5, and $Q_{301}$ to $Q_{303}$ may each independently be the same as described in connection with $Q_1$.

For example, when xb11 in Formula 301 is 2 or more, two or more of $Ar_{301}$ may be linked together via a single bond.

In embodiments, the host may include a compound represented by Formula 301-1, a compound represented by Formula 301-2, or any combination thereof:

[Formula 301-1]

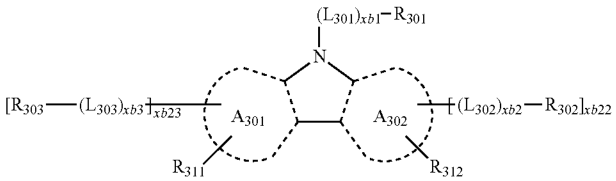

-continued

[Formula 301-2]

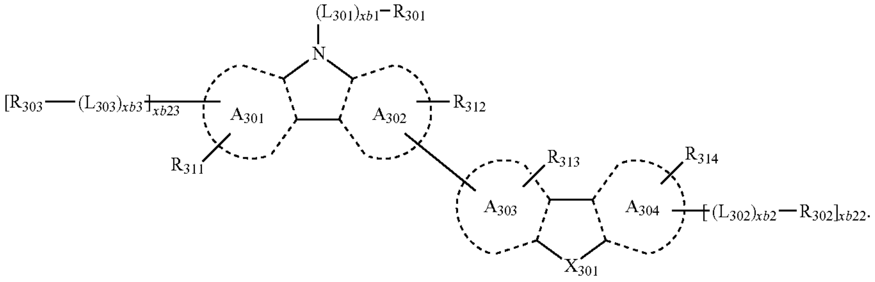

In Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[$(L_{304})_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ may each be the same as described herein, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each independently be the same as described in connection with $R_{301}$.

In embodiments, the host may include an alkali earth metal complex, a post-transition metal complex, or any combination thereof. For example, the host may include a Be complex (for example, Compound H55), an Mg complex, a Zn complex, or any combination thereof.

In embodiments, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

H1

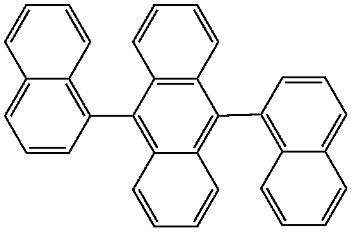

H2

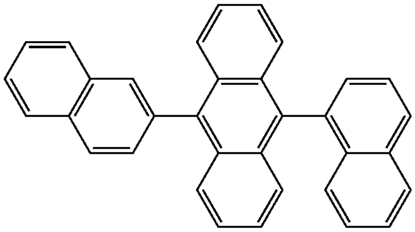

-continued

H3

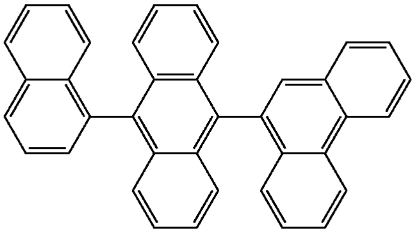

H4

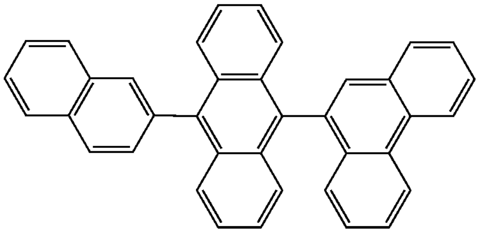

H5

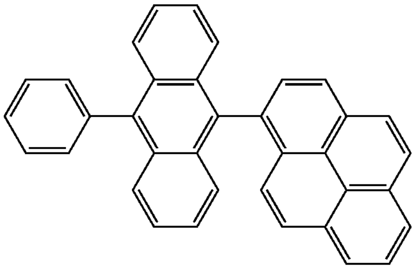

H6

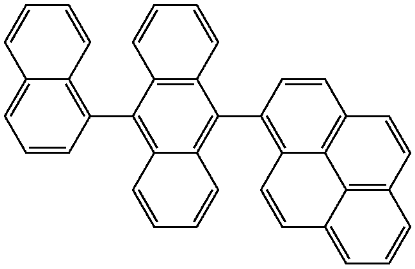

-continued
H7
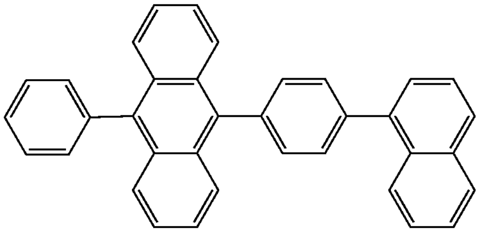
H8
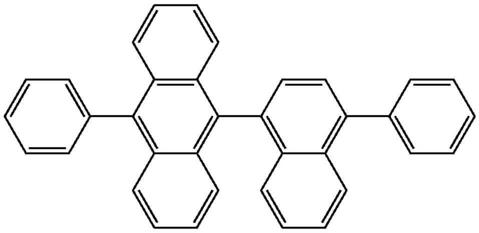
H9
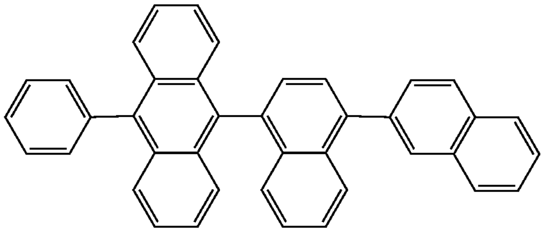
H10
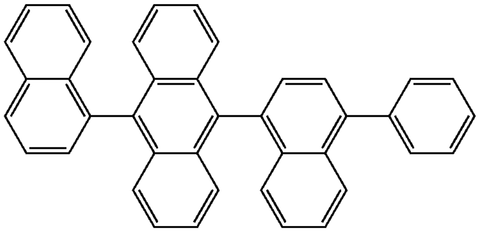
H11
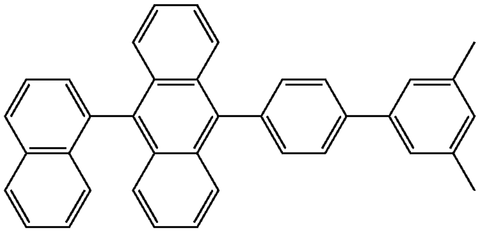
H12
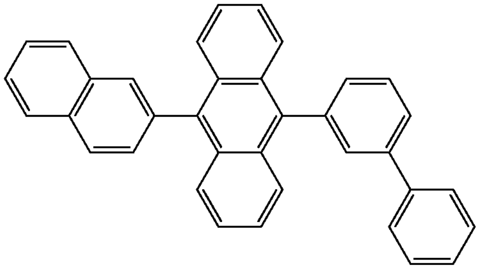
-continued
H13
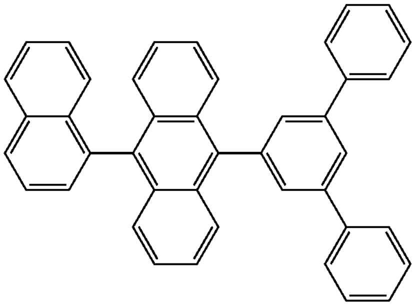
H14
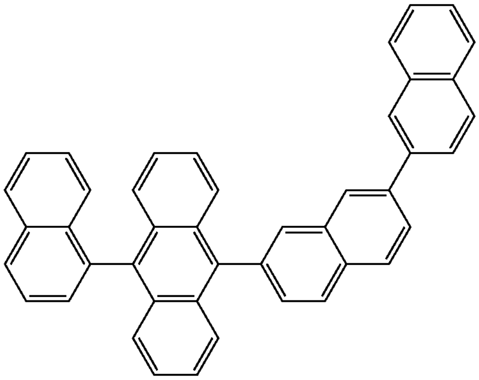
H15
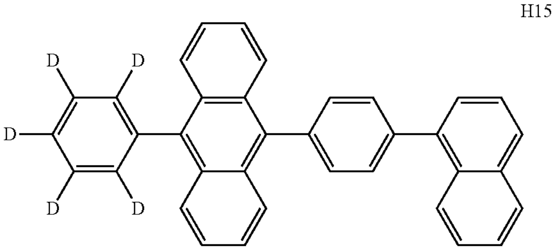
H16
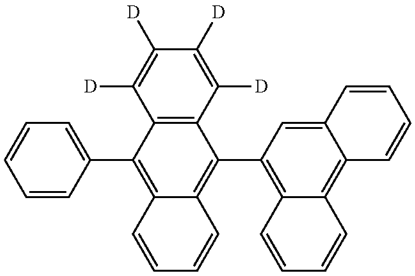
H17
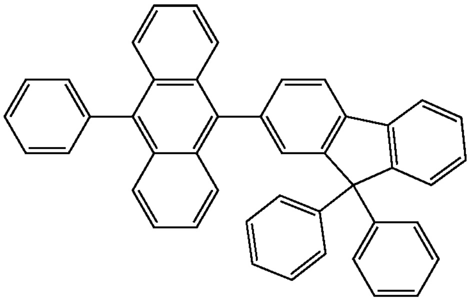

-continued
H18
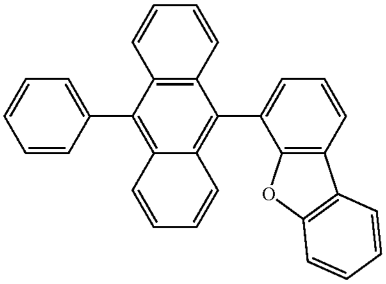
H19
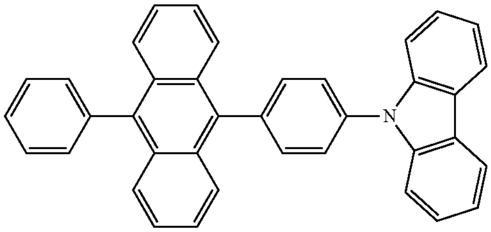
H20
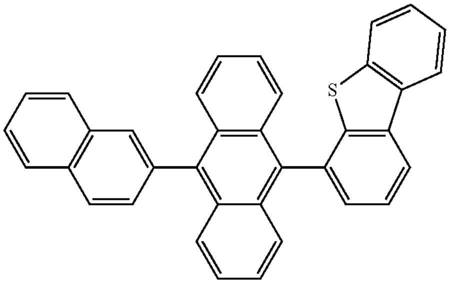
H21
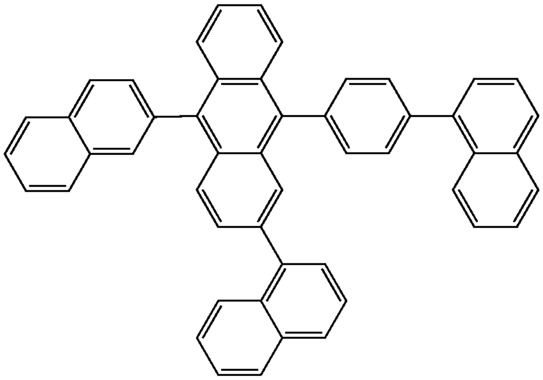
H22
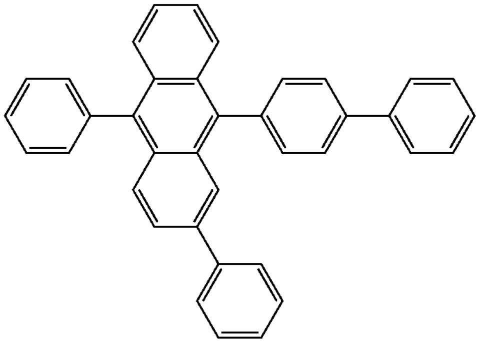
-continued
H23
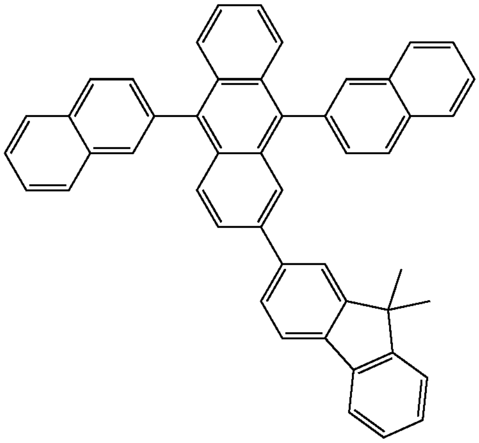
H24
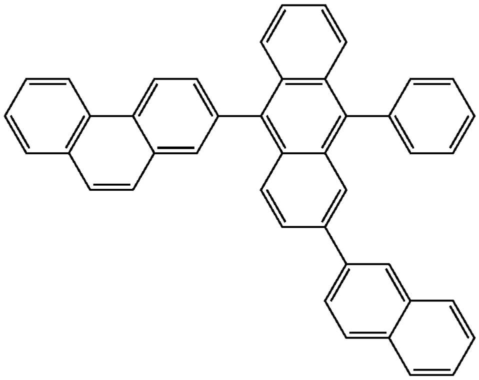
H25
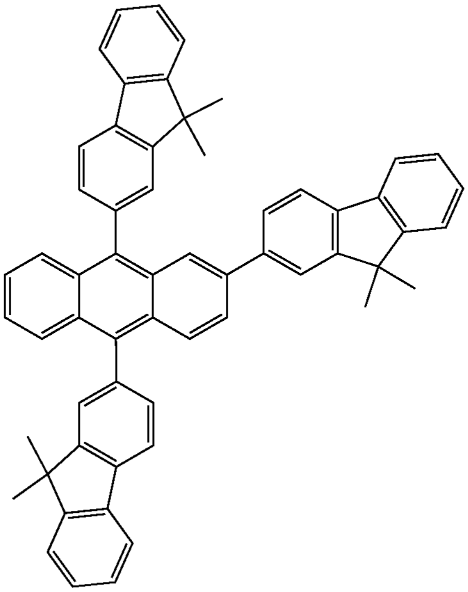

-continued
H26
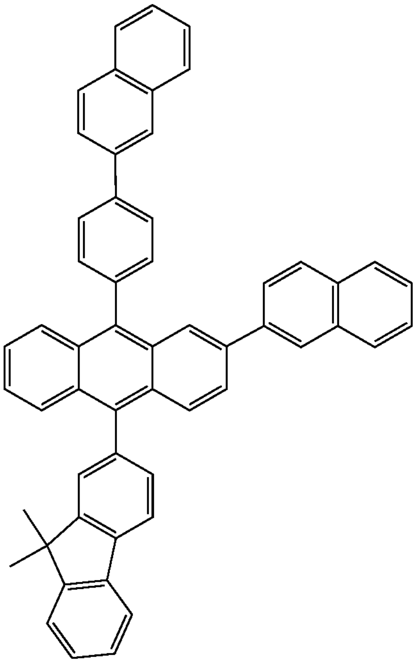
H27
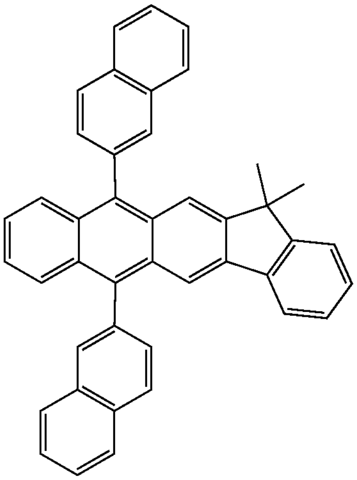
H28
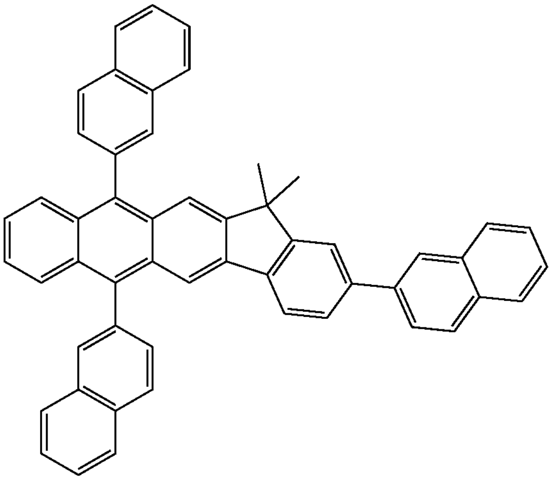
-continued
H29
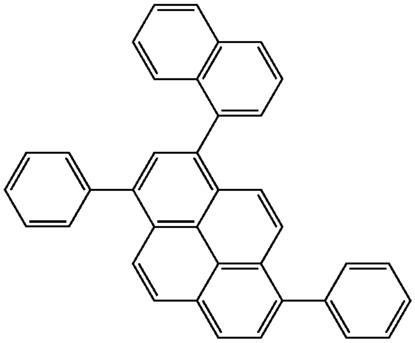
H30
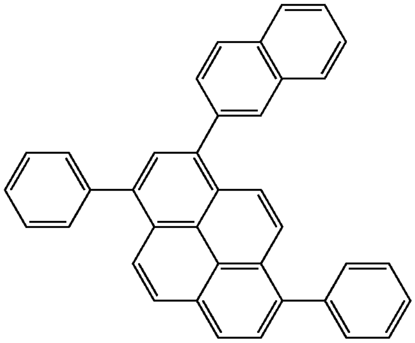
H31
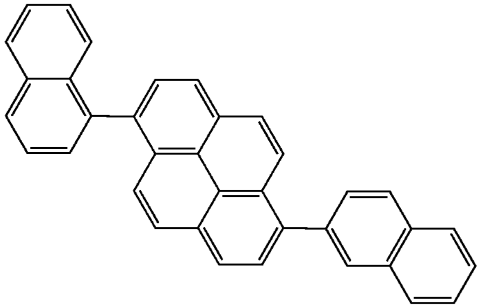
H32
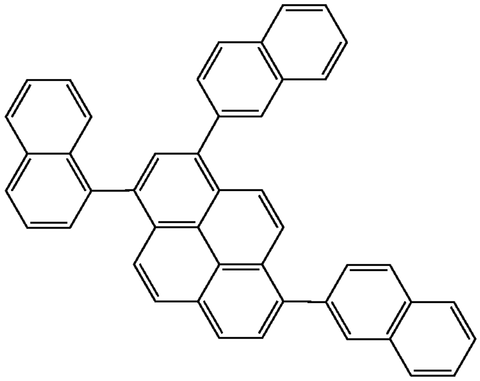
H33
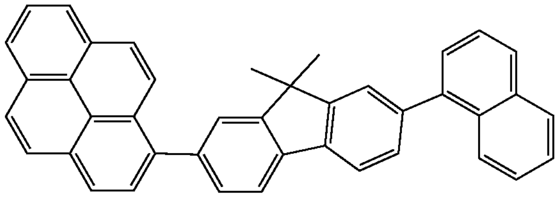

-continued
H34
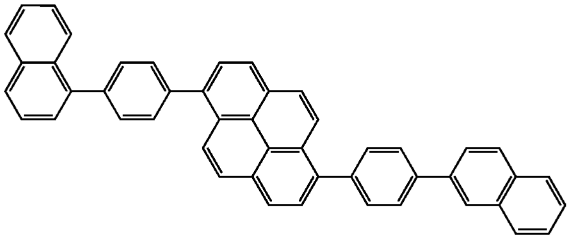
H35
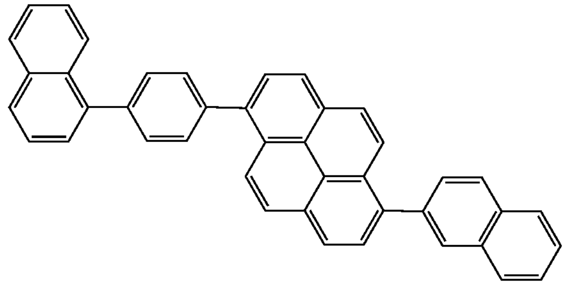
H36
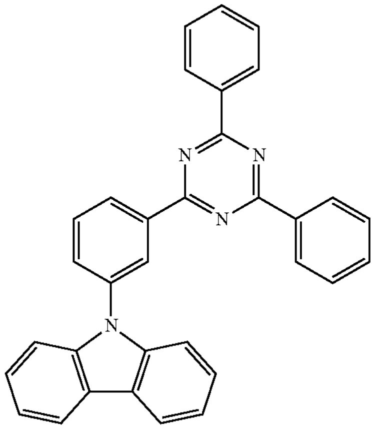
H37
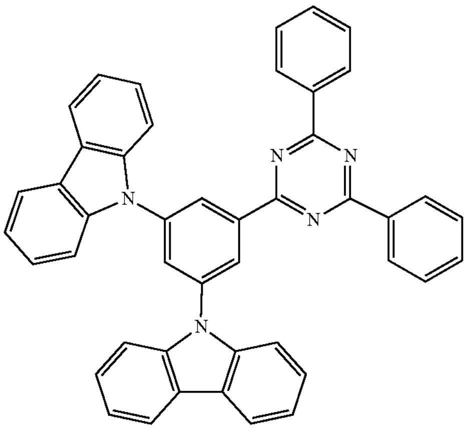
-continued
H38
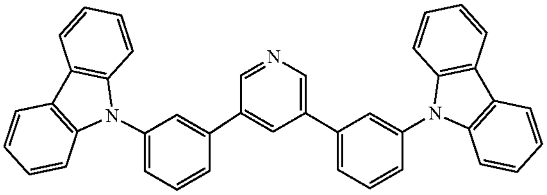
H39
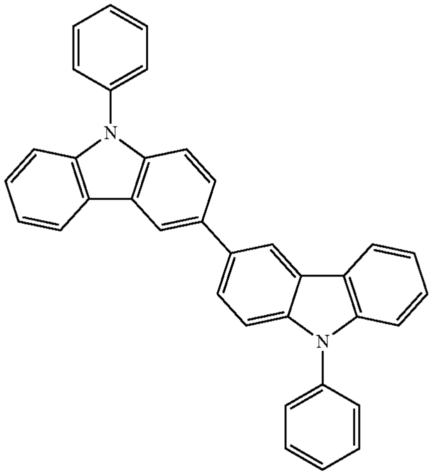
H40
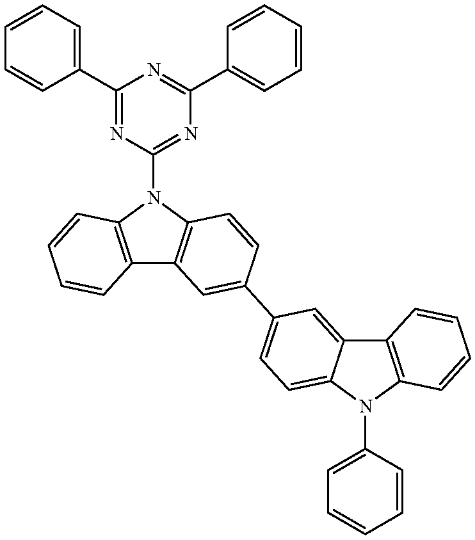

-continued
H41
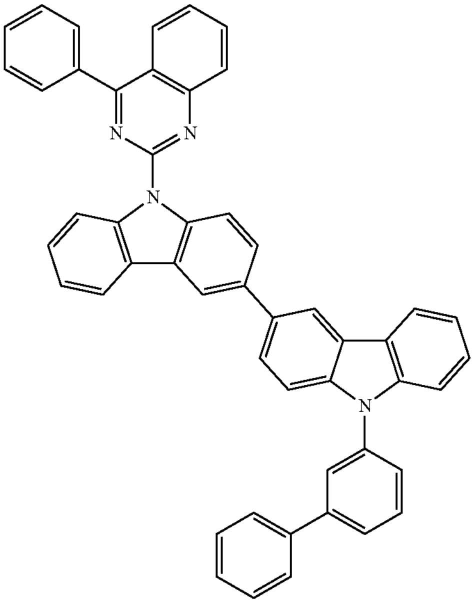
H42
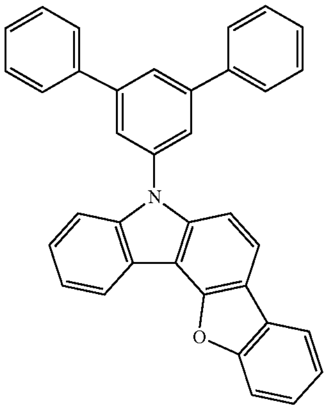
H43
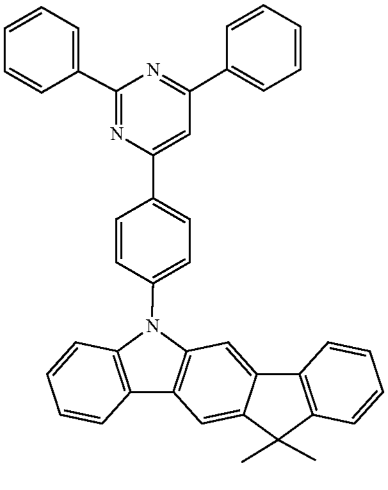
-continued
H44
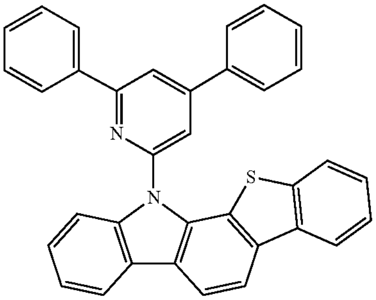
H45
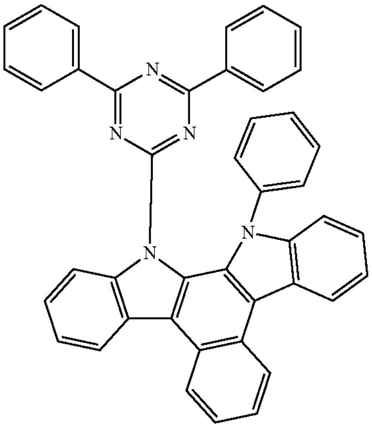
H46
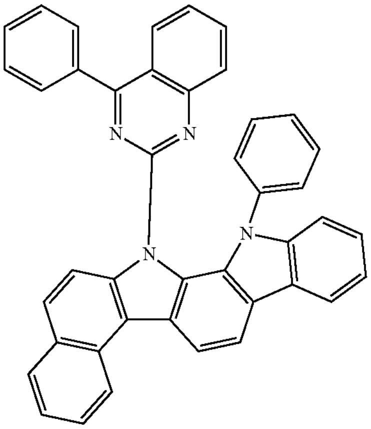
H47
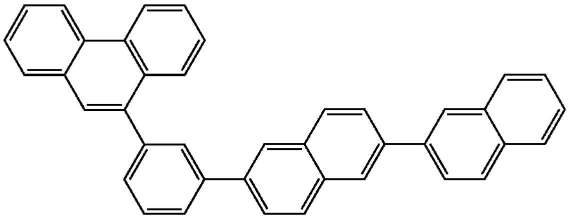
H48
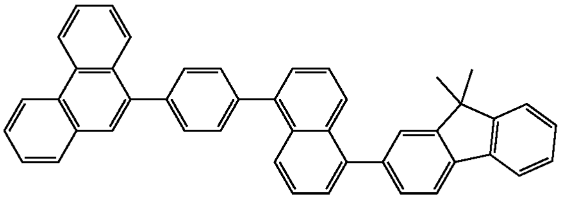

-continued
H49
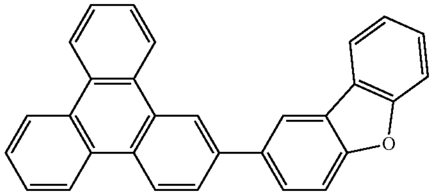
H50
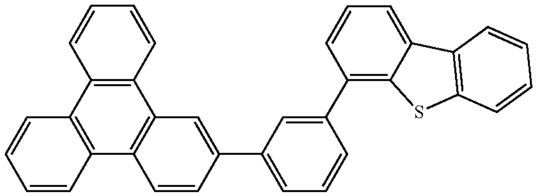
H51
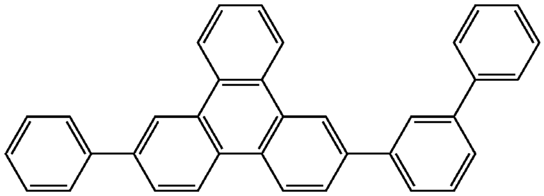
H52
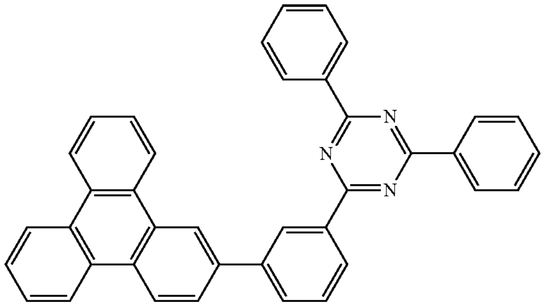
H53
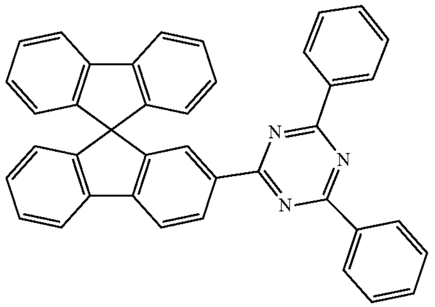
-continued
H54
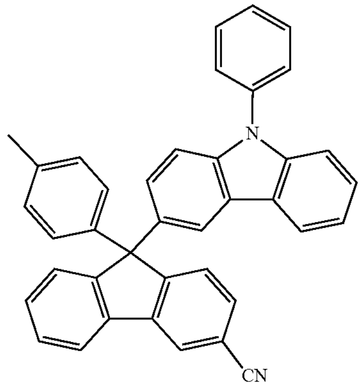
H55
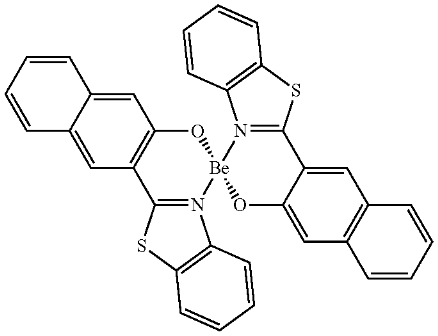
H56
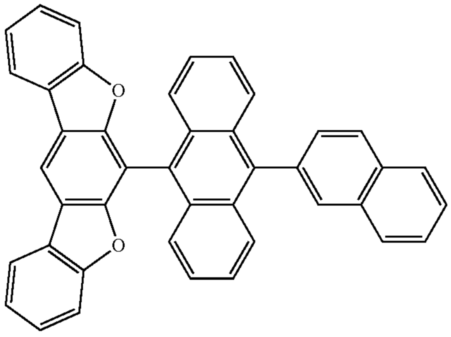
H57
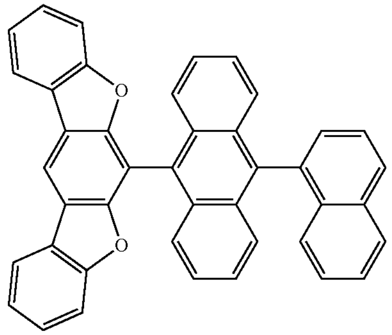

-continued
H58
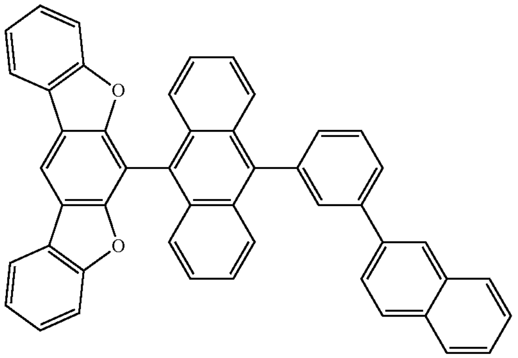
H59
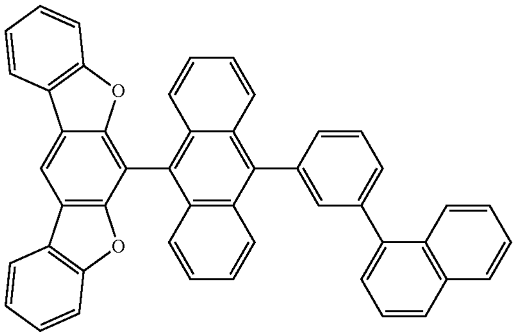
H60
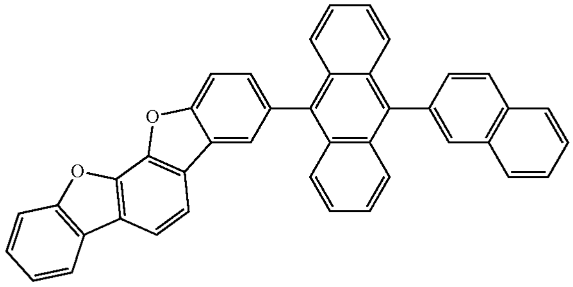
H61
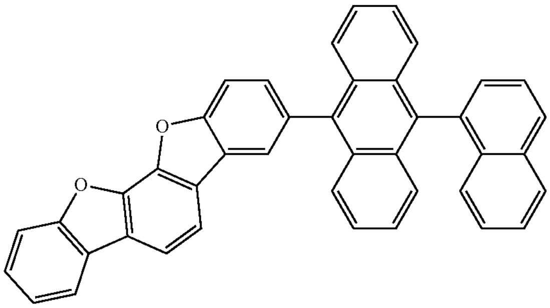
H62
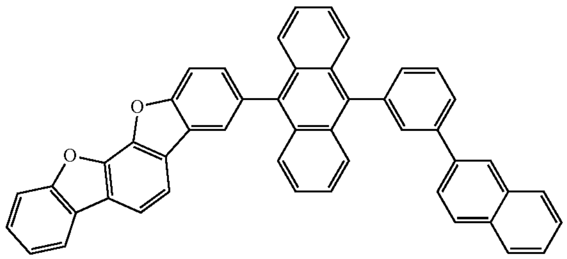
-continued
H63
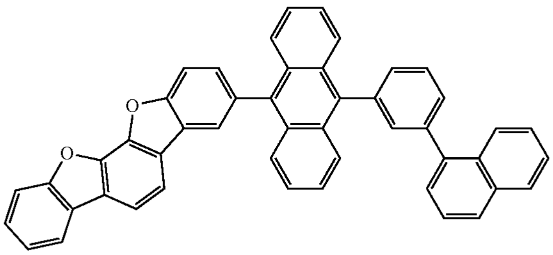
H64
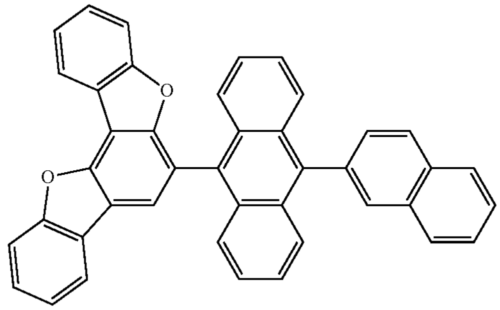
H65
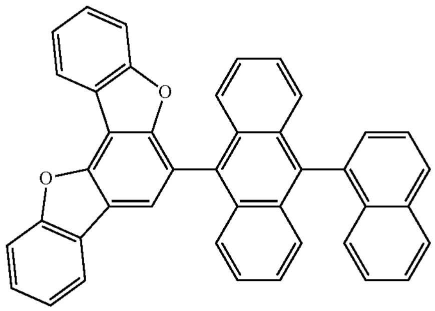
H66
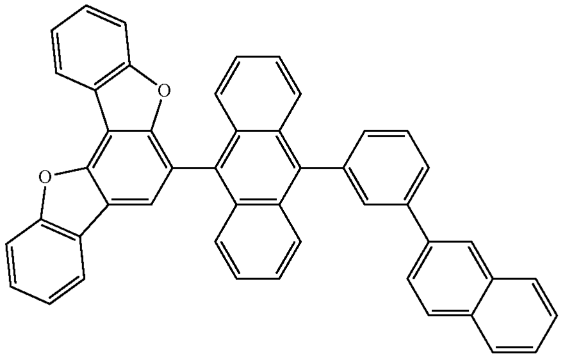
H67
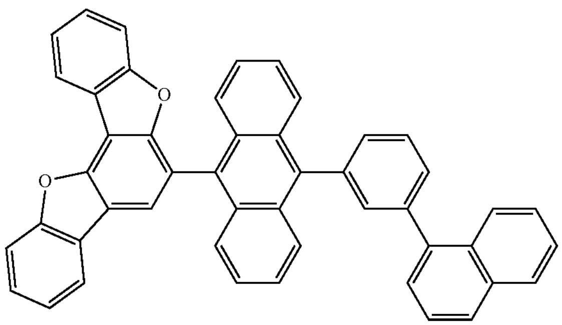

-continued
H68
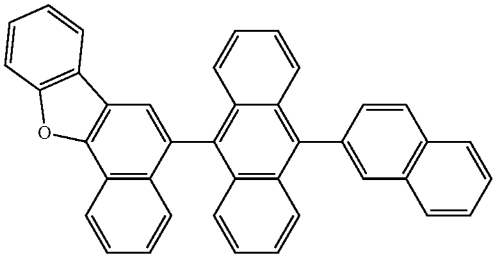
H69
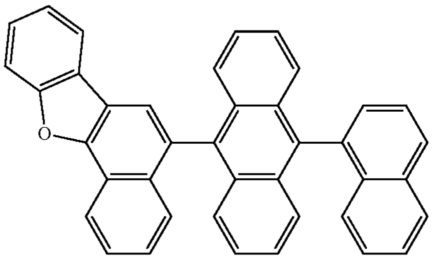
H70
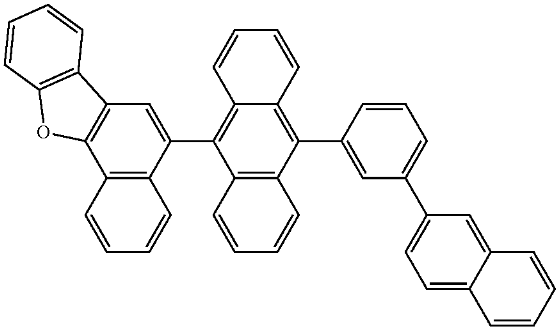
H71
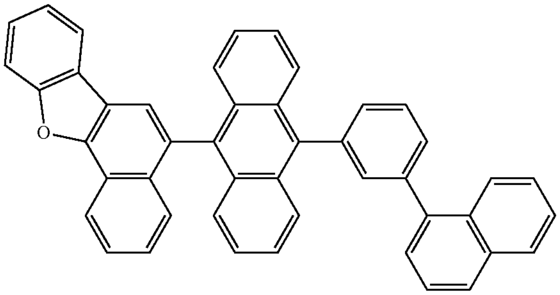
H72
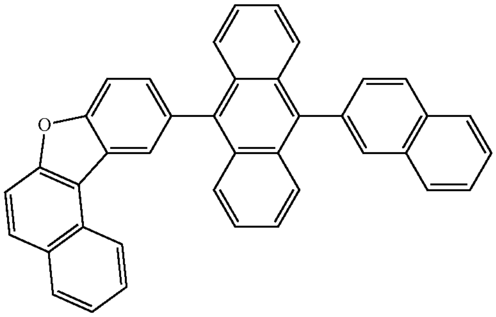
-continued
H73
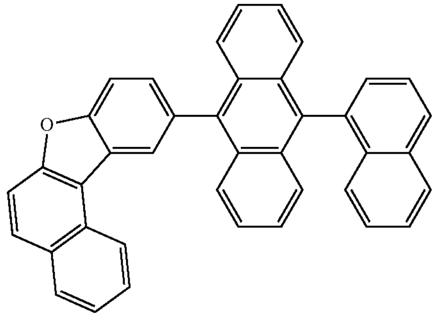
H74
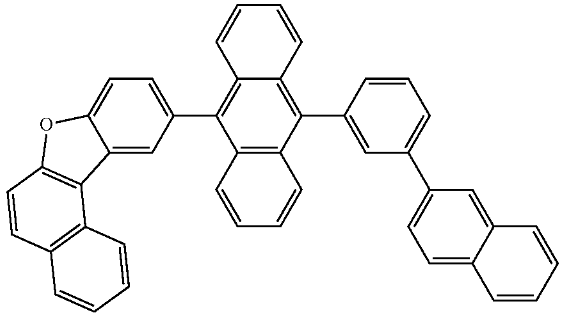
H75
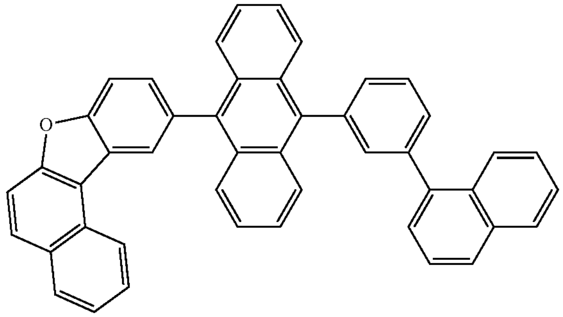
H76
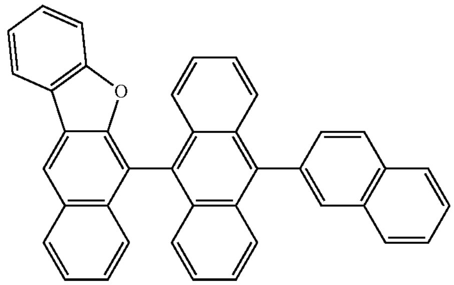
H77
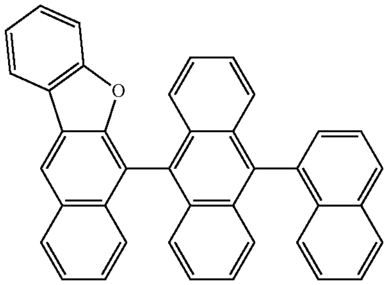

-continued
H78
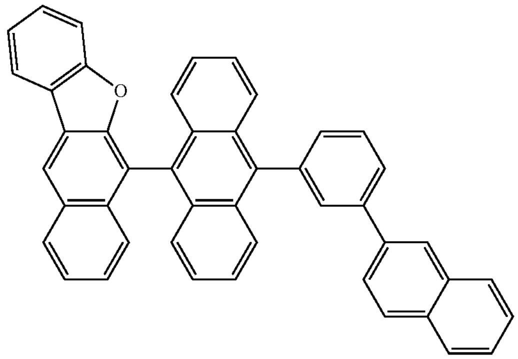
H79
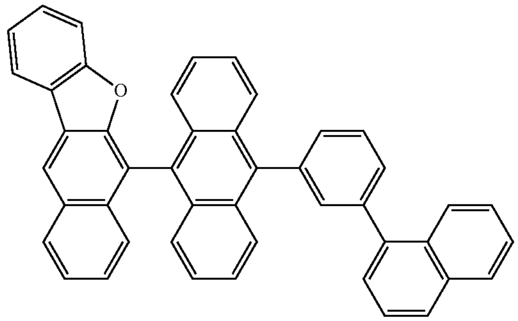
H80
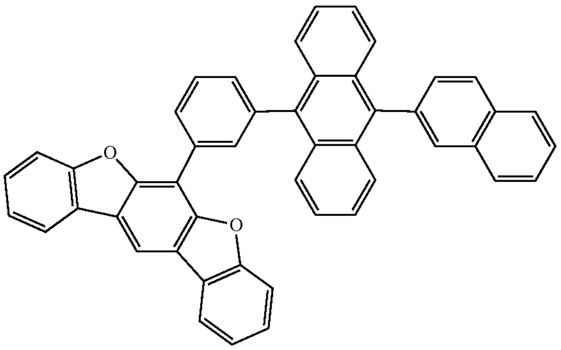
H81
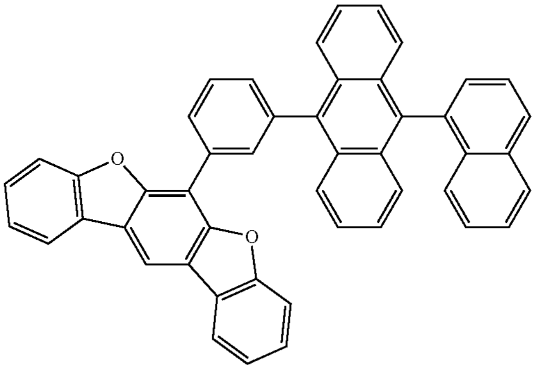
-continued
H82
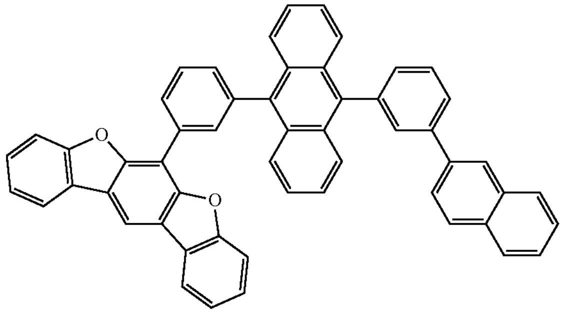
H83
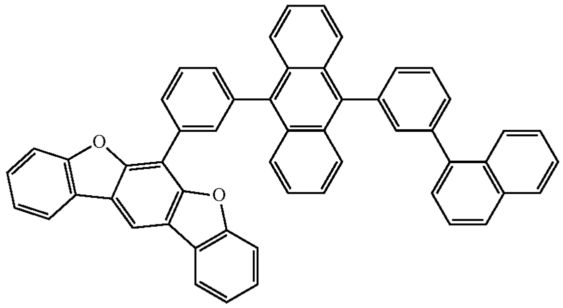
H84
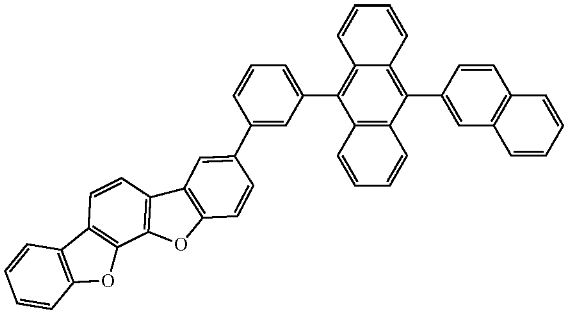
H85
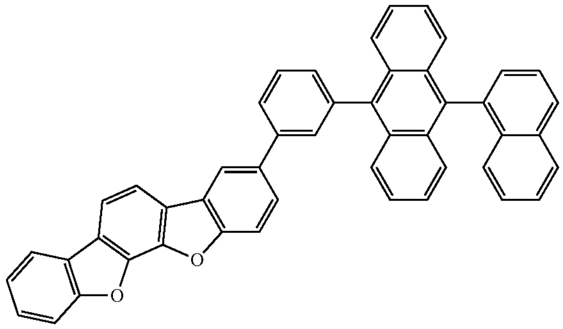

-continued
H86
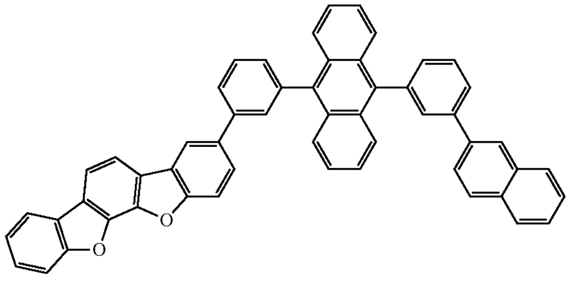
H87
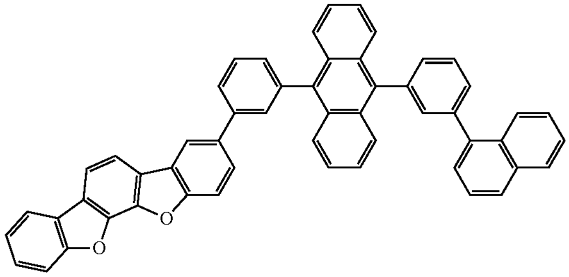
H88
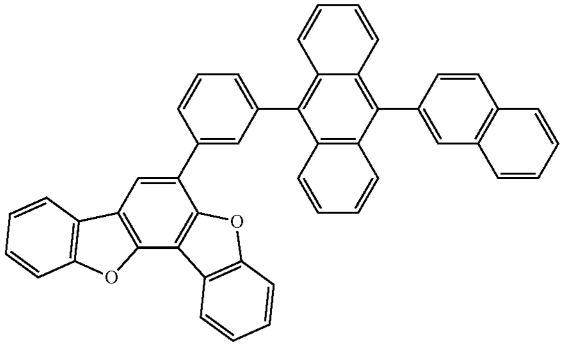
H89
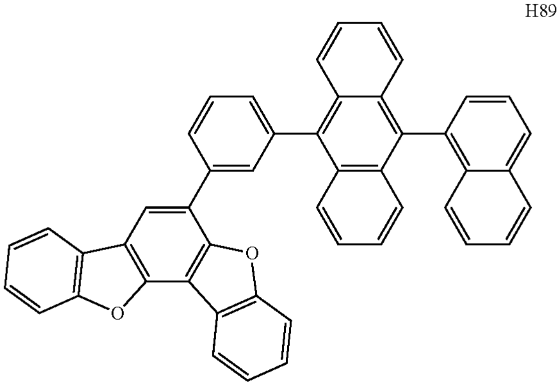
-continued
H90
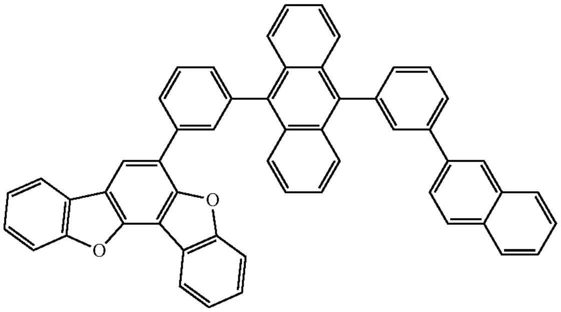
H91
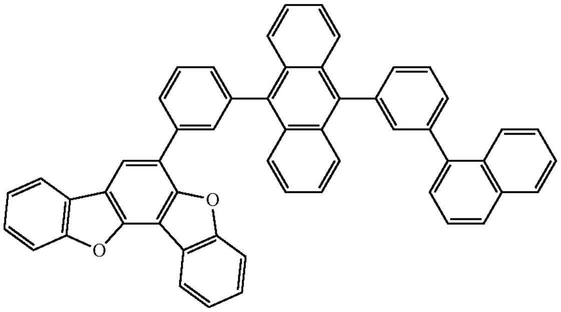
H92
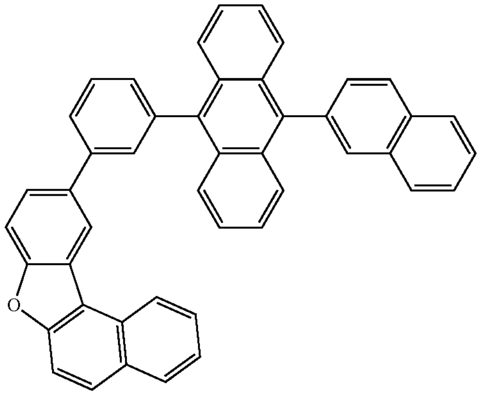
H93
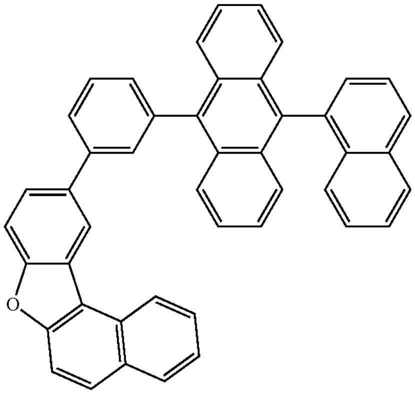

-continued
H94
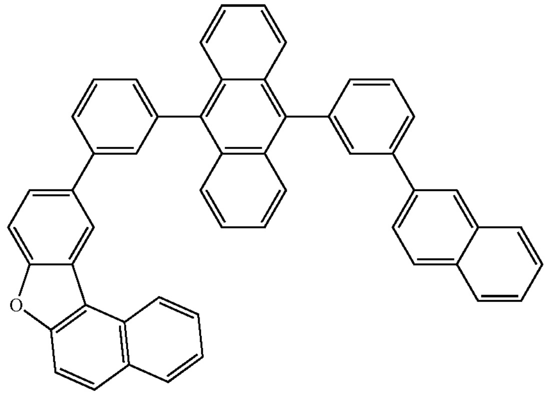
H95
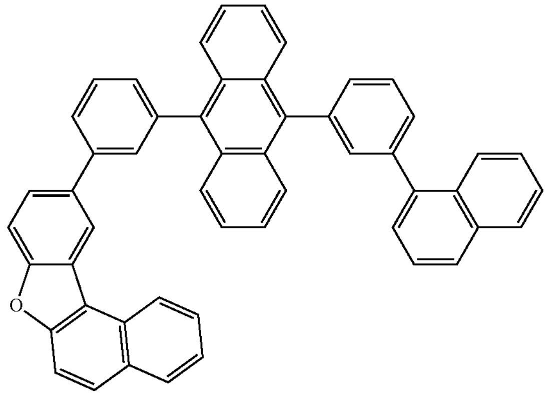
H96
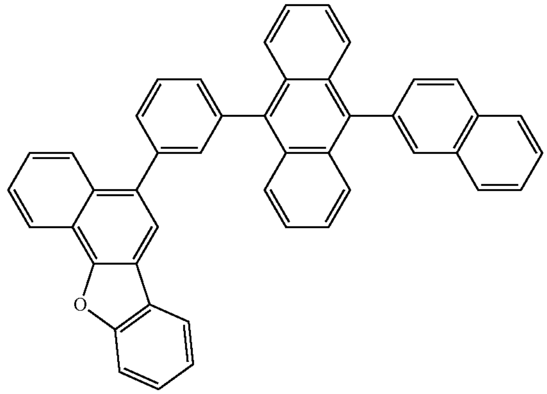
H97
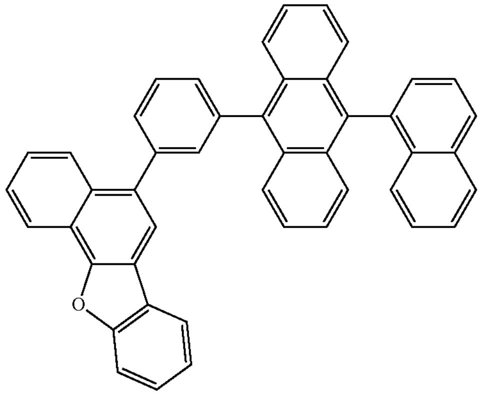
-continued
H98
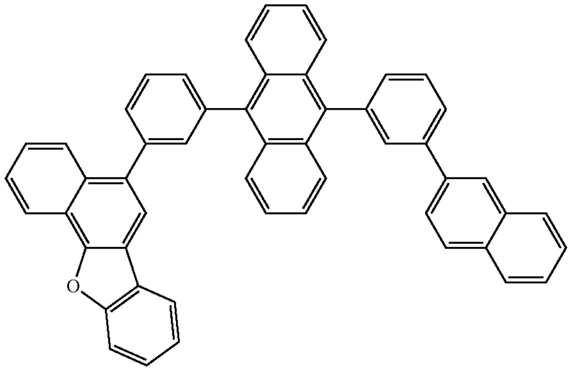
H99
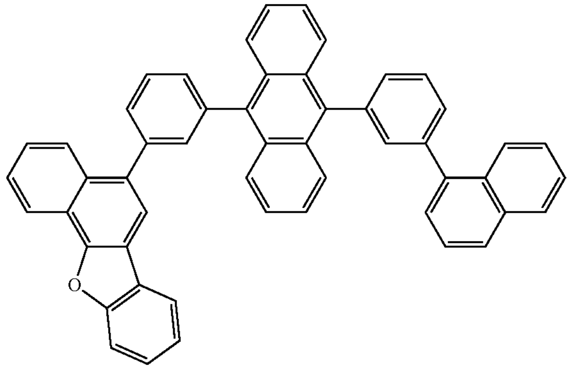
H100
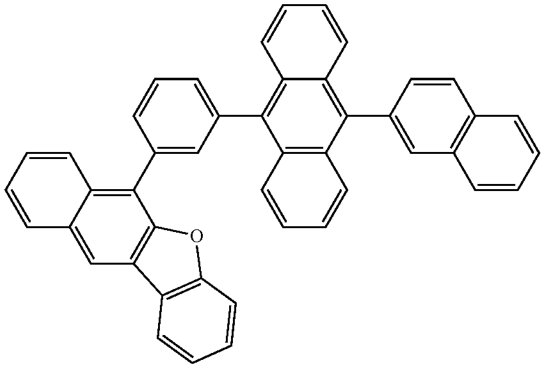
H101
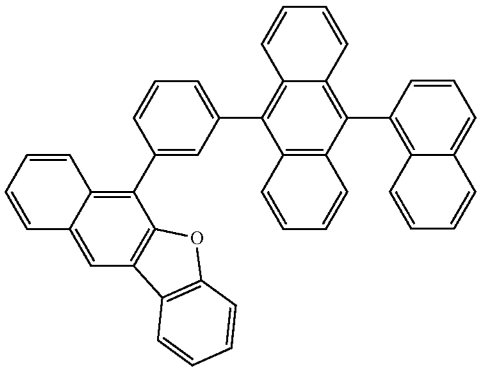

-continued
H102
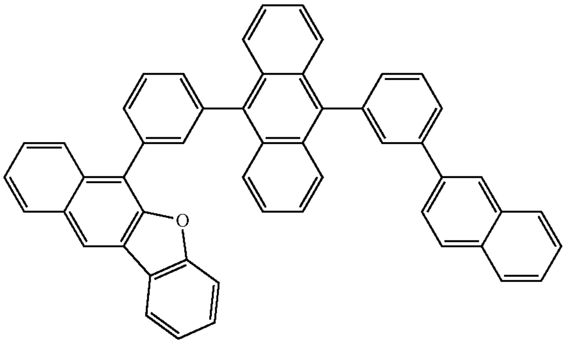
H103
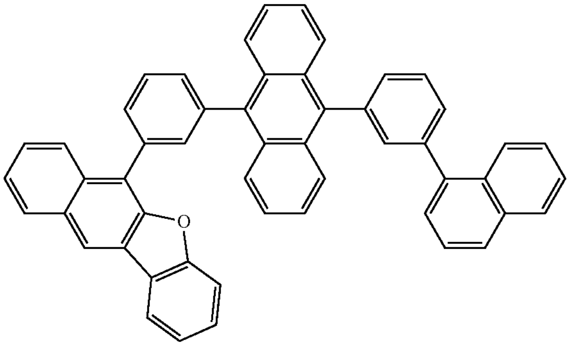
H104
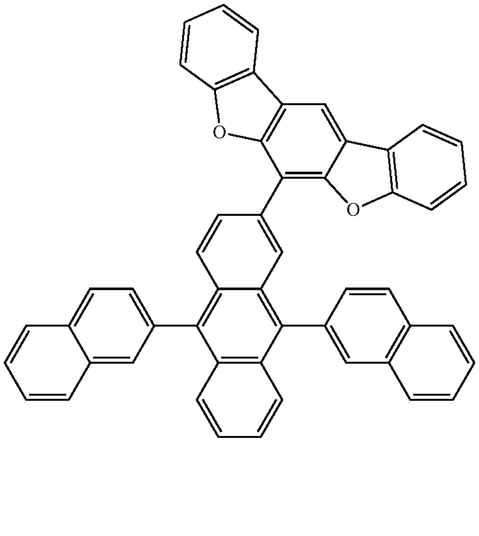
-continued
H105
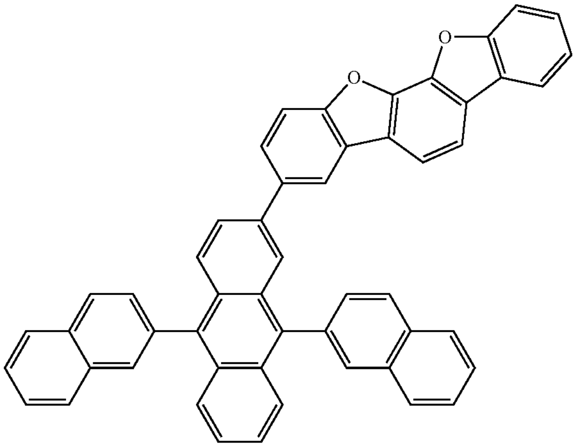
H106
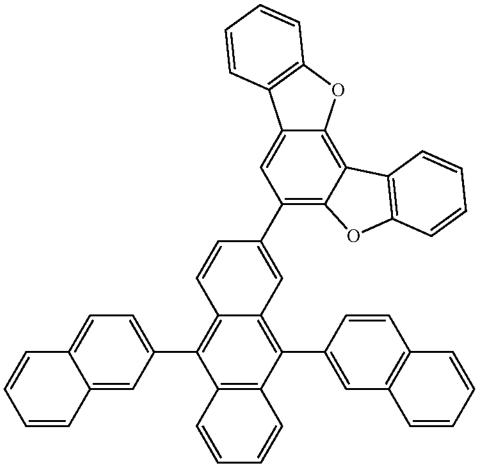
H107
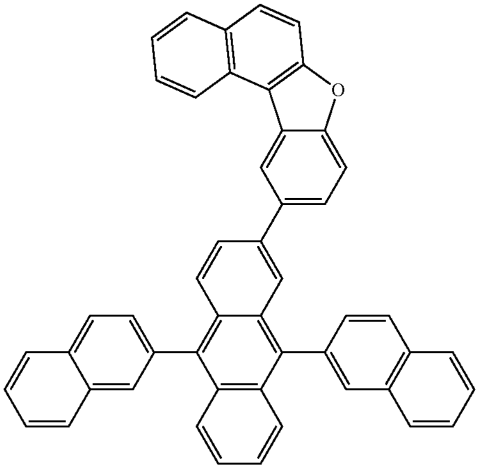

H108
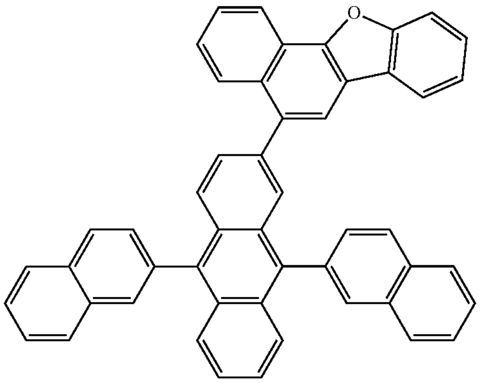
H109
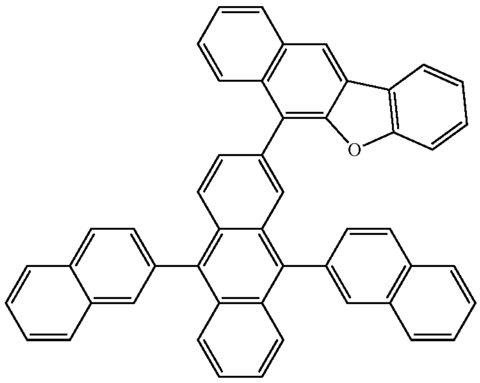
H110
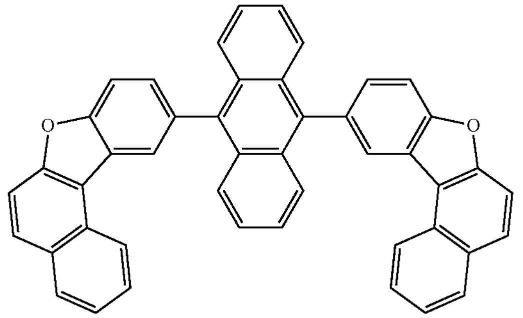
H111
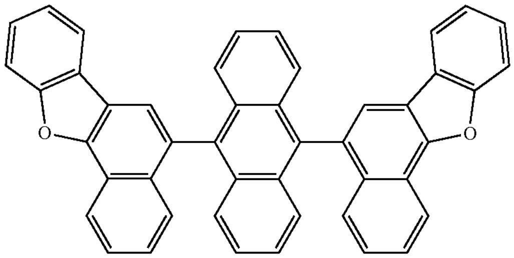
H112
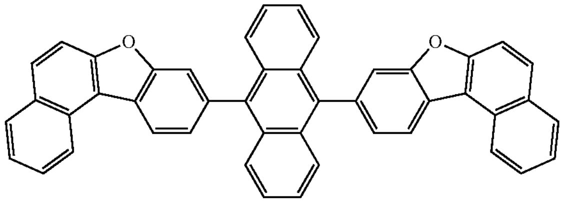
H113
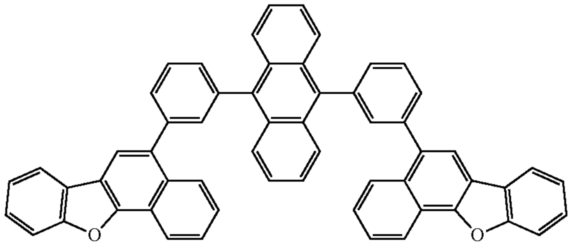
H114
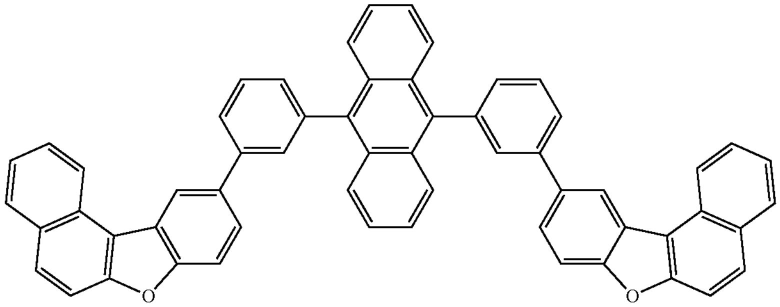

-continued
H115
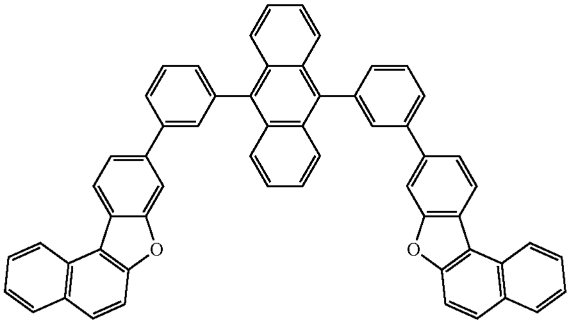
H116
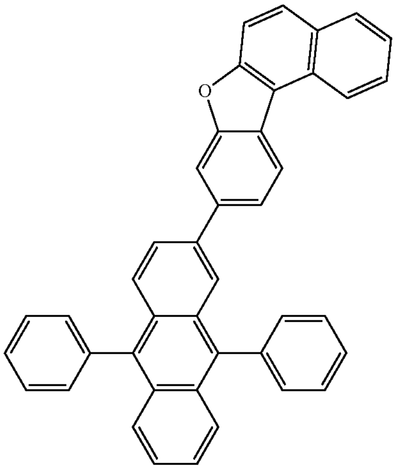
H117
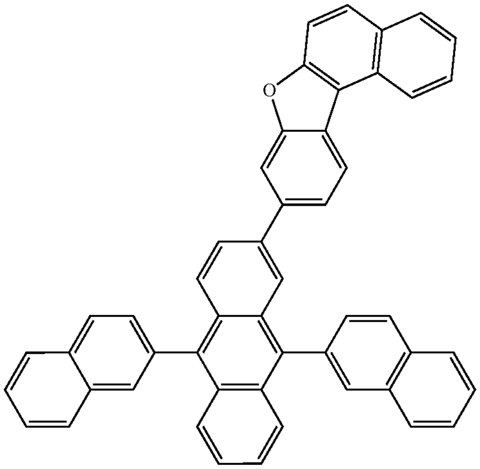
H118
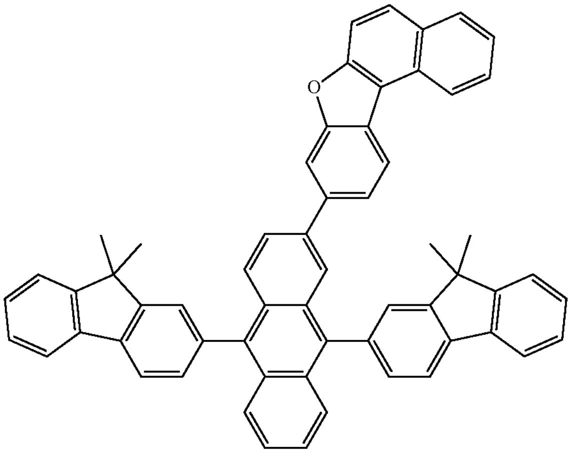
H119
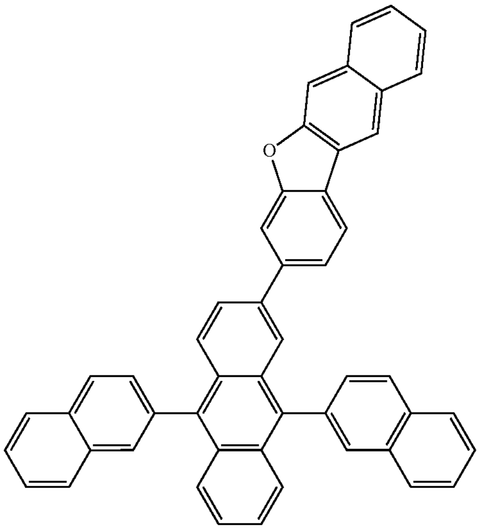
H120
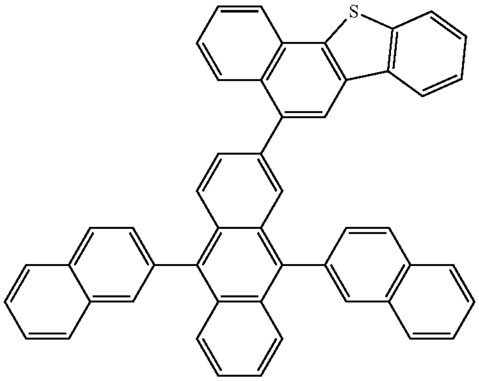

-continued

H121

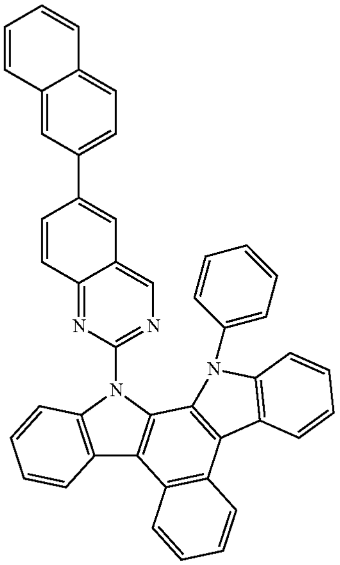

H122

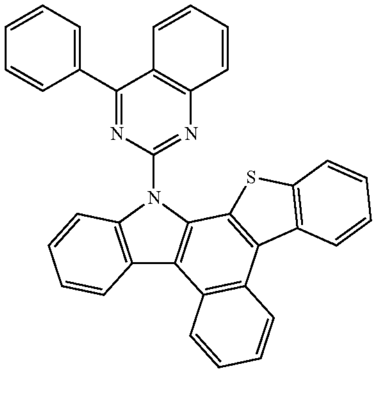

H123

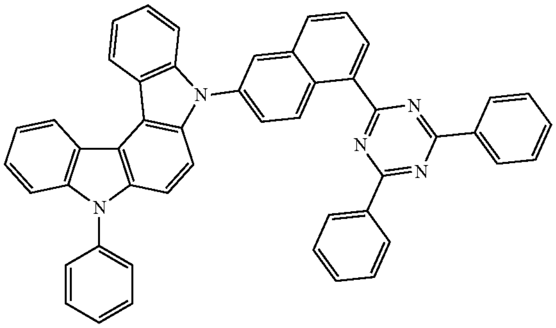

H124

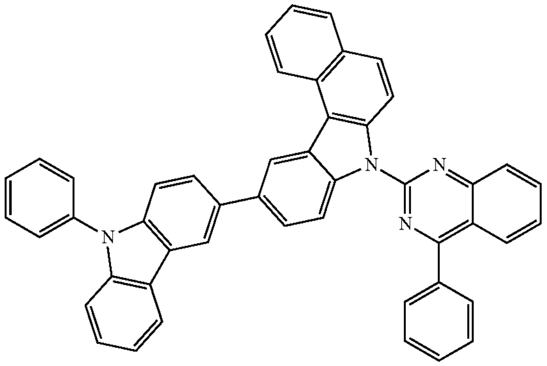

.

[Phosphorescent Dopant]

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In embodiments, the phosphorescent dopant may include an organometallic compound represented by Formula 401:

[Formula 401]

$$M(L_{401})_{xc1}(L_{402})_{xc2}$$

[Formula 402]

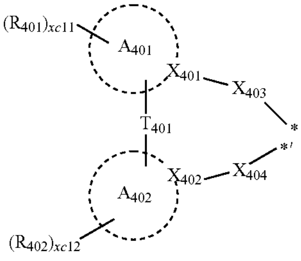

.

In Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is 2 or more, two or more of $L_{401}$ groups may be identical to or different from each other, $L_{402}$ may be an organic ligand, and xc2 may be 0, 1, 2, 3, or 4, wherein, when xc2 is 2 or more, two or more of $L_{402}$ groups may be identical to or different from each other, $X_{401}$ and $X_{402}$ may each independently be nitrogen (N) or carbon (C), ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S*', *—C(=O)—*', *—N($Q_{411}$)-*',*—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be the same as described in connection with $Q_1$, xc11 and xc12 may each independently be an integer from 0 to 10, and and *' in Formula 402 each indicate a binding site to M in Formula 401.

For example, in Formula 402, $X_{401}$ may be nitrogen and $X_{402}$ may be carbon, or each of $X_{401}$ and $X_{402}$ may be nitrogen.

In an embodiment, when xc1 in Formula 401 is 2 or more, two ring $A_{401}$(s) among two or more of $L_{401}$ may optionally be linked to each other via $T_{402}$, which is a linking group, and two ring $A_{402}$(s) among two or more of $L_{401}$ may optionally be linked to each other via $T_{403}$, which is a linking group (see Compounds PD1 to PD4 and PD7). $T_{402}$ and $T_{403}$ may each independently be the same as described in connection with $T_{401}$.

In Formula 401, $L_{402}$ may be an organic ligand. For example, $L_{402}$ may include a halogen group, a diketone group (for example, an acetylacetonate group), a carboxylic acid group (for example, a picolinate group), —C(=O), an isonitrile group, a —CN group, a phosphorus group (for example, a phosphine group, a phosphite group, and the like), or any combination thereof.

The phosphorescent dopant may include, for example, one of Compounds PD1 to PD39, or any combination thereof:

PD1

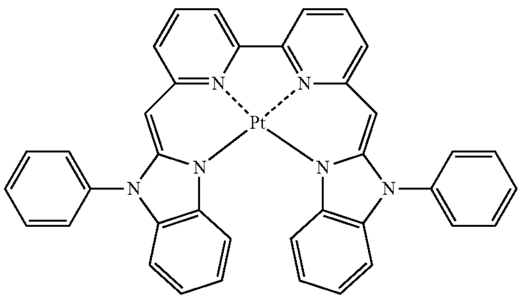

PD2

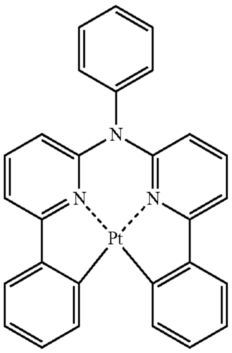

-continued

PD3

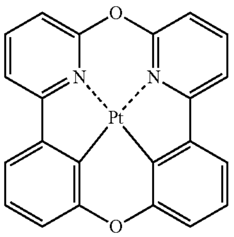

PD4

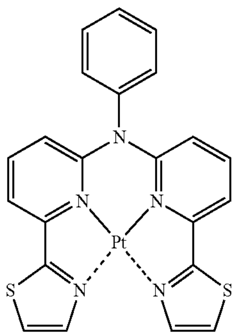

PD5

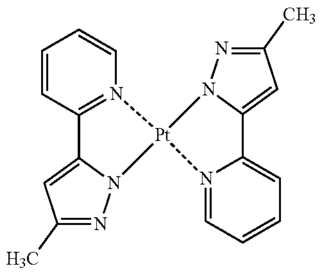

PD6

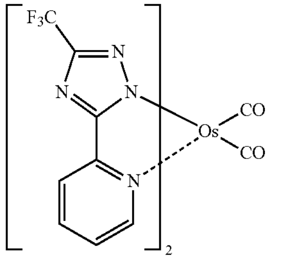

PD7

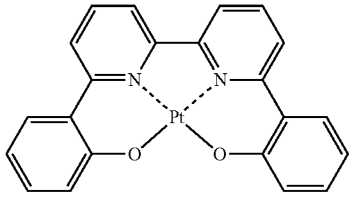

PD8

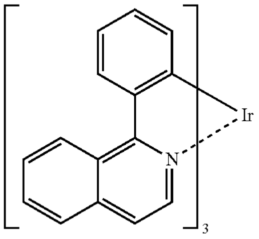

-continued
PD9
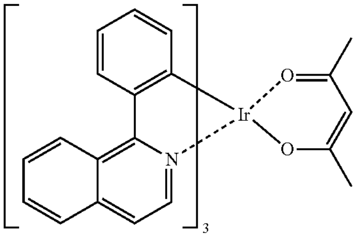
PD10
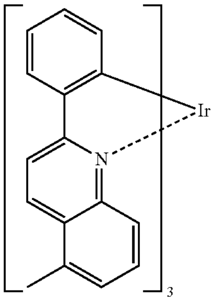
PD11
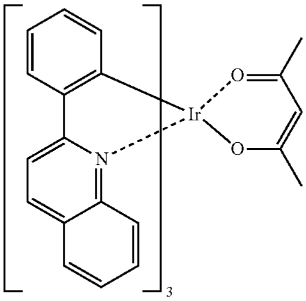
PD12
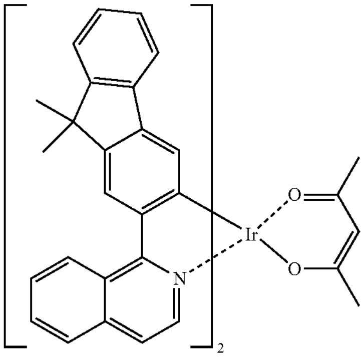
PD13
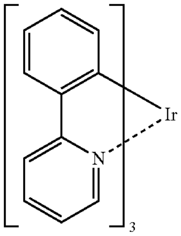
-continued
PD14
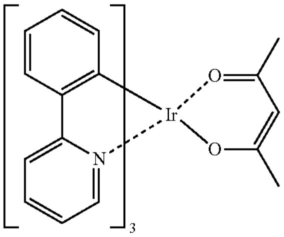
PD15
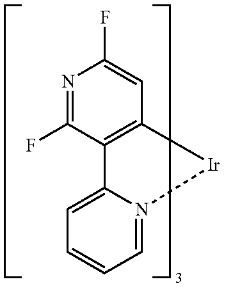
PD16
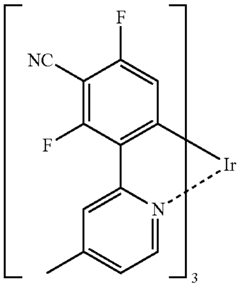
PD17
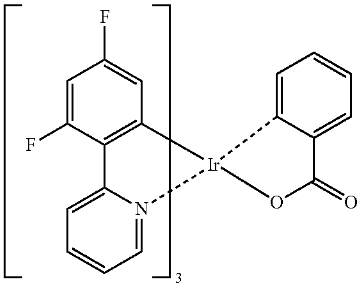
PD18
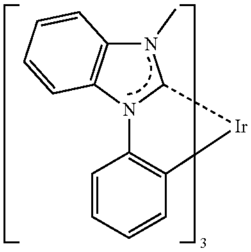

-continued
PD19
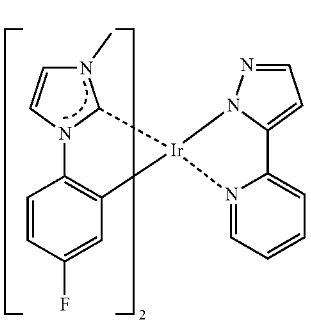
PD20
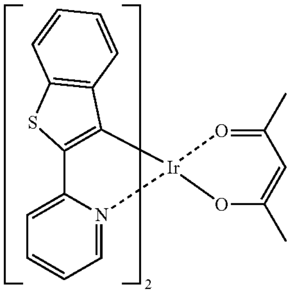
PD21
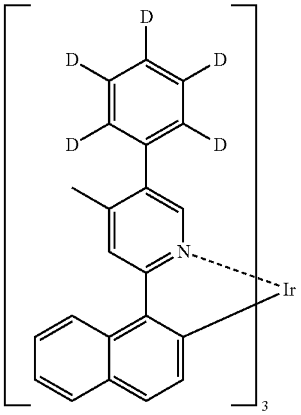
PD22
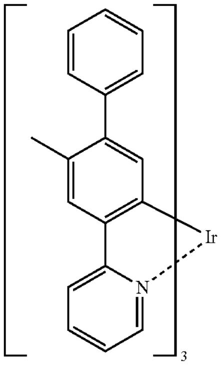
-continued
PD23
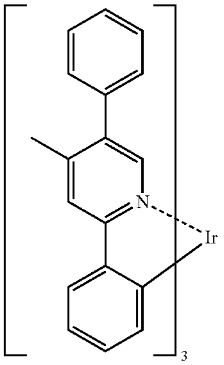
PD24
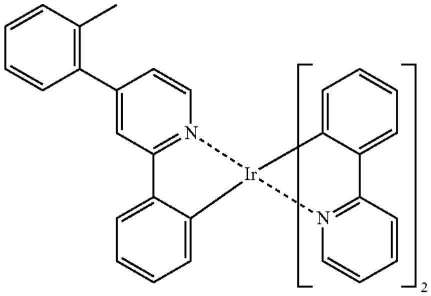
PD25
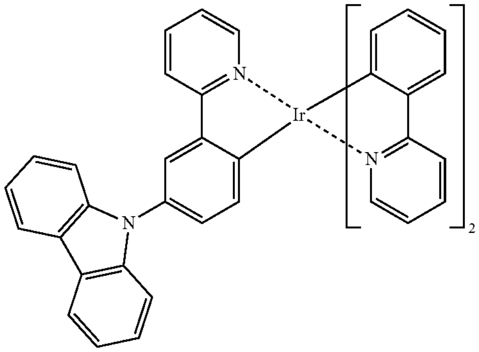
PD26
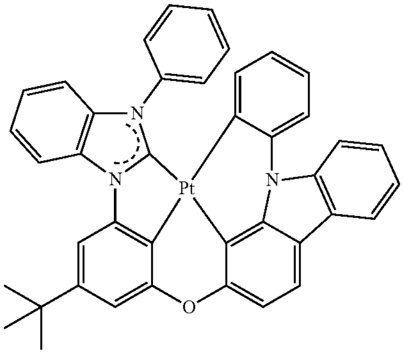

-continued
PD27
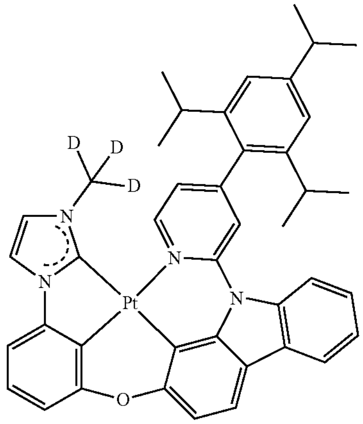
PD28
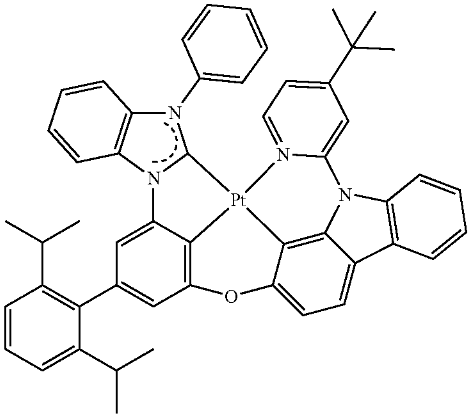
PD29
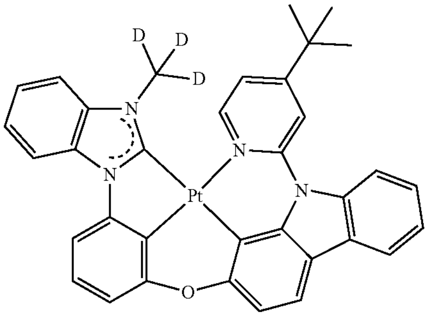
PD30
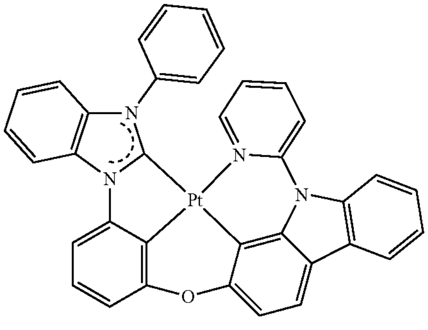
-continued
PD31
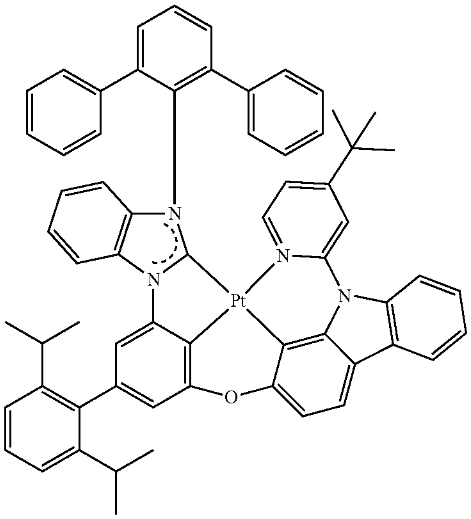
PD32
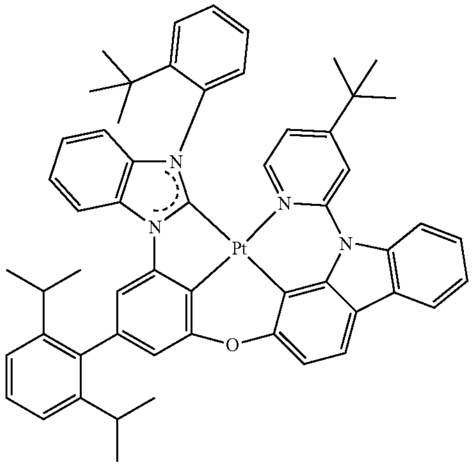
PD33
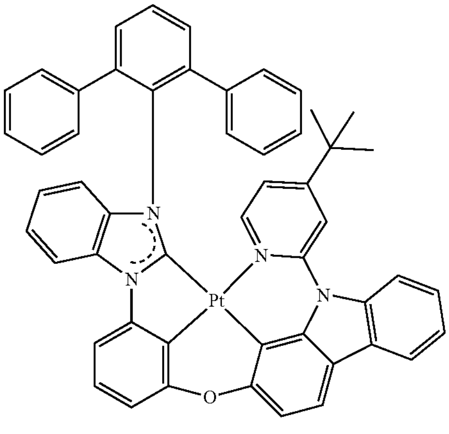

-continued
PD34
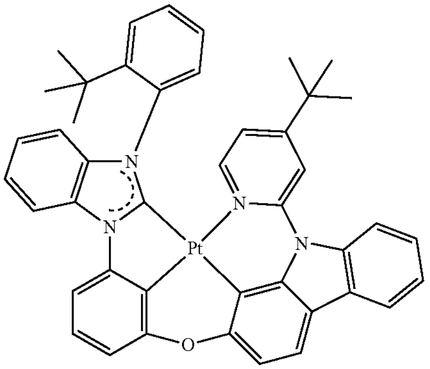
PD35
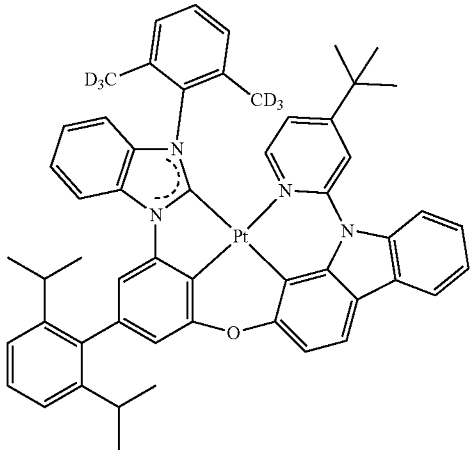
PD36
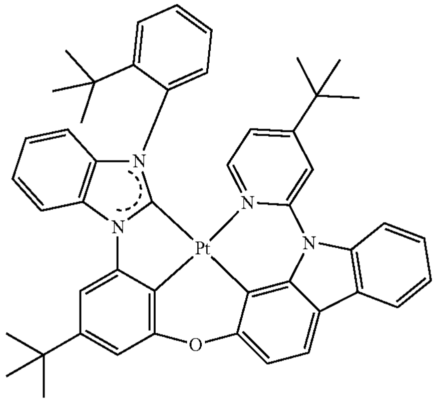
-continued
PD37
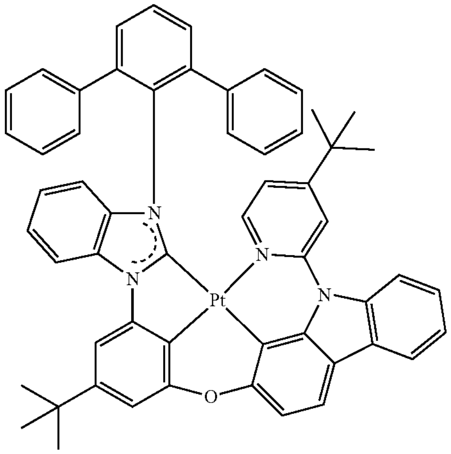
PD38
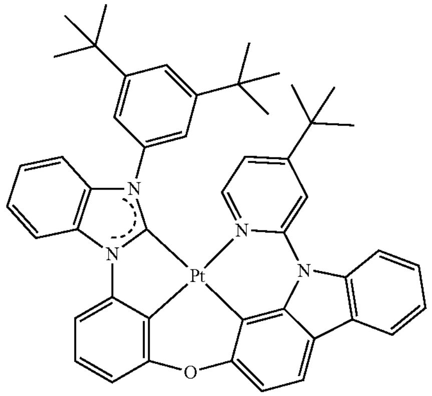
PD39
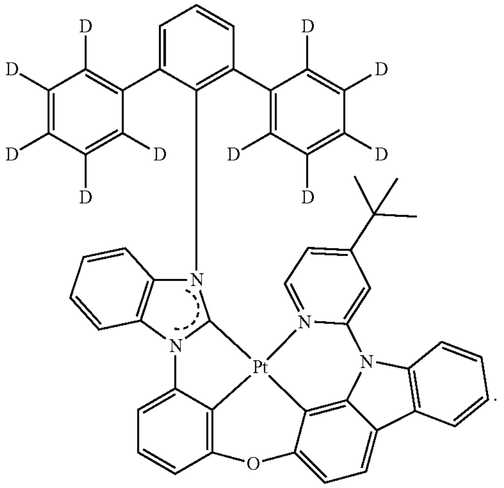
[Fluorescent Dopant]
The fluorescent dopant may include an amine group-containing compound, a styryl group-containing compound, or any combination thereof.

In an embodiment, the fluorescent dopant may include a compound represented by Formula 501:

Formula 501

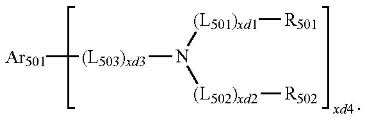

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

For example, $Ar_{501}$ in Formula 501 may include a condensed cyclic group (for example, an anthracene group, a chrysene group, a pyrene group, and the like) in which three or more monocyclic groups are condensed together.

For example, xd4 in Formula 501 may be 2.

In embodiments, the fluorescent dopant may include one of Compounds FD1 to FD36, DPVBi, DPAVBi, or any combination thereof:

FD1

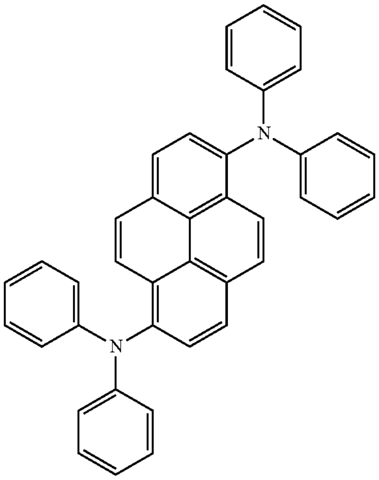

FD2

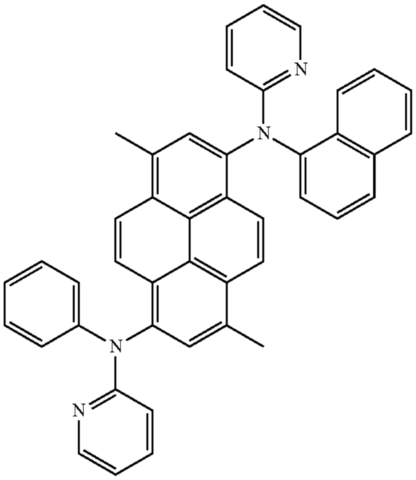

FD3

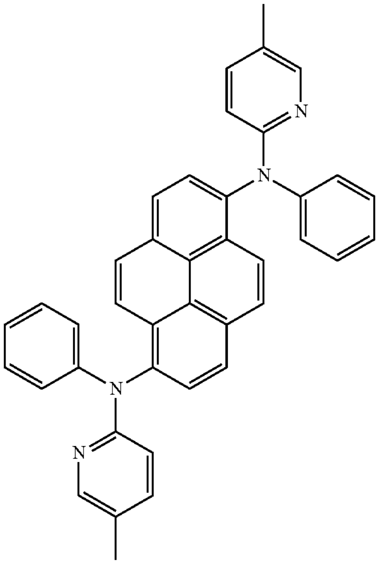

FD4

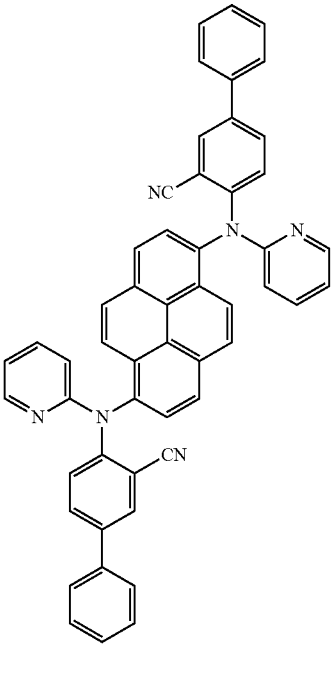

-continued
FD5
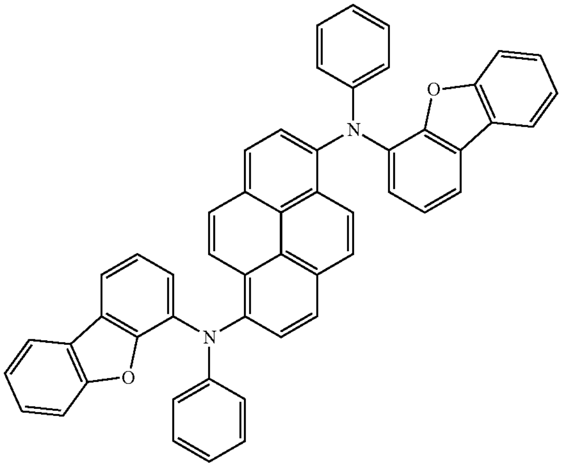
FD6
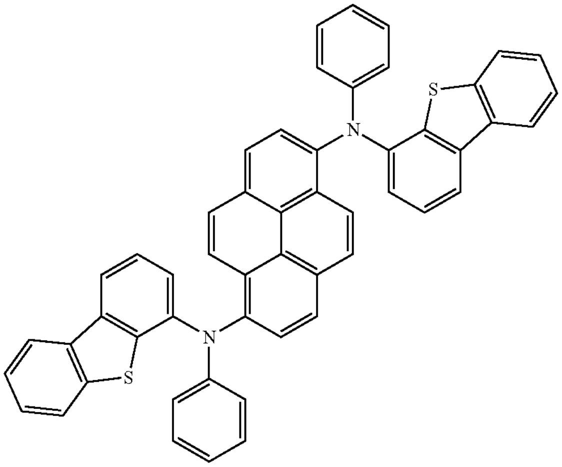
FD7
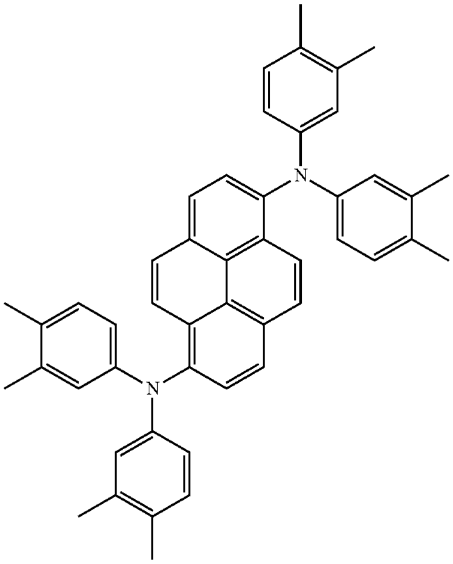
FD8
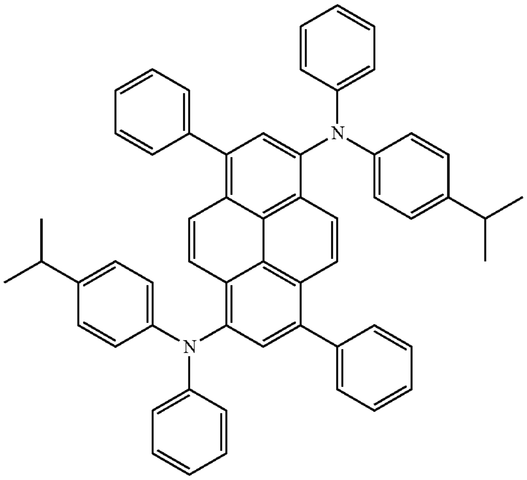
FD9
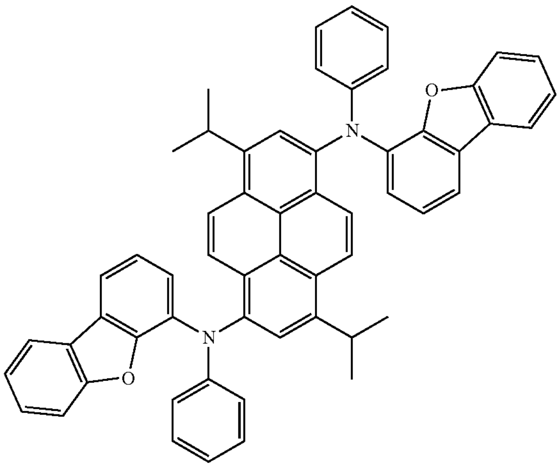
FD10
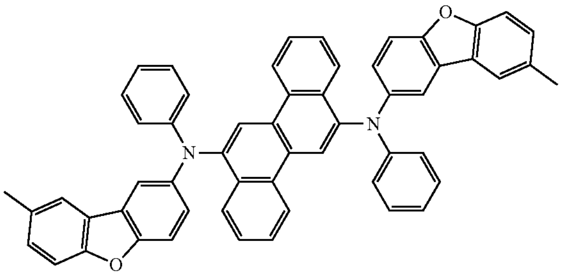

-continued
FD11
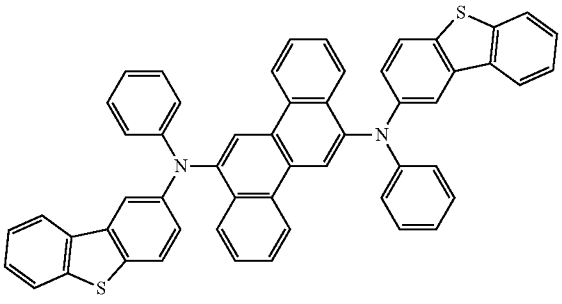
FD12
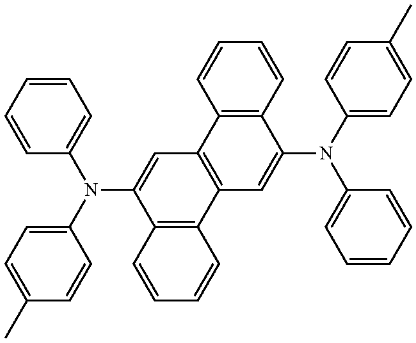
FD13
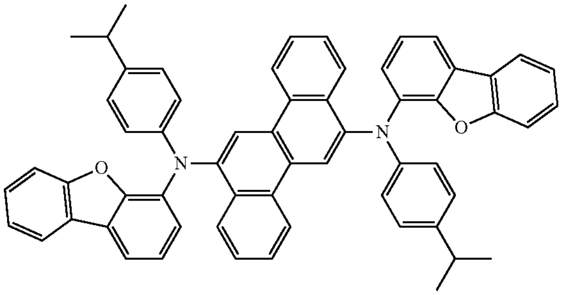
FD14
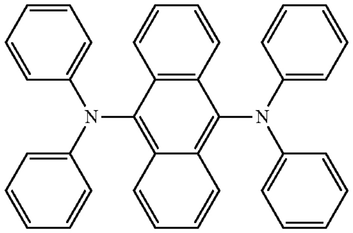
FD15
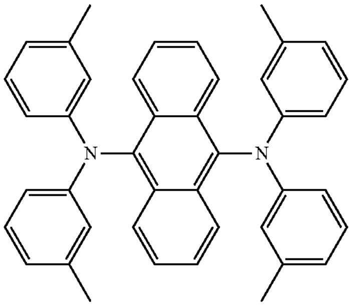
FD16
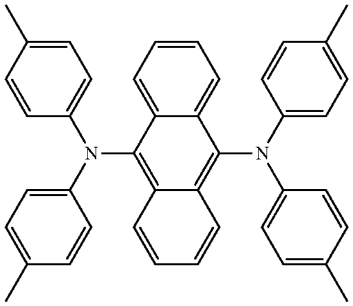
FD17
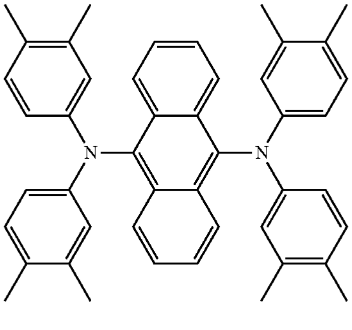
FD18
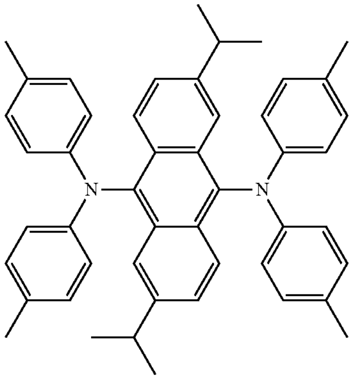

-continued
FD19
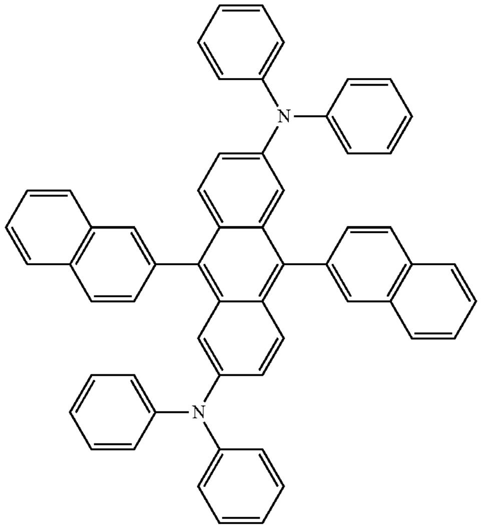
FD20
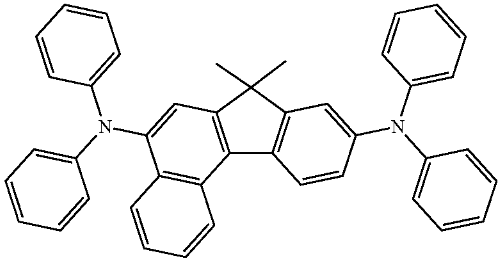
FD21
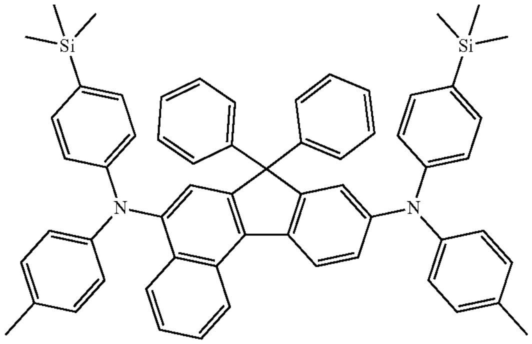
FD22
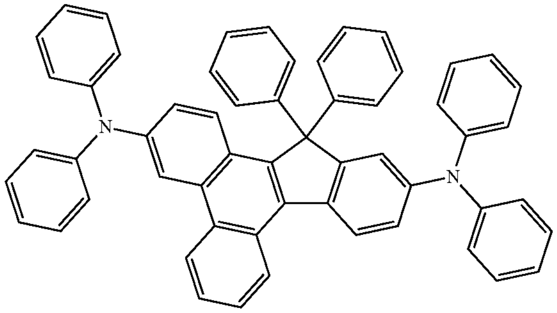
FD23
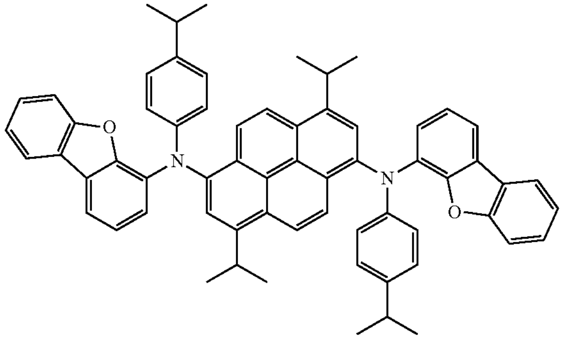
FD24
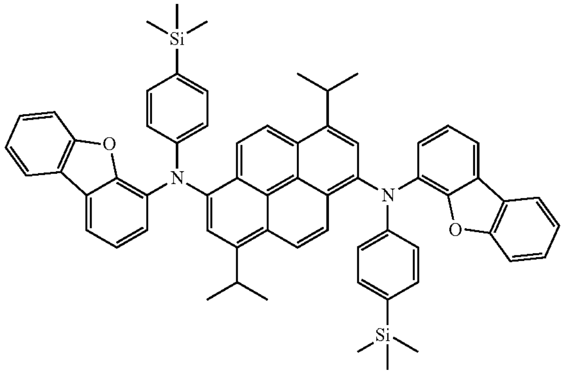

-continued
FD25
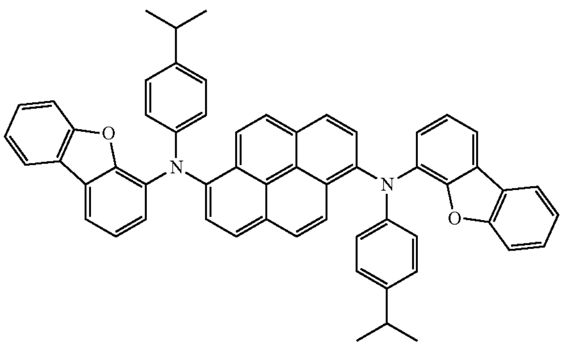
FD26
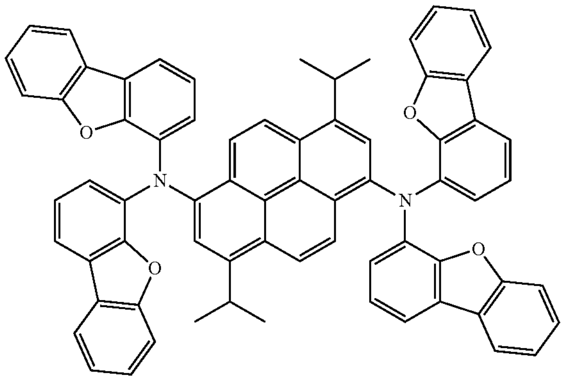
FD27
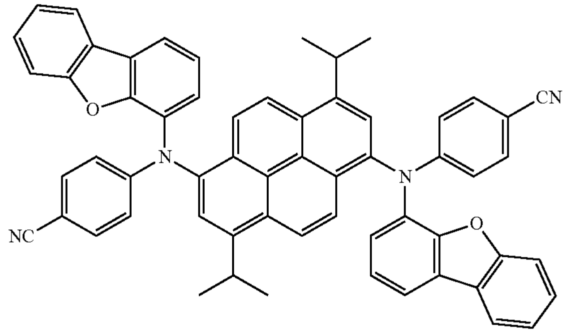
FD28
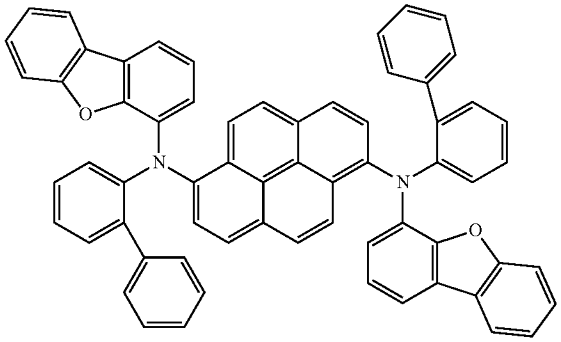
FD29
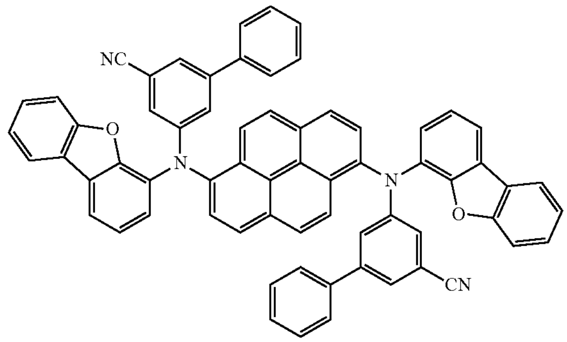
FD30
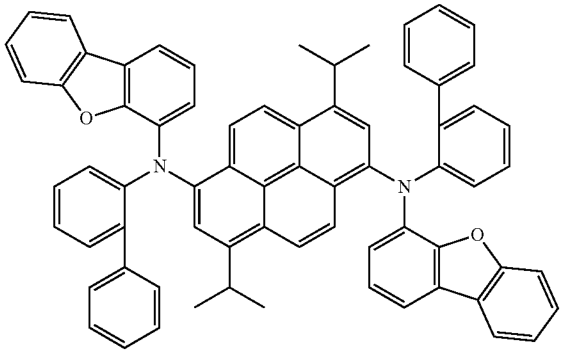
FD31
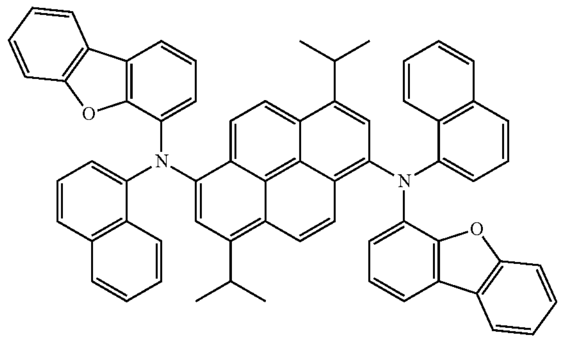
FD32
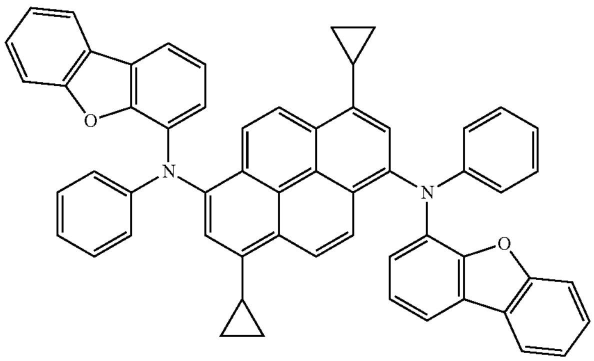

-continued

FD33

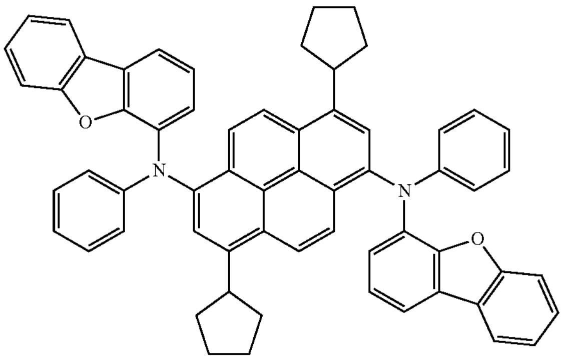

FD34

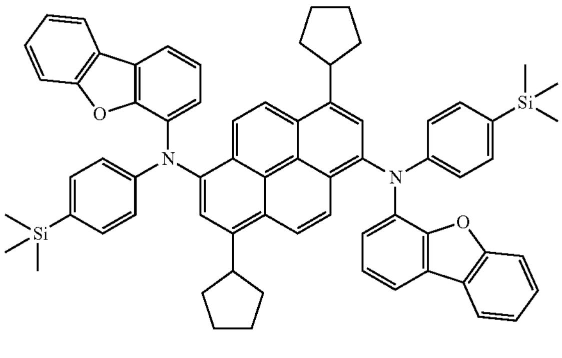

FD35

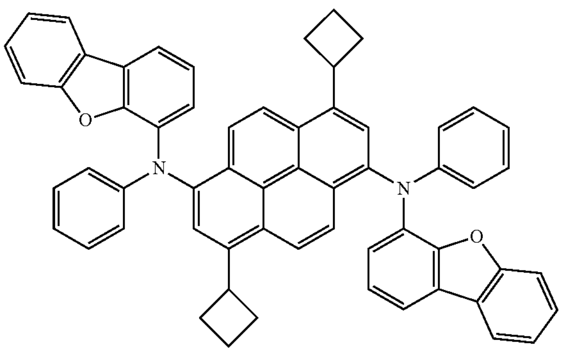

FD36

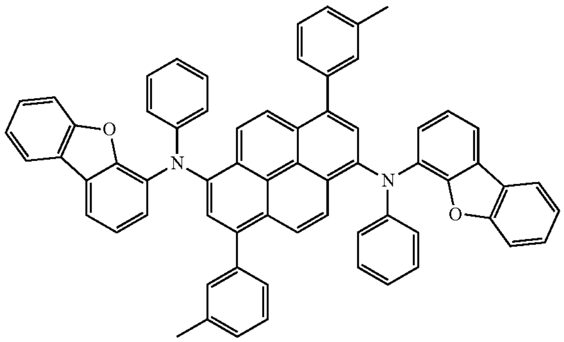

DPVBi

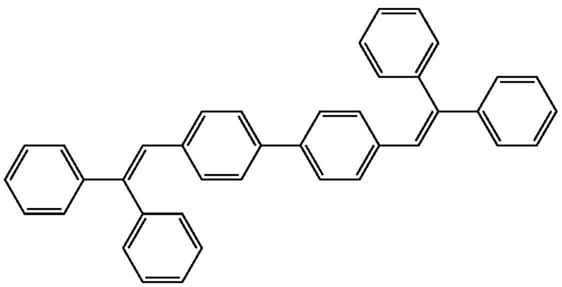

DPAVBi

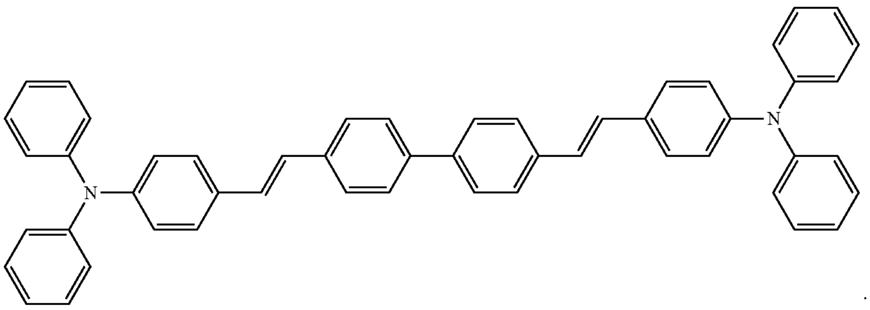

[Delayed Fluorescence Material]

The emission layer may include a delayed fluorescence material.

In the specification, the delayed fluorescence material may be selected from any compound capable of emitting delayed fluorescence by a delayed fluorescence emission mechanism.

The delayed fluorescence material included in the emission layer may serve as a host or as a dopant, depending on the type of other materials included in the emission layer.

In an embodiment, a difference between a triplet energy level (eV) of the delayed fluorescence material and a singlet energy level (eV) of the delayed fluorescence material may be in a range of about 0 eV to about 0.5 eV. When the difference between the triplet energy level (eV) of the delayed fluorescence material and the singlet energy level (eV) of the delayed fluorescence material is within the ranges above, up-conversion from the triplet state to the singlet state of the delayed fluorescence materials may effectively occur, thereby improving luminescence efficiency or the like of the light-emitting device 10.

For example, the delayed fluorescence material may include a material including at least one electron donor (for example, a π electron-rich $C_3$-$C_{60}$ cyclic group and the like, such as a carbazole group) and at least one electron acceptor (for example, a sulfoxide group, a cyano group, a π electron-deficient nitrogen-containing $C_1$-$C_{60}$ cyclic group, and the like); or a material including a $C_8$-$C_{60}$ polycyclic group in which two or more cyclic groups are condensed while sharing boron (B).

Examples of the delayed fluorescence material may include at least one of Compounds DF1 to DF9:

DF1

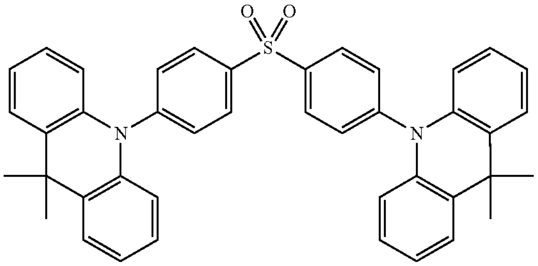

(DMAC-DPS)

DF2

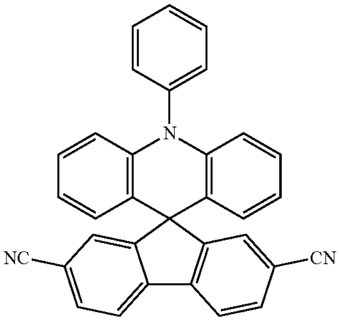

(ACRFLCN)

DF3

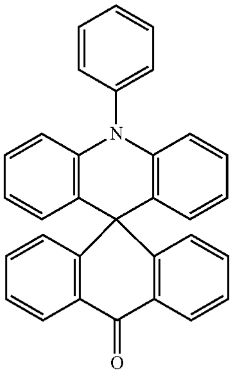

(ACRSA)

-continued

DF4

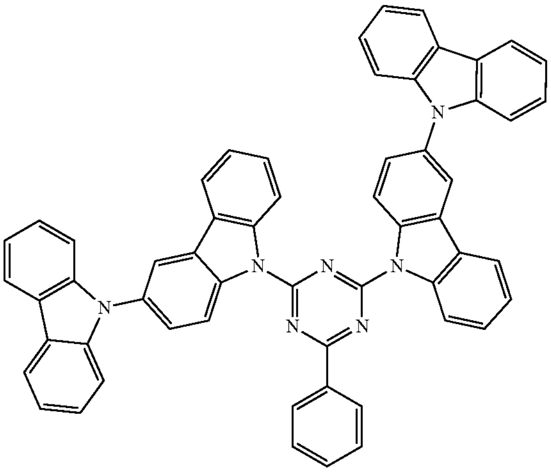

(CC2TA)

DF5

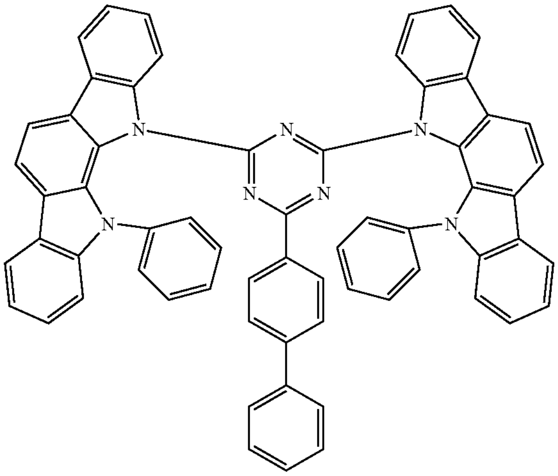

(PIC-TRZ)

DF6

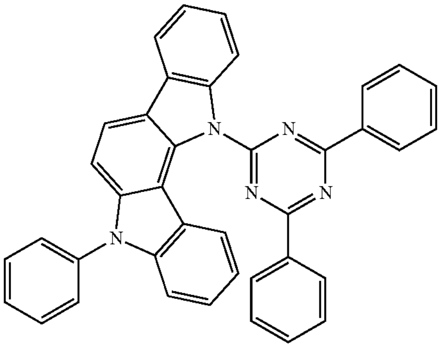

(PIC-TRZ2)

-continued

DF7

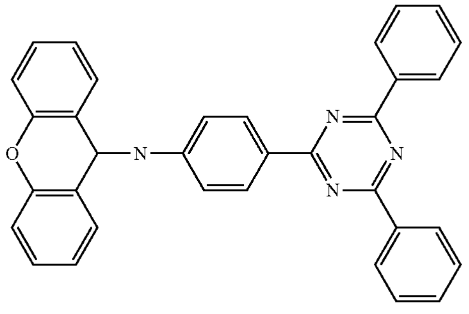

(PXZ-TRZ)

DF8

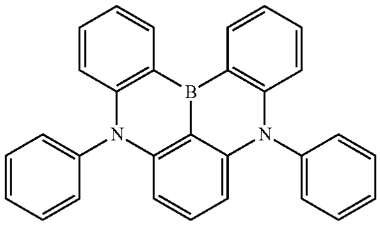

(DABNA-1)

DF9

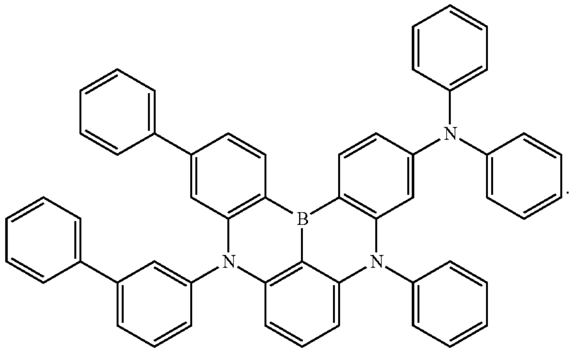

(DABNA-2)

[Quantum Dot]

The emission layer may include a quantum dot.

The term "quantum dot" as used herein refers to a crystal of a semiconductor compound, and may include any material capable of emitting light of various emission wavelengths according to a size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto.

The wet chemical process is a method including mixing a precursor material with an organic solvent and growing a quantum dot particle crystal. When the crystal grows, the organic solvent naturally acts as a dispersant coordinated on the surface of the quantum dot crystal and controls the growth of the crystal so that the growth of quantum dot particles can be controlled through a process which costs lower, and is easier than vapor deposition methods, such as metal organic chemical vapor deposition (MOCVD) or molecular beam epitaxy (MBE), The quantum dot may include a Group II-VI semiconductor compound, a Group III-V semiconductor compound, a Group III-VI semiconductor compound, a Group I-III-VI semiconductor compound, a Group IV-VI semiconductor compound, a Group IV element or compound, or any combination thereof.

Examples of the Group II-VI semiconductor compound may include a binary compound, such as CdSe, CdTe, ZnS, ZnSe, ZnTe, ZnO, HgS, HgSe, HgTe, MgSe, MgS, and the like; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and the like; a quaternary compound, such as CdZnSeS, CdZnSeTe, CdZnSTe, CdHgSeS, CdHgSeTe, CdHgSTe, HgZnSeS, HgZnSeTe, HgZnSTe, and the like; or any combination thereof.

Examples of the Group III-V semiconductor compound may include a binary compound, such as GaN, GaP, GaAs, GaSb, AlN, AlP, AlAs, AlSb, InN, InP, InAs, InSb, and the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and the like; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and the like; or any combination thereof. The Group III-V semiconductor compound may further include a Group II element. Examples of the Group III-V semiconductor compound further including a Group II element may include InZnP, InGaZnP, InAlZnP, and the like.

Examples of the Group III-VI semiconductor compound may include a binary compound, such as GaS, GaSe, $Ga_2Se_3$, GaTe, InS, InSe, $In_2S_3$, $In_2Se_3$, InTe, and the like; a ternary compound, such as $InGaS_3$, $InGaSe_3$, and the like; or any combination thereof.

Examples of the Group I-III-VI semiconductor compound may include a ternary compound, such as AgInS, $AgInS_2$, CuInS, $CuInS_2$, $CuGaO_2$, $AgGaO_2$, $AgAlO_2$, and the like; or any combination thereof.

Examples of the Group IV-VI semiconductor compound may include a binary compound, such as SnS, SnSe, SnTe, PbS, PbSe, PbTe, and the like; a ternary compound, such as SnSeS, SnSeTe, SnSTe, PbSeS, PbSeTe, PbSTe, SnPbS, SnPbSe, SnPbTe, and the like; a quaternary compound, such as SnPbSSe, SnPbSeTe, SnPbSTe, and the like; or any combination thereof.

The Group IV element or compound may include a single element compound, such as Si, Ge, and the like; a binary compound, such as SiC, SiGe, and the like; or any combination thereof.

Each element included in a multi-element compound, such as a binary compound, a ternary compound, and a quaternary compound, may exist in a particle thereof at a uniform concentration or at a non-uniform concentration.

The quantum dot may have a single structure or a core-shell structure. When the quantum dot has a single structure, a concentration of each element included in the quantum dot may be uniform. In embodiments, a material included in the core and a material included in the shell may be different from each other.

The shell of the quantum dot may be a protective layer that prevents chemical degeneration of the core to maintain semiconductor characteristics, and/or may be a charging layer that imparts electrophoretic characteristics to the quantum dot. The shell may be a single layer or a multi-layer. An interface between the core and the shell may have a concentration gradient in which the concentration of an element in the shell decreases toward the core.

Examples of the shell of the quantum dot may include a metal oxide, a metalloid oxide, a non-metal oxide, a semiconductor compound, or any combination thereof. Examples of the metal oxide, the metalloid oxide, or the non-metal oxide may include a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, NiO, and the like; a ternary compound, such as $MgAl_2O_4$, $CoFe_2O_4$, $NiFe_2O_4$, $CoMn_2O_4$, and the like; or any combination thereof.

Examples of the semiconductor compound may include a Group II-VI semiconductor compound, a Group III-V semiconductor compound, a Group III-VI semiconductor compound, a Group 1-III-VI semiconductor compound, a Group IV-VI semiconductor compound, or any combination thereof. Examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AIAs, AlP, AISb, or any combination thereof.

A full width of half maximum (FWHM) of an emission wavelength spectrum of the quantum dot may be equal to or less than about 45 nm. For example, a FWHM of an emission wavelength spectrum of the quantum dot may be equal to or less than about 40 nm. For example, a FWHM of an emission wavelength spectrum of the quantum dot may be equal to or less than about 30 nm. Within these ranges, color purity or color reproducibility may be increased. Light emitted through the quantum dot may be emitted in all directions, and thus, a wide viewing angle may be improved.

The quantum dot may be a spherical particle, a pyramidal particle, a multi-arm particle, or a cubic particle, or the quantum dot may be in the form of nanoparticles, nanotubes, nanowires, nanofibers, or nanoplates.

Since the energy band gap may be adjusted by controlling the size of the quantum dot, light having various wavelength bands may be obtained from the emission layer including the quantum dot. Accordingly, by using quantum dots of different sizes, a light-emitting device that emits light of various wavelengths may be implemented. For example, the size of the quantum dot may be selected such that the quantum dot may emit red light, green light, and/or blue light. The size of the quantum dot may be selected so that the quantum dot emits white light by the combination of light of various colors.

[Electron Transport Region in Interlayer 130]

The electron transport region may have a structure consisting of a layer consisting of a single material, a structure consisting of a layer consisting of different materials, or a structure including multiple layers including different materials.

The electron transport region may include a buffer layer, a hole blocking layer, an electron control layer, an electron transport layer, an electron injection layer, or any combination thereof.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein the layers of each structure may be stacked from the emission layer in its respective stated order, but the structure of the electron transport region is not limited thereto.

The electron transport region (for example, a buffer layer, a hole blocking layer, an electron control layer, or an electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

[Formula 601]

$$[Ar_{601}]_{xe11}-[(L_{601})_{xe1}-R_{601}]_{xe21}$$

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{601})(Q_{602})(Q_{603})$, $-C(=O)(Q_{601})$, $-S(=O)_2(Q_{601})$, or $-P(=O)(Q_{601})(Q_{602})$, $Q_{601}$ to $Q_{603}$ may each independently be the same as described in connection with $Q_1$ as described herein, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$ may be linked together via a single bond.

In embodiments, $Ar_{601}$ in Formula 601 may be a substituted or unsubstituted anthracene group.

In embodiments, the electron transport region may include a compound represented by Formula 601-1:

[Formula 601-1]

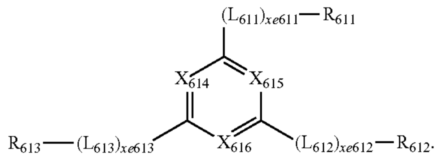

In Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, xe1 and xe611 to xe613 in Formulae 601 and 601-1 may each independently be 0, 1, or 2.

In embodiments, the electron transport region may include one of Compounds ET1 to ET45, 2,9-dimethyl-4, 7-diphenyl-1,10-phenanthroline (BCP), 4,7-diphenyl-1,10-phenanthroline (Bphen), $Alq_3$, BAlq, TAZ, NTAZ, or any combination thereof:
ET1
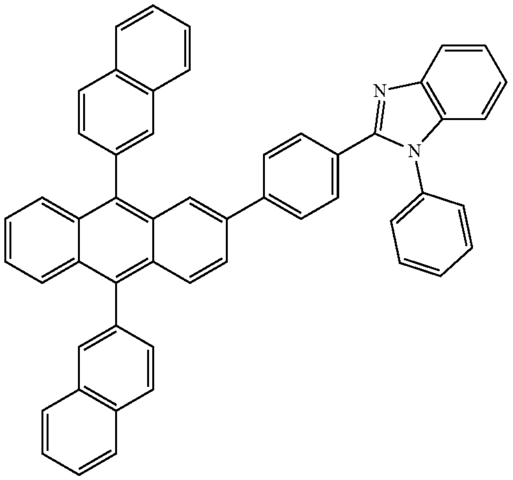
ET2
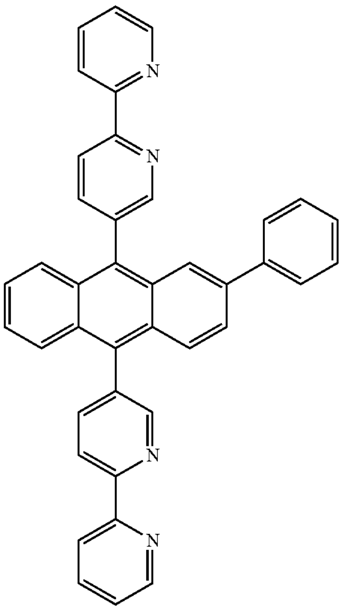
-continued
ET3
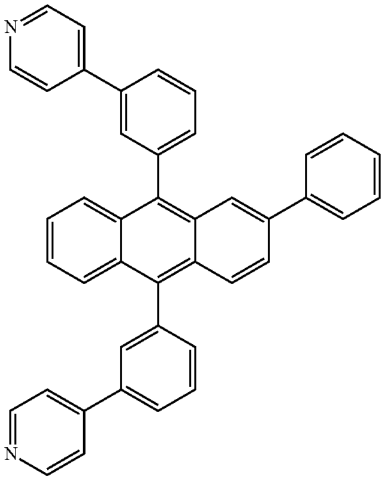
ET4
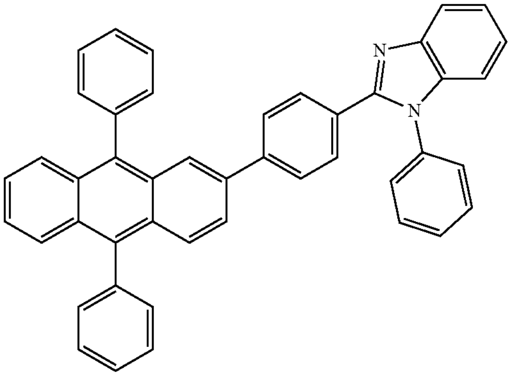
ET5
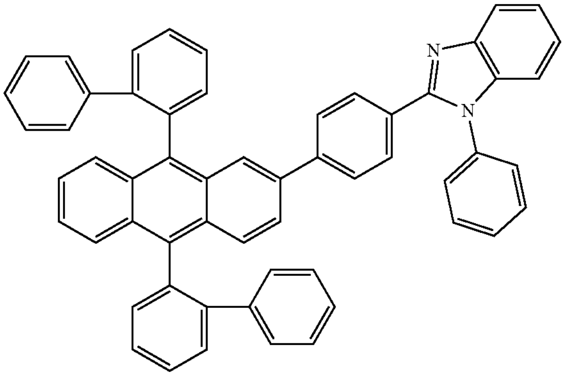
ET6
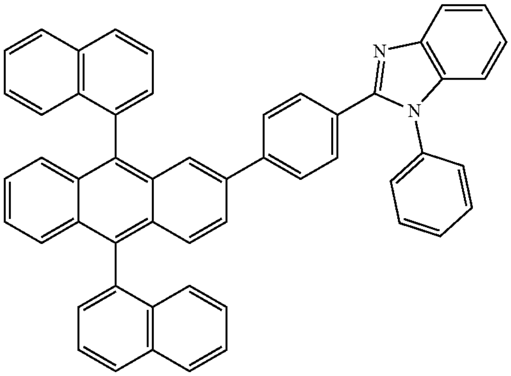

-continued
ET7
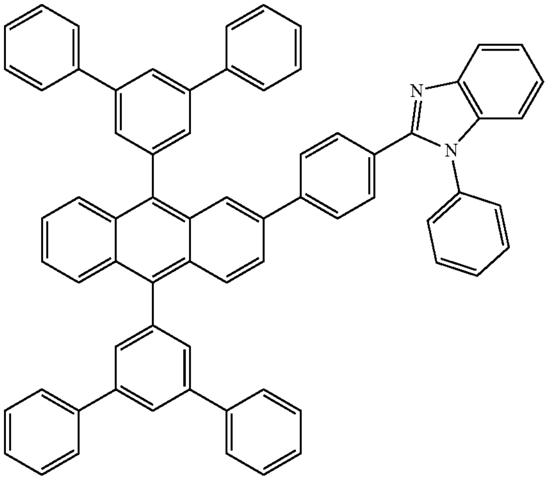
ET8
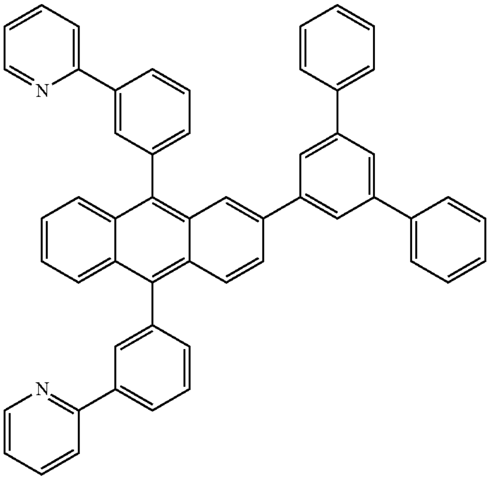
ET9
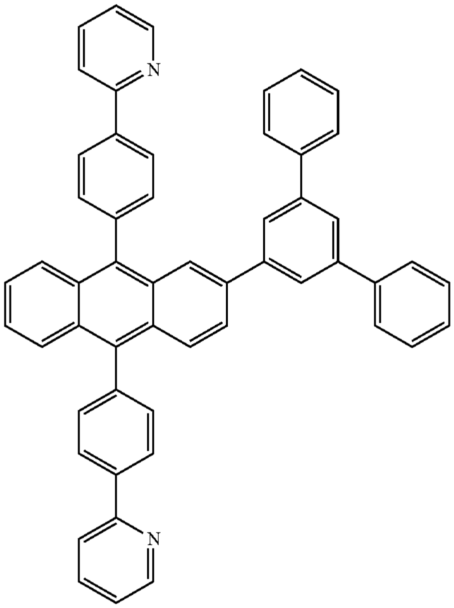
-continued
ET10
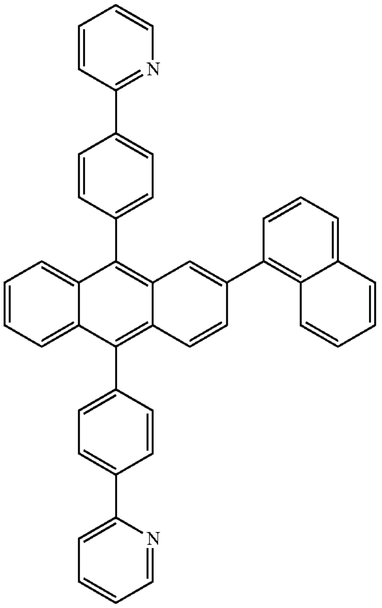
ET11
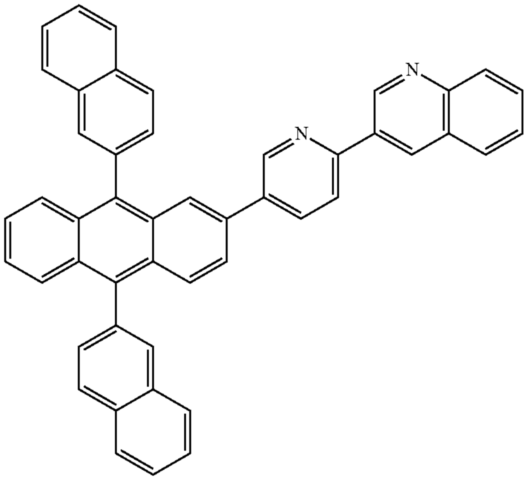
ET12
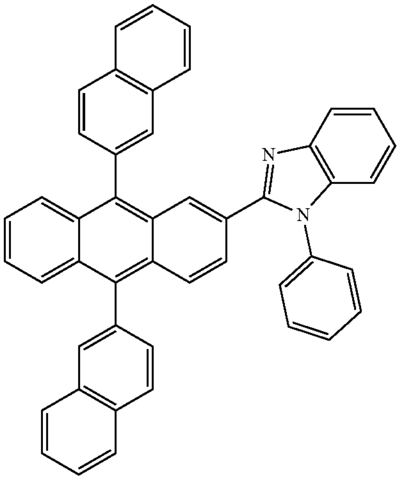

-continued
ET13
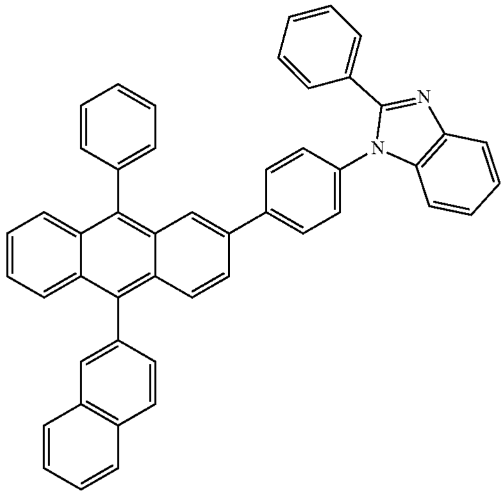
ET14
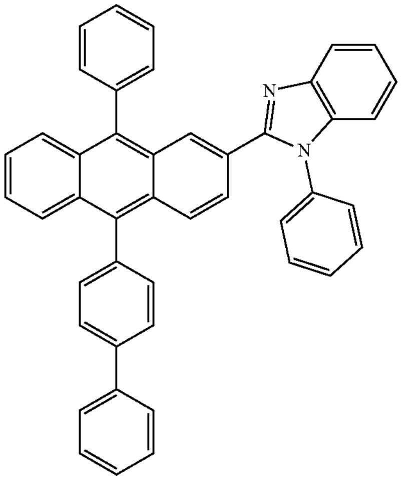
ET15
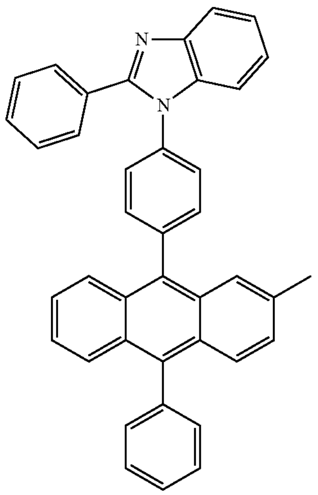
-continued
ET16
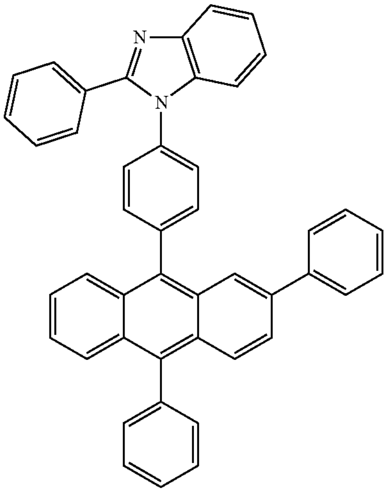
ET17
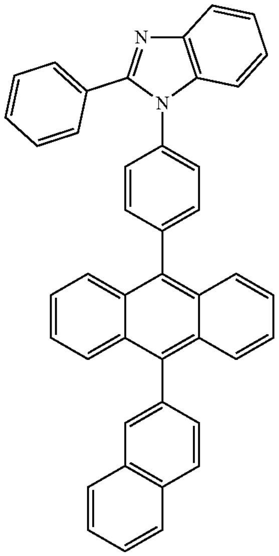
ET18
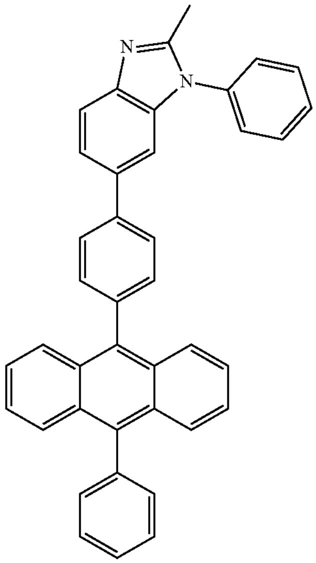

-continued
ET19
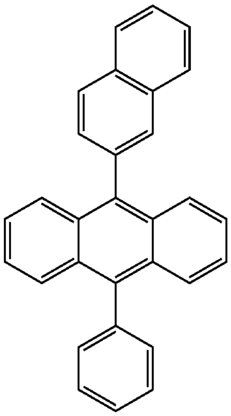
ET20
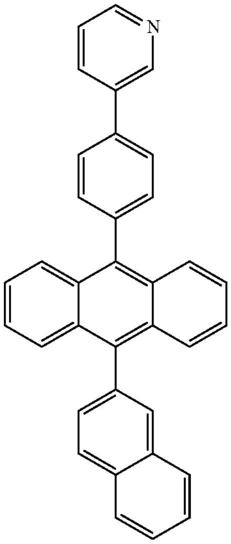
ET21
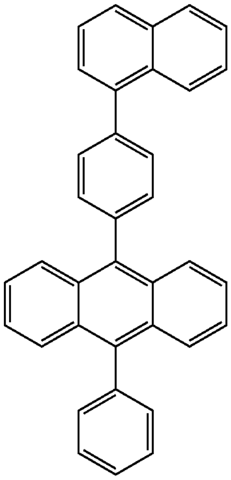
-continued
ET22
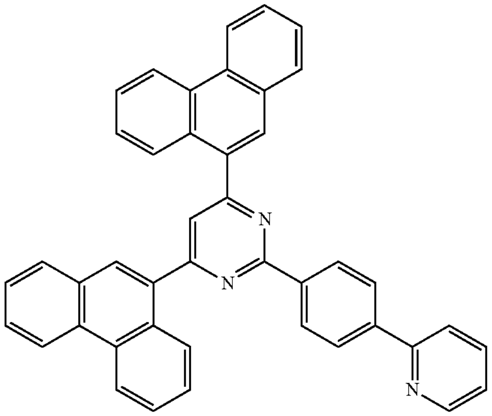
ET23
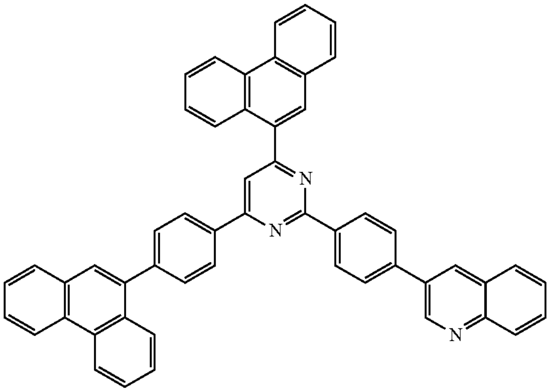
ET24
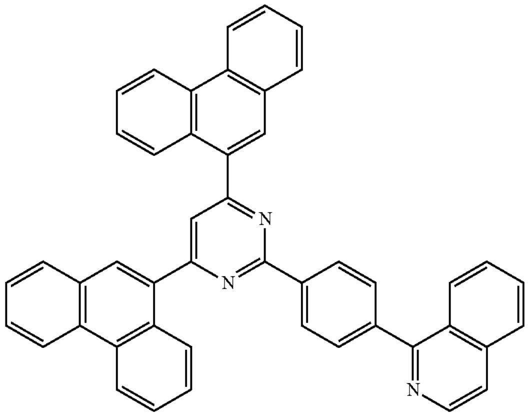

-continued
ET25
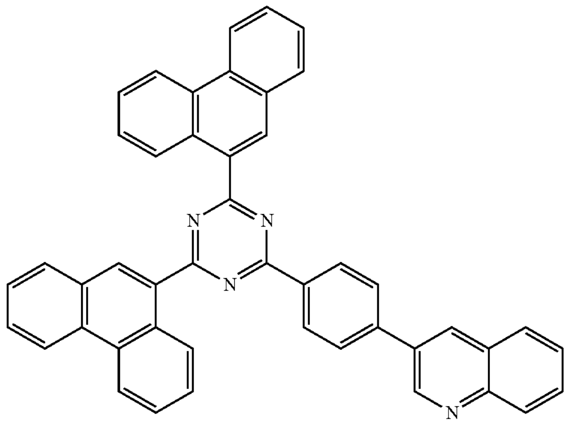
ET26
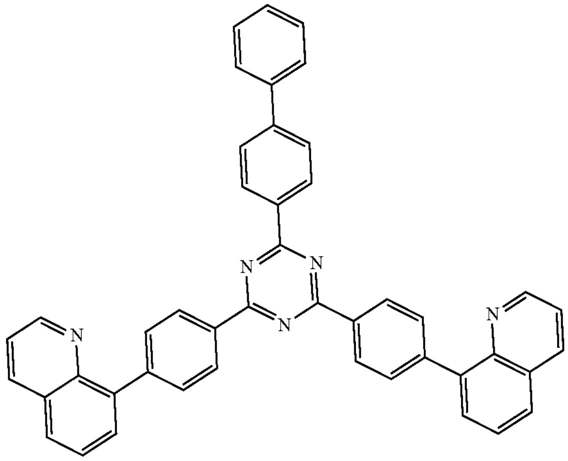
ET27
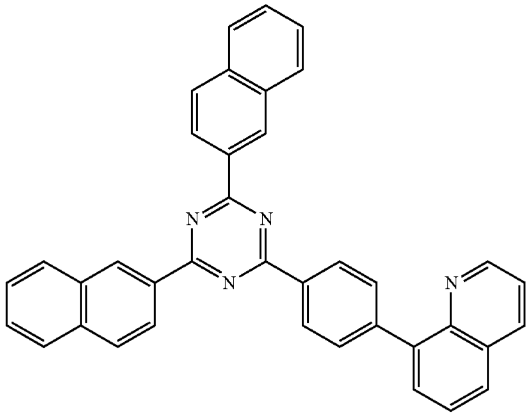
-continued
ET28
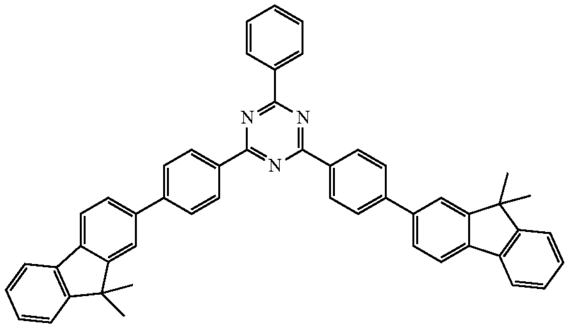
ET29
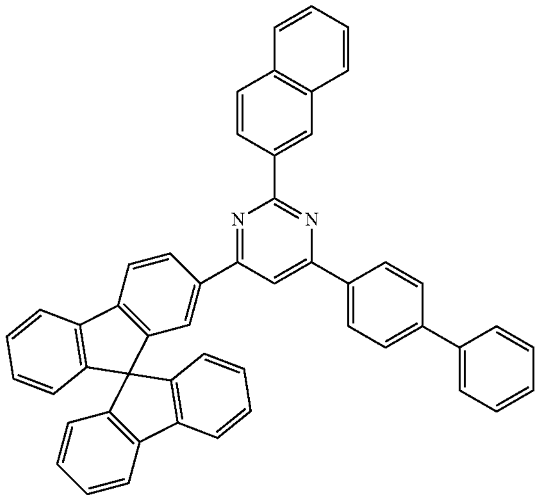
ET30
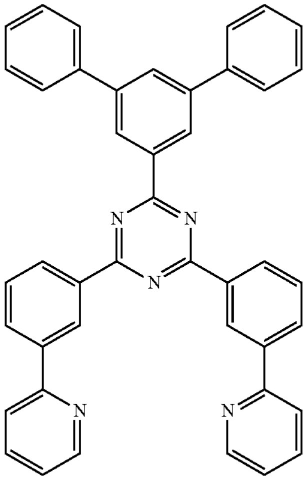

-continued
ET31
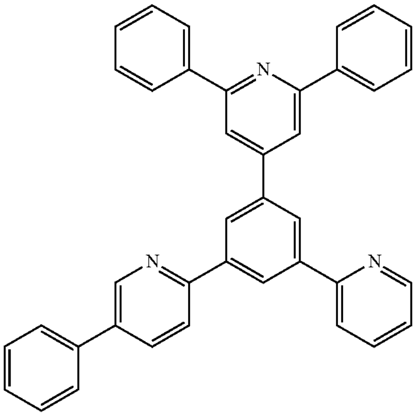
ET32
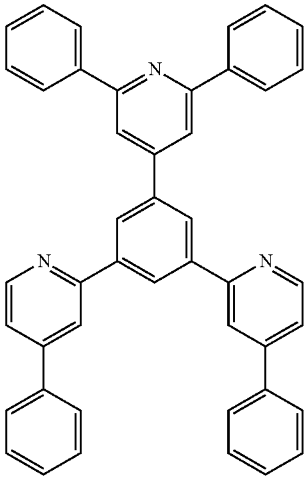
ET33
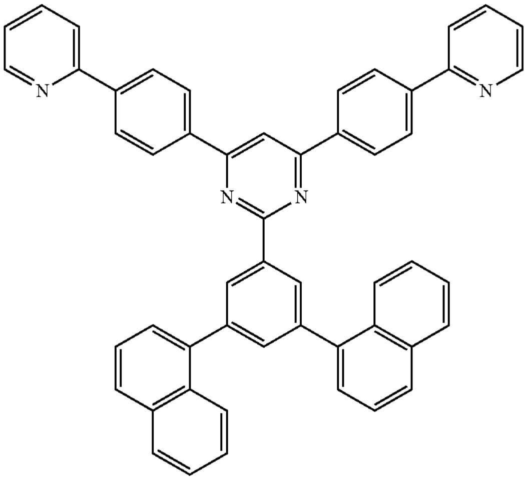
-continued
ET34
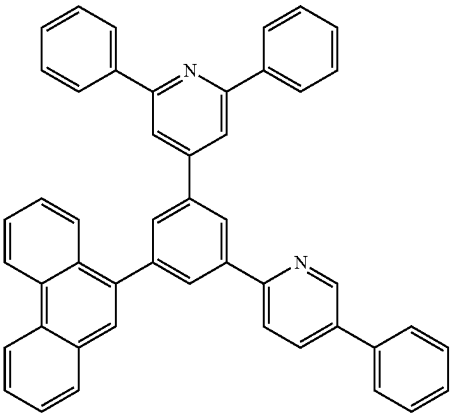
ET35
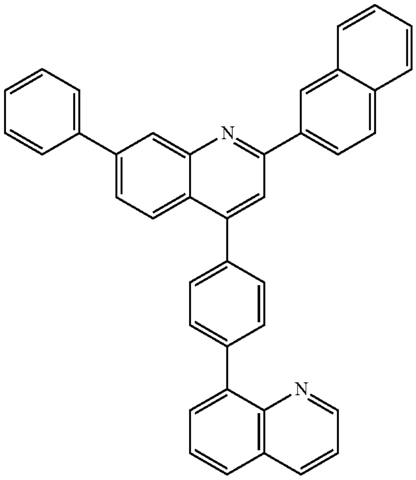
ET36
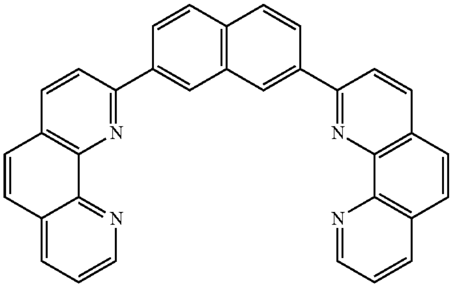
ET37
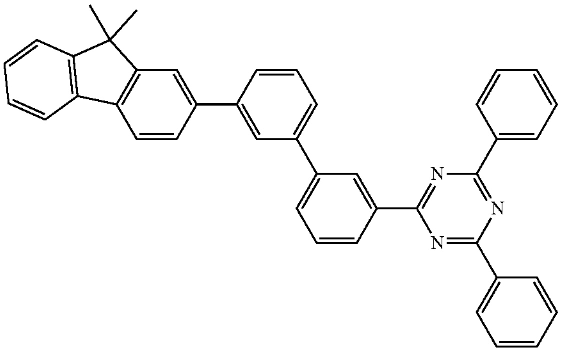

ET38
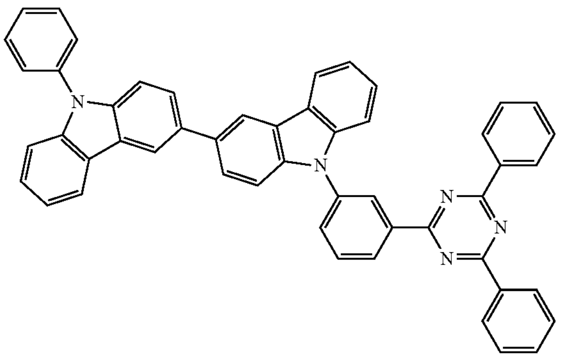
ET39
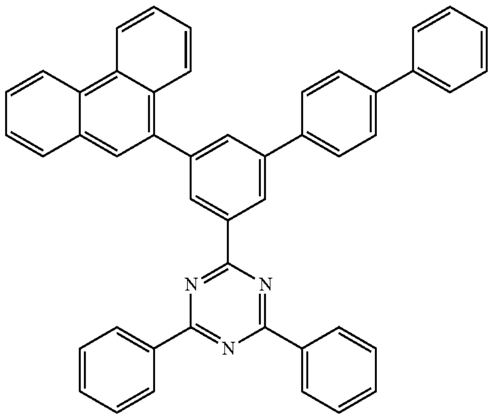
ET40
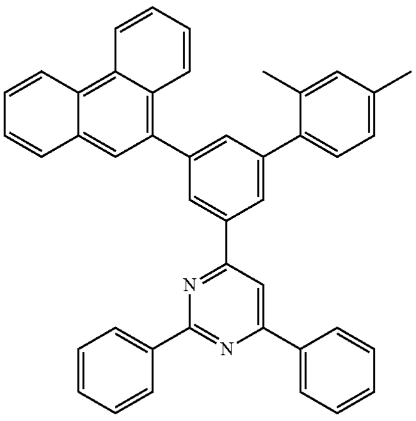
ET41
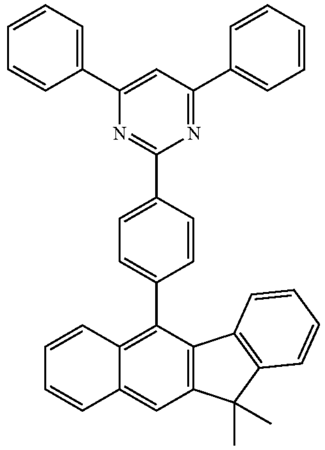
ET42
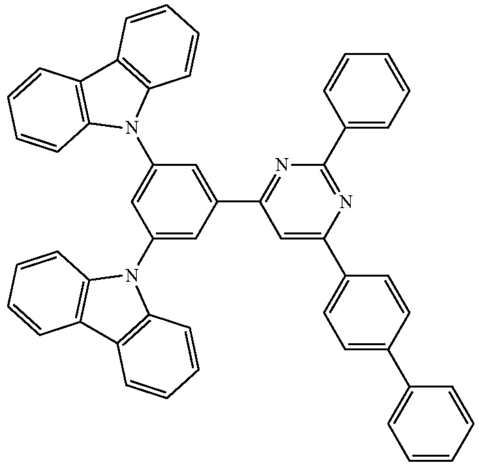
ET43
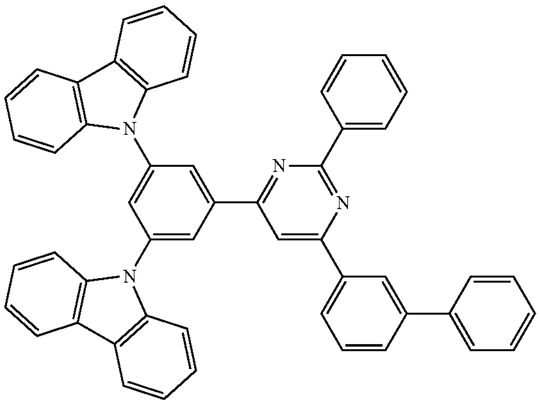

-continued

ET44

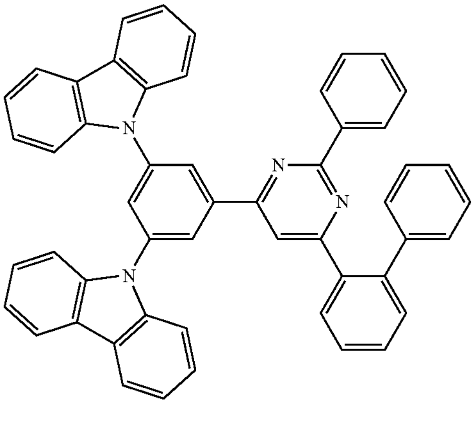

ET45

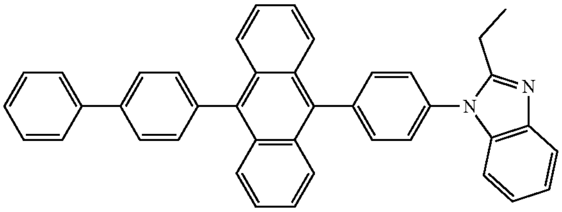

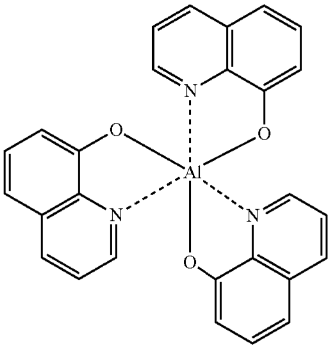

Alq3

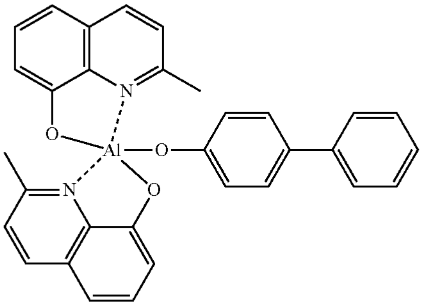

Balq

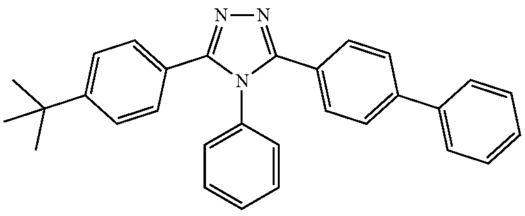

TAZ

-continued

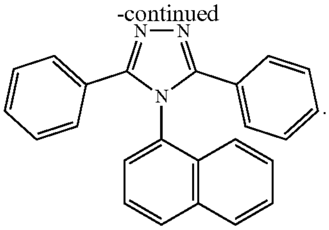

NTAZ

A thickness of the electron transport region may be in a range of about 100 Å to about 5,000 Å. For example, the thickness of the electron transport region may be in a range of about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, and a thickness of the electron transport layer may be in a range of about 100 Å to about 1,000 Å. For example, the thickness of the buffer layer, the hole blocking layer, or the electron control layer may each independently be in a range of about 30 Å to about 300 Å. For example, the thickness of the electron transport layer may be in a range of about 150 Å to about 500 Å. When the thicknesses of the buffer layer, the hole blocking layer, the electron control layer, the electron transport layer, and/or the electron transport region are within these ranges, satisfactory electron transporting characteristics may be obtained without a substantial increase in driving voltage.

The electron transport region (for example, an electron transport layer in the electron transport region) may further include, in addition to the materials described above, a metal-containing material.

The metal-containing material may include an alkali metal complex, an alkaline earth metal complex, or any combination thereof. A metal ion of an alkali metal complex may be a Li ion, a Na ion, a K ion, a Rb ion, or a Cs ion, and a metal ion of an alkaline earth metal complex may be a Be ion, a Mg ion, a Ca ion, a Sr ion, or a Ba ion. A ligand coordinated with the metal ion of the alkali metal complex or the metal ion of the alkaline earth-metal complex may each independently include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (LiQ) or Compound ET-D2:

ET-D1

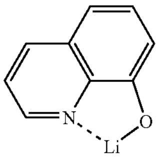

-continued

ET-D2

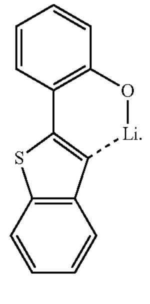

The electron transport region may include an electron injection layer that facilitates the injection of electrons from the second electrode 150. The electron injection layer may directly contact the second electrode 150.

The electron injection layer may have a structure consisting of a layer consisting of a single material, a structure consisting of a layer consisting of different materials, or a structure including multiple layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may respectively include oxides, halides (for example, fluorides, chlorides, bromides, iodides, and the like), or tellurides of the alkali metal, the alkaline earth metal, and the rare earth metal, or any combination thereof.

The alkali metal-containing compound may include alkali metal oxides, such as $Li_2O$, $Cs_2O$, $K_2O$, and the like; alkali metal halides, such as LiF, NaF, CsF, KF, LiI, NaI, CsI, KI, and the like; or any combination thereof. The alkaline earth metal-containing compound may include an alkaline earth metal compound, such as BaO, SrO, CaO, $BaxSr_{1-x}O$ (wherein x is a real number satisfying the condition of $0<x<1$), $BaxCa_{1-x}O$ (wherein x is a real number satisfying the condition of $0<x<1$), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. For example, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, $Lu_2Te_3$, and the like.

The alkali metal complex, the alkaline earth-metal complex, and the rare earth metal complex may include one of ions of the alkali metal, ions of the alkaline earth metal, and ions of the rare earth metal, and a ligand linked to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

In an embodiment, the electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In embodiments, the electron injection layer may further include an organic material (for example, the compound represented by Formula 601).

In embodiments, the electron injection layer may consist of an alkali metal-containing compound (for example, an alkali metal halide); or the electron injection layer may consist of an alkali metal-containing compound (for example, an alkali metal halide), and an alkali metal, an alkaline earth metal, a rare earth metal, or any combination thereof. In embodiments, the electron injection layer may be a KI:Yb co-deposited layer, an RbI:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be uniformly or non-uniformly dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within any of these ranges, satisfactory electron injection characteristics may be obtained without a substantial increase in driving voltage.

[Second Electrode 150]

The second electrode 150 may be on the interlayer 130 having a structure as described above. The second electrode 150 may be a cathode, which is an electron injection electrode. When the second electrode 150 is a cathode, a material for forming the second electrode 150 may be a material having a low work function, for example, a metal, an alloy, an electrically conductive compound, or any combination thereof.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

[Capping Layer]

A first capping layer may be located outside the first electrode 110, and/or a second capping layer may be located outside the second electrode 150. For example, the light-emitting device 10 may have a structure in which the first capping layer, the first electrode 110, the interlayer 130, and the second electrode 150 are stacked in this stated order, a structure in which the first electrode 110, the interlayer 130, the second electrode 150, and the second capping layer are stacked in this stated order, or a structure in which the first capping layer, the first electrode 110, the interlayer 130, the second electrode 150, and the second capping layer are stacked in this stated order.

Light generated in the emission layer of the interlayer 130 of the light-emitting device 10 may be extracted toward the outside through the first electrode 110 (which may be a semi-transmissive electrode or a transmissive electrode) and through the first capping layer. Light generated in the emission layer of the interlayer 130 of the light-emitting device 10 may be extracted toward the outside through the second electrode 150 (which may be a semi-transmissive electrode or a transmissive electrode) and through the second capping layer.

The first capping layer and the second capping layer may each increase external emission efficiency according to the principle of constructive interference. Accordingly, the light extraction efficiency of the light-emitting device 10 may be increased, so that the luminescence efficiency of the light-emitting device 10 may be improved.

The first capping layer and the second capping layer may each include a material having a refractive index equal to or greater than about 1.6 (at a wavelength of about 589 nm).

The first capping layer and the second capping layer may each independently be an organic capping layer including an organic material, an inorganic capping layer including an inorganic material, or an organic-inorganic composite capping layer including an organic material and an inorganic material.

In an embodiment, at least one of the first capping layer and the second capping layer may each independently include a carbocyclic compound, a heterocyclic compound, an amine group-containing compound, a porphine derivative, a phthalocyanine derivative, a naphthalocyanine derivative, an alkali metal complex, an alkaline earth metal complex, or any combination thereof. The carbocyclic compound, the heterocyclic compound, and the amine group-containing compound may each optionally be substituted with a substituent including O, N, S, Se, Si, F, Cl, Br, I, or any combination thereof. In embodiments, at least one of the first capping layer and the second capping layer may each independently include an amine group-containing compound.

In embodiments, at least one of the first capping layer and the second capping layer may each independently include a compound represented by Formula 201, a compound represented by Formula 202, or any combination thereof.

In embodiments, at least one of the first capping layer and the second capping layer may each independently include one of Compounds HT28 to HT33, one of Compounds CP1 to CP6, β-NPB, or any combination thereof:

CP1

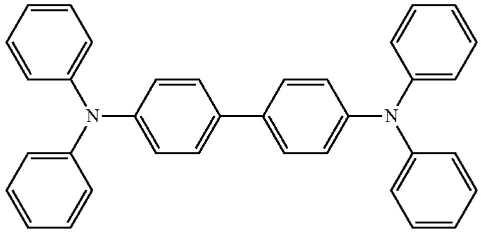

-continued

CP2

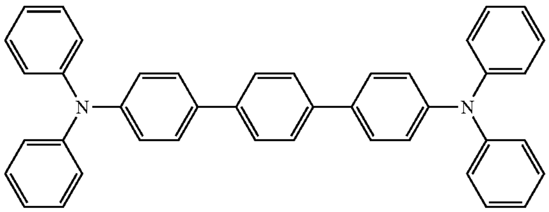

CP3

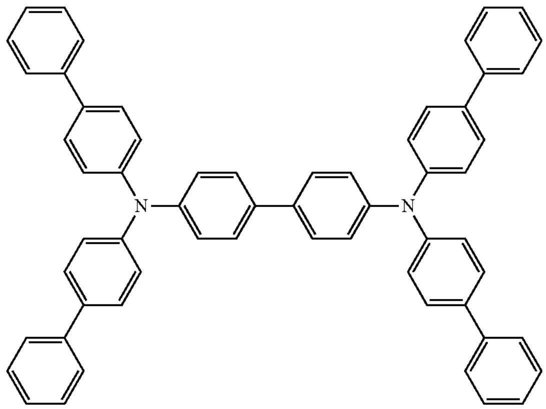

CP4

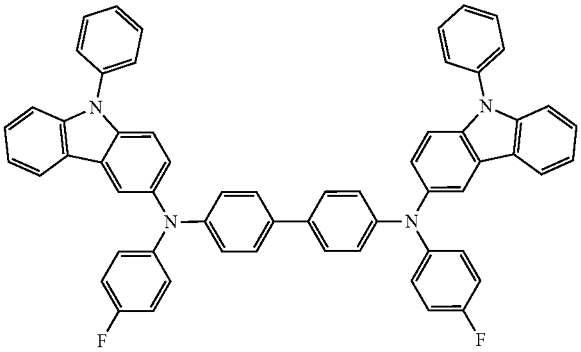

CP5

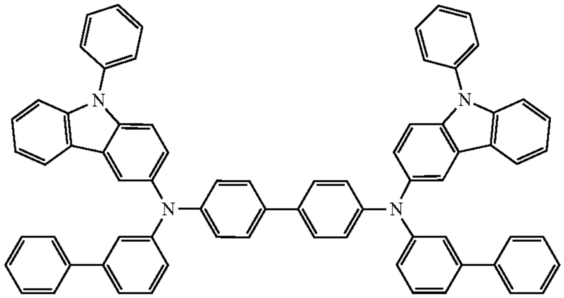

-continued

CP6

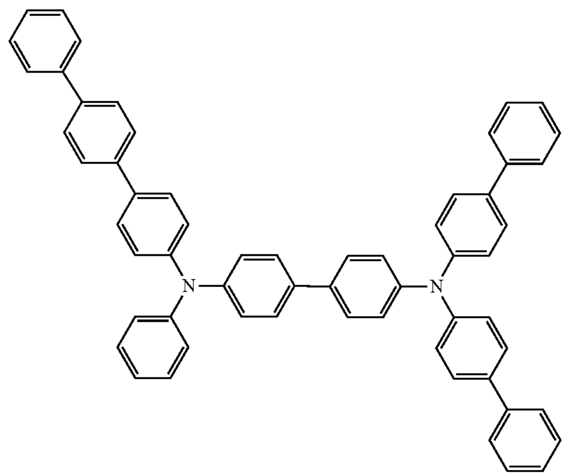

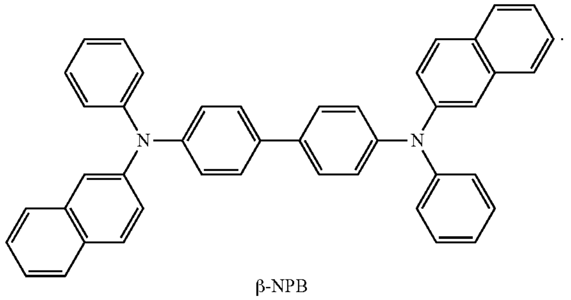

β-NPB

[Film]

The heterocyclic compound represented by Formula 1 may be included in various films. Accordingly, another aspect of the disclosure provides a film including the heterocyclic compound represented by Formula 1. The film may be, for example, an optical member (or a light control means) (for example, a color filter, a color conversion member, a capping layer, a light extraction efficiency enhancement layer, a selective light absorbing layer, a polarizing layer, a quantum dot-containing layer, or like), a light-blocking member (for example, a light reflective layer, a light absorbing layer, or the like), or a protective member (for example, an insulating layer, a dielectric layer, or the like).

[Electronic Apparatus]

The light-emitting device may be included in various electronic apparatuses. For example, an electronic apparatus including the light-emitting device may be a light-emitting apparatus, an authentication apparatus, or the like.

The electronic apparatus (for example, a light-emitting apparatus) may further include, in addition to the light-emitting device, a color filter, a color conversion layer, or a color filter and a color conversion layer. The color filter and/or the color conversion layer may be located in at least one traveling direction of light emitted from the light-emitting device. For example, light emitted from the light-emitting device may be blue light or white light. Details for the light-emitting device may be the same as described herein. In an embodiment, the color conversion layer may include a quantum dot. The quantum dots may be, for example, the same as described herein.

The electronic apparatus may include a first substrate. The first substrate may include subpixels, the color filter may include color filter areas respectively corresponding to the subpixels, and the color conversion layer may include color conversion areas respectively corresponding to the subpixels.

A pixel-defining film may be located between the subpixels to define each subpixel.

The color filter may further include color filter areas and light-shielding patterns located between the color filter areas, and the color conversion layer may further include color conversion areas and light-shielding patterns located between the color conversion areas.

The color filter areas (or the color conversion areas) may include a first area emitting first color light, a second area emitting second color light, and/or a third area emitting third color light, wherein the first color light, the second color light, and/or the third color light may have different maximum emission wavelengths from one another. For example, the first color light may be red light, the second color light may be green light, and the third color light may be blue light. In embodiments, the color filter areas (or the color conversion areas) may include quantum dots. For example, the first region may include red quantum dots, the second region may include green quantum dots, and the third region may not include quantum dots. Details for the quantum dots may be the same as described herein. The first region, the second region, and/or the third region may each include a scatterer.

For example, the light-emitting device may emit first light, the first region may absorb the first light to emit first-first color light, the second region may absorb the first light to emit second-first color light, and the third region may absorb the first light to emit third-first color light. In this regard, the first-first color light, the second-first color light, and the third-first color light may have different maximum emission wavelengths from each other. For example, the first light may be blue light, the first-first color light may be red light, the second-first color light may be green light, and the third-first color light may be blue light.

The electronic apparatus may further include a thin-film transistor, in addition to the light-emitting device as described above. The thin-film transistor may include a source electrode, a drain electrode, and an active layer, wherein any one of the source electrode or the drain electrode may be electrically connected to any one of the first electrode or the second electrode of the light-emitting device.

The thin-film transistor may further include a gate electrode, a gate insulating film, or the like.

The active layer may include crystalline silicon, amorphous silicon, an organic semiconductor, an oxide semiconductor, or the like.

The electronic apparatus may further include a sealing portion for sealing the light-emitting device. The sealing portion may be located between the color conversion layer and/or color filter and the light-emitting device. The sealing portion may allow light from the light-emitting device to be extracted to the outside, and may simultaneously prevent ambient air and/or moisture from penetrating into the light-emitting device. The sealing portion may be a sealing substrate including a transparent glass substrate or a plastic substrate. The sealing portion may be a thin-film encapsulation layer including an organic layer and/or an inorganic layer. When the sealing portion is a thin film encapsulation layer, the electronic apparatus may be flexible.

Various functional layers may be further included on the sealing portion, in addition to the color filter and/or the color conversion layer, according to a use of the electronic apparatus. Examples of the functional layers may include a touch screen layer, a polarizing layer, an authentication apparatus, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, and the like).

The authentication apparatus may further include, in addition to the light-emitting device as described above, a biometric information collector.

The electronic apparatus may be applied to various displays, such as light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
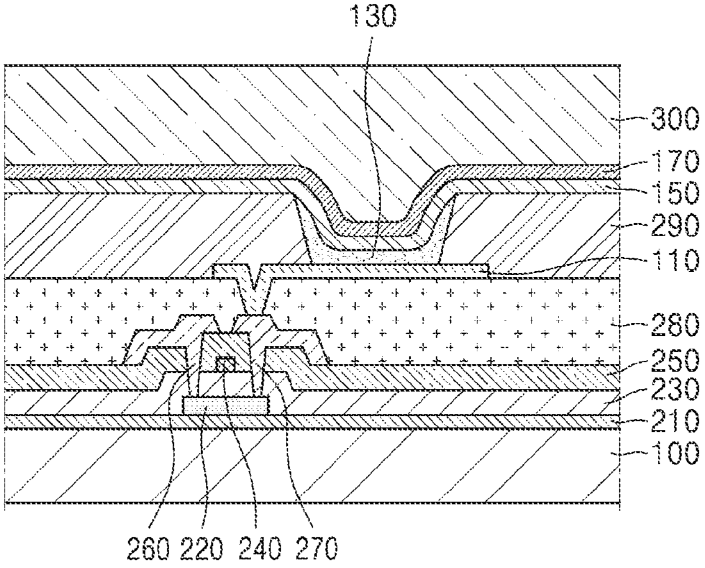
FIG. 2 is a schematic cross-sectional view of an electronic apparatus according to an embodiment.
Figure 3:
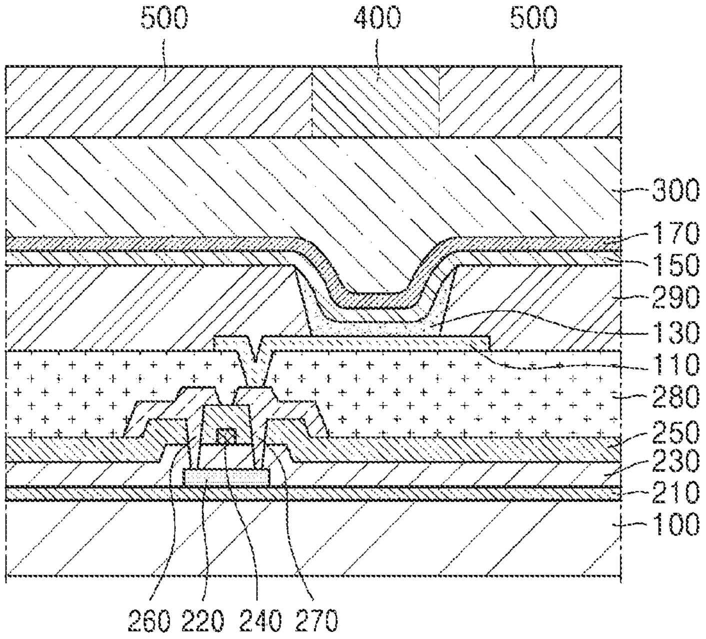
FIG. 3 is a schematic cross-sectional view of an electronic apparatus according to another embodiment.

[Description of FIGS. 2 and 3]

FIG. 2 is a schematic cross-sectional view showing an electronic apparatus according to an embodiment.

The electronic apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be located on the substrate 100. The buffer layer 210 may prevent penetration of impurities through the substrate 100 and may provide a flat surface on the substrate 100.

A TFT may be located on the buffer layer 210. The TFT may include an active layer 220, a gate electrode 240, a source electrode 260, and a drain electrode 270.

The active layer 220 may include an inorganic semiconductor such as silicon or polysilicon, an organic semiconductor, or an oxide semiconductor, and may include a source region, a drain region, and a channel region.

A gate insulating film 230 for insulating the active layer 220 from the gate electrode 240 may be located on the active layer 220, and the gate electrode 240 may be located on the gate insulating film 230.

An interlayer insulating film 250 may be located on the gate electrode 240. The interlayer insulating film 250 may be located between the gate electrode 240 and the source electrode 260 and between the gate electrode 240 and the drain electrode 270, to insulate from one another.

The source electrode 260 and the drain electrode 270 may be located on the interlayer insulating film 250. The interlayer insulating film 250 and the gate insulating film 230 may be formed to expose the source region and the drain region of the active layer 220, and the source electrode 260 and the drain electrode 270 may respectively contact the exposed portions of the source region and the drain region of the active layer 220.

The TFT may be electrically connected to a light-emitting device to drive the light-emitting device, and may be covered and protected by a passivation layer 280. The passivation layer 280 may include an inorganic insulating film, an organic insulating film, or any combination thereof. A light-emitting device is provided on the passivation layer 280. The light-emitting device may include a first electrode 110, an interlayer 130, and a second electrode 150.

The first electrode 110 may be located on the passivation layer 280. The passivation layer 280 may expose a portion of the drain electrode 270, not fully covering the drain electrode 270, and the first electrode 110 may be electrically connected to the exposed portion of the drain electrode 270.

A pixel defining layer 290 including an insulating material may be located on the first electrode 110. The pixel defining layer 290 may expose a region of the first electrode 110, and an interlayer 130 may be formed in the exposed region of the first electrode 110. The pixel defining layer 290 may include a polyimide or polyacrylic organic film. Although not shown in FIG. 2, at least one layer of the interlayer 130 may extend beyond the upper portion of the pixel defining layer 290 to be provided in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device to protect the light-emitting device from moisture and/or oxygen. The encapsulation portion 300 may include an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and the like), an epoxy-based resin (for example, aliphatic glycidyl ether (AGE), and the like), or any combination thereof; or any combination of the inorganic films and the organic films.

FIG. 3 is a schematic cross-sectional view showing an electronic apparatus according to another embodiment.

The electronic apparatus of FIG. 3 differs from the electronic apparatus of FIG. 2, at least in that a light-shielding pattern 500 and a functional region 400 are further included on the encapsulation portion 300. The functional region 400 may be a color filter area, a color conversion area, or a combination of the color filter area and the color conversion area. In an embodiment, the light-emitting device included in the electronic apparatus of FIG. 3 may be a tandem light-emitting device.

[Manufacturing Method]

The layers included in the hole transport region, the emission layer, and the layers included in the electron transport region may be formed in a certain region by using various methods such as vacuum deposition, spin coating, casting, Langmuir-Blodgett (LB) deposition, ink-jet printing, laser-printing, laser-induced thermal imaging, and the like.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definitions of Terms

The term "$C_3$-$C_{60}$ carbocyclic group" as used herein may be a cyclic group consisting of carbon as the only ring-forming atoms and having three to sixty carbon atoms, and the term "$C_1$-$C_{60}$ heterocyclic group" as used herein may be a cyclic group that has one to sixty carbon atoms and further has, in addition to carbon, at least one heteroatom as ring-forming atoms. The $C_3$-$C_{60}$ carbocyclic group and the $C_1$-$C_{60}$ heterocyclic group may each be a monocyclic group consisting of one ring or a polycyclic group in which two or more rings are condensed with each other. For example, the $C_1$-$C_{60}$ heterocyclic group may have 3 to 61 ring-forming atoms.

The "cyclic group" as used herein may include the $C_3$-$C_{60}$ carbocyclic group, or the $C_1$-$C_{60}$ heterocyclic group.

The term "Tr electron-rich $C_3$-$C_{60}$ cyclic group" as used herein may be a cyclic group that has three to sixty carbon atoms and may not include *—N=*' as a ring-forming moiety, and the term "Tr electron-deficient nitrogen-containing $C_1$-$C_{60}$ cyclic group" as used herein may be a heterocyclic group that has one to sixty carbon atoms and may include *—N=*' as a ring-forming moiety.

In embodiments, the $C_3$-$C_{60}$ carbocyclic group may be a T1 group or a group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be a T2 group, a group in which two or more T2 groups are condensed with each other, or a group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), the π electron-rich $C_3$-$C_{60}$ cyclic group may be a T1 group, a group in which two or more T1 groups are condensed with each other, a T3 group, a group in which two or more T3 groups are condensed with each other, or a group in which at least one T3 group and at least one T1 group are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, and the like), the π electron-deficient nitrogen-containing $C_1$-$C_{60}$ cyclic group may be a T4 group, a group in which two or more T4 groups are condensed with each other, a group in which at least one T4 group and at least one T1 group are condensed with each other, a group in which at least one T4 group and at least one T3 group are condensed with each other, or a group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein may each be a group condensed to any cyclic group, a monovalent group, or a polyvalent group (for example, a divalent group, a trivalent group, a tetravalent group, and the like) according to the structure of a formula for which the corresponding term is used. For example, the "benzene group" may be a benzo group, a phenyl group, a phenylene group, or the like, which may be readily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. Examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein may be a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, and the like. The term "$C_1$-$C_{60}$ alkylene group" as used herein may be a divalent group having a same structure as the $C_1$-$C_{60}$ alkyl group.

The term "$C_2$-$C_{60}$ alkenyl group" as used herein may be a monovalent hydrocarbon group having at least one carbon-carbon double bond in the middle or at a terminus of a $C_2$-$C_{60}$ alkyl group, and examples thereof may include an ethenyl group, a propenyl group, a butenyl group, and the like. The term "$C_2$-$C_{60}$ alkenylene group" as used herein may be a divalent group having a same structure as the $C_2$-$C_{60}$ alkenyl group.

The term "$C_2$-$C_{60}$ alkynyl group" as used herein may be a monovalent hydrocarbon group having at least one carbon-carbon triple bond in the middle or at a terminus of a $C_2$-$C_{60}$ alkyl group, and examples thereof may include an ethynyl group, a propynyl group, and the like. The term "$C_2$-$C_{60}$ alkynylene group" as used herein may be a divalent group having a same structure as the $C_2$-$C_{60}$ alkynyl group.

The term "$C_1$-$C_{60}$ alkoxy group" as used herein may be a monovalent group represented by —O($A_{101}$) (wherein $A_{101}$ may be a $C_1$-$C_{60}$ alkyl group), and examples thereof may include a methoxy group, an ethoxy group, an isopropyloxy group, and the like.

The term "$C_3$-$C_{10}$ cycloalkyl group" as used herein may be a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, a bicyclo[2.2.2]octyl group, and the like. The term "$C_3$-$C_{10}$ cycloalkylene group" as used herein may be a divalent group having a same structure as the $C_3$-$C_{10}$ cycloalkyl group.

The term "$C_1$-$C_{10}$ heterocycloalkyl group" as used herein may be a monovalent cyclic group of 1 to 10 carbon atoms, further including, in addition to carbon atoms, at least one heteroatom, as ring-forming atoms, and examples thereof may include a 1,2,3,4-oxatriazolidinyl group, a tetrahydrofuranyl group, a tetrahydrothiophenyl group, and the like. The term "$C_1$-$C_{10}$ heterocycloalkylene group" as used herein may be a divalent group having a same structure as the $C_1$-$C_{10}$ heterocycloalkyl group.

The term "$C_3$-$C_{10}$ cycloalkenyl group" as used herein may be a monovalent cyclic group that has three to ten carbon atoms and at least one carbon-carbon double bond in the cyclic structure thereof and no aromaticity, and examples thereof may include a cyclopentenyl group, a cyclohexenyl group, a cycloheptenyl group, and the like. The term "$C_3$-$C_{10}$ cycloalkenylene group" as used herein may be a divalent group having a same structure as the $C_3$-$C_{10}$ cycloalkenyl group.

The term "$C_1$-$C_{10}$ heterocycloalkenyl group" as used herein may be a monovalent cyclic group of 1 to 10 carbon atoms, further including, in addition to carbon atoms, at least one heteroatom, as ring-forming atoms, and having at least one carbon-carbon double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, a 2,3-dihydrothiophenyl group, and the like. The term "$C_1$-$C_{10}$ heterocycloalkenylene group" as used herein may be a divalent group having a same structure as the $C_1$-$C_{10}$ heterocycloalkenyl group.

The term "$C_6$-$C_{60}$ aryl group" as used herein may be a monovalent group having a carbocyclic aromatic system of 6 to 60 carbon atoms, and the term "$C_6$-$C_{60}$ arylene group"

as used herein may be a divalent group having a carbocyclic aromatic system of 6 to 60 carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, an ovalenyl group, and the like. When the $C_6$-$C_{60}$ aryl group and the $C_6$-$C_{60}$ arylene group each independently include two or more rings, the two or more rings may respectively be condensed with each other.

The term "$C_1$-$C_{60}$ heteroaryl group" as used herein may be a monovalent group having a heterocyclic aromatic system of 1 to 60 carbon atoms, further including, in addition to carbon atoms, at least one heteroatom, as ring-forming atoms. The term "$C_1$-$C_{60}$ heteroarylene group" as used herein may be a divalent group having a heterocyclic aromatic system of 1 to 60 carbon atoms, further including, in addition to carbon atoms, at least one heteroatom, as ring-forming atoms. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, a naphthyridinyl group, and the like. When the $C_1$-$C_{60}$ heteroaryl group and the $C_1$-$C_{60}$ heteroarylene group each include two or more rings, the two or more rings may respectively be condensed with each other.

The term "monovalent non-aromatic condensed polycyclic group" as used herein may be a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group may include an indenyl group, a fluorenyl group, a spiro-bifluorenyl group, a benzofluorenyl group, an indenophenanthrenyl group, and an indeno anthracenyl group. The term "divalent non-aromatic condensed polycyclic group" as used herein may be to a divalent group having a same structure as the monovalent non-aromatic condensed polycyclic group described above.

The term "monovalent non-aromatic condensed heteropolycyclic group" as used herein may be a monovalent group (for example, having 1 to 60 carbon atoms) having two or more rings condensed to each other, further including, in addition to carbon atoms, at least one heteroatom, as ring-forming atoms, and having non-aromaticity in its entire molecular structure. Examples of the monovalent non-aromatic condensed heteropolycyclic group may include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, a benzothienodibenzothiophenyl group, and the like. The term "divalent non-aromatic condensed heteropolycyclic group" as used herein may be a divalent group having a same structure as the monovalent non-aromatic condensed heteropolycyclic group described above.

The term "$C_6$-$C_{60}$ aryloxy group" as used herein may be represented by —O($A_{102}$) (wherein $A_{102}$ may be a $C_6$-$C_{60}$ aryl group), and the term "$C_6$-$C_{60}$ arylthio group" as used herein may be represented by —S($A_{103}$) (wherein $A_{103}$ may be a $C_6$-$C_{60}$ aryl group).

The term "$C_7$-$C_{60}$ aryl alkyl group" used herein may be represented by -($A_{104}$)($A_{105}$) (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" used herein may be represented by -($A_{106}$)($A_{107}$) (where $A_{106}$ may be a $C_1$-$C_{59}$ alkylene group, and $A_{107}$ may be a $C_1$-$C_{59}$ heteroaryl group).

The term "$R_{10a}$" as used herein may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$).

In the specification, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein may be any atom other than a carbon atom or a hydrogen atom. Examples of the heteroatom may include O, S, N, P, Si, B, Ge, Se, or any combinations thereof.

The term "third-row transition metal" as used herein may include hafnium (Hf), tantalum (Ta), tungsten (W), rhenium (Re), osmium (Os), iridium (Ir), platinum (Pt), gold (Au), and the like.

The term "Ph" as used herein refers to a phenyl group, the term "Me" as used herein refers to a methyl group, the term "Et" as used herein refers to an ethyl group, the terms "ter-Bu" or "$Bu^t$" as used herein refers to a tert-butyl group, and the term "OMe" as used herein refers to a methoxy group.

The term "biphenyl group" as used herein may be a phenyl group substituted with a phenyl group. For example, the "biphenyl group" may be a substituted phenyl group having a $C_6$-$C_{60}$ aryl group as a substituent.

The term "terphenyl group" as used herein may be a phenyl group substituted with a biphenyl group. For example, the "terphenyl group" may be a substituted phenyl group having, as a substituent, a $C_6$-$C_{60}$ aryl group substituted with a $C_6$-$C_{60}$ aryl group.

The symbols * and *' as used herein, unless defined otherwise, each refer to a binding site to a neighboring atom in a corresponding formula or moiety.

Hereinafter, compounds according to embodiments and light-emitting devices according to embodiments will be described in detail with reference to the Synthesis Examples and the Examples. The wording "B was used instead of A" used in describing Synthesis Examples means that an identical molar equivalent of B was used in place of A.

EXAMPLES

Synthesis Example 1: Synthesis of Compound 2

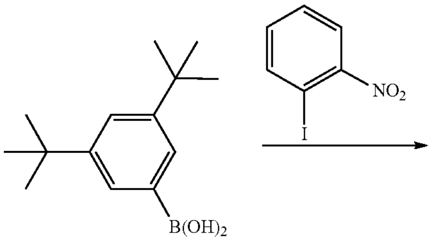

-continued

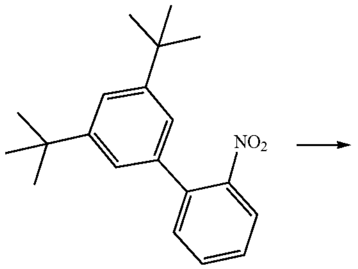

2-1

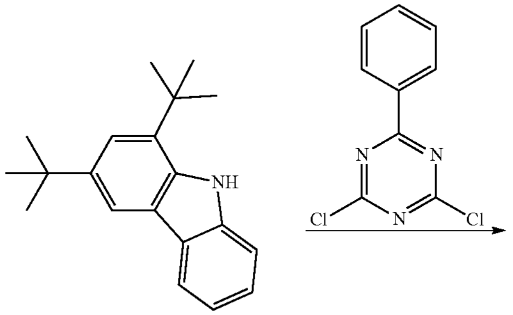

2-2

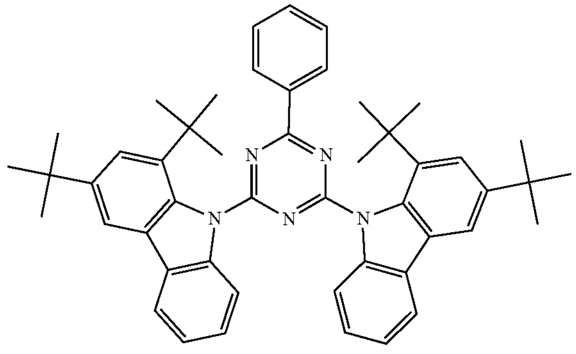

2

Synthesis of Intermediate 2-1

(3,5-di-tert-butylphenyl)boronic acid (CAS #=197223-39-5, 1.2 eq) and 1-iodo-2-nitrobenzene were reacted in the presence of $Pd(PPh_3)_4$ catalyst, so as to obtain Intermediate 2-1. Intermediate 2-1 was identified by LC/MS. $C_{20}H_{25}NO_2$ M+1: 312.21

Synthesis of Intermediate 2-2

Intermediate 2-1 was dissolved in a solution (0.2 M) in which o-dichlorobenzene and $P(OEt)_3$ were mixed at a volume ratio of 1:1 for a reaction at 180° C., so as to obtain Intermediate 2-2. Intermediate 2-2 was identified by LC/MS.

$C_{20}H_{25}N$ M + 1:280.21

Synthesis of Compound 2

2.9 g of Intermediate 2-2 was added to RBF, and 30 mL of THF was added dropwise thereto under nitrogen conditions. nBuLi (2.0 M, 5.2 mL) was added to the reaction solution at 0° C., and stirred for 30 minutes. To the resultant reaction solution, a mixed solution in which 2.3 g of 2,4-dichloro-6-phenyl-1,3,5-triazine was dissolved in 30 mL of THF was slowly added dropwise. The reaction solution was stirred overnight at 70° C. After the reaction was completed, an extraction process was performed on the reaction solution by using ethylacetate. An organic layer collected therefrom was dried with magnesium sulfate, and a solvent was evaporated therefrom. A residue thus obtained was separated and purified by silica gel column chromatography, so as to obtain 4.9 g (yield: 67%) of Compound 2. Compound 2 was identified by LC-MS and $^1$H-NMR.

Synthesis Example 2: Synthesis of Compound 4

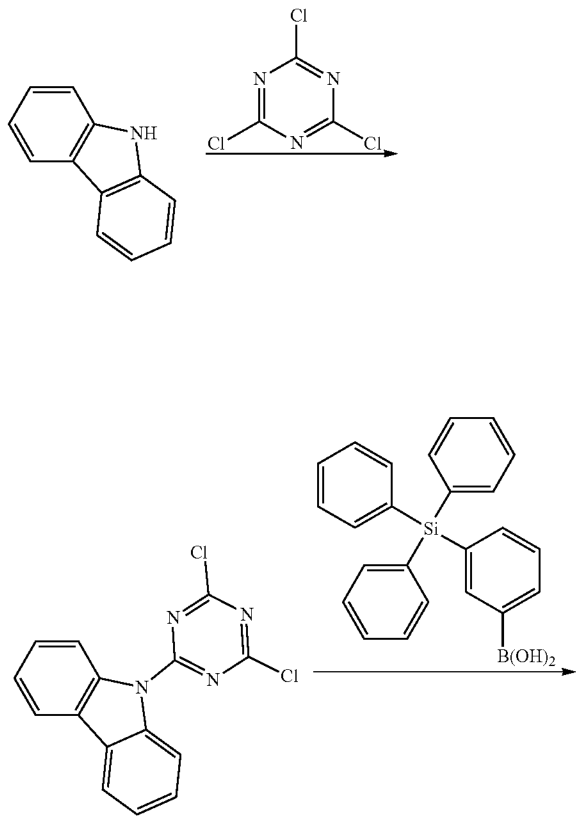

4-1

-continued

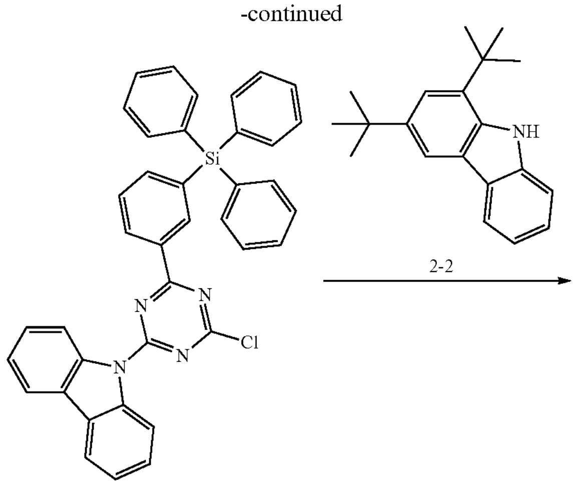

4-2

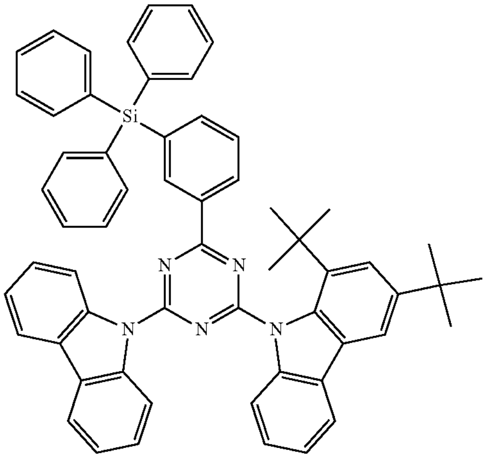

4

Synthesis of Intermediate 4-1

Carbazole and nBuLi were reacted, and cyanuric chloride was added thereto and stirred overnight at 70° C., so as to obtain Intermediate 4-1. Intermediate 4-1 was identified by LC/MS. $C_{15}H_8Cl_2N_4$ M+1: 315.07

Synthesis of Intermediate 4-2

Intermediate 4-1 and (3-(triphenylsilyl)phenyl)boronic acid (CAS #=1253912-58-1) were reacted in the presence of $Pd(PPh_3)_2Cl_2$ (0.01 eq) catalyst, so as to obtain Intermediate 4-2. Intermediate 4-2 was identified by LC/MS.

$C_{39}H_{27}ClN_4Si$ M + 1:615.11

Synthesis of Compound 4

3.4 g of Intermediate 4-2, 1.54 g of Intermediate 2-2, 0.2 g of $Pd_2(dba)_3$, 0.2 mL of $P(tBu)_3$ (50 wt % in xylene), 1.6 g of NaOtBu, and 50 mL of o-xylene were added to RBF, and stirred overnight at 160° C. After the reaction was completed, an extraction process was performed on the reaction solution by using ethylacetate. An organic layer collected therefrom was dried with magnesium sulfate, and a solvent was evaporated therefrom. A residue thus obtained was separated and purified by silica gel column chromatography, so as to obtain 3.4 g (yield: 72%) of Compound 4. Compound 4 was identified by LC-MS and $^1$H-NMR.

Synthesis Example 3: Synthesis of Compound 5

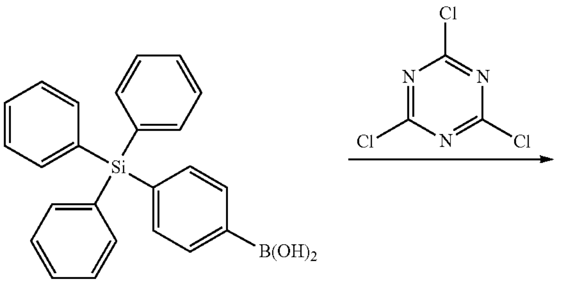

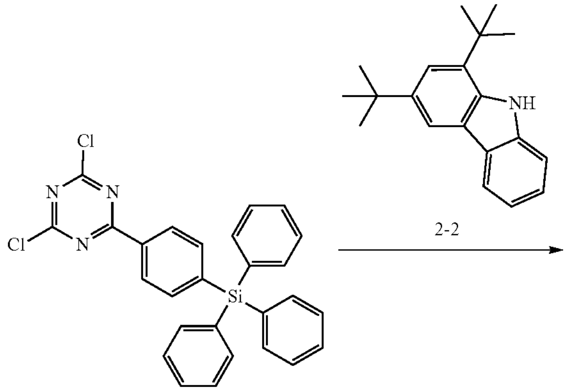

5-1

-continued

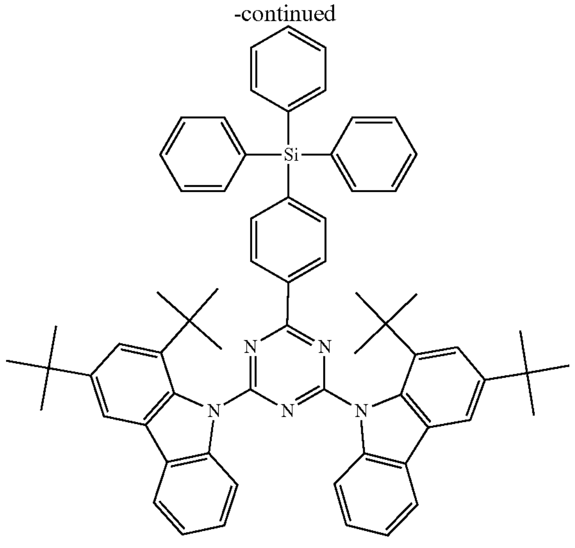

5

Synthesis of Intermediate 5-1

Cyanuric chloride (1 eq) and (4-(triphenylsilyl)phenyl) boronic acid (CAS #=852475-03-7, 1 eq) were reacted in the presence of $Pd(PPh_3)_2Cl_2$ (0.01 eq), so as to obtain Intermediate 5-1. Intermediate 5-1 was identified by LC/MS.

$C_{27}H_{19}Cl_2N_3Si$ M + 1:484.01

Synthesis of Compound 5

5.2 g of Intermediate 5-1, 3.0 g of Intermediate 2-2, 0.39 g of $Pd_2(dba)_3$, 0.2 mL of $P(tBu)_3$, 3 g of NaOtBu, and 50 mL of o-xylene were added to RBF, and stirred overnight at 160° C. After the reaction was completed, an extraction process was performed on the reaction solution by using ethylacetate. An organic layer collected therefrom was dried with magnesium sulfate, and a solvent was evaporated therefrom.

A residue thus obtained was separated and purified by silica gel column chromatography, so as to obtain 5.7 g (yield: 55%) of Compound 5. Compound 5 was identified by LC-MS and $^1$H-NMR.

Synthesis Example 4: Synthesis of Compound 23

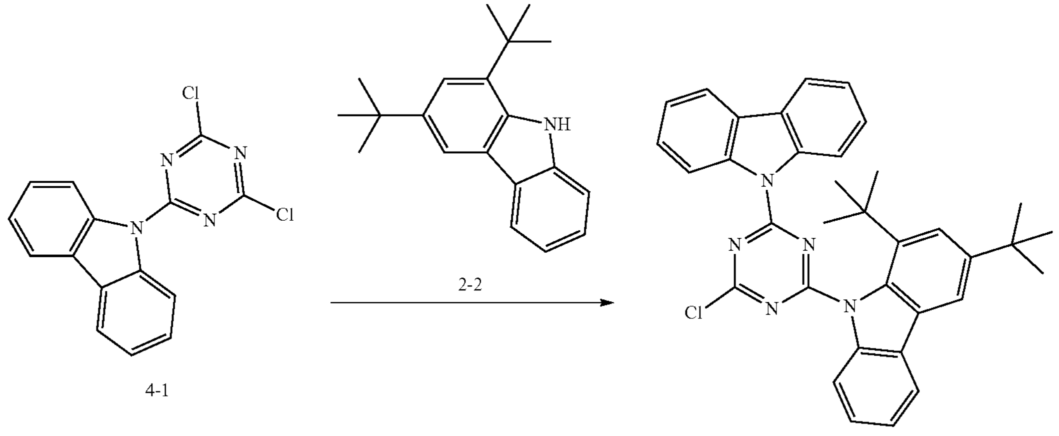

4-1

2-2

23-1

+

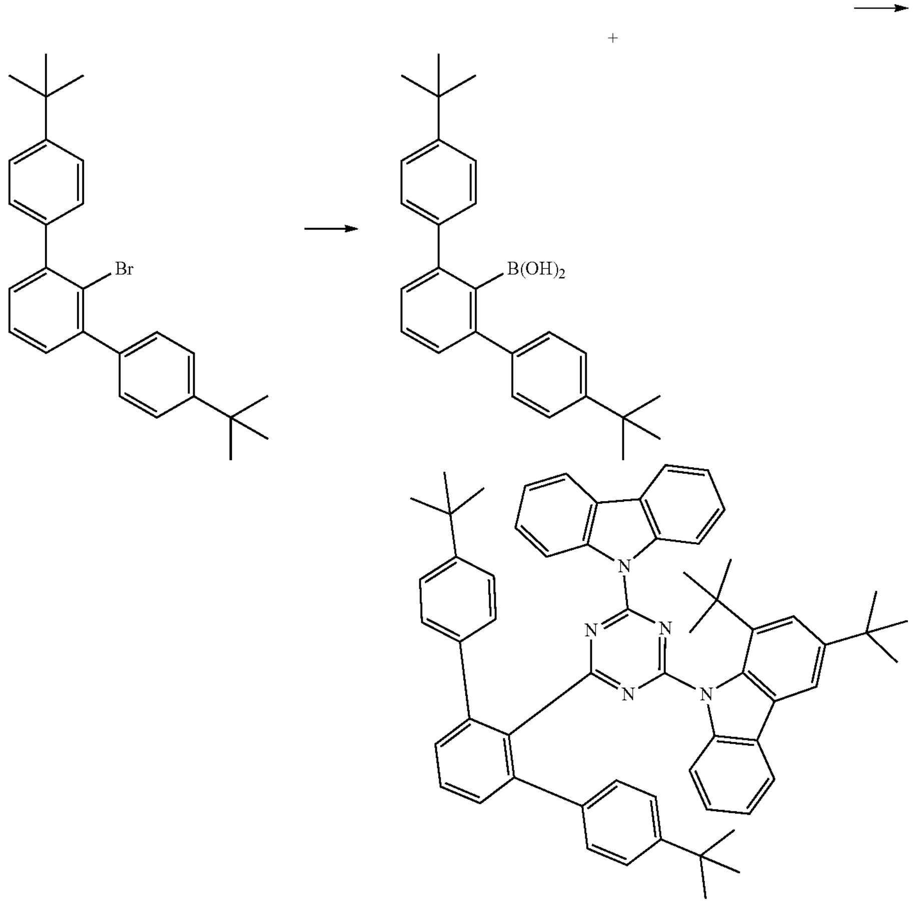

23

Synthesis of Intermediate 23-1

Intermediate 4-1 and Intermediate 2-2 were reacted, so as to synthesize Intermediate 23-1. Intermediate 23-1 was identified by LC/MS. $C_{35}H_{32}ClN_5$ M+1: 558.21

Synthesis of Intermediate 23-2

2'-bromo-4,4"-di-tert-butyl-1,1':3',1"-terphenyl (CAS #=332104-80-0) and nBuLi were reacted, and $B(OMe)_3$ was added dropwise thereto. The mixed solution was stirred overnight, so as to obtain Intermediate 23-2. Intermediate 23-2 was identified by LC/MS. $C_{21}H_{31}BO_2$ M+1:387.19

Synthesis of Compound 23

2.6 g of Intermediate 23-1, 2.2 g of Intermediate 23-2, 0.21 g of tetrakis(triphenylphosphine)palladium, and 1.6 g of potassium carbonate were added to a reaction vessel, and dissolved in 40 mL of toluene, 10 mL of ethanol, and 10 mL of distilled water. The mixed solution was refluxed for 24 hours. After the reaction was completed, an extraction process was performed on the reaction solution by using ethylacetate. An organic layer collected therefrom was dried with magnesium sulfate, and a solvent was evaporated therefrom. A residue thus obtained was separated and purified by silica gel column chromatography, so as to obtain 2.5 g (yield: 61%) of Compound 23. Compound 23 was identified by LC-MS and $^1$H-NMR.

Synthesis Example 5: Synthesis of Compound 28

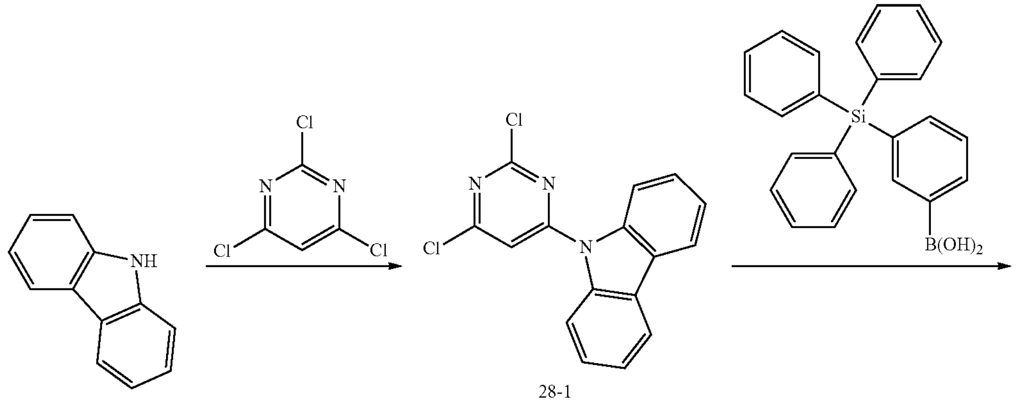

28-1

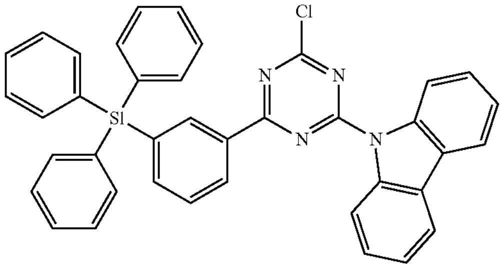

28-2

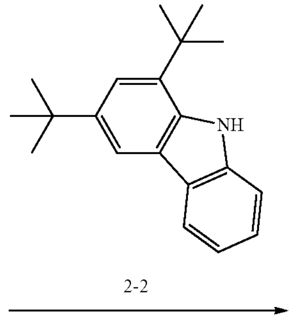

2-2

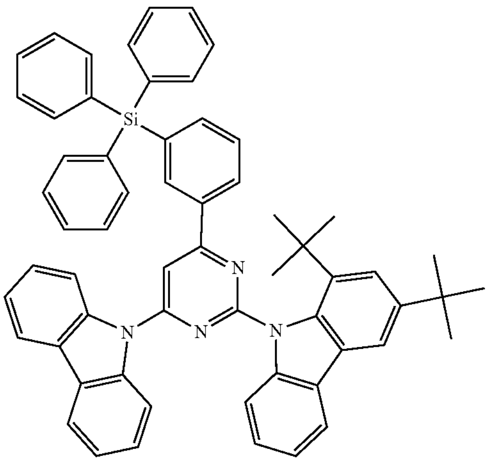

28

Synthesis of Intermediate 28-1

Carbazole (1 eq) and n-BuLi (1 eq) were reacted, and trichloripyrimidine (1 eq) was also reacted therewith, so as to obtain Intermediate 28-1. Intermediate 28-1 was identified by LC/MS. $C_{16}H_9Cl_2N_3$ M+1: 314.07

Synthesis of Intermediate 28-2

Intermediate 2-2 and Intermediate 28-1 were reacted in the presence of $Pd(PPh_3)_2Cl_2$ catalyst, so as to obtain Intermediate 28-2. Intermediate 28-2 was identified by LC/MS.

C40H28ClN3Si M + 1:614.11

Synthesis of Compound 28

1.9 g of Intermediate 28-2, 0.9 g of Intermediate 2-2, 0.11 g of $Pd_2(dba)_3$, 0.05 mL of $P(tBu)_3$, 0.9 g of NaOtBu, and 30 mL of o-xylene were added to RBF, and stirred overnight at 160° C. After the reaction was completed, an extraction process was performed on the reaction solution by using ethylacetate. An organic layer collected therefrom was dried with magnesium sulfate, and a solvent was evaporated therefrom.

A residue thus obtained was separated and purified by silica gel column chromatography, so as to obtain 1.2 g (yield: 44%) of Compound 28. Compound 28 was identified by LC-MS and $^1$H-NMR.

Synthesis Example 6: Synthesis of Compound 30

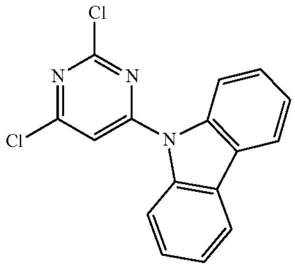

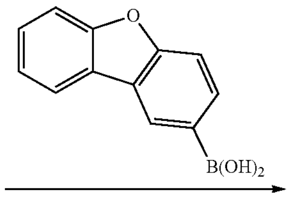

28-1

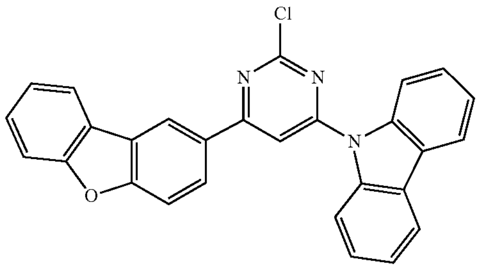

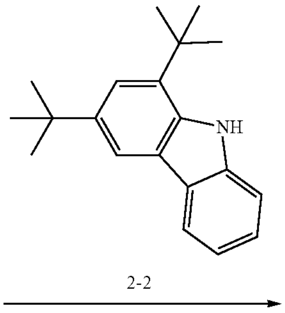

2-2

30-1

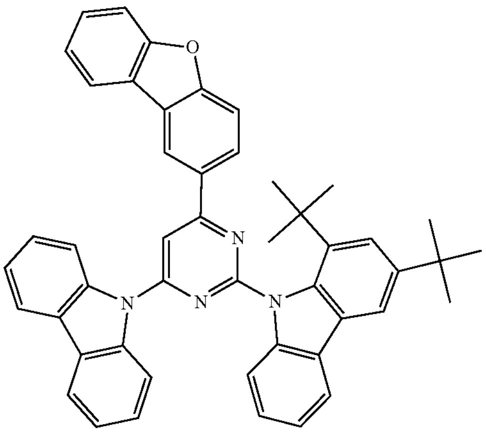

30

Synthesis of Intermediate 30-1

Intermediate 28-1 and dibenzo[b,d]furan-2-ylboronic acid (CAS #=402936-15-6) were reacted in the presence of $Pd(PPh_3)_2Cl_2$ catalyst, so as to obtain Intermediate 30-1. Intermediate 30-1 was identified by LC/MS. $C_{28}H_{16}ClN_3O$ M+1: 446.13

Synthesis of Compound 30

4.5 g of Intermediate 30-1, 2.8 g of Intermediate 2-2, 0.37 g of $Pd_2(dba)_3$, 0.2 mL of $P(tBu)_3$, 2.9 g of NaOtBu, and 50 mL of o-xylene were added to RBF, and stirred overnight at 160° C. After the reaction was completed, an extraction process was performed on the reaction solution by using ethylacetate. An organic layer collected therefrom was dried with magnesium sulfate, and a solvent was evaporated therefrom.

A residue thus obtained was separated and purified by silica gel column chromatography, so as to obtain 1.8 g (yield: 86%) of Compound 30. Compound 30 was identified by LC-MS and $^1$H-NMR.

Synthesis Example 7: Synthesis of Compound 41

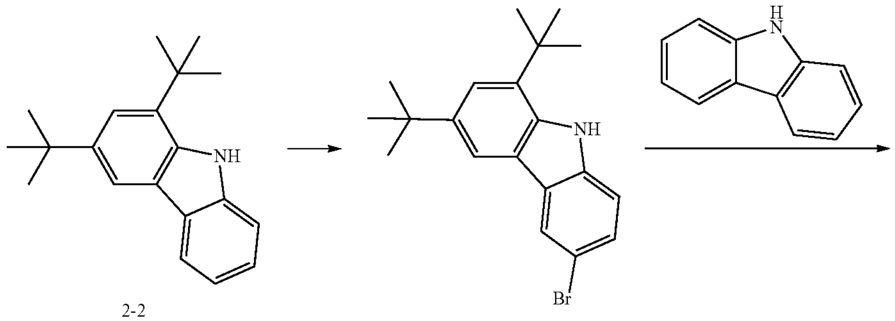

2-2

41-1

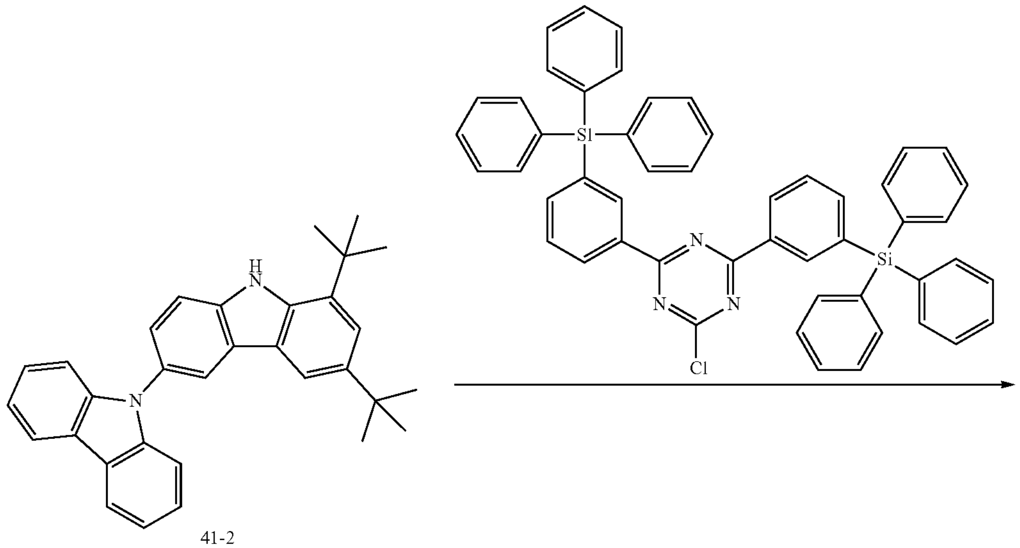

41-2

-continued

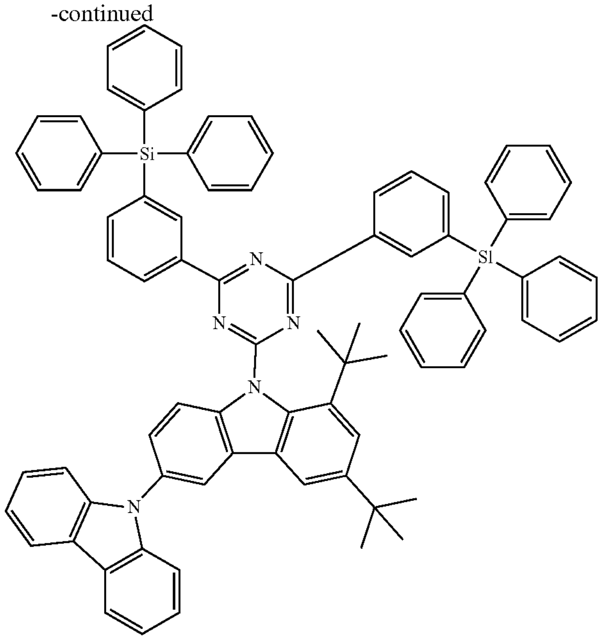

41

Synthesis of Intermediate 41-1

Intermediate 2-2 and N-bromosuccinimide were reacted in the presence of DMF solvent, so as to obtain Intermediate 41-1. Intermediate 41-1 was identified by LC/MS. $C_{20}H_{24}BrN$ M+1: 358.12

Synthesis of Intermediate 41-2

Intermediate 41-1 and carbazole were reacted in the presence of $Pd_2dba_3$ catalyst, so as to obtain Intermediate 41-2. Intermediate 41-2 was identified by LC/MS.

$C_{32}H_{32}N_2$ M + 1:334.23

Synthesis of Compound 41

1.8 g of Intermediate 41-2, 3.9 g of 2-chloro-4,6-bis(3-(triphenylsilyl)phenyl)-1,3,5-triazine (CAS #=2422046-28-2), 0.15 g of $Pd_2(dba)_3$, 0.1 mL of $P(tBu)_3$, 0.1 g of NaOtBu, and 30 mL of o-xylene were added to RBF, and stirred overnight at 160° C. After the reaction was completed, an extraction process was performed on the reaction solution by using ethylacetate. An organic layer collected therefrom was dried with magnesium sulfate, and a solvent was evaporated therefrom. A residue thus obtained was separated and purified by silica gel column chromatography, so as to obtain 1.33 g (yield: 49%) of Compound 41. Compound 41 was identified by LC-MS and $^1$H-NMR.

Table 1 shows $^1$H NMR and LC-MS of the synthesized compounds. Synthesis methods for other compounds than the compounds shown in Table 1 may be readily recognized by those skilled in the technical field by referring to the synthesis paths and source materials described above.

TABLE 1

| | | LC-MS | |
|---|---|---|---|
| Compound | $^1$H-NMR ($CDCl_3$, 500 MHZ) | calc. | Found [M + 1] |
| 2 | 8.56 (d) 2H, 8.37 (d) 2H, 8.15 (d) 2H, 7.93 (d) 2H, 7.51 (t) 3H, 7.36 (t) 2H, 7.18-11 (m) 4H, 1.36 (s) 18H, 1.31 (s) 18H | 711.43 | 712.41 |
| 4 | 8.57-8.53 (m) 3H, 8.37 (d) 1H, 8.17 (d) 1H, 7.96-7.92 (m) 3H, 7.88 (d) 1H, 7.64 (t) 1H, 7.56 (d) 1H, 7.48-7.32 (m) 18H, 7.18-7.13 (m) 4H, 1.34 (s) 18H, 1.32 (s) 18H | 857.39 | 858.37 |
| 5 | 8.56 (d) 2H, 8.15 (d) 2H, 7.93 (d) 2H, 7.88-7.4 (m) 2H, 7.67-7.63 (m) 2H, 7.48-7.32 (m) 17H, 7.17-7.13 (m) 4H, 1.36 (s) 18H, 1.31 (s) 18H | 969.62 | 970.61 |
| 23 | 8.57-8.54 (m) 3H, 8.17 (d) 1H, 8.05 (d) 2H, 7.96-7.93 (m) 3H, 7.82 (t) 1H, 7.38-7.30 (m) 11H, 7.17-7.14 (m) 4H, 1.36 (s) 9H, 1.32 (s) 18H, 1.30 (s) 9H | 863.49 | 864.43 |
| 28 | 8.57-8.53 (m) 3H, 8.16 (d) 1H, 7.95-7.92 (m) 4H, 7.87 (s) 1H, 7.63 (t) 1H, 7.62 (s) 1H, 7.54 (d) 1H, 7.48-7.35 (m) 15H, 7.37-7.32 (m) 2H, 7.17-7.12 (m) 4H, 1.35 (s) 9H, 1.32 (s) 9H | 856.40 | 857.41 |
| 30 | 8.54 (d) 1H, 8.19-8.15 (m) 3H, 7.99-7.95 (m) 2H, 7.90 (d) 1H, 7.83 (s) 1H, 7.77 (d) 1H, 7.58-7.50 (m) 5H, 7.40 (t) 1H, 7.35 (t) 1H, 7.29 (t) 1H, 7.20 (t) 2H, 7.17-7.12 (m) 2H, 1.36 (s) 9H, 1.32 (s) 9H | 688.32 | 689.31 |
| 41 | 8.58 (d) 2H, 8.32 (d) 1H, 8.16 (s) 1H, 8.09 (d) 1H, 7.93 (d) 2H, 7.87 (s) 1H, 7.75 (d) 1H, 7.67-7.62 (m) 2H, 7.48-7.35 (m) 30H, 7.34 (t) 2H, 7.15 (t) 2H, 7.11 (s) 1H, 1.36 (s) 9H, 1.31 (s) 9H | 1191.51 | 1192.49 |

Example 1

As an anode, a Corning 15 $\Omega/cm^2$ (1,200 Å) ITO glass substrate was cut to a size of 50 mm×50 mm×0.7 mm, sonicated with isopropyl alcohol and pure water each for 15 minutes, and cleaned by exposure to ultraviolet rays and ozone for 30 minutes. The ITO glass substrate was loaded onto a vacuum deposition apparatus.

NPB was vacuum-deposited on the ITO anode formed on the ITO glass substrate to form a hole injection layer having a thickness of 300 Å, and mCP was vacuum-deposited on the hole injection layer to form a hole transport layer having a thickness of 250 Å.

Compound 2 (host) and $Ir(pmp)_3$ (dopant) were co-deposited at a weight ratio of 92:8 on the hole transport layer to form an emission layer having a thickness of 250 Å.

TAZ was deposited on the emission layer to form an electron transport layer having a thickness of 200 Å, LiF was deposited on the electron transport layer to form an electron injection layer having a thickness of 10 Å, and Al was vacuum-deposited on the electron injection layer to form a LiF/Al electrode having a thickness of 100 Å, thereby completing the manufacture of a light-emitting device.

NPB

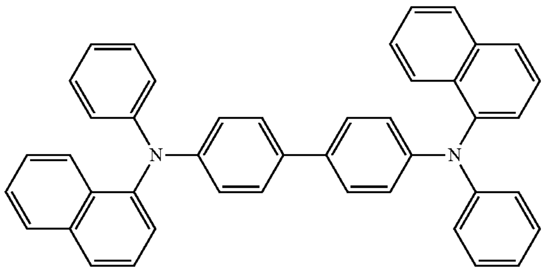

mCP

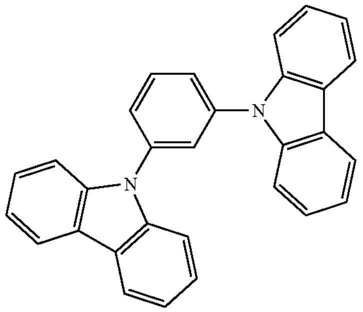

TAZ

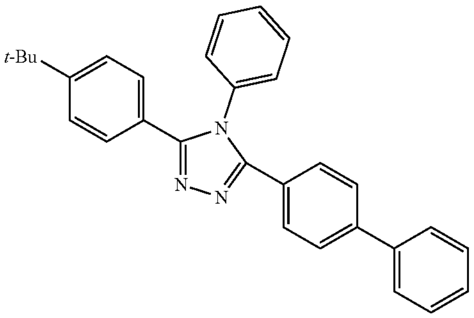

-continued

Ir(pmp)3

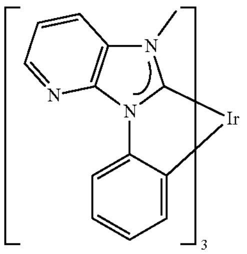

Examples 2 to 7 and Comparative Example 1

Light-emitting devices were manufactured in the same manner as in Example 1, except that compounds shown in Table 2 were respectively used instead of Compound 2 in forming an emission layer.

Evaluation Example 1

To evaluate characteristics of the light-emitting devices manufactured according to Examples 1 to 7 and Comparative Example 1, the driving voltage at the current density of 10 mA/ci, luminescence efficiency, and maximum external quantum efficiency (EQE) thereof were measured. The driving voltage of each of the light-emitting devices was measured using a source meter (Keithley Instrument Inc., 2400 series), and the EQE of each of the light-emitting devices was measured using an EQE measurement apparatus C9920-2-12 of Hamamatsu Photonics Inc. In evaluating the EQE, the luminance/current density was measured using a luminance meter that was calibrated for wavelength sensitivity, and the measured luminance/current density was converted into the EQE by assuming an angular luminance distribution (Lambertian) which introduced a perfect reflecting diffuser. The evaluation results of the characteristics of the light-emitting devices are shown in Table 2.

TABLE 2

| | Host in emission layer | Driving voltage (V) | Current density ($mA/cm^2$) | EQE (%) | Emission color |
|---|---|---|---|---|---|
| Example 1 | Compound 2 | 4.1 | 10 | 23.1 | Blue |
| Example 2 | Compound 4 | 4.1 | 10 | 21.1 | Blue |
| Example 3 | Compound 5 | 4.2 | 10 | 24.2 | Blue |
| Example 4 | Compound 23 | 4.2 | 10 | 22.3 | Blue |
| Example 5 | Compound 28 | 4.5 | 10 | 24.9 | Blue |
| Example 6 | Compound 30 | 4.3 | 10 | 25.8 | Blue |
| Example 7 | Compound 41 | 3.8 | 10 | 22.1 | Blue |
| Comparative Example 1 | Compound A | 4.8 | 10 | 17.2 | Blue |

TABLE 2-continued

| Host in emission layer | Driving voltage (V) | Current density ($mA/cm^2$) | EQE (%) | Emission color |
|---|---|---|---|---|
| 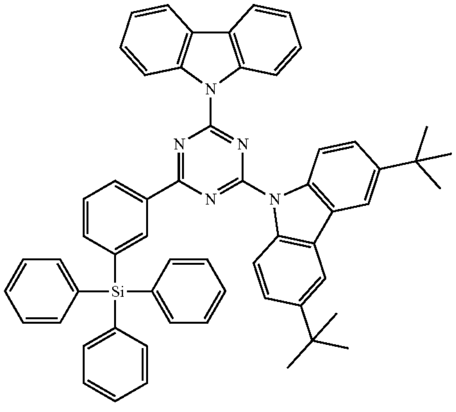 A | | | | |

Referring to Table 2, it was confirmed that the light-emitting devices of Examples 1 to 7 had low driving voltage and excellent EQE, as compared with the light-emitting device of Comparative Example 1.

According to the embodiments, the disclosure relates to a novel heterocyclic compound, a light-emitting device including the heterocyclic compound, and an electronic apparatus including the light-emitting device. The heterocyclic compound disclosed herein may have excellent characteristics in terms of electrical stability, molecular polarity, and luminescence efficiency, and accordingly, the light-emitting device and the electronic apparatus that include the heterocyclic compound may have high luminescence efficiency and a long lifespan.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the claims.

What is claimed is:

1. A light-emitting device comprising:

a first electrode;

a second electrode facing the first electrode;

an interlayer between the first electrode and the second electrode and comprising an emission layer; and at least one heterocyclic compound represented by Formula 1:

[Formula 1]

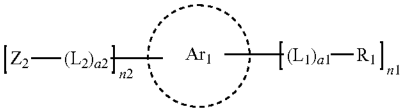

-continued

[Formula 2]

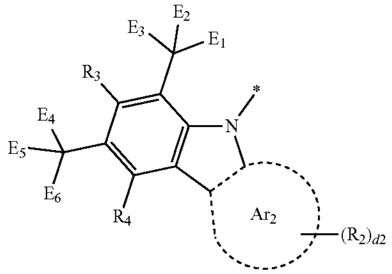

wherein in Formulae 1 and 2, $Z_2$ is a group represented by Formula 2, $Ar_1$ and $Ar_2$ are each independently a $C_5$-$C_{60}$ carbocyclic group or a $C_1$-$C_{60}$ heterocyclic group, provided that $Ar_1$ is not a benzene group or a pyridine qroup, $L_1$ is a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, $L_2$ is a single bond, a $C_1$-$C_{60}$ heterocyclic group unsubstituted or substituted with at least one $R_{10a}$, a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, provided that the benzene group is not substituted with a $C_3$-$C_{60}$ carbocyclic group, a1 and a2 are each independently an integer from 1 to 3, $R_1$ to $R_4$ are each independently:

hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$B(Q_1)(Q_2)$, —$C(=O)(Q_1)$, —$S(=O)_2(Q_1)$, or —$P(=O)(Q_1)(Q_2)$; or a group represented by Formula 2, $E_1$ to $E_6$ are each independently a $C_1$-$C_{60}$ alkyl group unsubstituted or substituted with at least one $R_{10a}$, a $C_2$-$C_{60}$ alkenyl group unsubstituted or substituted with at least one $R_{10a}$, or a $C_2$-$C_{60}$ alkynyl group unsubstituted or substituted with at least one $R_{10a}$, d2 is an integer from 0 to 10, n1 is an integer from 1 to 10, n2 is an integer from 1 to 5,

* indicates a binding site to a neighboring atom, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or a combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or a combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —$C_1$; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a $C_3$-$C_{60}$ carbocyclic group, a $C_1$-$C_{60}$ heterocyclic group, or a combination thereof.

2. The light-emitting device of claim 1, wherein the first electrode is an anode, the second electrode is a cathode, the interlayer further comprises:

a hole transport region between the emission layer and the second electrode; and an electron transport region between the emission layer and the second electrode, the hole transport region comprises a hole injection layer, a hole transport layer, an emission auxiliary layer, an electron blocking layer, or a combination thereof, and the electron transport region comprises a buffer layer, a hole blocking layer, an electron control layer, an electron transport layer, an electron injection layer, or a combination thereof.

3. The light-emitting device of claim 1, wherein the emission layer comprises the at least one heterocyclic compound represented by Formula 1.

4. The light-emitting device of claim 3, wherein the emission layer further comprises an organometallic compound represented by Formula 401:

$$M(L_{401})_{xc1}(L_{402})_{xc2}$$ [Formula 401]

[Formula 402]

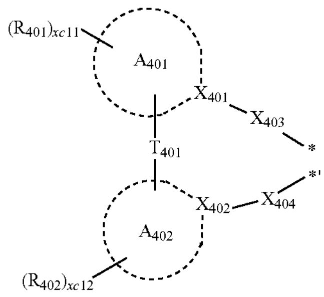

wherein in Formulae 401 and 402,

M is a transition metal, $L_{401}$ is a ligand represented by Formula 402, xc1 is 1, 2, or 3, when xc1 is 2 or more, two or more of $L_{401}$ groups are identical to or different from each other, $L_{402}$ is an organic ligand, xc2 is 0, 1, 2, 3, or 4, when xc2 is 2 or more, two or more of $L_{402}$ groups are identical to or different from each other, $X_{401}$ and $X_{402}$ are each independently nitrogen (N) or carbon (C), ring $A_{401}$ and ring $A_{402}$ are each independently a $C_3$-$C_{60}$ carbocyclic group or a $C_1$-$C_{60}$ heterocyclic group, $T_{401}$ is a single bond, *—O—*', *—S*', *—C(=O)—*', *—$N(Q_{411})$-*' *—$C(Q_{411})(Q_{412})$-*', *—$C(Q_{411})$=$C(Q_{412})$-*', *—$C(Q_{411})$=*', or *=C=*', $X_{403}$ and $X_{404}$ are each independently a chemical bond, O, S, $N(Q_{413})$, $B(Q_{413})$, $P(Q_{413})$, $C(Q_{413})(Q_{414})$, or $Si(Q_{413})(Q_{414})$, $Q_{411}$ to $Q_{414}$ are each independently the same as described in connection with $Q_1$ in Formula 1, $R_{401}$ and $R_{402}$ are each independently hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, or —$P(=O)(Q_{401})(Q_{402})$, $Q_{401}$ to $Q_{403}$ are each independently the same as described in connection with $Q_1$ in Formula 1, xc11 and xc12 are each independently an integer from 0 to 10, and

* and *' in Formula 402 each indicate a binding site to M in Formula 401.

5. An electronic apparatus comprising the light-emitting device of claim 1.

6. The electronic apparatus of claim 5, further comprising a thin-film transistor, wherein the thin-film transistor comprises a source electrode and a drain electrode, and the first electrode of the light-emitting device is electrically connected to the source electrode or the drain electrode.

7. The electronic apparatus of claim 5, further comprising:

a color filter, a color conversion layer, a touch screen layer, a polarizing layer, or a combination thereof.

8. A heterocyclic compound represented by Formula 1:

[Formula 1]

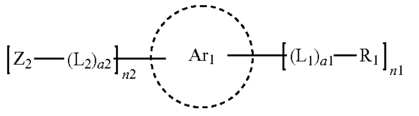

[Formula 2]

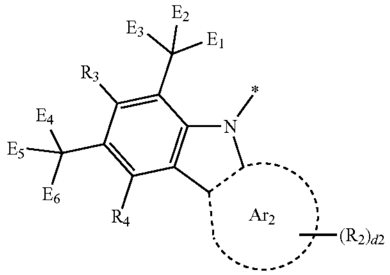

wherein in Formulae 1 and 2, $Z_2$ is a group represented by Formula 2, $Ar_1$ and $Ar_2$ are each independently a $C_5$-$C_{60}$ carbocyclic group or a $C_1$-$C_{60}$ heterocyclic group, provided that $Ar_1$ is not a benzene group or a pyridine group, $L_1$ is a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, $L_2$ is a single bond, a $C_1$-$C_{60}$ heterocyclic group unsubstituted or substituted with at least one $R_{10a}$, a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, provided that the benzene group is not substituted with a $C_3$-$C_{60}$ carbocyclic group, a1 and a2 are each independently an integer from 1 to 3, $R_1$ to $R_4$ are each independently:

hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$B(Q_1)(Q_2)$, —$C(=O)(Q_1)$, —$S(=O)_2(Q_1)$, or —$P(=O)(Q_1)(Q_2)$; or a group represented by Formula 2, $E_1$ to $E_6$ are each independently a $C_1$-$C_{60}$ alkyl group unsubstituted or substituted with at least one $R_{10a}$, a $C_2$-$C_{60}$ alkenyl group unsubstituted or substituted with at least one $R_{10a}$, or a $C_2$-$C_{60}$ alkynyl group unsubstituted or substituted with at least one $R_{10a}$, d2 is an integer from 0 to 10, n1 is an integer from 1 to 10, n2 is an integer from 1 to 5,

* indicates a binding site to a neighboring atom, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})$ ($Q_{12}$), —C(=O)($Q_{11}$), —S(=O)$_2$($Q_{11}$), —P(=O)($Q_{11}$)($Q_{12}$), or a combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or a combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —$C_1$; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a $C_3$-$C_{60}$ carbocyclic group, a $C_1$-$C_{60}$ heterocyclic group, or a combination thereof.

9. The heterocyclic compound of claim 8, wherein the heterocyclic compound represented by Formula 1 satisfies at least one of Conditions 1 and 2:

[Condition 1]

$Ar_1$ is a π electron-deficient nitrogen-containing $C_1$-$C_{60}$ cyclic group,

[Condition 2]

at least one of $R_1$(s) in the number of n1 is —Si($Q_1$)($Q_2$)($Q_3$).

10. The heterocyclic compound of claim 8, wherein n2 is an integer from 1 to 3.

11. The heterocyclic compound of claim 8, wherein the heterocyclic compound represented by Formula 1 is represented by Formula 1-A:

[Formula 1-A]

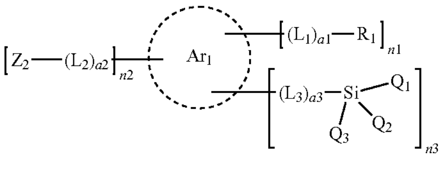

wherein in Formula 1-A, $Z_2$, $Ar_1$, $L_1$, $L_2$, n1, n2, a1, a2, $R_1$, and $Q_1$ to $Q_3$ are each the same as described in Formula 1, $L_3$ is the same as described in connection with Li in Formula 1, a3 is the same as described in connection with a1 in Formula 1, and n3 is an integer from 0 to 10.

12. The heterocyclic compound of claim 8, wherein $Ar_1$ is a cyclopentadiene group, an adamantane group, a norbornane group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, an indenoanthracene group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, or an azadibenzofuran group.

13. The heterocyclic compound of claim 8, wherein $L_1$ is:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ is the same as described in Formula 1.

14. The heterocyclic compound of claim 8, wherein $L_1$ is:

a single bond; or a group represented by one of Formulae 3-1 to 3-40:

3-1

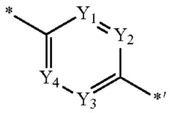

3-2

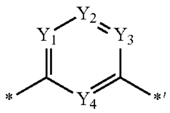

3-3

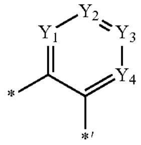

3-4

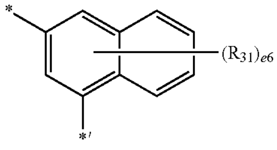

3-5

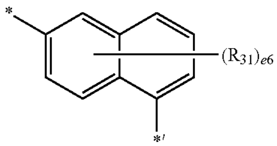

3-6

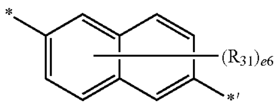

3-7

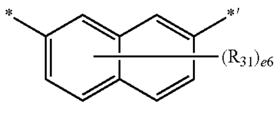

3-8

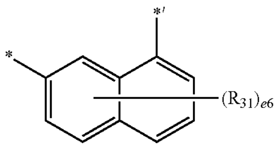

-continued 3-9

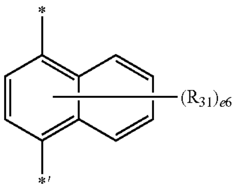

3-10

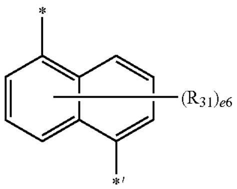

3-11

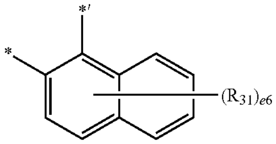

3-12

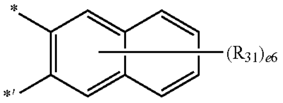

3-13

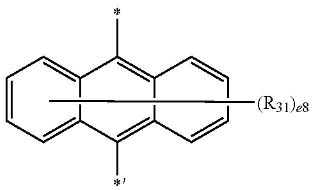

3-14

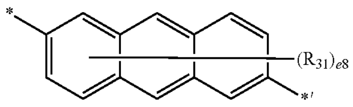

3-15

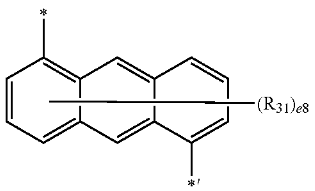

3-16

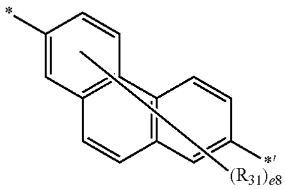

3-17

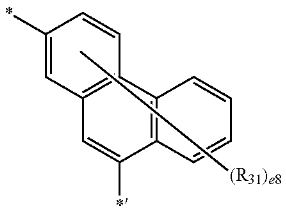

-continued
3-18
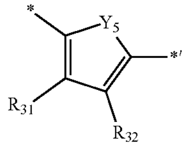
3-19
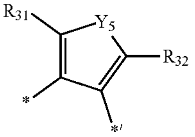
3-20
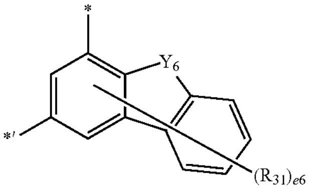
3-21
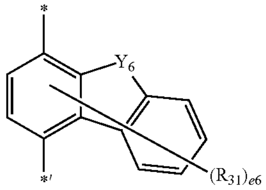
3-22
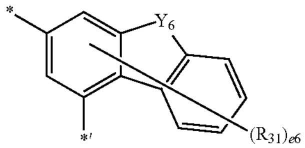
3-23
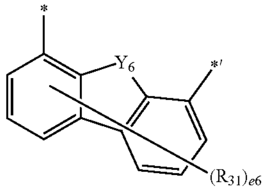
3-24
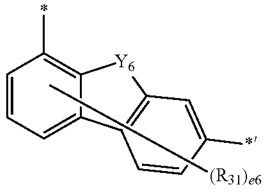
3-25
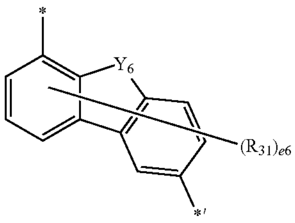
-continued
3-26
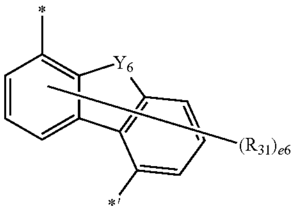
3-27
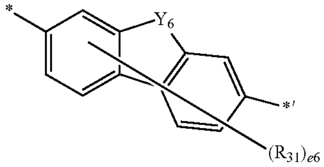
3-28
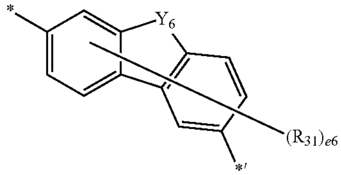
3-29
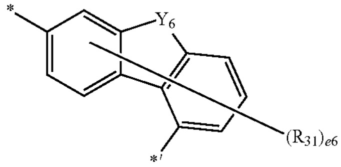
3-30
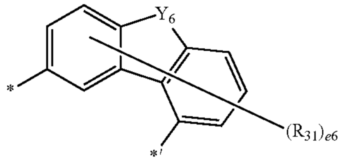
3-31
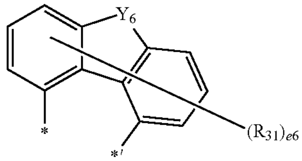
3-32
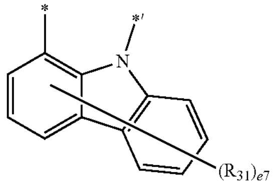
3-33
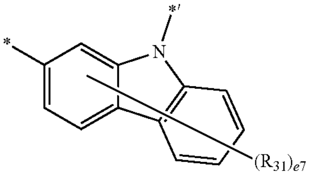

-continued 3-34

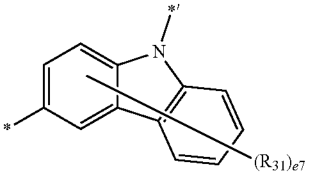

3-35

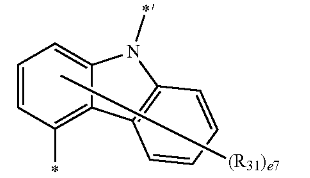

3-36

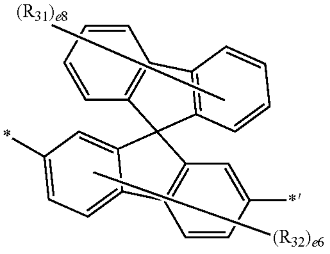

3-37

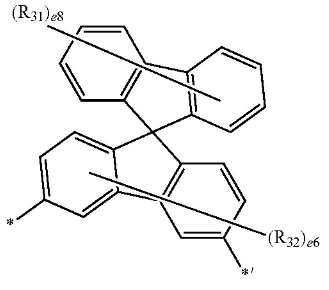

3-38

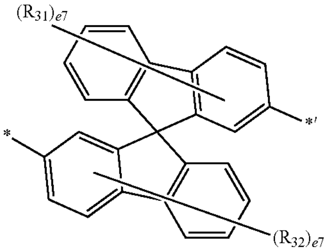

3-39

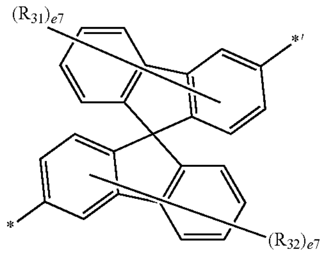

-continued 3-40

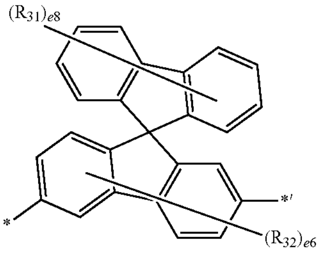

wherein in Formulae 3-1 to 3-40, $Y_1$ is N or $C(R_{33})$, $Y_2$ is N or $C(R_{34})$, $Y_3$ is N or $C(R_{35})$, $Y_4$ is N or $C(R_{36})$, $Y_5$ is O, S, or Se, $Y_6$ is O, S, Se, $N(R_{37})$, or $C(R_{37})(R_{38})$, $R_{31}$ to $R_{38}$ are each independently:

hydrogen, deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $—Si(Q_{11})(Q_{12})(Q_{13})$, $—B(Q_{11})(Q_{12})$, $—C(=O)(Q_{11})$, $—S(=O)_2(Q_{11})$, $—P(=O)(Q_{11})(Q_{12})$, or a combination thereof;

a $C_3$-$C_{60}$ carbocyclic group, a $C_1$-$C_{60}$ heterocyclic group, a $C_6$-$C_{60}$ aryloxy group; or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, $—Si(Q_{21})(Q_{22})(Q_{23})$, $—B(Q_{21})(Q_{22})$, $—C(=O)(Q_{21})$, $—S(=O)_2(Q_{21})$, $—P(=O)(Q_{21})(Q_{22})$, or a combination thereof; or $Si(Q_{31})(Q_{32})(Q_{33})$, $—B(Q_{31})(Q_{32})$, $—C(=O)(Q_{31})$, $—S(=O)_2(Q_{31})$, or $—P(=O)(Q_{31})(Q_{32})$, $Q_{11}$ to $Q_{13}$, $Q_{21}$ to $Q_{23}$, and $Q_{31}$ to $Q_{33}$ are each the same as described in Formula 1, e6 is an integer from 0 to 6, e7 is an integer from 0 to 7, e8 is an integer from 0 to 8, and

* and *' each indicate a binding site to a neighboring atom.

15. The heterocyclic compound of claim 8, wherein the heterocyclic compound represented by Formula 1 is represented by one of Formulae 1-1 to 1-5:

1-1

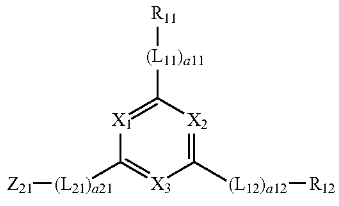

-continued 1-2

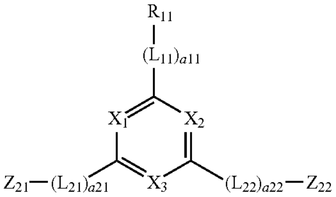

1-3

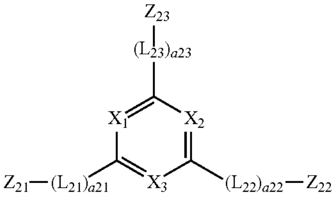

1-4

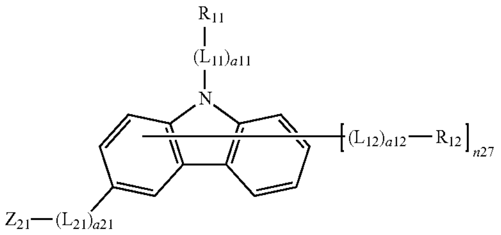

1-5

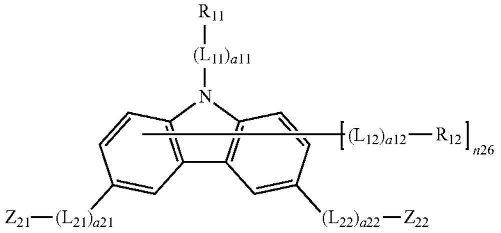

wherein in Formulae 1-1 to 1-5, $X_1$ is $C(R_{13})$ or N, $X_2$ is $C(R_{14})$ or N, $X_3$ is $C(R_{15})$ or N, $R_{11}$ to $R_{15}$ are each independently the same as described in connection with $R_1$ in Formula 1, $L_{11}$ and $L_{12}$ are each independently the same as described in connection with Li in Formula 1, a11 and a12 are each the same as described in connection with a1 in Formula 1, n26 is an integer from 1 to 6, n27 is an integer from 1 to 7, $L_{21}$ to $L_{23}$ are each independently the same as described in connection with $L_2$ in Formula 1, a21 to a23 are each independently the same as described in connection with a2 in Formula 1, and $Z_{21}$ to $Z_{23}$ are each independently the same as described in connection with $Z_2$ in Formula 1.

16. The heterocyclic compound of claim 15, wherein $R_{11}$ is $—Si(Q_1)(Q_2)(Q_3)$, and $Q_1$ to $Q_3$ are each the same as described in Formula 1.

17. The heterocyclic compound of claim 8, wherein $E_1$ to $E_6$ are each independently:

a $C_1$-$C_{20}$ alkyl group, a $C_2$-$C_{60}$ alkenyl group, or a $C_2$-$C_{60}$ alkynyl group; or a $C_1$-$C_{20}$ alkyl group, a $C_2$-$C_{60}$ alkenyl group, or a $C_2$-$C_{20}$ alkynyl group, each substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or a combination thereof.

18. The heterocyclic compound of claim 8, wherein the group represented by Formula 2 is represented by Formula 2-1:

[Formula 2-1]

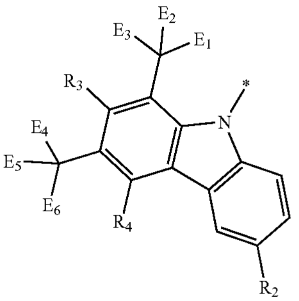

wherein in Formula 2-1, $E_1$ to $E_6$ and $R_2$ to $R_4$ are each the same as described in Formula 2, and

* indicates a binding site to a neighboring atom.

19. A heterocyclic compound, wherein the heterocyclic compound is one of Compounds 1 to 50:

1

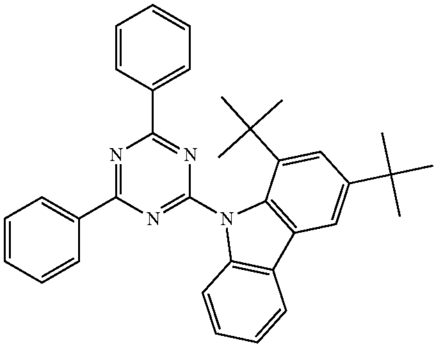

2

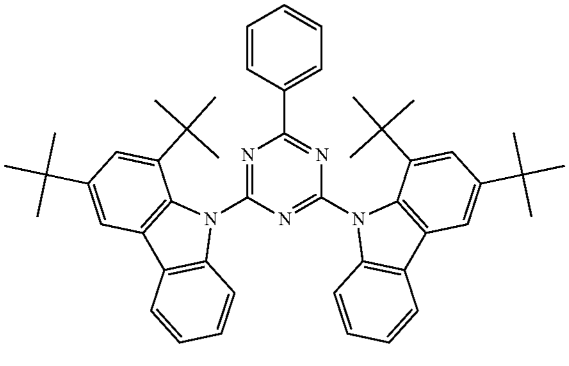

-continued
3
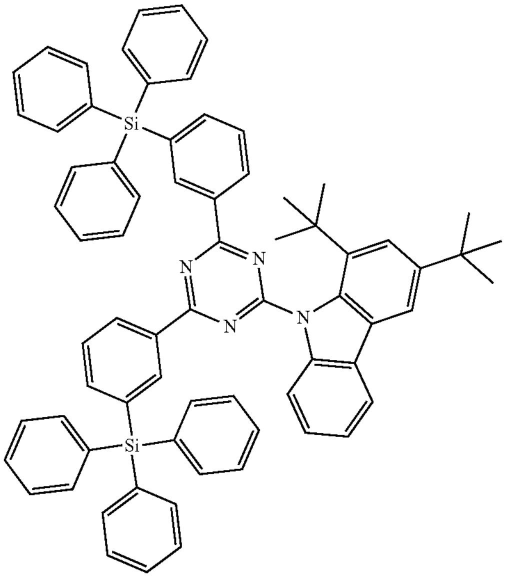
4
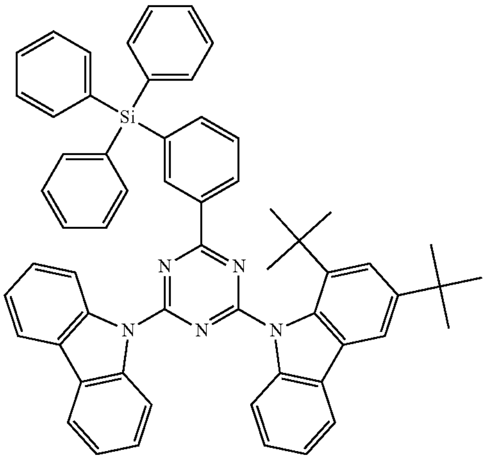
5
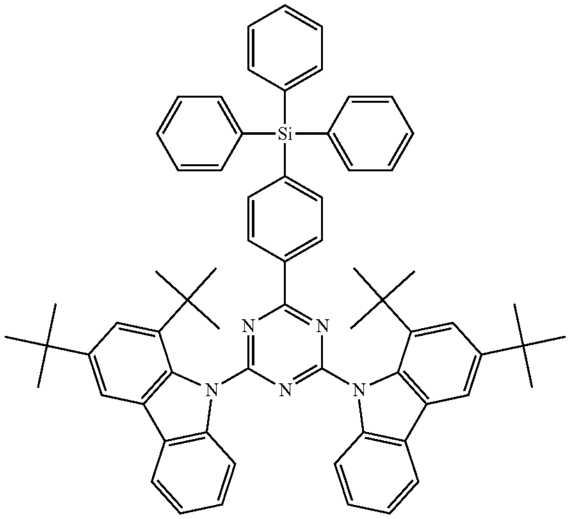
-continued
6
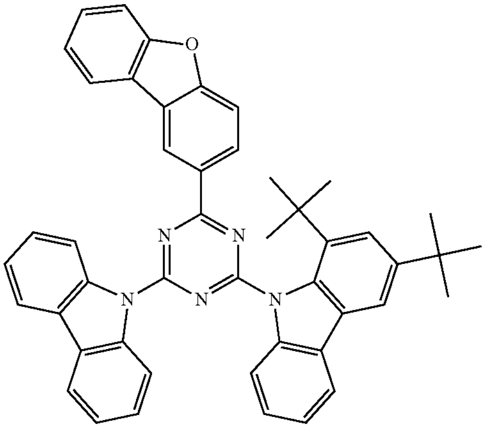
7
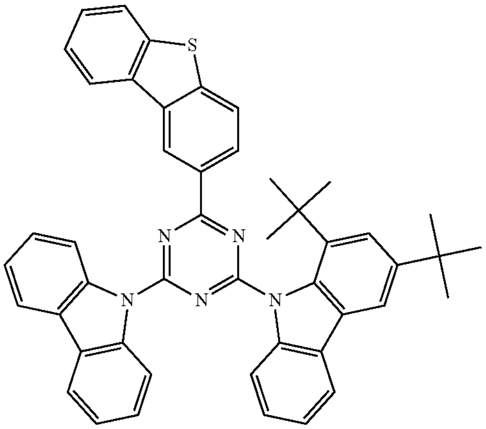
8
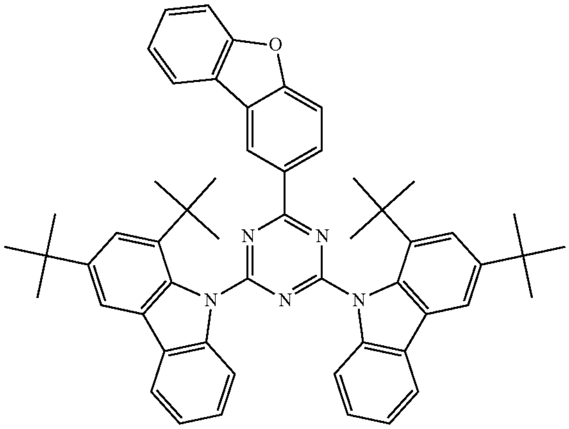

-continued
9
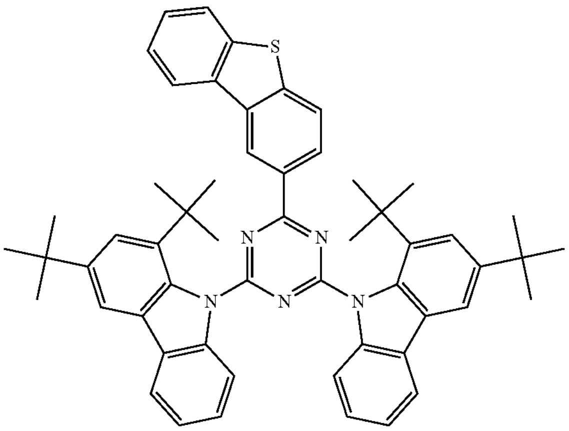
10
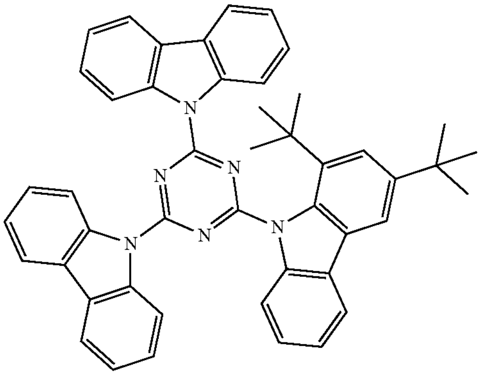
11
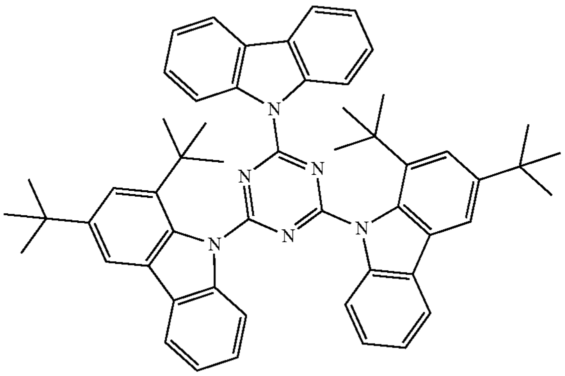
12
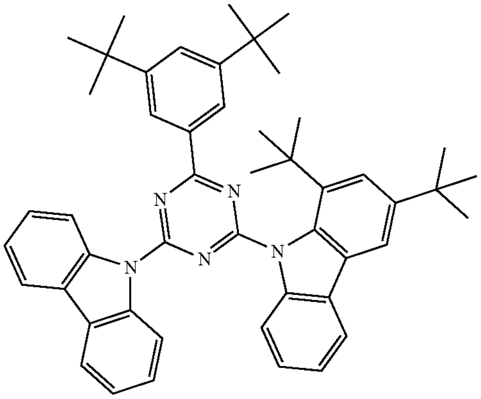
-continued
13
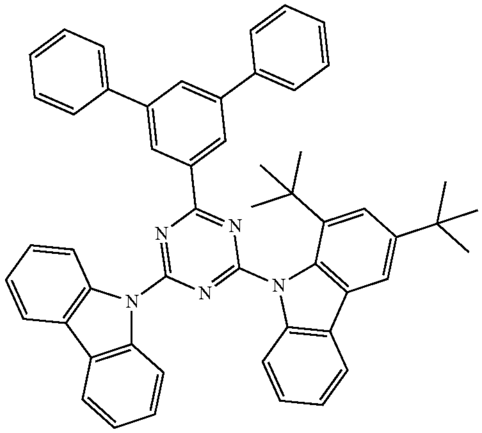
14
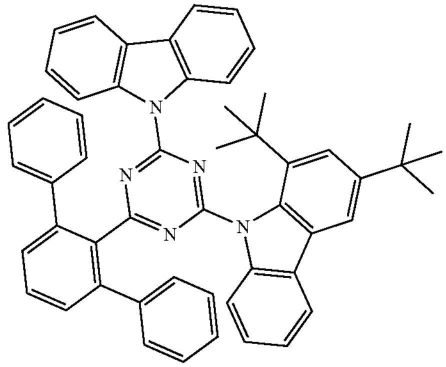
15
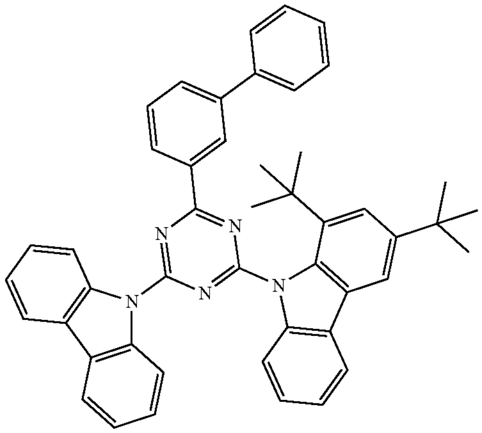

-continued
16
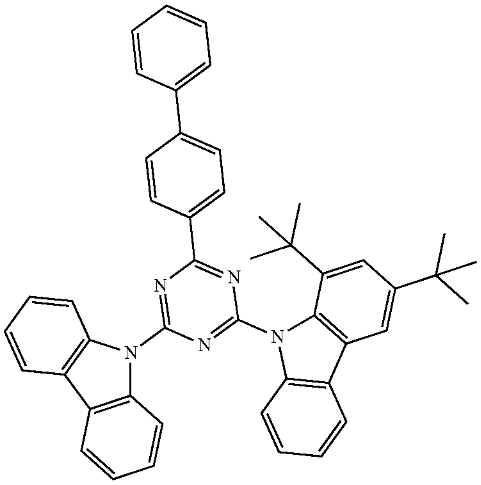
17
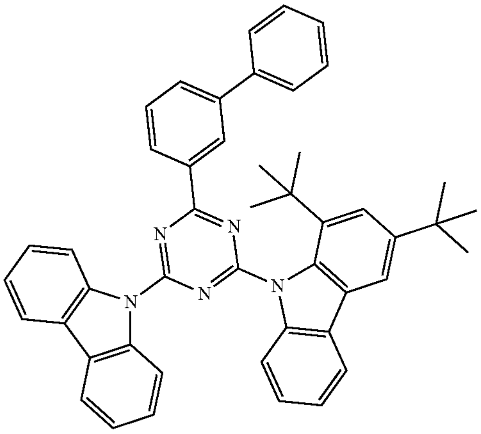
18
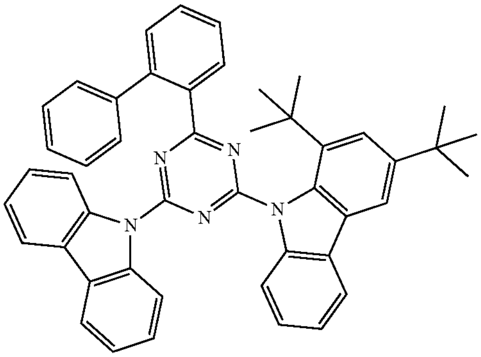
-continued
19
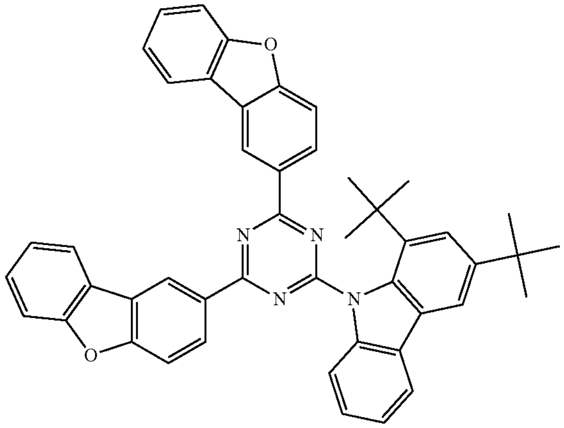
20
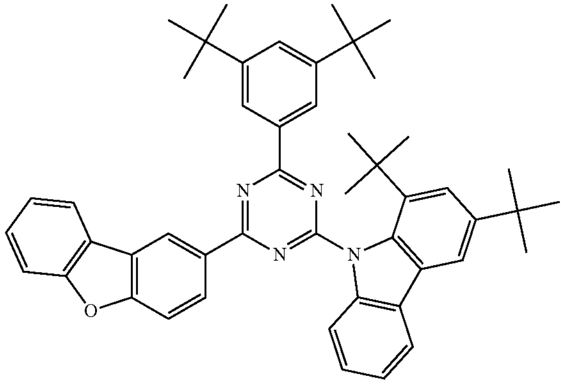
21
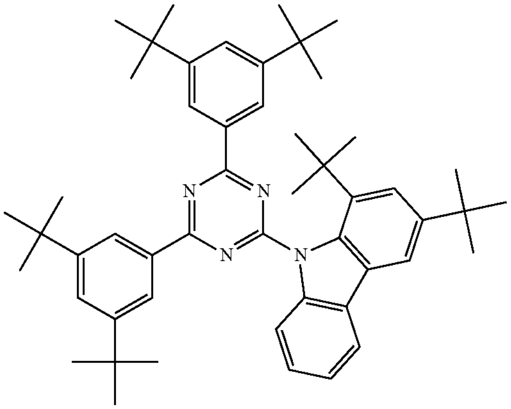

-continued
22
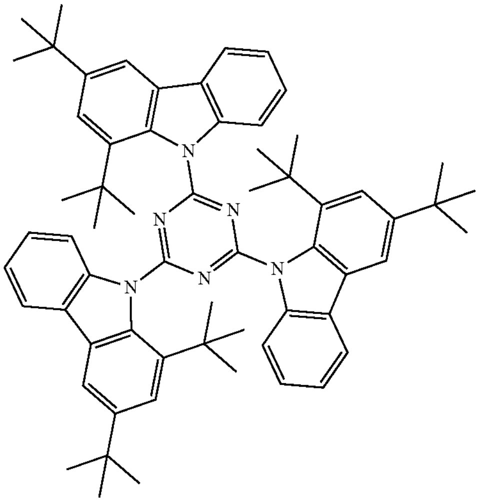
23
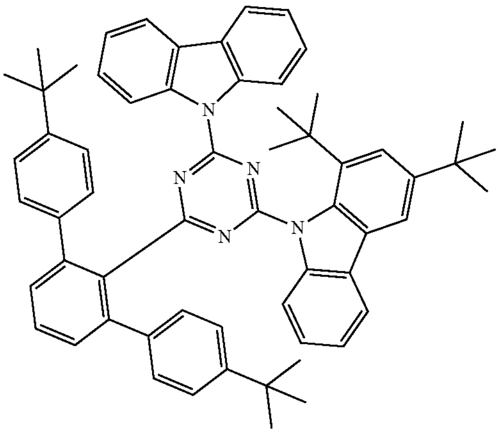
24
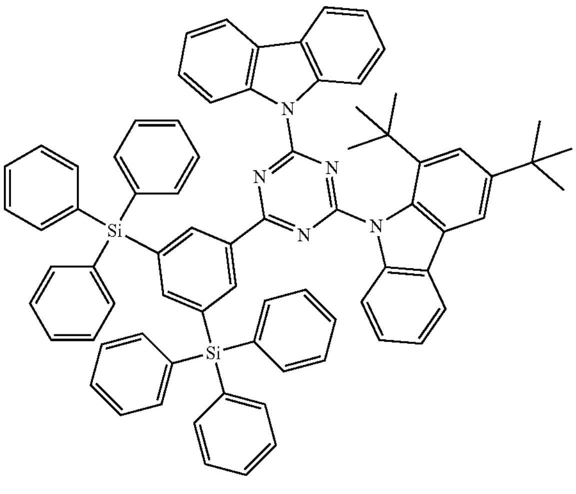
-continued
25
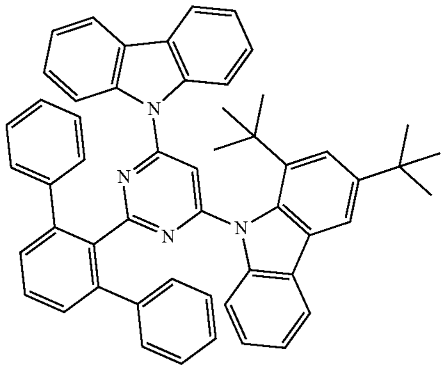
26
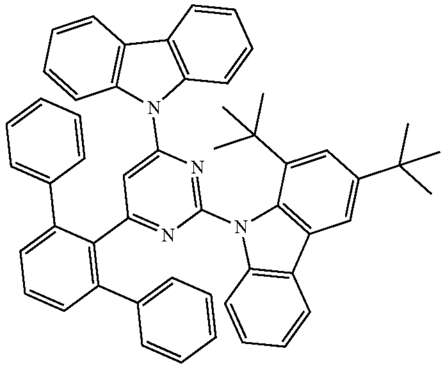
27
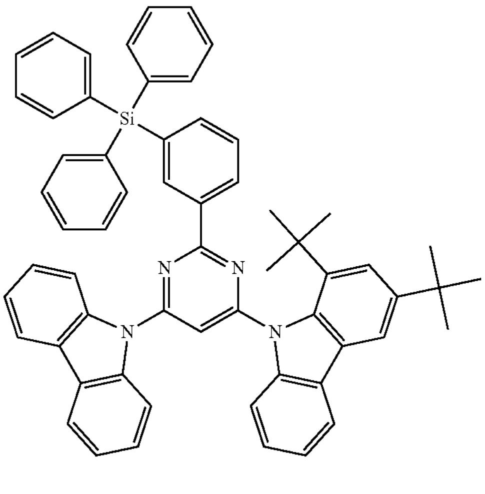

-continued
28
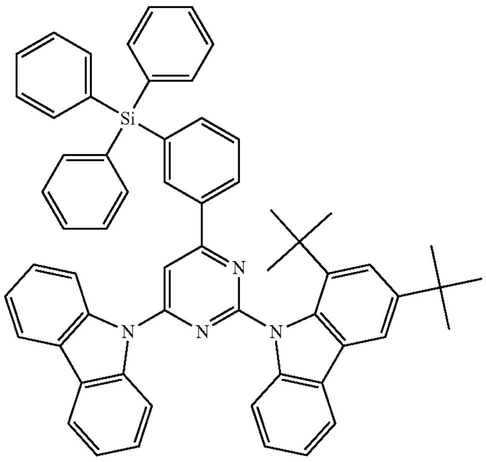
29
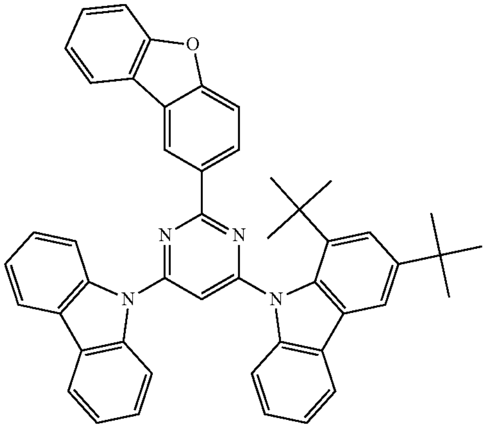
30
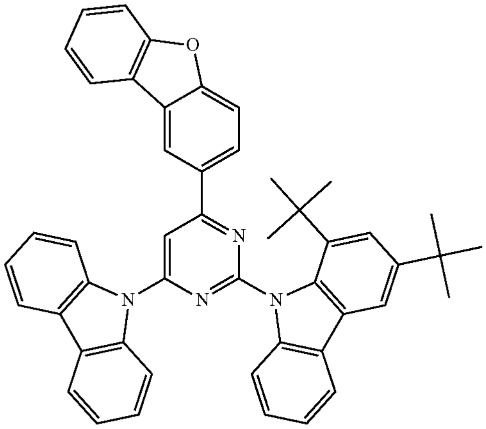
-continued
31
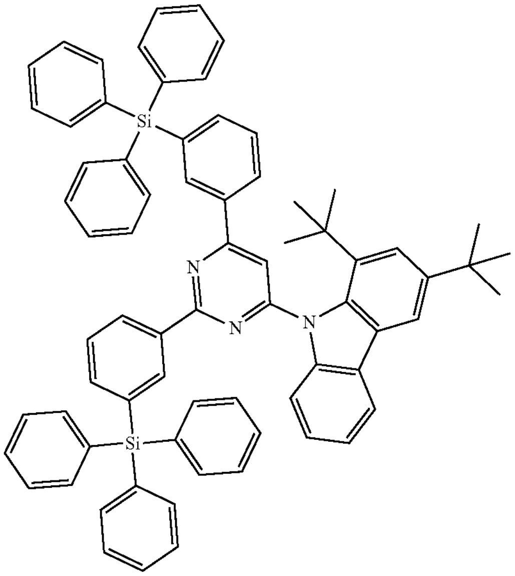
32
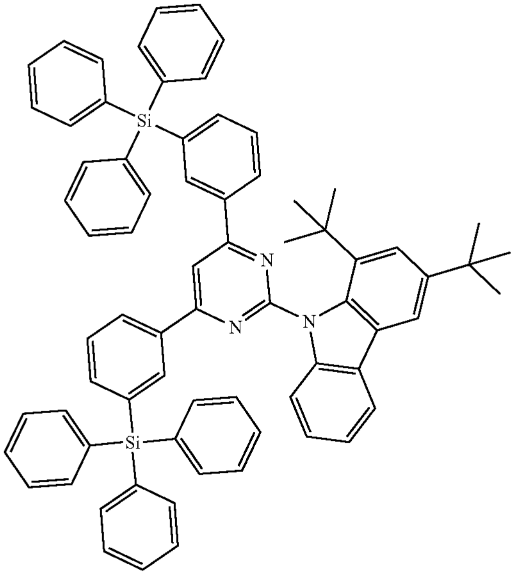

-continued
33
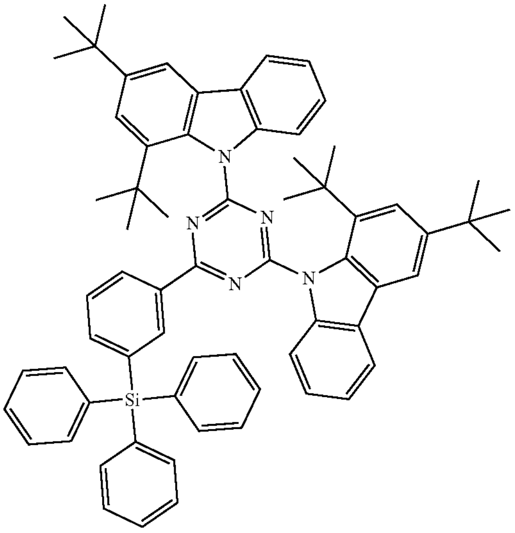
34
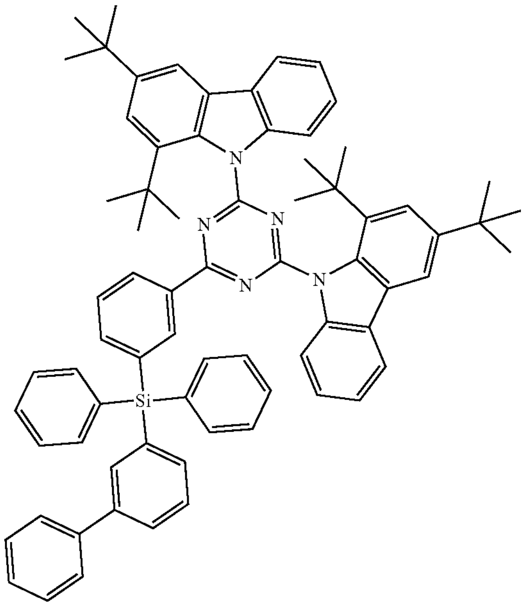
-continued
35
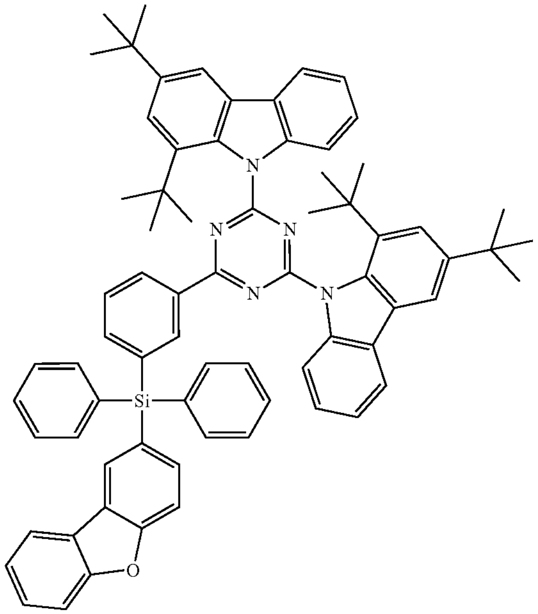
36
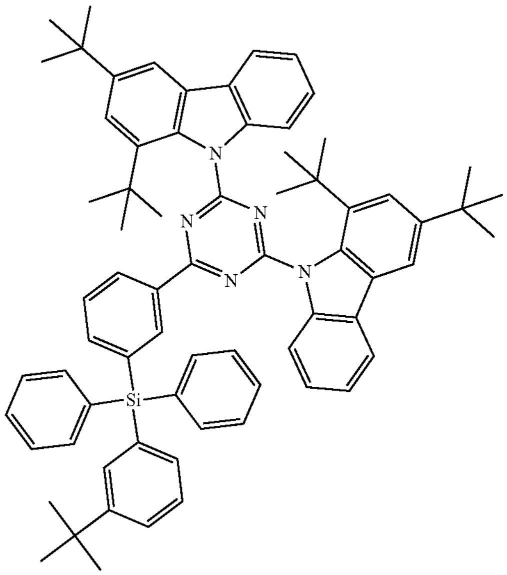

-continued
37
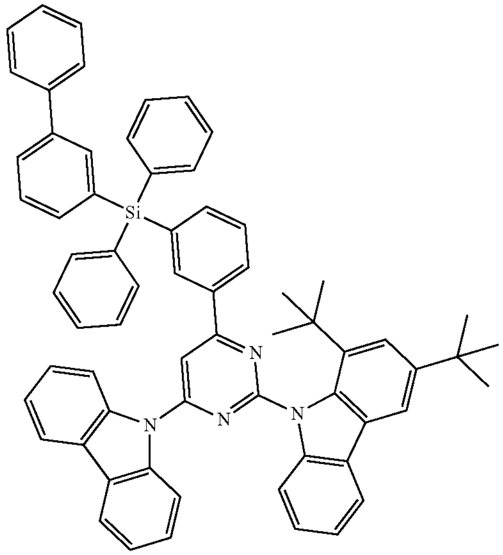
38
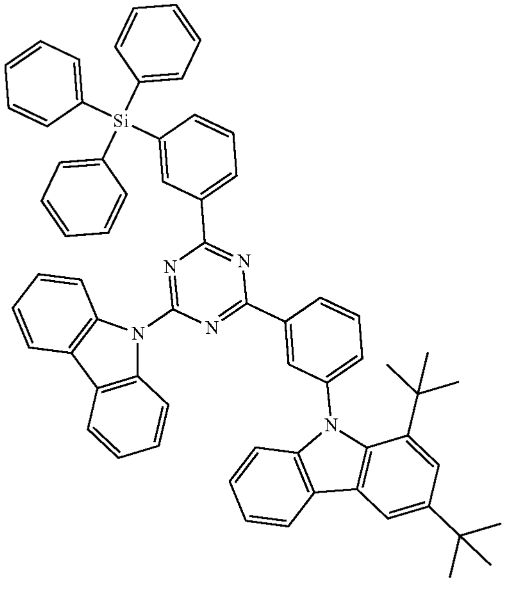
-continued
39
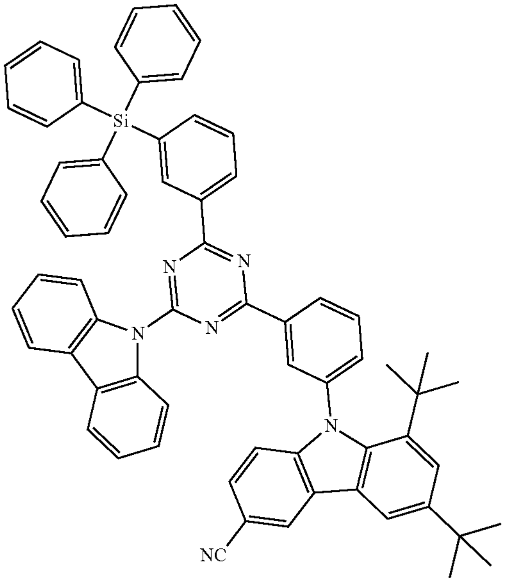
40
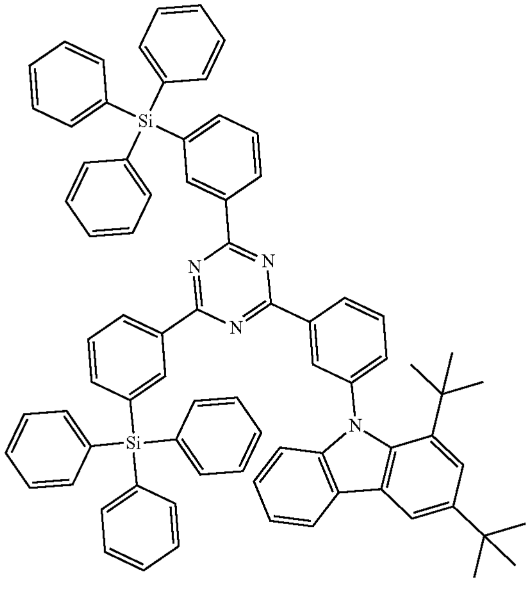

-continued
41
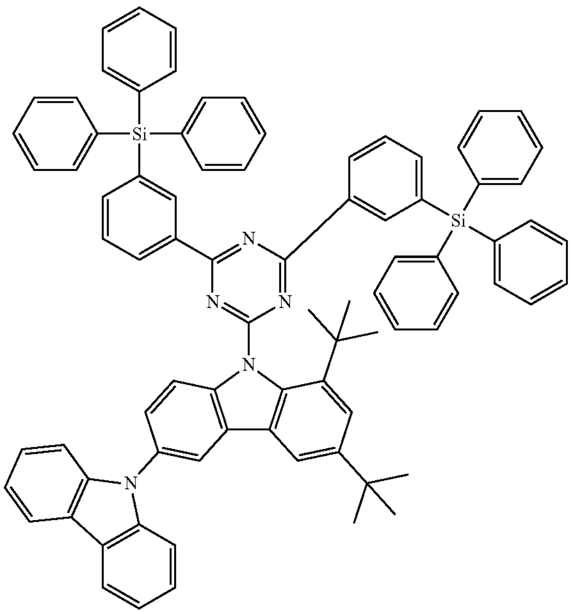
42
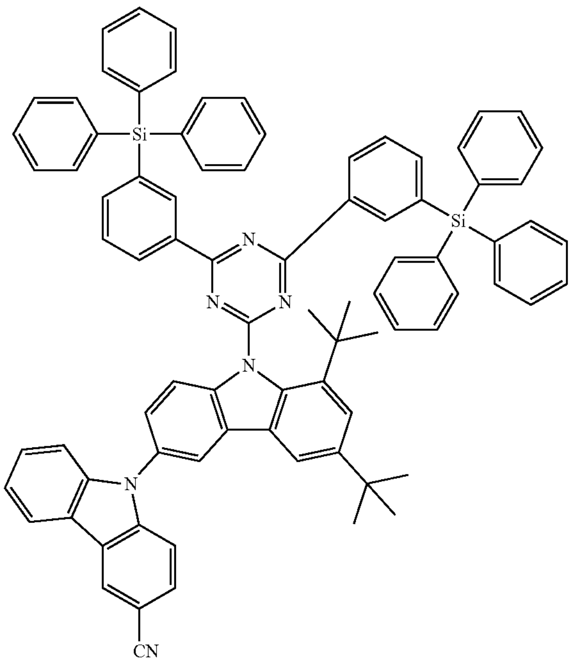
-continued
43
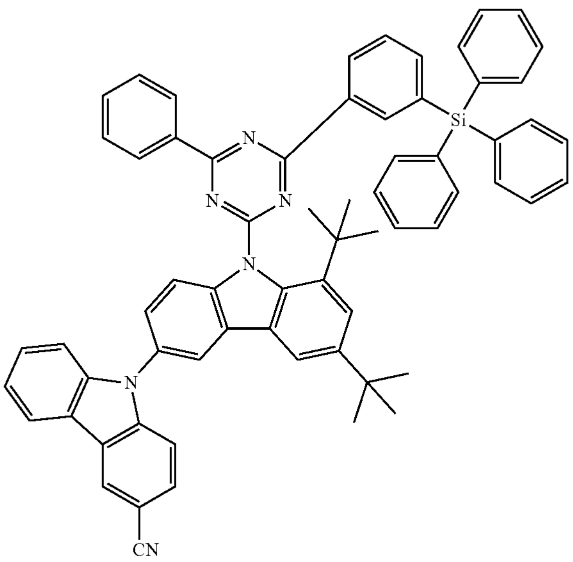
44
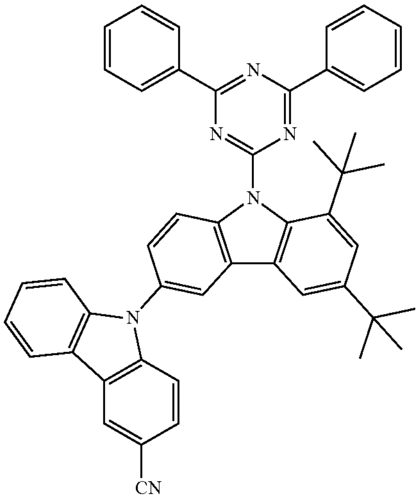
45
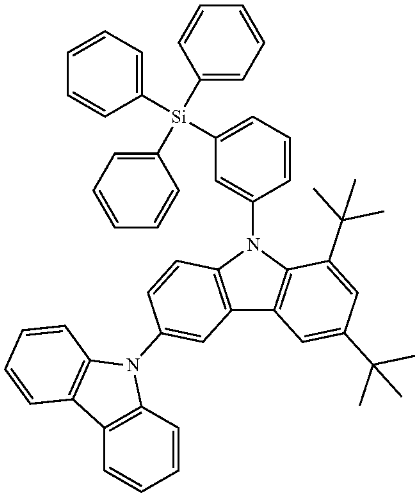

-continued
46
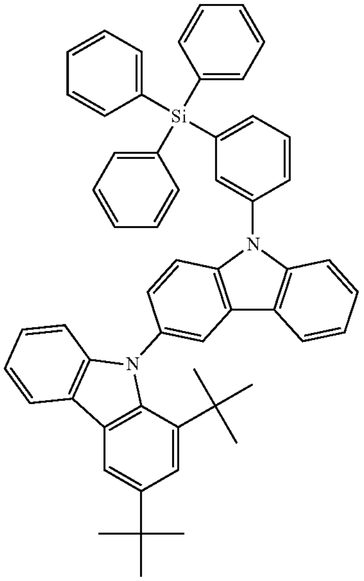
48
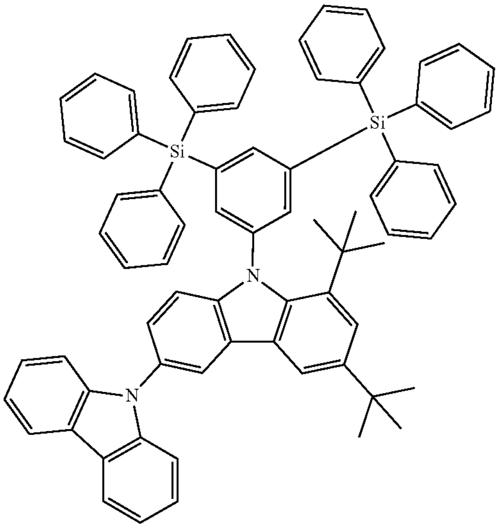
47
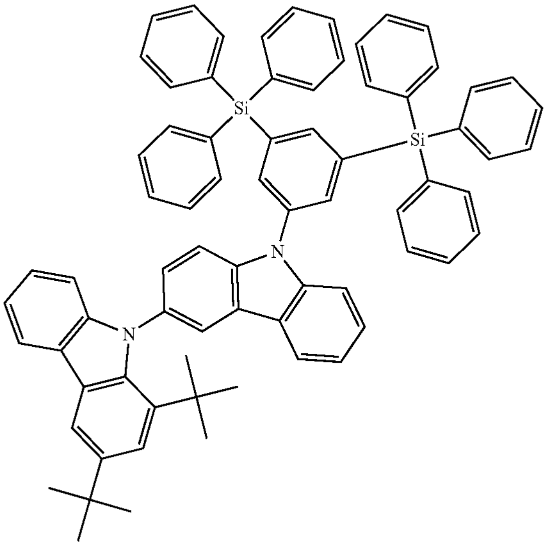
49
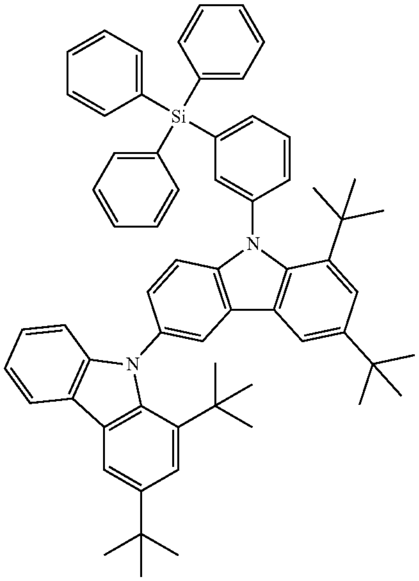

-continued
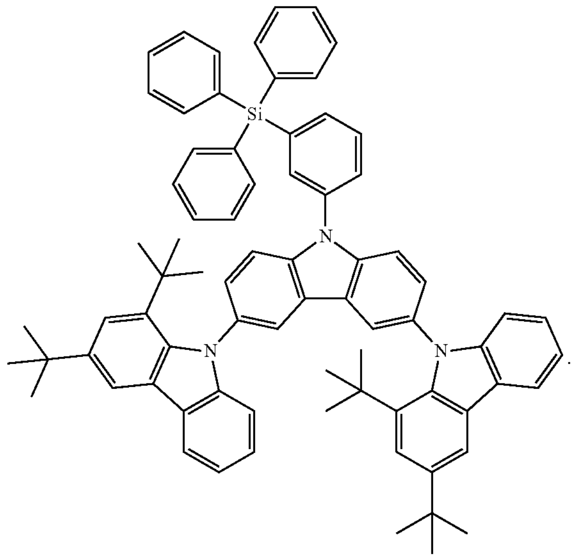
.
* * * * *